US012453773B2

(12) United States Patent
Liu

(10) Patent No.: US 12,453,773 B2
(45) Date of Patent: Oct. 28, 2025

(54) EXPANSION OF NATURAL KILLER AND CHIMERIC ANTIGEN RECEPTOR-MODIFIED CELLS

(71) Applicants: Rutgers, The State University of New Jersey, New Brunswick, NJ (US); Houston Methodist Hospital, Houston, TX (US)

(72) Inventor: Dongfang Liu, Millburn, NJ (US)

(73) Assignees: Rutgers, The State University of New Jersey, New Brunswick, NJ (US); Houston Methodist Hospital, Houston, TX (US)

(*) Notice: Subject to any disclaimer, the term of this patent is extended or adjusted under 35 U.S.C. 154(b) by 1015 days.

(21) Appl. No.: 17/432,380

(22) PCT Filed: Feb. 19, 2020

(86) PCT No.: PCT/US2020/018897

§ 371 (c)(1),
(2) Date: Aug. 19, 2021

(87) PCT Pub. No.: WO2020/172328

PCT Pub. Date: Aug. 27, 2020

(65) Prior Publication Data

US 2022/0152102 A1 May 19, 2022

Related U.S. Application Data

(60) Provisional application No. 62/808,031, filed on Feb. 20, 2019.

(51) Int. Cl.

| | |
|---|---|
| ***A61K 40/15*** | (2025.01) |
| ***A61K 38/17*** | (2006.01) |
| ***A61K 38/20*** | (2006.01) |
| ***A61K 40/31*** | (2025.01) |
| ***A61K 40/42*** | (2025.01) |
| ***A61P 35/00*** | (2006.01) |
| ***C12N 5/0781*** | (2010.01) |
| ***C12N 5/0783*** | (2010.01) |
| ***C12N 15/86*** | (2006.01) |

(52) U.S. Cl.

CPC .......... *A61K 40/15* (2025.01); *A61K 38/1774* (2013.01); *A61K 38/20* (2013.01); *A61K 40/31* (2025.01); *A61K 40/4211* (2025.01); *A61P 35/00* (2018.01); *C12N 5/0635* (2013.01); *C12N 5/0636* (2013.01); *C12N 5/0646* (2013.01); *C12N 15/86* (2013.01); *A61K 2239/31* (2023.05); *A61K 2239/38* (2023.05); *A61K 2239/48* (2023.05); *C12N 2501/2302* (2013.01); *C12N 2501/2315* (2013.01); *C12N 2501/2321* (2013.01); *C12N 2502/1107* (2013.01); *C12N 2740/10043* (2013.01)

(58) Field of Classification Search

CPC ... A61K 39/46; A61K 39/4612; C12N 5/0635
See application file for complete search history.

(56) References Cited

U.S. PATENT DOCUMENTS

2010/0330053 A1 12/2010 Song et al.

FOREIGN PATENT DOCUMENTS

| | | | |
|---|---|---|---|
| CN | 102911918 B | 12/2014 | |
| CN | 106574244 A | 4/2017 | |
| WO | WO 2015/154012 A1 | 10/2015 | |
| WO | WO 2018/022646 A1 | 2/2018 | |
| WO | WO 2018/081470 A1 | 5/2018 | |
| WO | WO-2018182511 A1 * | 10/2018 | ............ A61K 35/17 |

OTHER PUBLICATIONS

Haryadi et al. Optimization of Heavy Chain and Light Chain Signal Peptides for High Level Expression of Therapeutic Antibodies in CHO Cells. PLoS One 2015, 10;2:e0116878. (Year: 2015).*

Klöß et al. Optimization of Human NK Cell Manufacturing: Fully Automated Separation, Improved Ex Vivo Expansion Using IL-21 with Autologous Feeder Cells, and Generation of Anti-CD123-CAR-Expressing Effector Cells. Human Gene Therapy 2017, 28;10:1-21. (Year: 2017).*

Denman et al., "Membrane-Bound IL-21 Promotes Sustained Ex Vivo Proliferation of Human Natural Killer Cells," *PLoS One*, 7:e30264, 2012 (13 pages).

Lisovsky et al., "Functional analysis of NK cell subsets activated by 721.221 and K562 HLA-null cells," *J. Leukocyte Biol.*, vol. 97, pp. 761-767, 2015.

Singh et al., "Reprogramming CD19-Specific T Cells with IL-21 Signaling Can Improve Adoptive Immunotherapy of B-lineage Malignancies," *Cancer Research*, vol. 71, No. 10, pp. 3516-3527, 2011.

Anton et al., "NK Cell Proliferation Induced by IL-15 Transpresentation Is Negatively Regulated by Inhibitory Receptors," *J. Immunol.*, vol. 195, No. 10, pp. 4810-4821, 2015 (Author manuscript version, 29 pages).

Lindemann et al. "Versatile Retrovirus Vector Systems for Regulated Gene Expression In Vitro and In Vivo," *Molecular Medicine*, vol. 3, No. 7, pp. 466-476, 1997.

Xiong et al. "Immunological Synapse Predicts Effectiveness of Chimeric Antigen Receptor Cells," *Mol. Ther.*, vol. 26, No. 4, pp. 963-975, 2018.

* cited by examiner

*Primary Examiner* — Christopher M Babic
*Assistant Examiner* — Jennifer S Spence
(74) *Attorney, Agent, or Firm* — Klarquist Sparkman, LLP

(57) ABSTRACT

Disclosed herein are methods and compositions for generating immunotherapeutic cells (e.g., NK and T cells) with enhanced cytotoxicity and capacity for expansion thereof. The methods and compositions disclosed herein can further be used for enhanced expansion of CAR-modified NK and T cells with increased cytotoxicity.

20 Claims, 76 Drawing Sheets

Specification includes a Sequence Listing.

FIG. 7B
PBS
K562-mIL21-CD19-CAR-NK
221-mIL21-CD19-CAR-NK
D1
D9
D15
D22
$2\times10^6$
$1\times10^5$

SEQUENCE LISTING

<160> NUMBER OF SEQ ID NOS: 27

<210> SEQ ID NO 1
<211> LENGTH: 462
<212> TYPE: DNA
<213> ORGANISM: Artificial Sequence
<220> FEATURE:
<223> OTHER INFORMATION: Exemplary nucleic acid sequence of the extracellular domain from interleukin (IL)-21

<400> SEQUENCE: 1
atggagtttg ggctgagctg gctttttctt gtggctattt taaaaggtgt ccagtgcgtc 60
gaccaaggtc aagatcgcca catgattaga atgcgtcaac ttatagatat tgttgatcag 120
ctgaaaaatt atgtgaatga cttggtccct gaatttctgc cagctccaga agatgtagag 180
acaaactgtg agtggtcagc tttttcctgc tttcagaagg cccaactaaa gtcagcaaat 240
acaggaaaca atgaaaggat aatcaatgta tcaattaaaa agctgaagag gaaaccacct 300
tccacaaatg cagggagaag acagaaacac agactaacat gcccttcatg tgattcttat 360
gagaaaaaac cacccaaaga attcctagaa agattcaaat cacttctcca aaagatgatt 420
catcagcatc tgtcctctag aacacacgga agtgaagatt cc 462

<210> SEQ ID NO 2
<211> LENGTH: 154
<212> TYPE: PRT
<213> ORGANISM: Artificial Sequence
<220> FEATURE:
<223> OTHER INFORMATION: Exemplary amino acid sequence of the extracellular domain from IL-21

<400> SEQUENCE: 2

Met Glu Phe Gly Leu Ser Trp Leu Phe Leu Val Ala Ile Leu Lys Gly
1 5 10 15

Val Gln Cys Val Asp Gln Gly Gln Asp Arg His Met Ile Arg Met Arg
20 25 30

Gln Leu Ile Asp Ile Val Asp Gln Leu Lys Asn Tyr Val Asn Asp Leu
35 40 45

Val Pro Glu Phe Leu Pro Ala Pro Glu Asp Val Glu Thr Asn Cys Glu
50 55 60

Trp Ser Ala Phe Ser Cys Phe Gln Lys Ala Gln Leu Lys Ser Ala Asn
65 70 75 80

Thr Gly Asn Asn Glu Arg Ile Ile Asn Val Ser Ile Lys Lys Leu Lys
85 90 95

Arg Lys Pro Pro Ser Thr Asn Ala Gly Arg Arg Gln Lys His Arg Leu
100 105 110

Thr Cys Pro Ser Cys Asp Ser Tyr Glu Lys Lys Pro Pro Lys Glu Phe
115 120 125

Leu Glu Arg Phe Lys Ser Leu Leu Gln Lys Met Ile His Gln His Leu
130 135 140

Ser Ser Arg Thr His Gly Ser Glu Asp Ser
145 150

<210> SEQ ID NO 3
<211> LENGTH: 1881
<212> TYPE: DNA
<213> ORGANISM: Artificial Sequence
<220> FEATURE:
<223> OTHER INFORMATION: Exemplary nucleic acid sequence of a construct for transducing cells with membrane-bound (m)IL-21

<400> SEQUENCE: 3
atggagtttg ggctgagctg gctttttctt gtggctattt taaaaggtgt ccagtgcgtc 60
gaccaaggtc aagatcgcca catgattaga atgcgtcaac ttatagatat tgttgatcag 120
ctgaaaaatt atgtgaatga cttggtccct gaatttctgc cagctccaga agatgtagag 180
acaaactgtg agtggtcagc tttttcctgc tttcagaagg cccaactaaa gtcagcaaat 240
acaggaaaca atgaaaggat aatcaatgta tcaattaaaa agctgaagag gaaaccacct 300
tccacaaatg cagggagaag acagaaacac agactaacat gcccttcatg tgattcttat 360
gagaaaaaac cacccaaaga attcctagaa agattcaaat cacttctcca aaagatgatt 420
catcagcatc tgtcctctag aacacacgga agtgaagatt ccctgcggcc gccgtacgtc 480
accgtctctt cacaggatcc cgccgagccc aaatctcctg acaaaactca cacatgccca 540
ccgtgcccag cacctgaact cctgggggga ccgtcagtct tcctcttccc cccaaaaccc 600
aaggacaccc tcatgatctc ccggacccct gaggtcacat gcgtggtggt ggacgtgagc 660
cacgaagacc ctgaggtcaa gttcaactgg tacgtggacg gcgtggaggt gcataatgcc 720
aagacaaagc cgcgggagga gcagtacaac agcacgtacc gtgtggtcag cgtcctcacc 780
gtcctgcacc aggactggct gaatggcaag gagtacaagt gcaaggtctc caacaaagcc 840
ctcccagccc ccatcgagaa aaccatctcc aaagccaaag ggcagccccg agaaccacag 900
gtgtacaccc tgcccccatc ccgggatgag ctgaccaaga accaggtcag cctgacctgc 960
ctggtcaaag gcttctatcc cagcgacatc gccgtggagt gggagagcaa tgggcaaccg 1020
gagaacaact acaagaccac gcctcccgtg ctggactccg acggctcctt cttcctctac 1080
agcaagctca ccgtggacaa gagcaggtgg cagcagggga acgtcttctc atgctccgtg 1140
atgcatgagg ctctgcacaa ccactacacg cagaagagcc tctccctgtc tccgggtaaa 1200
aaagatccca aattttgggt gctggtggtg gttggtggag tcctggcttg ctatagcttg 1260
ctagtaacag tggcctttat tatttttggg gtgaggagta agaggagcag gctcctgcac 1320
agtgactaca tgaacatgac tccccgccgc cccgggccca cccgcaagca ttaccagccc 1380
tatgccccac cacgcgactt cgcagcctat cgctccaaac ggggcagaaa gaaactcctg 1440
tatatattca aacaaccatt tatgagacca gtacaaacta ctcaagagga agatggctgt 1500
agctgccgat ttccagaaga agaagaagga ggatgtgaac tgagagtgaa gttcagcagg 1560
agcgcagacg cccccgcgta ccagcagggc cagaaccagc tctataacga gctcaatcta 1620
ggacgaagag aggagtacga tgttttggac aagagacgtg gccgggaccc tgagatgggg 1680
ggaaagccga gaaggaagaa ccctcaggaa ggcctgtaca atgaactgca gaaagataag 1740
atggcggagg cctacagtga gattgggatg aaaggcgagc gccggagggg caaggggcac 1800
gatggccttt accagggtct cagtacagcc accaaggaca cctacgacgc ccttcacatg 1860
caggccctgc cccctcgcta a 1881

<210> SEQ ID NO 4
<211> LENGTH: 1566
<212> TYPE: DNA
<213> ORGANISM: Artificial Sequence
<220> FEATURE:
<223> OTHER INFORMATION: Exemplary nucleic acid sequence of IL-15Ralpha

<400> SEQUENCE: 4
ctgggcagcg ctcgcccggg gagtccagcg gtgtcctgtg gagctgccgc catggccccg 60
cggcgggcgc gcggctgccg gaccctcggt ctcccggcgc tgctactgct gctgctgctc 120

```
cggccgccgg cgacgcgggg catcacgtgc cctcccccca tgtccgtgga acacgcagac    180

atctgggtca agagctacag cttgtactcc agggagcggt acatttgtaa ctctggtttc    240

aagcgtaaag ccggcacgtc cagcctgacg gagtgcgtgt tgaacaaggc cacgaatgtc    300

gcccactgga caacccccag tctcaaatgc attagagacc ctgccctggt tcaccaaagg    360

ccagcgccac cctccacagt aacgacggca ggggtgaccc cacagccaga gagcctctcc    420

ccttctggaa aagagcccgc agcttcatct cccagctcaa acaacacagc ggccacaaca    480

gcagctattg tcccgggctc ccagctgatg ccttcaaaat caccttccac aggaaccaca    540

gagataagca gtcatgagtc ctcccacggc accccctctc agacaacagc caagaactgg    600

gaactcacag catccgcctc ccaccagccg ccaggtgtgt atccacaggg ccacagcgac    660

accactgtgg ctatctccac gtccactgtc ctgctgtgtg ggctgagcgc tgtgtctctc    720

ctggcatgct acctcaagtc aaggcaaact cccccgctgg ccagcgttga aatggaagcc    780

atggaggctc tgccggtgac ttgggggacc agcagcagag atgaagactt ggaaaactgc    840

tctcaccacc tatgaaactc ggggaaacca gcccagctaa gtccggagtg aaggagcctc    900

tctgctttag ctaaagacga ctgagaagag gtgcaaggaa gcgggctcca ggagcaagct    960

caccaggcct ctcagaagtc ccagcaggat ctcacggact gccgggtcgg cgcctcctgc   1020

gcgagggagc aggttctccg cattcccatg ggcaccacct gcctgcctgt cgtgccttgg   1080

acccagggcc cagcttccca ggagagacca aaggcttctg agcaggattt ttatttcatt   1140

acagtgtgag ctgcctggaa tacatgtggt aatgaaataa aaaccctgcc ccgaatcttc   1200

cgtccctcat cctaactttc agttcacaga gaaaagtgac atacccaaag ctctctgtca   1260

attacaaggc ttctcctggc gtgggagacg tctacaggga agacaccagc gtttgggctt   1320

ctaaccaccc tgtctccagc tgctctgcac acatggacag ggacctggga aaggtgggag   1380

agatgctgag cccagcgaat cctctccatt gaaggattca ggaagaagaa aactcaactc   1440

agtgccattt tacgaatata tgcgtttata tttatacttc cttgtctatt atatctatac   1500

attatatatt atttgtattt tgacattgta ccttgtataa acaaaataaa acatctattt   1560

tcaata                                                              1566
```

<210> SEQ ID NO 5
<211> LENGTH: 267
<212> TYPE: PRT
<213> ORGANISM: Artificial Sequence
<220> FEATURE:
<223> OTHER INFORMATION: Exemplary amino acid sequence of IL-15Ralpha.

<400> SEQUENCE: 5

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95
```

```
Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

<210> SEQ ID NO 6
<211> LENGTH: 2333
<212> TYPE: DNA
<213> ORGANISM: Artificial Sequence
<220> FEATURE:
<223> OTHER INFORMATION: Exemplary nucleic acid sequence of IL-15

<400> SEQUENCE: 6

```
gttgggactc cgggtggcag gcgcccgggg gaatcccagc tgactcgctc actgccttcg     60

aagtccggcg ccccccggga gggaactggg tggccgcacc ctcccggctg cggtggctgt    120

cgcccccac cctgcagcca ggactcgatg gagaatccat tccaatatat ggccatgtgg    180

ctctttggag caatgttcca tcatgttcca tgctgctgac gtcacatgga gcacagaaat    240

caatgttagc agatagccag cccatacaag atcgttttca actagtggcc ccactgtgtc    300

cggaattgat gggttcttgg tctcactgac ttcaagaatg aagccgcgga ccctcgcggt    360

gagtgttaca gctcttaagg tggcgcatct ggagtttgtt ccttctgatg ttcggatgtg    420

ttcggagttt cttccttctg gtgggttcgt ggtctcgctg gctcaggagt gaagctacag    480

accttcgcgg aggcattgtg gatggatggc tgctggaaac cccttgccat agccagctct    540

tcttcaatac ttaaggattt accgtggctt tgagtaatga gaatttcgaa accacatttg    600

agaagtattt ccatccagtg ctacttgtgt ttacttctaa acagtcattt tctaactgaa    660

gctggcattc atgtcttcat tttgggatgc agctaatata cccagttggc ccaaagcacc    720

taacctatag ttatataatc tgactctcag ttcagtttta ctctactaat gccttcatgg    780

tattgggaac catagatttg tgcagctgtt tcagtgcagg gcttcctaaa acagaagcca    840

actgggtgaa tgtaataagt gatttgaaaa aaattgaaga tcttattcaa tctatgcata    900

ttgatgctac tttatatacg gaaagtgatg ttcaccccag ttgcaaagta acagcaatga    960

agtgctttct cttggagtta caagttattt cacttgagtc cggagatgca agtattcatg   1020

atacagtaga aaatctgatc atcctagcaa acaacagttt gtcttctaat gggaatgtaa   1080
```

```
cagaatctgg atgcaaagaa tgtgaggaac tggaggaaaa aaatattaaa gaatttttgc   1140
agagttttgt acatattgtc caaatgttca tcaacacttc ttgattgcaa ttgattcttt   1200
ttaaagtgtt tctgttatta acaaacatca ctctgctgct tagacataac aaaacactcg   1260
gcatttcaaa tgtgctgtca aaacaagttt ttctgtcaag aagatgatca gaccttggat   1320
cagatgaact cttagaaatg aaggcagaaa aatgtcattg agtaatatag tgactatgaa   1380
cttctctcag acttacttta ctcatttttt taatttatta ttgaaattgt acatatttgt   1440
ggaataatgt aaaatgttga ataaaaatat gtacaagtgt tgttttttaa gttgcactga   1500
tattttacct cttattgcaa aatagcattt gtttaagggt gatagtcaaa ttatgtattg   1560
gtggggctgg gtaccaatgc tgcaggtcaa cagctatgct ggtaggctcc tgccagtgtg   1620
gaaccactga ctactggctc tcattgactt ccttactaag catagcaaac agaggaagaa   1680
tttgttatca gtaagaaaaa gaagaactat atgtgaatcc tcttctttat actgtaattt   1740
agttattgat gtataaagca actgttatga aataaagaaa ttgcaataac tggcatataa   1800
tgtccatcag taaatcttgg tggtggtggc aataataaac ttctactgat aggtagaatg   1860
gtgtgcaagc ttgtccaatc acggattgca ggccacatgc ggcccaggac aactttgaat   1920
gtggcccaac acaaattcat aaactttcat acatctcgtt tttagctcat cagctatcat   1980
tagcggtagt gtatttaaag tgtggcccaa gacaattctt cttattccaa tgtggcccag   2040
ggaaatcaaa agattggatg cccctggtat agaaaactaa tagtgacagt gttcatattt   2100
catgctttcc caaatacagg tattttattt tcacattctt tttgccatgt ttatataata   2160
ataaagaaaa accctgttga tttgttggag ccattgttat ctgacagaaa ataattgttt   2220
atatttttg cactacactg tctaaaatta gcaagctctc ttctaatgga actgtaagaa   2280
agatgaaata tttttgtttt attataaatt tatttcacct taaaaaaaaa aaa          2333
```

```
<210> SEQ ID NO 7
<211> LENGTH: 135
<212> TYPE: PRT
<213> ORGANISM: Artificial Sequence
<220> FEATURE:
<223> OTHER INFORMATION: Exemplary amino acid sequence of IL-15

<400> SEQUENCE: 7

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135
```

<210> SEQ ID NO 8
<211> LENGTH: 822
<212> TYPE: DNA
<213> ORGANISM: Artificial Sequence
<220> FEATURE:
<223> OTHER INFORMATION: Exemplary nucleic acid sequence of IL-2

<400> SEQUENCE: 8

```
agttccctat cactctcttt aatcactact cacagtaacc tcaactcctg ccacaatgta      60

caggatgcaa ctcctgtctt gcattgcact aagtcttgca cttgtcacaa acagtgcacc     120

tacttcaagt tctacaaaga aaacacagct acaactggag catttactgc tggatttaca     180

gatgattttg aatggaatta ataattacaa gaatcccaaa ctcaccagga tgctcacatt     240

taagttttac atgcccaaga aggccacaga actgaaacat cttcagtgtc tagaagaaga     300

actcaaacct ctggaggaag tgctaaattt agctcaaagc aaaaactttc acttaagacc     360

cagggactta atcagcaata tcaacgtaat agttctggaa ctaaagggat ctgaaacaac     420

attcatgtgt gaatatgctg atgagacagc aaccattgta gaatttctga acagatggat     480

taccttttgt caaagcatca tctcaacact gacttgataa ttaagtgctt cccacttaaa     540

acatatcagg ccttctattt atttaaatat ttaaatttta tatttattgt tgaatgtatg     600

gtttgctacc tattgtaact attattctta atcttaaaac tataaatatg gatcttttat     660

gattcttttt gtaagcccta ggggctctaa aatggtttca cttatttatc ccaaaatatt     720

tattattatg ttgaatgtta aatatagtat ctatgtagat tggttagtaa aactatttaa     780

taaatttgat aaatataaaa aaaaaaaaaa aaaaaaaaaa aa                        822
```

<210> SEQ ID NO 9
<211> LENGTH: 153
<212> TYPE: PRT
<213> ORGANISM: Artificial Sequence
<220> FEATURE:
<223> OTHER INFORMATION: Amino acid sequence of IL-2

<400> SEQUENCE: 9

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 10
<211> LENGTH: 1044
<212> TYPE: DNA
<213> ORGANISM: Artificial Sequence
<220> FEATURE:
<223> OTHER INFORMATION: Exemplary nucleic acid sequence of IL-27

<400> SEQUENCE: 10
gaccaaagag gctgggcccc gccatgggcc agacggcagg cgaccttggc tggcggctca 60
gcctgttgct gcttcccttg ctcctggttc aagctggtgt ctggggattc ccaaggcccc 120
cagggaggcc ccagctgagc ctgcaggagc tgcggaggga gttcacagtc agcctgcatc 180
tcgccaggaa gctgctctcc gaggttcggg gccaggccca ccgctttgcg gaatctcacc 240
tgccaggagt gaacctgtac ctcctgcccc tgggagagca gctccctgat gtttccctga 300
ccttccaggc ctggcgccgc ctctctgacc cggagcgtct ctgcttcatc tccaccacgc 360
ttcagccctt ccatgccctg ctgggagggc tggggaccca gggccgctgg accaacatgg 420
agaggatgca gctgtgggcc atgaggctgg acctccgcga tctgcagcgg cacctccgct 480
tccaggtgct ggctgcagga ttcaacctcc cggaggagga ggaggaggaa gaggaggagg 540
aggaggagga gaggaagggg ctgctcccag gggcactggg cagcgcctta cagggcccgg 600
cccaggtgtc ctggccccag ctcctctcca cctaccgcct gctgcactcc ttggagctcg 660
tcttatctcg ggccgtgcgg gagttgctgc tgctgtccaa ggctgggcac tcagtctggc 720
ccttggggtt cccaacattg agcccccagc cctgatcggt ggcttcttag ccccctgccc 780
cccacccttt agaactttag gactggagtc ttggcatcag ggcagccttc gcatcatcag 840
ccttggacaa gggagggctc ttccagcccc ctgccccagg ctctacccag taactgaaag 900
cccctctggt cctcgccagc tatttatttc ttggatattt atttattgtt tagggagatg 960
atggtttatt tattgtcttg gggcccgatg gtcctcctcg ggccaagccc ccatgctggg 1020
tgcccaataa agcactctca tcca 1044

<210> SEQ ID NO 11
<211> LENGTH: 243
<212> TYPE: PRT
<213> ORGANISM: Artificial Sequence
<220> FEATURE:
<223> OTHER INFORMATION: Exemplary amino acid sequence of IL-27

<400> SEQUENCE: 11

Met Gly Gln Thr Ala Gly Asp Leu Gly Trp Arg Leu Ser Leu Leu Leu
1 5 10 15

Leu Pro Leu Leu Leu Val Gln Ala Gly Val Trp Gly Phe Pro Arg Pro
20 25 30

Pro Gly Arg Pro Gln Leu Ser Leu Gln Glu Leu Arg Arg Glu Phe Thr
35 40 45

Val Ser Leu His Leu Ala Arg Lys Leu Leu Ser Glu Val Arg Gly Gln
50 55 60

Ala His Arg Phe Ala Glu Ser His Leu Pro Gly Val Asn Leu Tyr Leu
65 70 75 80

Leu Pro Leu Gly Glu Gln Leu Pro Asp Val Ser Leu Thr Phe Gln Ala
85 90 95

Trp Arg Arg Leu Ser Asp Pro Glu Arg Leu Cys Phe Ile Ser Thr Thr
100 105 110

Leu Gln Pro Phe His Ala Leu Leu Gly Gly Leu Gly Thr Gln Gly Arg
115 120 125

```
Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro


<210> SEQ ID NO 12
<211> LENGTH: 2347
<212> TYPE: DNA
<213> ORGANISM: Artificial Sequence
<220> FEATURE:
<223> OTHER INFORMATION: Exemplary nucleic acid sequence of IL-12B

<400> SEQUENCE: 12

ctgtttcagg gccattggac tctccgtcct gcccagagca agatgtgtca ccagcagttg     60

gtcatctctt ggttttccct ggtttttctg gcatctcccc tcgtggccat atgggaactg    120

aagaaagatg tttatgtcgt agaattggat tggtatccgg atgcccctgg agaaatggtg    180

gtcctcacct gtgacacccc tgaagaagat ggtatcacct ggaccttgga ccagagcagt    240

gaggtcttag gctctggcaa aaccctgacc atccaagtca aagagtttgg agatgctggc    300

cagtacacct gtcacaaagg aggcgaggtt ctaagccatt cgctcctgct gcttcacaaa    360

aaggaagatg gaatttggtc cactgatatt ttaaaggacc agaaagaacc caaaaataag    420

acctttctaa gatgcgaggc caagaattat tctggacgtt tcacctgctg gtggctgacg    480

acaatcagta ctgatttgac attcagtgtc aaaagcagca gaggctcttc tgacccccaa    540

ggggtgacgt gcggagctgc tacactctct gcagagagag tcagagggga caacaaggag    600

tatgagtact cagtggagtg ccaggaggac agtgcctgcc cagctgctga ggagagtctg    660

cccattgagg tcatggtgga tgccgttcac aagctcaagt atgaaaacta caccagcagc    720

ttcttcatca gggacatcat caaacctgac ccacccaaga acttgcagct gaagccatta    780

aagaattctc ggcaggtgga ggtcagctgg gagtaccctg acacctggag tactccacat    840

tcctacttct ccctgacatt ctgcgttcag gtccagggca agagcaagag agaaaagaaa    900

gatagagtct tcacggacaa gacctcagcc acggtcatct gccgcaaaaa tgccagcatt    960

agcgtgcggg cccaggaccg ctactatagc tcatcttgga gcgaatgggc atctgtgccc   1020

tgcagttagg ttctgatcca ggatgaaaat ttggaggaaa agtggaagat attaagcaaa   1080

atgtttaaag acacaacgga atagacccaa aaagataatt tctatctgat ttgctttaaa   1140

acgttttttt aggatcacaa tgatatcttt gctgtatttg tatagttaga tgctaaatgc   1200

tcattgaaac aatcagctaa tttatgtata gattttccag ctctcaagtt gccatgggcc   1260

ttcatgctat ttaaatattt aagtaattta tgtatttatt agtatattac tgttatttaa   1320

cgtttgtctg ccaggatgta tggaatgttt catactctta tgacctgatc catcaggatc   1380
```

```
agtccctatt atgcaaaatg tgaatttaat tttatttgta ctgacaactt ttcaagcaag   1440

gctgcaagta catcagtttt atgacaatca ggaagaatgc agtgttctga taccagtgcc   1500

atcatacact tgtgatggat gggaacgcaa gagatactta catggaaacc tgacaatgca   1560

aacctgttga gaagatccag gagaacaaga tgctagttcc catgtctgtg aagacttcct   1620

ggagatggtg ttgataaagc aatttagggc cacttacact tctaagcaag tttaatcttt   1680

ggatgcctga attttaaaag ggctagaaaa aaatgattga ccagcctggg aaacataaca   1740

agaccccgtc tctacaaaaa aaatttaaaa ttagccaggc gtggtggctc atgcttgtgg   1800

tcccagctgt tcaggaggat gaggcaggag gatctcttga gcccaggagg tcaaggctat   1860

ggtgagccgt gattgtgcca ctgcatacca gcctaggtga cagaatgaga ccctgtctca   1920

aaaaaaaaaa tgattgaaat taaaattcag ctttagcttc catggcagtc ctcaccccca   1980

cctctctaaa agacacagga ggatgacaca gaaacaccgt aagtgtctgg aaggcaaaaa   2040

gatcttaaga ttcaagagag aggacaagta gttatggcta aggacatgaa attgtcagaa   2100

tggcaggtgg cttcttaaca gccctgtgag aagcagacag atgcaaagaa aatctggaat   2160

ccctttctca ttagcatgaa tgaacctgat acacaattat gaccagaaaa tatggctcca   2220

tgaaggtgct acttttaagt aatgtatgtg cgctctgtaa agtgattaca tttgtttcct   2280

gtttgtttat ttatttattt atttttgcat tctgaggctg aactaataaa aactcttctt   2340

tgtaatc                                                             2347
```

<210> SEQ ID NO 13
<211> LENGTH: 328
<212> TYPE: PRT
<213> ORGANISM: Artificial Sequence
<220> FEATURE:
<223> OTHER INFORMATION: Exemplary amino acid sequence of IL-12B

<400> SEQUENCE: 13

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190
```

```
Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 14
<211> LENGTH: 823
<212> TYPE: DNA
<213> ORGANISM: Artificial Sequence
<220> FEATURE:
<223> OTHER INFORMATION: Exemplary nucleic acid sequence of IL-12 p35

<400> SEQUENCE: 14

agaaagcaag agaccagagt cccgggaaag tcctgccgcg cctcgggaca attataaaaa      60

tgtggccccc tgggtcagcc tcccagccac cgccctcacc tgccgcggcc acaggtctgc     120

atccagcggc tcgccctgtg tccctgcagt gccggctcag catgtgtcca gcgcgcagcc     180

tcctccttgt ggctaccctg gtcctcctgg accacctcag tttggccaga aacctccccg     240

tggccactcc agacccagga atgttcccat gccttcacca ctcccaaaac ctgctgaggg     300

ccgtcagcaa catgctccag aaggccagac aaactctaga attttaccct tgcacttctg     360

aagagattga tcatgaagat atcacaaaag ataaaaccag cacagtggag gcctgtttac     420

cattggaatt aaccaagaat gagagttgcc taaattccag agagacctct ttcataacta     480

atgggagttg cctggcctcc agaaagacct cttttatgat ggccctgtgc cttagtagta     540

tttatgaaga cttgaagatg taccaggtgg agttcaagac catgaatgca aagcttctga     600

tggatcctaa gaggcagatc tttctagatc aaaacatgct ggcagttatt gatgagctga     660

tgcaggccct gaatttcaac agtgagactg tgccacaaaa atcctccctt gaagaaccgg     720

atttttataa aactaaaatc aagctctgca tacttcttca tgctttcaga attcgggcag     780

tgactattga tagagtgatg agctatctga atgcttccta aaa                       823


<210> SEQ ID NO 15
<211> LENGTH: 253
<212> TYPE: PRT
<213> ORGANISM: Artificial Sequence
<220> FEATURE:
<223> OTHER INFORMATION: Exemplary amino acid sequence of IL-12 p35

<400> SEQUENCE: 15

Met Trp Pro Pro Gly Ser Ala Ser Gln Pro Pro Pro Ser Pro Ala Ala
1               5                   10                  15
```

-continued

```
Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```

<210> SEQ ID NO 16
<211> LENGTH: 1007
<212> TYPE: DNA
<213> ORGANISM: Artificial Sequence
<220> FEATURE:
<223> OTHER INFORMATION: Exemplary nucleic acid sequence of IL-12 p40

<400> SEQUENCE: 16

```
agcaagatgt gtcaccagca gttggtcatc tcttggtttt ccctggtttt tctggcatct      60

cccctcgtgg ccatatggga actgaagaaa gatgtttatg tcgtagaatt ggattggtat     120

ccggatgccc ctggagaaat ggtggtcctc acctgtgaca cccctgaaga agatggtatc     180

acctggacct tggaccagag cagtgaggtc ttaggctctg gcaaaaccct gaccatccaa     240

gtcaaagagt ttggagatgc tggccagtac acctgtcaca aaggaggcga ggttctaagc     300

cattcgctcc tgctgcttca caaaaaggaa gatggaattt ggtccactga tattttaaag     360

gaccagaaag aacccaaaaa taagaccttt ctaagatgcg aggccaagaa ttattctgga     420

cgtttcacct gctggtggct gacgacaatc agtactgatt tgacattcag tgtcaaaagc     480

agcagaggct cttctgaccc ccaaggggtg acgtgcggag ctgctacact ctctgcagag     540

agagtcagag gggacaacaa ggagtatgag tactcagtgg agtgccagga ggacagtgcc     600

tgcccagctg ctgaggagag tctgcccatt gaggtcatgg tggatgccgt tcacaagctc     660

aagtatgaaa actacaccag cagcttcttc atcagggaca tcatcaaacc tgacccaccc     720
```

```
aagaacttgc agctgaagcc attaaagaat tctcggcagg tggaggtcag ctgggagtac    780

cctgacacct ggagtactcc acattcctac ttctccctga cattctgcgt tcaggtccag    840

ggcaagagca agagagaaaa gaaagataga gtcttcacgg acaagacctc agccacggtc    900

atctgccgca aaaatgccag cattagcgtg cgggcccagg accgctacta tagctcatct    960

tggagcgaat gggcatctgt gccctgcagt taggttctga tccagga                 1007


<210> SEQ ID NO 17
<211> LENGTH: 328
<212> TYPE: PRT
<213> ORGANISM: Artificial Sequence
<220> FEATURE:
<223> OTHER INFORMATION: Exemplary amino acid sequence of IL-12 p40.

<400> SEQUENCE: 17

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320
```

```
Glu Trp Ala Ser Val Pro Cys Ser
                325

<210> SEQ ID NO 18
<211> LENGTH: 1151
<212> TYPE: DNA
<213> ORGANISM: Artificial Sequence
<220> FEATURE:
<223> OTHER INFORMATION: Exemplary nucleic acid sequence of IL-18

<400> SEQUENCE: 18

attctctccc cagcttgctg agccctttgc tcccctggcg actgcctgga cagtcagcaa     60

ggaattgtct cccagtgcat tttgccctcc tggctgccaa ctctggctgc taaagcggct    120

gccacctgct gcagtctaca cagcttcggg aagaggaaag gaacctcaga ccttccagat    180

cgcttcctct cgcaacaaac tatttgtcgc aggaataaag atggctgctg aaccagtaga    240

agacaattgc atcaactttg tggcaatgaa atttattgac aatacgcttt actttataga    300

aaacctggaa tcagattact ttggcaagct tgaatctaaa ttatcagtca taagaaattt    360

gaatgaccaa gttctcttca ttgaccaagg aaatcggcct ctatttgaag atatgactga    420

ttctgactgt agagataatg caccccggac catatttatt ataagtatgt ataaagatag    480

ccagcctaga ggtatggctg taactatctc tgtgaagtgt gagaaaattt caactctctc    540

ctgtgagaac aaaattattt cctttaagga aatgaatcct cctgataaca tcaaggatac    600

aaaaagtgac atcatattct ttcagagaag tgtcccagga catgataata agatgcaatt    660

tgaatcttca tcatacgaag gatactttct agcttgtgaa aaagagagag accttttaa     720

actcattttg aaaaaagagg atgaattggg ggatagatct ataatgttca ctgttcaaaa    780

cgaagactag ctattaaaat ttcatgccgg gcgcagtggc tcacgcctgt aatcccagcc    840

ctttgggagg ctgaggcggg cagatcacca gaggtcaggt gttcaagacc agcctgacca    900

acatggtgaa acctcatctc tactaaaaat acaaaaaatt agctgagtgt agtgacgcat    960

gccctcaatc ccagctactc aagaggctga ggcaggagaa tcacttgcac tccggaggta   1020

gaggttgtgg tgagccgaga ttgcaccatt gcgctctagc ctgggcaaca acagcaaaac   1080

tccatctcaa aaaataaaat aaataaataa acaaataaaa aattcataat gtgaaaaaaa   1140

aaaaaaaaaa a                                                        1151


<210> SEQ ID NO 19
<211> LENGTH: 189
<212> TYPE: PRT
<213> ORGANISM: Artificial Sequence
<220> FEATURE:
<223> OTHER INFORMATION: Exemplary amino acid sequence of IL-18

<400> SEQUENCE: 19

Met Ala Ala Glu Pro Val Glu Asp Asn Cys Ile Asn Phe Val Ala Met
1               5                   10                  15

Lys Phe Ile Asp Asn Thr Leu Tyr Phe Ile Glu Asn Leu Glu Ser Asp
            20                  25                  30

Tyr Phe Gly Lys Leu Glu Ser Lys Leu Ser Val Ile Arg Asn Leu Asn
        35                  40                  45

Asp Gln Val Leu Phe Ile Asp Gln Gly Asn Arg Pro Leu Phe Glu Asp
    50                  55                  60

Met Thr Asp Ser Asp Cys Arg Asp Asn Ala Pro Arg Thr Ile Phe Ile
65                  70                  75                  80
```

```
Ile Ser Met Tyr Lys Asp Ser Gln Pro Arg Gly Met Ala Val Thr Ile
                85                  90                  95

Ser Val Lys Cys Glu Lys Ile Ser Thr Leu Ser Cys Glu Asn Lys Ile
            100                 105                 110

Ile Ser Phe Lys Glu Met Asn Pro Pro Asp Asn Ile Lys Asp Thr Lys
        115                 120                 125

Ser Asp Ile Ile Phe Phe Gln Arg Ser Val Pro Gly His Asp Asn Lys
    130                 135                 140

Met Gln Phe Glu Ser Ser Ser Tyr Glu Gly Tyr Phe Leu Ala Cys Glu
145                 150                 155                 160

Lys Glu Arg Asp Leu Phe Lys Leu Ile Leu Lys Lys Glu Asp Glu Leu
                165                 170                 175

Gly Asp Arg Ser Ile Met Phe Thr Val Gln Asn Glu Asp
            180                 185
```

<210> SEQ ID NO 20
<211> LENGTH: 1115
<212> TYPE: DNA
<213> ORGANISM: Artificial Sequence
<220> FEATURE:
<223> OTHER INFORMATION: Exemplary nucleic acid sequence of IL-18

<400> SEQUENCE: 20

```
cctttgctcc cctggcgact gcctggacag tcagcaagga attgtctccc agtgcatttt     60

gccctcctgg ctgccaactc tggctgctaa agcggctgcc acctgctgca gtctacacag    120

cttcgggaag aggaaaggaa cctcagacct tccagatcgc ttcctctcgc aacaaactat    180

ttgtcgcagg aataaagatg gctgctgaac cagtagaaga caattgcatc aactttgtgg    240

caatgaaatt tattgacaat acgctttact ttatagctga agatgatgaa aacctggaat    300

cagattactt tggcaagctt gaatctaaat tatcagtcat aagaaatttg aatgaccaag    360

ttctcttcat tgaccaagga aatcggcctc tatttgaaga tatgactgat tctgactgta    420

gagataatgc accccggacc atatttatta taagtatgta taaagatagc cagcctagag    480

gtatggctgt aactatctct gtgaagtgtg agaaaatttc aactctctcc tgtgagaaca    540

aaattatttc ctttaaggaa atgaatcctc ctgataacat caaggataca aaaagtgaca    600

tcatattctt tcagagaagt gtcccaggac atgataataa gatgcaattt gaatcttcat    660

catacgaagg atactttcta gcttgtgaaa aagagagaga cctttttaaa ctcattttga    720

aaaaagagga tgaattgggg gatagatcta taatgttcac tgttcaaaac gaagactagc    780

tattaaaatt tcatgccggg cgcagtggct cacgcctgta atcccagccc tttgggaggc    840

tgaggcgggc agatcaccag aggtcaggtg ttcaagacca gcctgaccaa catggtgaaa    900

cctcatctct actaaaaata caaaaaatta gctgagtgta gtgacgcatg ccctcaatcc    960

cagctactca agaggctgag gcaggagaat cacttgcact ccggaggtag aggttgtggt   1020

gagccgagat tgcaccattg cgctctagcc tgggcaacaa cagcaaaact ccatctcaaa   1080

aaataaaata aataaataaa caaataaaaa attca                              1115
```

<210> SEQ ID NO 21
<211> LENGTH: 193
<212> TYPE: PRT
<213> ORGANISM: Artificial Sequence
<220> FEATURE:
<223> OTHER INFORMATION: Exemplary amino acid sequence of IL-18

<400> SEQUENCE: 21

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

<210> SEQ ID NO 22
<211> LENGTH: 2612
<212> TYPE: DNA
<213> ORGANISM: Artificial Sequence
<220> FEATURE:
<223> OTHER INFORMATION: Exemplary nucleic acid sequence of IL-33

<400> SEQUENCE: 22

```
ctgctgcctt ccaccatcag atgatcctca ccagatgcca gcataatatt cttggatttg     60

cctgcctcta gaagtaatcc caacagaagg ccaaagaagt ttgccccatg tactttatga    120

agctccgctc tggccttatg ataaaaaagg aggcctgtta ctttaggaga gaaaccacca    180

aaaggccttc actgaaaaca ggtagaaagc acaaaagaca tctggtactc gctgcctgtc    240

aacagcagtc tactgtggag tgctttgcct ttggtatatc aggggtccag aaatatacta    300

gagcacttca tgattcaagt atcacaggaa tttcacctat tacagagtat cttgcttctc    360

taagcacata caatgatcaa tccattactt ttgctttgga ggatgaaagt tatgagatat    420

atgttgaaga cttgaaaaaa gatgaaaaga aagataaggt gttactgagt tactatgagt    480

ctcaacaccc ctcaaatgaa tcaggtgacg gtgttgatgg taagatgtta atggtaaccc    540

tgagtcctac aaaagacttc tggttgcatg ccaacaacaa ggaacactct gtggagctcc    600

ataagtgtga aaaaccactg ccagaccagg ccttctttgt ccttcataat atgcactcca    660

actgtgtttc atttgaatgc aagactgatc ctggagtgtt tataggtgta aaggataatc    720

atcttgctct gattaaagta gactcttctg agaatttgtg tactgaaaat atcttgttta    780

agctctctga aacttagttg atggaaacct gtgagtcttg ggttgagtac ccaaatgcta    840

ccactggaga aggaatgaga gataaagaaa gagacaggtg acatctaagg gaaatgaaga    900

gtgcttagca tgtgtggaat gttttccata ttatgtataa aaatattttt tctaatcctc    960
```

cagttattct tttatttccc tctgtataac tgcatcttca atacaagtat cagtatatta 1020
aatagggtat tggtaaagaa acggtcaaca ttctaaagag atacagtctg acctttactt 1080
ttctctagtt tcagtccaga aagaacttca tatttagagc taaggccact gaggaaagag 1140
ccatagctta agtctctatg tagacaggga tccattttaa agagctactt agagaaataa 1200
ttttccacag ttccaaacga taggctcaaa cactagagct gctagtaaaa agaagaccag 1260
atgcttcaca gaattatcat tttttcaact ggaataaaac accaggtttg tttgtagatg 1320
tcttaggcaa cactcagagc agatctccct tactgtcagg ggatatggaa cttcaaaggc 1380
ccacatggca agccaggtaa cataaatgtg tgaaaaagta aagataacta aaaaatttag 1440
aaaaataaat ccagtatttg taaagtgaat aacttcattt ctaattgttt aatttttaaa 1500
attctgattt ttatatattg agtttaagca aggcattctt acacgaggaa gtgaagtaaa 1560
ttttagttca gacataaaat ttcacttatt aggaatatgt aacatgctaa aacttttttt 1620
tttttaaaga gtactgagtc acaacatgtt ttagagcatc caagtaccat ataatccaac 1680
tatcatggta aggccagaaa tcttctaacc taccagagcc tagatgagac accgaattaa 1740
cattaaaatt tcagtaactg actgtccctc atgtccatgg cctaccatcc cttctgaccc 1800
tggcttccag ggacctatgt cttttaatac tcactgtcac attgggcaaa gttgcttcta 1860
atccttattt cccatgtgca caagtctttt tgtattccag cttcctgata acactgctta 1920
ctgtggaata ttcatttgac atctgtctct tttcatttct tttaactacc atgcccttga 1980
tatatctttt gcacctgctg aacttcattt ctgtatcacc tgacctctgg atgccaaaac 2040
gtttattctg ctttgtctgt tgtagaattt tagataaagc tattaatggc aatatttttt 2100
tgctaaacgt tttgttttt tactgtcact agggcaataa aatttatact caaccatata 2160
ataacatttt ttaactacta aaggagtagt ttttatttta aagtcttagc aatttctatt 2220
acaacttttc ttagacttaa cacttatgat aaatgactaa catagtaaca gaatctttat 2280
gaaatatgac cttttctgaa aatacatact tttacatttc tactttattg agacctatta 2340
gatgtaagtg ctagtagaat ataagataaa agaggctgag aattaccata caagggtatt 2400
acaactgtaa aacaatttat ctttgtttca ttgttctgtc aataattgtt accaaagaga 2460
taaaaataaa agcagaatgt atatcatccc atctgaaaaa cactaattat tgacatgtgc 2520
atctgtacaa taaacttaaa atgattatta aataatcaaa tatatctact acattgttta 2580
tattattgaa taaagtatat tttccaaatg ta 2612

<210> SEQ ID NO 23
<211> LENGTH: 229
<212> TYPE: PRT
<213> ORGANISM: Artificial Sequence
<220> FEATURE:
<223> OTHER INFORMATION: Exemplary amino acid sequence of IL-33

<400> SEQUENCE: 23

Met Tyr Phe Met Lys Leu Arg Ser Gly Leu Met Ile Lys Lys Glu Ala
1 5 10 15

Cys Tyr Phe Arg Arg Glu Thr Thr Lys Arg Pro Ser Leu Lys Thr Gly
20 25 30

Arg Lys His Lys Arg His Leu Val Leu Ala Ala Cys Gln Gln Gln Ser
35 40 45

Thr Val Glu Cys Phe Ala Phe Gly Ile Ser Gly Val Gln Lys Tyr Thr
50 55 60

Arg Ala Leu His Asp Ser Ser Ile Thr Gly Ile Ser Pro Ile Thr Glu
65 70 75 80

Tyr Leu Ala Ser Leu Ser Thr Tyr Asn Asp Gln Ser Ile Thr Phe Ala
85 90 95

Leu Glu Asp Glu Ser Tyr Glu Ile Tyr Val Glu Asp Leu Lys Lys Asp
100 105 110

Glu Lys Lys Asp Lys Val Leu Leu Ser Tyr Tyr Glu Ser Gln His Pro
115 120 125

Ser Asn Glu Ser Gly Asp Gly Val Asp Gly Lys Met Leu Met Val Thr
130 135 140

Leu Ser Pro Thr Lys Asp Phe Trp Leu His Ala Asn Asn Lys Glu His
145 150 155 160

Ser Val Glu Leu His Lys Cys Glu Lys Pro Leu Pro Asp Gln Ala Phe
165 170 175

Phe Val Leu His Asn Met His Ser Asn Cys Val Ser Phe Glu Cys Lys
180 185 190

Thr Asp Pro Gly Val Phe Ile Gly Val Lys Asp Asn His Leu Ala Leu
195 200 205

Ile Lys Val Asp Ser Ser Glu Asn Leu Cys Thr Glu Asn Ile Leu Phe
210 215 220

Lys Leu Ser Glu Thr
225

<210> SEQ ID NO 24
<211> LENGTH: 2016
<212> TYPE: DNA
<213> ORGANISM: Artificial Sequence
<220> FEATURE:
<223> OTHER INFORMATION: Exemplary nucleic acid sequence of IL-7

<400> SEQUENCE: 24
acacttgtgg cttccgtgca cacattaaca actcatggtt ctagctccca gtcgccaagc 60
gttgccaagg cgttgagaga tcatctggga agtcttttac ccagaattgc tttgattcag 120
gccagctggt tttcctgcg gtgattcgga aattcgcgaa ttcctctggt cctcatccag 180
gtgcgcggga agcaggtgcc caggagagag gggataatga agattccatg ctgatgatcc 240
caaagattga acctgcagac caagcgcaaa gtagaaactg aaagtacact gctggcggat 300
cctacggaag ttatggaaaa ggcaaagcgc agagccacgc cgtagtgtgt gccgcccccc 360
ttgggatgga tgaaactgca gtcgcggcgt gggtaagagg aaccagctgc agagatcacc 420
ctgcccaaca cagactcggc aactccgcgg aagaccaggg tcctgggagt gactatgggc 480
ggtgagagct tgctcctgct ccagttgcgg tcatcatgac tacgcccgcc tcccgcagac 540
catgttccat gtttctttta ggtatatctt tggacttcct cccctgatcc ttgttctgtt 600
gccagtagca tcatctgatt gtgatattga aggtaaagat ggcaaacaat atgagagtgt 660
tctaatggtc agcatcgatc aattattgga cagcatgaaa gaaattggta gcaattgcct 720
gaataatgaa tttaactttt ttaaaagaca tatctgtgat gctaataagg aaggtatgtt 780
tttattccgt gctgctcgca agttgaggca atttcttaaa atgaatagca ctggtgattt 840
tgatctccac ttattaaaag tttcagaagg cacaacaata ctgttgaact gcactggcca 900
ggttaaagga agaaaaccag ctgccctggg tgaagcccaa ccaacaaaga gtttggaaga 960
aaataaatct ttaaaggaac agaaaaaact gaatgacttg tgtttcctaa agagactatt 1020
acaagagata aaaacttgtt ggaataaaat tttgatgggc actaaagaac actgaaaaat 1080

```
atggagtggc aatatagaaa cacgaacttt agctgcatcc tccaagaatc tatctgctta   1140

tgcagttttt cagagtggaa tgcttcctag aagttactga atgcaccatg gtcaaaacgg   1200

attagggcat ttgagaaatg catattgtat tactagaaga tgaatacaaa caatggaaac   1260

tgaatgctcc agtcaacaaa ctatttctta tatatgtgaa catttatcaa tcagtataat   1320

tctgtactga tttttgtaag acaatccatg taaggtatca gttgcaataa tacttctcaa   1380

acctgtttaa atatttcaag acattaaatc tatgaagtat ataatggttt caaagattca   1440

aaattgacat tgctttactg tcaaaataat tttatggctc actatgaatc tattatactg   1500

tattaagagt gaaaattgtc ttcttctgtg ctggagatgt tttagagtta acaatgatat   1560

atggataatg ccggtgagaa taagagagtc ataaacctta agtaagcaac agcataacaa   1620

ggtccaagat acctaaaaga gatttcaaga gatttaatta atcatgaatg tgtaacacag   1680

tgccttcaat aaatggtata gcaaatgttt tgacatgaaa aaaggacaat ttcaaaaaaa   1740

taaaataaaa taaaaataaa ttcacctagt ctaaggatgc taaaccttag tactgagtta   1800

cattgtcatt tatatagatt ataacttgtc taaataagtt tgcaatttgg gagatatatt   1860

tttaagataa taatatatgt ttacctttta attaatgaaa tatctgtatt taattttgac   1920

actatatctg tatataaaat attttcatac agcattacaa attgcttact ttggaataca   1980

tttctccttt gataaaataa atgagctatg tattaa                             2016
```

<210> SEQ ID NO 25
<211> LENGTH: 177
<212> TYPE: PRT
<213> ORGANISM: Artificial Sequence
<220> FEATURE:
<223> OTHER INFORMATION: Exemplary amino acid sequence of IL-7

<400> SEQUENCE: 25

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 26

<211> LENGTH: 12846
<212> TYPE: DNA
<213> ORGANISM: Artificial Sequence
<220> FEATURE:
<223> OTHER INFORMATION: Exemplary nucleic acid sequence of MICA

<400> SEQUENCE: 26
tggtctgagc ggttctactg cggcaggtgc ttctgagagg cagaggtggc tgagatctgg 60
aaacaggtct gcaaatctgg tcactggtct cattgccagt aacgctgtgc gcggttgagg 120
gagtgtgttg ggagaatagc cacgcgttgt ctgtcctgga aggaacaagc cagtgagagc 180
cggtttaatg gggcggccgg cgaaaggggc ttggtgaggc ccgcgctcct cggggtgggg 240
gcgcggggat gggtggtcgc gatgccggga gggcaggcag ggccctgccc gtgcttatga 300
agttggagct gtactctcag ctactcgaag ctggtccctg ctttaggctg cgctcccgcg 360
tgctccccat tttctgggcc ccaggtcccg ccttctaaat ctccccaggt ctccagccca 420
ctggaatttt ctcttccaag cgtggccccg ccctctccgc tcgtgattgg ccctaagttc 480
cgggccccag tttcattgga tgagcggtcg ggggaccggg ccaggtgact aagtttccgc 540
ggcgccttct ccccggccac tgcttgagcc gctgagaggg tggcgacgtc ggggccatgg 600
ggctgggccc ggtcttcctg cttctggctg gcatcttccc ttttgcacct ccgggagctg 660
ctgctggtga gtggcgttcc tggcggtcct cggcggagcg ggagcagtgg gacgtttccg 720
ggggtcgggt gggtagcggc gagcgctgtg cggtcagggc gggcctcctg tgcgctgtcg 780
gtggcgcagg gagctggacg cggcccgtta ccgccacact tcagccctgc ttccccgtca 840
cttttcagtc ctcctcggga tcgcgcatca cctgcacttt ctggtctcct cctgctcttt 900
ctctcctcgc gtctcctccg cttcctctca cttttcggac aaaccagtcc ttctgaggcc 960
catgggttcc cgggctgcct ccggggctgc tcctgtgaat ggcattcgag tgcccttcca 1020
gcgcggccac tgaagcagcc acaacccccg gtgctcgggg cggctctcag gtccctgaag 1080
tcctgtcctc tcccggagcc gacgtgttct cagctcctgg gccgcagctc ctggagtagg 1140
ggccctcctt tctcgggacc cggagctggt gcttcctgct gctgtgggga ctgtgggggg 1200
tcctgactct caagctgagg ggttggagtc tgcaggctcc gggcagagga ttcttcctgc 1260
gacttctctc atccccagct cattctcccc tcgcctctgg ctccgagggt cctctcctct 1320
ctctcatccc accccctacta atgaccagtg atctaaggac accagattcc ctctcacctc 1380
ctccctgccc atctcagggc ccgctgagtc cttttgccct cccagctccc tgctacccct 1440
tcctgtgtgc tgttctctga tccatttcta gggtgtcctc tgccctcatc ccctgtcccc 1500
gccaccgaag gtccctcctg cacccccttat gggcctttcc tacaagcagc cttcacccag 1560
tgctgcccct atgcctcccc gttcccaaat gtccctgact ctaactttct ggtgctgcct 1620
tttatccggg ggggtcttcc ctccatccca ctcccctcca cacccccaag gggaaccctg 1680
atgctaatgg cagttgggcc ttaggcaggg cgcagggcag cgcagatgcc ccctcccctc 1740
cagtgcagat gcctgctctg gaccctgcct cattgtggcc ccttccccac tccttcatcc 1800
tcagcctcac cctcttgagg accccaccct ccagcccaca ggtgctggac catccctccc 1860
tggtccctcc gcccctctcc accttgggac cttgtgctgc tcctatctct tgcccagctg 1920
ccttgggccc tcagcacgtt ctcatctttc agtgggaaag tgggagtgct ggagcatatg 1980
acagtgctga gcatctttcc caagccccac cctcccccag agcaccctcc cctcctgtcc 2040
tcaccctacc ccaagttctc ccacagtcac tcctgcccca tgctcatgcc gccctccagt 2100
tcttgctctg cccatctccc ctccccaacc cagacctaaa acaggctgtt gggccagctg 2160

```
ttccttgacc ttccttcttt tcttttggtt ccttgacccc agtgggctct cactccccac   2220
accgcatatc taaaatctgt tttgcctgct cttggggtgc cactgctccc cctccagcat   2280
tactcctttt ggcaggtcct tcctcaggct gagaatctcc ccctctacct tggttttctc   2340
tctctggcca gcacccccac cccttgcttt gtttttaatt tttaactttt gtttgggtac   2400
gtagtagata tatatgtata tatttatggg gtacatggga tattttcaca caggcctaca   2460
atatgtaata atcacatcag ggtaaatggg ttatatcaca acaagcattt atcctttctt   2520
tgtgctacaa acaatcccat tatgctcttt cagttatttt taaatgtaca ataaattatt   2580
gttgactgta ctcaccctgc tgtgctatct actagatctt attcattcta attatatttt   2640
tgtacccatt attaaccatc cctgctcccc cactccccac tacccttctc agcctctggt   2700
aatcatcatt ctattgtctc tccccatgag gtccattgtt ttaaattttg gctgccacaa   2760
ataagtgaga acatgcaaag tttgtctgtc tgggcctggg gcttatttca cttcacagga   2820
tgacctccag ttctttgcaa atgacacgat ggctgaatag ttctccacat acacatgtac   2880
accacatttt ctttatccat gcgtctgttg atggacactt agattgcttg cagatcttgg   2940
ctactttgaa tagtgctgca ataaacatgg aaaagtagat agctctttaa tataccgatt   3000
tcctttcttt ggagtatatg cctaacagtg ggagtgctgg agcatatgac agctctattg   3060
tatttttagt ttttggaaga acctccacat tgtttcccat agtggttgta ctagtttacg   3120
ttcccaccaa cagtgtacat cctcaccagc attccttatt tctacatcct cgccagcatt   3180
ccttattgcc tgtcttctgg ataaaagcca gtttatctgg ggtgggatgt tatctcgtag   3240
gagttttgat ttgccttcat ctgttgacga atgatgttga gcaccttttc atatacctgt   3300
ttgccattta tatgtcttct tttgagaaat gactattcag atcttttctc atttttaaat   3360
tggattatta tatttttttt tcctatagtt gttcgagctc cttatatgtt tcagttactg   3420
atcctttgtc agatgaatag tttgaaaata ttttctccca ttcttggatg gtctcttcat   3480
tttgtttatt gtttcctttg ctgtgcagaa gccttttttac ttgatatgat cccatttatg   3540
caattttact ttggttacct gtgcttgtgg ggtattactt taaaaatctt tgcccagtcc   3600
aatatcctag agagtttccc caatgttttc ttgtatagtt tcatagtttg aggtcataga   3660
tttacatctt taatccactt tgatttgatt tttgtatatg gtgaaagaca gggtctagtt   3720
tcattcttct gcataaggat atctagtttc cccagcacca tttttgaaga gactctcctt   3780
tgccaatgtg tgttcttggt acctttgttg gaaatgagtt tactgtagat gtatggaatt   3840
gtttctgggt tctctattct gtttcattgg tctgtgtgtc tgtttttatg ccagtatcat   3900
gctgttttgg ttactgtagc tctgtagtat aatttgaagt cagataatgt gattcctcta   3960
gttttgttca ttttgctcag gatagcttta tctattctgg ttttttttgtg gttccatatg   4020
cattttagga ttatttttat tatttctgtg aagaatgtca ttagtgtttt gatagggatt   4080
gcattgaatc tgtagattac tttgggtagt atggatattt caacaaaact gattcttcca   4140
atccatgaac gtggactatc ttttccattt tttgtgtcct tcaatttttt gcatcagtgt   4200
tttttgtttt tggtttttga gatggagttt cactcttgtt gcccaggcta gaatgcaagg   4260
gtgtgatctt ggctcaccgc aacctccgcc tcccaggttc aagcgattct tctgcctcag   4320
cctcccaagt agctgggatt acaggcatgt gccactgtgc ctggctaatt ttctattttt   4380
attagagatg ggtttctct atgttggcca ggctagtctt gaactcctga cctcaggtga   4440
tccacctgcc tcggcctccc aaagtgctgg gattacaggc atgagccacc acgcccagcc   4500
```

```
acatcactgt tttatagttt ttattggaga ggtctttcac ttcttcagtt aggtttattc   4560
ctcagtattt tattttattt gtagctattg taaatgggat tcgtttcttg atttcttttt   4620
cagattattt gctgttagca ctgatttttg catgttgatt ttgtatcctg caactttact   4680
gaatttgttc ttcagttcta atggtttttt ggtggagtct ttaggttttt ccaaatatca   4740
gaccacatga tctgcaaaca aggataattt gacttcttct tttccagttt taatgccctt   4800
tctttctttc tcctgtctga ttgctctagt taggatctgc agtactgtgt tgcataactg   4860
tggtaaaatt agtcatcctt gtcttattcc agatcttaga gaaaaggctt tcagttttcc   4920
cccattcagt atgttactag ctgtgagttt gtcatatatg gcttttatta tattgaggtc   4980
tgttccttgt atacttagtt ttttgagagt ttttatcatg aagggatgtt gaatttatca   5040
aatgcttttt cagtatcaat tgaatgatac tggcttttgt cctttattct gttgatatga   5100
cgtattacat tgattgattt gtgtatgtta aatcatcctt gcatacctgg aatacattcc   5160
acttgctcat aaagaatgat ctttttaat gtattgttga atgtggtttg ctagtatttc   5220
cttgacgatt tttgcatcgg tgttcatcag ggatataggc ctgtagtttt cttttttatg   5280
atgtgtcttt gcctggtttt tgtatcagga tattcctggc tttgtaaaat gagtttggaa   5340
gtattccctc ctcctctatt tttcagaaca gtttgaatag gactgacata tgttgttctt   5400
taaaagttta attgtggtaa attatacatt acataaattt tactgtttta accactttta   5460
agtgtatact cggtggcatt agatacattc acatttttgt gcaacccaaa actctgtgcc   5520
cattaatcgg taactcccca ttcctcccta cctctggccc ctggtaacca ccattctact   5580
ttttgtttct atgaatttga ccactctagg tacctcattt aagcagaatc atgtaatgtt   5640
tgtctttttg tttctggctt atttcactta taatattttt gaggttcggt gggcacagtg   5700
gctcacgcct ggatttccag cactttggga ggctgaagca ggtggatcac ctgagtttcg   5760
gagttcgaaa ccagcctggc caacatggtg aaaccccatc tctactaaaa ataataaaag   5820
ttagccgggc gtgatggcgg gtgcctgtaa tcccaactac ttgggaggct gaggcaggag   5880
aatcgcttga atccgggaag tggaggttgc agtgagctga gatcaggcca ctgcactcca   5940
gcctgggcaa caagagtgaa attccatctc caaaaaaaaa aataaaacaa taataataat   6000
aatattttg aggttcatcc aagttgtagt atgggtcaga atttcattcc ttttaaggat   6060
ggataatact cattatatgt atgtaccaca tcttggttat ccatccctca gacaacggac   6120
acttgggtta cttctacctt ttggatattg gcaaatattt catttccttt gggtatatat   6180
ttatttcctt tgggtatttc ttttgggtat atatccagaa atagaagcag tacataggg   6240
cttcattttc tctgtctctt tgccaacctt gctctgtgtg tgtgtgtgta tgtgtgtgtg   6300
taggtgtgtg ataacagcca tcctgattgg tttcaggtgg catctcattg tggtttggat   6360
ttgcattttc ctaatgagtg ctgatattga gcatcttttc atgtgtttgt tgatcatttg   6420
taattttctt tgaagaattg gccatttaag tcttttgccc attttttccc ccacatagct   6480
tctcttatca gatatatgac ttgcaatatt tatttcattt cggggttgat tgctttttca   6540
ctctgattgt gccctttgat gcatagatgt tttgaatttt catcagtcta ctttgtcagt   6600
tctttctatt ctatctgtgc tttggtgtca tatccatgaa agcactgtca aatcctatgt   6660
catgaacatt atccccaatg tttgcttcta agaaattttt aggttttagt tcttgagtgt   6720
agagtttagg tctttgattc attttgagtt aatttttgta tatagtgcaa attaagggtc   6780
caattttatt ttaacacccc ctgcccccag aactatttgc tgaaaagatc aactgactct   6840
ttgtcacctg ctcaccccag tggacactag ctgttccatc caattgctgt cctggggcct   6900
```

-continued

```
tgtcatgcca ctcttccact ttgaacccaa gcccacaccg ttgctcccct ctgggatact   6960
gaccccacta taaacttcac tggggctaca accttcctac cctttgtgcc tcatgaccac   7020
cccctccctt gtccccacca tgcccatgat gagtctcttc tcgaggcagc tccccttgcc   7080
tccatctcac cctcacctat gcaccacagc cacactggac atgggtccct ctgagcctga   7140
gtcccttccc attcccacca tcccctctgg caagaccttc cttccaccac cttcatgctc   7200
ctccccttgcc cctgcagggc agcctctccc cttggcccct attcccttag ggggcttgtg   7260
gccacccagt ccttgcacct ggcctacaag tttgccatct tcattccccc ttcttctgtt   7320
catcagcccc ctcctctatc ctcccaccct cacagttttc tttgtatatg aaatcctcgt   7380
tcttgtccct ttgcccgtgt gcatttcctg cctcctcagg aaggttggga cagcagacct   7440
gtgtgttaaa catcaatgtg aagttacttc caggaagaag tttcacctgt gatttcctct   7500
tccccagagc cccacagtct tcgttataac ctcacggtgc tgtccgggga tggatctgtg   7560
cagtcagggt ttctcgctga ggtacatctg gatggtcagc ccttcctgcg ctgtgacagg   7620
cagaaatgca gggcaaagcc ccagggacag tgggcagaag atgtcctggg aaataagaca   7680
tgggacagag agaccaggga cttgacaggg aacggaaagg acctcaggat gaccctggct   7740
catatcaagg accagaaaga aggtgagagt cggcaggggc aagagtgact ggagaggcct   7800
tttccagaaa agttaggggc agagagcagg gacctgtatc tacccactgg atctggctca   7860
ggctggggt gaggaatggg ggtcagtgga actcagcagg gaggtgagcc ggcactcagc   7920
ccacacaggg aggcatggag gagggccagg gaggcgtacc ccctgggctg agttcctcac   7980
ttgggtggaa aggtgatggg ttcgggaatg gagaagtcac tgctgggtgg gggcaggctt   8040
gcattccctc caggagatta gggtctgtga gatccatgaa gacaacagca ccaggagctc   8100
ccagcatttc tactacgatg gggagctctt cctctcccaa aacctggaga ctgaggaatg   8160
gacaatgccc cagtcctcca gagctcagac cttggccatg aacgtcagga atttcttgaa   8220
ggaagatgcc atgaagacca agacacacta tcacgctatg catgcagact gcctgcagga   8280
actacggcga tatctaaaat ccggcgtagt cctgaggaga acaggtaccg acgctggcca   8340
ggggctctcc tctccttcca attctgctag agttgcctca cctcccagat gtgtccaggg   8400
aaaccctccc tgtgctatgg atgaaggcat ttcctgttgg cacatcgtgt cctgattttc   8460
ctctattgtt agagccactg gataaagaca gtgggtcagg gactggacca tccagtgttg   8520
taatcagggc aagtagagga ccctccgaca gaatcctgag cctggggtgg gtgtcaggca   8580
ggagaggaag gcttcagggc cagggctgcc ccctctgcct cccagcctgc ccatcctgga   8640
gagttccctc ctggccccac aacccaggag tccacccctg acatccccct cctcagcatc   8700
aatgtgggga tcccagagcc tgaggccaca gtcccatggc ccatcctcct gccagcctgg   8760
aagaactggg ccccagagtg aggacagact tgcaggtcag gggtcccaga gggcttcagc   8820
cagagtgaga acagtgaaga gaaacagccc tgttcctctc ccctccttag aggggagcag   8880
ggcttcactg gctctgccct ttcttctcca gtgcccccca tggtgaatgt cacccgcagc   8940
gaggcctcag agggcaacat taccgtgaca tgcagggctt ctggcttcta tccctggaat   9000
atcacactga gctggcgtca ggatggggta tctttgagcc acgacaccca gcagtggggg   9060
gatgtcctgc ctgatgggaa tggaacctac cagacctggg tggccaccag gatttgccaa   9120
ggagaggagc agaggttcac ctgctacatg gaacacagcg ggaatcacag cactcaccct   9180
gtgccctctg gtgagcctag ggtgaccctg gagagggtca ggccagggta gggacagcag   9240
```

ggatggctgt ggctctctgc ccagtgtata acaagtccct ttttttttcag ggaaagtgct 9300
ggtgcttcag agtcattggc agacattcca tgtttctgct gttgctgctg ctgctgctgc 9360
tgctgctgct atttttgtta ttattatttt ctacgtctgt tgttgtaaga agaaaacatc 9420
agctgcagag ggtccaggtg agaaaagcgg gcagtttctg gagatggtaa ggcccctgtc 9480
tgggcagtag ggtcccctca ttgctcctgc aaagataggc atgttggtga caaggcttct 9540
gtaacagggg atgaaagttg gggaatttgg gaagggaatg gggcaacat ctccatctac 9600
acccataagt gctgcccaag cgagggtcaa acgcccagct gtggcatctt cctgctgcag 9660
gtgaggagtg ggcagcaggg agggctgcgg cgcctgctct gtccccatcc cggtctctgt 9720
gtctcttgga ctcactaggg cgcatccagg tggggtgagc tgggaatcac gtgctgaatg 9780
ctgaggacct ggatgatcac ggcctcagag ggagcaaata gtaaaggcag ctgtgatctg 9840
gggagggcca gaaactggag aggaatctga ggagaggcgg tgcccctatt cccttcctct 9900
ctgcatccct ctcccctatt tctccagcca ttggggcgga caccaagaaa aagacctatg 9960
aggcccagcc tgggggccct gcctgtgtag ccctttggag accccttgta acagggaggg 10020
tcctgagcac acatggccat ctctgtccac ttttcagctc cccatgcacc tcctccagga 10080
gctttcttgg ggttgtcgtg tcctctgcac cattcgaggc cctactcttt ccaggttccc 10140
acagcctggt ctccctgagt ttcttgcaga tgagatggat gagtagataa gcagatgtcc 10200
ctgggccatt tgaggagtgg ggcccagccc ctcatcaggg cagctgtggt ccctgttttc 10260
atcctacctc cgagtgtttt cttctccagt ccctgaggga cacagtcctc agggcccatg 10320
tttttggggc tttaatctgt gctctgtggc ctcaccttgc cctccctgag ccaatttccc 10380
tttctaaagg tggtcactgc ctggtaagtt tggagtaagg gacggtcaga atcatttccc 10440
ctacagtcag gttgtttgat gggggatgaa aagagacagc aggaagtttt gtgtttctgc 10500
aaagacagaa gcagttcagg ggacagtaag aggctggggt gtccaggagg gtgtgtctgg 10560
cagtagggtc gctggtttct catccttgaa cctaattgca ctgtcagtcg gcccctcagg 10620
cctgagcaga tgggaaggtt tgtcccctgc cctgcagtaa gagggccctg tccaggaggc 10680
acccataaca ggggcagtgc aggtctgtgg tcgctcctgc tctcacctgt ggcgtctccc 10740
gtagagggat tatcagttct ggttccctgt gggcaggaat ggtttcctca taggtcactg 10800
gagttttggc caggaaaaga gtatgaagtt catgtgccag tttctcaaaa ttcctgcttt 10860
caatgttgat gtcaagcaaa gatattcgta atttcagctc tataatctta ataggatttc 10920
ccctaatatt gtaaagcatc ttatatgaaa caggaacaca aatttctcaa aattcctgcg 10980
atgtccaata aagattttca taatttcggc tctccaatct taataggatt tcctaatact 11040
gtaaagcata ttaaatgaaa caggaaccca aatttggagc cccctctcca ggaggttctg 11100
tgtggagatg gtggctgtgg cagtggcagt tcccaggtgc agagggtggg cagaggcagc 11160
ctcaggctaa ggggtctccc ctactccaca tggagaaaat cccttgtagg ttgcaagggc 11220
agtggccggg tggaatccct gctagggaca gagcaggaag gcctcgcagc ctcaccaagc 11280
agcagccctg gggtggagct gcgtttccag ggttaagcgg accaggcagg agcagtggtt 11340
actcaacagc aggtcacagg cttgggttgt gagggtcagg agaggccagg cctcctcgag 11400
caaggtgggg gtcccagggt caggtcaggt gcagatcctg tggcagccac gtctttccat 11460
gctgggcctg ctgggccccc caggctttct gatggggtcc ccagttagga gctgcctgct 11520
cagggctggg aggggaggag cgctgagctg cagatagagg gcagagccca cagtgggcag 11580
ggcctgccct ggtgtgtagg tgcctctgca ggagaggagg gcctggggac tgagagcaag 11640

```
ggtcagggcc tctctttgag gaggcctctc actgtaacag gactggtcag gcctgagagg  11700

aggtcactgg gttccctctt gggtcttgtc ctttagtctt ggggcccttt ccctccctgc  11760

acgatgagtg gtgggcacag ggcaggggct gatgttgatg gagtgatggg agggaactgg  11820

taggggctgg gaaaagcaag gagggaggaa gaaaaaagtg gggcctcat cttctctcag  11880

agaaagggcg aatctggttt tggagcaact gaagagagaa aagtccccag ggaataaaca  11940

caacactgca cccagtggag catttacccg tttccctctt ttctccagag ctcgtgagcc  12000

tgcaggtcct ggatcaacac ccagttggga cgagtgacca cagggatgcc acacagctcg  12060

gatttcagcc tctgatgtca gatcttgggt ccactggctc cactgagggc gcctagactc  12120

tacagccagg cagctgggat tcaattccct gcctggatct cacgagcact ttccctcttg  12180

gtgcctcagt ttcatgacct atgaaacaga gaaaataaaa gcacttattt attgttgttg  12240

gaggctgcaa aatgttagta gatatgaggc gtttgcagct gtaccatatt aattggtgtc  12300

attgtttctg ttgttttcgt attattattt ttttttttta agacagagtc tcaggccagg  12360

cacggtggct cacgcctgta atcccagcac tttgggaggc cgaggcgggc ggatcacaag  12420

gtcaagagat cgagaccacc ctgatcaaca tggtgaaacc ctgtctctac taaaaataca  12480

aaaaattagc tgggcctggt ggcatgtgcc tgtagtccca gctactcagg agctgaggca  12540

ggaaaatcac ttgaacctgg gaggtggaga ttgcagtgag ctgagatcgc gccactgcac  12600

tccagcctgg cgacagagcg agactctgtc tcaaaaaaaa aaaaaaaaaa aaaaaaagac  12660

agagtctcac tctgtcaccc aggctgcagt tcagtgacat gatctcagct cgttgcagcc  12720

tccgcctccc gggttcaagc acttcttgtg cctcagcctc ccgagtagct ggggttacag  12780

acatgcacca ccatacccgg ctaatttttg catttttcat agagacagga ttttgccatg  12840

ttggcc                                                             12846
```

```
<210> SEQ ID NO 27
<211> LENGTH: 388
<212> TYPE: PRT
<213> ORGANISM: Artificial Sequence
<220> FEATURE:
<223> OTHER INFORMATION: Exemplary amino acid sequence of MICA

<400> SEQUENCE: 27

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Gly Asp Gly Ser Val Gln Ser Gly Phe Leu Ala Glu
        35                  40                  45

Val His Leu Asp Gly Gln Pro Phe Leu Arg Cys Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140
```

-continued

```
Leu Glu Thr Glu Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Lys Ser Gly Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ala
305                 310                 315                 320

Ala Ala Ala Ala Ile Phe Val Ile Ile Ile Phe Tyr Val Cys Cys Cys
                325                 330                 335

Lys Lys Lys Thr Ser Ala Ala Glu Gly Pro Glu Leu Val Ser Leu Gln
            340                 345                 350

Val Leu Asp Gln His Pro Val Gly Thr Ser Asp His Arg Asp Ala Thr
        355                 360                 365

Gln Leu Gly Phe Gln Pro Leu Met Ser Asp Leu Gly Ser Thr Gly Ser
    370                 375                 380

Thr Glu Gly Ala
385
```

EXPANSION OF NATURAL KILLER AND CHIMERIC ANTIGEN RECEPTOR-MODIFIED CELLS

CROSS REFERENCE TO RELATED APPLICATIONS

This application is the § 371 U.S. National Stage of International Application No. PCT/US2020/018897, filed Feb. 19, 2020, which was published in English under PCT Article 21(2), which in turn claims the benefit of U.S. Provisional Application No. 62/808,031, filed Feb. 20, 2019, which is incorporated herein in its entirety.

ACKNOWLEDGMENT OF GOVERNMENT SUPPORT

This invention was made with government support under grant number AI130197 awarded by National Institutes of Health. The government has certain rights in the invention.

FIELD

This disclosure relates to methods of producing modified feeder cells, compositions comprising the modified feeder cells, and methods of their use.

BACKGROUND

NK cells are an important subset of lymphocytes that provide the body's first line of defense. NK cells were originally described for their capacity to spontaneously kill tumor cells (Rosenberg et al., J Natl Cancer Inst 52: 345-52 (1974); Kiessling et al., Eur J Immunol 5:117-21 (1975); Kiessling et al., Eur J Immuol 5:112-7 (1975); Herberman et al., Int J Cancer 16:230-9 (1975); Herberman et al., Int J Cancer 16: 216-29 (1975)) and differ from T cells, which require prior sensitization. NK cells kill tumor cells or virus-infected cells via several pathways (Liu et al., Immunity 31:99-109 (2012); Liu et al., Immunity 36:600-11 (2012); Long et al., Annu Rev Immunol 31:227-58 (2013)), which include direct cytotoxicity (natural cytotoxicity and ADCC) and indirect effects (e.g., cytokine production and interacting with adaptive immunity). Among these functions, one important application of NK cells is use of primary ex vivo expanded NK cells or genetically modified NK cells to treat a variety of cancers. A number of clinical trials showed that NK cell infusion has less severe graft-versus-host disease (GvHD) than does T cell infusion.

There are two major clinical applications of NK cells. The first is to use the primary ex vivo expanded NK with genetic modification to treat cancers. Specifically, NK cells are used to treat ALL and AML in clinic (Miller et al., Blood 105:3051-7 (2005); Rubnitz et al., J Clin Oncol 28:955-9 (2010)). Second, genetically modified NK cells, such as chimeric antigen receptor (CAR)-modified NK cells, have become an emerging tool for cancer immunotherapy (Liu et al., Leukemia 32:520-31 (2018); Liu et al., Protein Cell 9:902 (2018)). Clinical investigation of CAR-modified NK cell-based immunotherapy has been intensively conducted for several types of cancer (Rezvani K and Rouce R H, Front Immunol 6:578 (2015)). Similar to CAR-T cell-based immunotherapy, genetically modified NK cells using various CAR molecules to redirect different antigen specificity has been investigated by different groups (Rezvani K and Rouce R H, Front Immunol 6:578 (2015); Hermanson D L and Kaufman D S, Front Immunol 6:195 (2015); Glienke et al., Front Pharmacol 6:21 (2015)).

CAR-modified T cell therapy has become a promising immunotherapeutic strategy for the treatment of blood cancers (Porter et al., N Engl J Med 365: 725-33 (2011); Kim et al., Arch Pharm Res 39:437-52 (2016); Maude S and Barrett D M, Br J Haematol 172:11-22 (2016)) and has gained significant attention from researchers in both academia and industry (Glienke et al., Front Pharmacol 6:21 (2015). Adoptive transfer of CAR-modified immune cells (including CAR-T, CAR-NK, and CAR-NKT cells) into patients has shown remarkable success in treating multiple blood cancers. Clinical trials treating multiple myeloma (Garfall et al., N Engl J Med 373:1040-7 (2015); Atanackovic et al., Br J Haematol 172:685-98 (2016)), leukemia (Porter et al., N Engl J Med 365: 725-33 (2011); Maude et al., N Engl J Med 371:1507-17 (2014); Lee et al., Lancet 385:517-28 (2015)), sarcoma (Ahmed et al., J Clin Oncol 33:1688-96 (2015)), and neuroblastoma (Pule et al., Nat Med 14:1264-70 (2008); Louis et al., Blood 118:6050-6 (2011)) using CAR products have shown promising results. Scientists and pharmaceutical companies worldwide have invested considerable effort and funds into CAR development and optimization (Casucci et al., Cancer Immunol Immunother 64:123-30 (2015); Gottschalk et al., Ernst Schering Found Symp Proc 69-82 (2006); Ramos et al, Cancer J 20:112-8 (2014); Savoldo B and Dotti G, Cancer J 20:112-8 (2014)).

Adoptive CAR T cell therapy combines tumor antigen specificity with immune cell activation in a single receptor, which includes isolating a patient's own T-cells, engineering them to express chimeric antigen receptors (CAR) that recognize tumor proteins, and re-infusing them back into the patient. One potential problem with adoptive CART cell therapy is use of autologous T cells isolated from patients. Autologous T cells isolated from patients face two major issues. 1) T cells directly isolated from immune-compromised cancer patients usually have poor cytotoxicity and functionality, precluding their use. 2) Autologous T cells cannot be used for other patients due to the potential for GVHD.

SUMMARY

There remains a need for improved cytotoxic cell-mediated immunotherapies, for example, to mitigate the disadvantages of CAR-modified cell immunotherapy, such as poor cytotoxicity. Disclosed herein are methods and compositions for expanding cells for immunotherapies, such as NK and T cells, with improved cytotoxicity and capacity for cell expansion.

Disclosed herein are modified 721.221 cells. In some examples, the modified 721.221 cells express at least one of membrane-bound IL-21 (mIL-21), IL-2, IL-12, IL-33, IL-27, IL-18, IL-7, mIL-7, IL-15, membrane-bound IL-15 (mIL-15), a TLR ligand, UL16-binding protein (ULBP)-1, ULPB-2, and/or major histocompatibility complex (MHC) class I chain-related protein A (MIC-A). In specific, non-limiting examples, the modified 721.221 cells express mIL-21, such as including an amino acid sequence with 90% or 95% sequence identity to SEQ ID NO: 2 (and/or as encoded by a nucleic acid sequence with 90% or 95% sequence identity to SEQ ID NO: 1), for example, using a viral (such as retroviral) vector (e.g., a lentivirus, such as a Moloney murine leukemia virus (MoMLV) vector, such as an SFG retroviral vector). Additional heterologous cytokines, including activating receptor ligands, TRL ligands, or receptors thereof, can be included in the modified 721.221 cell (e.g., IL-15 receptor alpha (IL-15Ra)). In some examples, the modified 721.221 cells include a heterologous nucleic acid encoding at least one of mIL-21, IL-2, IL-12, IL-33, IL-27, IL-18, IL-7, mIL-7, IL-15, mIL-15, a TLR ligand, ULBP-1, ULPB-2, and/or MIC-A. In particular examples, the modified 721.221 cells express mIL-21 or mIL-21 and IL-15Rα.

Further disclosed herein are methods of producing modified 721.221 cells, for example, including transducing or transfecting a population of 721.221 cells with a nucleic acid encoding mIL-21, IL-2, IL-12, IL-33, IL-27, IL-18, IL-7, mIL-7, IL-15, membrane-bound IL-15 (mIL-15), a TLR ligand, ULBP-1, ULPB-2, and/or MIC-A; isolating the cells that express mIL-21, IL-2, IL-12, IL-33, IL-27, IL-18, IL-7, mIL-7, IL-15, membrane-bound IL-15 (mIL-15), a TLR ligand, ULBP-1, ULPB-2, and/or MIC-A; and irradiating the isolated cells, thereby producing the modified 721.221 cells. In some examples, the cells are modified through transduction (e.g., using a viral vector such as a retrovirus or a lentivirus). In specific, non-limiting examples, the modified 721.221 cells express mIL-21, such as including an amino acid sequence with 90% or 95% sequence identity to SEQ ID NO: 2 (and/or as encoded by a nucleic acid sequence with 90% or 95% sequence identity to SEQ ID NO: 1), for example, using a retroviral vector (e.g., a Moloney murine leukemia virus (MoMLV) vector, such as a SFG retroviral vector). The methods can further include modifying the 721.221 cells to express one or more than one additional heterologous cytokine, activating receptor ligand, TRL ligand, or receptor thereof (e.g., IL-15Rα).

Also disclosed herein are methods of expanding a population of natural killer (NK) cells or T cells, for example, by contacting a population of lymphocytes with a modified 721.221 cell disclosed herein and at least one cytokine (e.g., an interleukin, such as IL-15 or IL-2) for 1-40 (e.g., 14-21 days) days under conditions sufficient for cell expansion. The population of lymphocytes can be from any sample type, such as peripheral blood, cord blood, ascites, menstrual blood, or bone marrow, and can, for example, include peripheral blood mononuclear cells (PBMCs). The population of cells contacted with the modified 721.221 cells can further include modified cells for immunotherapies, such as chimeric antigen receptor (CAR)-modified cells (e.g., CAR-NK or CAR-T cells, such as CD19 CAR-modified NK cells). In some examples, the NK or T cell population is increased by at least 5000- to 90,000-fold (e.g., after contacting with the modified 721.221 for at least 14-21 days under conditions sufficient for cell expansion).

Additionally disclosed herein are methods of treating a cancer or an infectious or immune disease, for example, by administering the NK cells or T cells (e.g., CAR-modified NK or T cells, such as CD19 CAR-modified NK cells) produced using the methods disclosed herein to a subject with cancer or an infectious or immune disease, thereby treating the cancer or immune disease. In some examples, the cancer or immune or infectious disease includes an autoimmune disease, a transplant rejection, a solid tumor (such as lymphoma, breast cancer, hepatocellular carcinoma (HCC), and pancreatic cancer), a sarcoma, a neuroblastoma, blood cancer (e.g., multiple myeloma; lymphoma, such as non-Hodgkin's lymphoma; or leukemia; such as acute lymphocytic leukemia (ALL) or acute myeloid leukemia (AML)), HIV, hepatitis B virus (HBV), hepatitis C virus (HCV), tuberculosis (TB), or malaria.

The foregoing and other features of the disclosure will become more apparent from the following detailed description, which proceeds with reference to the accompanying figures.

BRIEF DESCRIPTION OF THE DRAWINGS

(FIG. 1A), Representative histograms show the expression of IL-21 and 4-1BBL by K562 (green) and K562 transduced with IL-21 (K562-mIL21, red) detected using flow cytometry. The mean fluorescence intensity (MFI) is noted in the respective histograms. (FIG. 1B), Representative histograms show the expression of IL-21 and 4-1BBL on 721.221 (green) and 721.221 transduced with IL-21 (721.221-mIL21, red) detected using flow cytometry. The MFI is noted in the respective histograms. (FIG. 1C) Confocal images of the expression of IL-21 on K562 cells transduced with IL-21 (K562-mIL21). (FIG. 1D) Confocal images of the expression of IL-21 on 221 cells transduced with IL-21 (221-mIL21). (FIG. 1E), representative histograms show the expression of ICAM-1, PD-L1, HLA-E, and MICB on K562 (green) and K562-mIL21 (red) cells detected using flow cytometry. The MFI is noted in the respective histograms. (FIG. 1F), Representative histograms show the expression of ICAM-1, PD-L1, HLA-E, and MICB on 721.221 (green) and 721.221-mIL21 (red) cells detected using flow cytometry. The MFI is noted in the respective histograms.

(FIG. 2A), Representative dot plots show the purity of NK cells expanded with different types of feeder cells on the indicated day post expansion detected using flow cytometry. PBMCs were stimulated with irradiated K562, K562-mIL21, 721.221, and 721.221-mIL21 on day 0, respectively. The purities of NK cells were examined on day 7 and then every 3 to 5 days. (FIGS. 2B and 2C), Quantitative data show fold-expansion (FIG. 2B) and purity (FIG. 2C) of NK cells from 11 donors expanded with irradiated K562, K562-mIL21, 721.221, and 721.221-mIL21, respectively, for 21 days. (FIGS. 2D and 2E), Quantitative data show fold-expansion (FIG. 2D) and purity (FIG. 2E) of NK cells from 11 donors expanded with the indicated feeder cells on day 21. Mean (solid lines) with 95% CI (gray band) are showed in (FIG. 2B) and (FIG. 2C). * $p<0.05$.  $p<0.01$, * $p<0.001$.

(FIG. 3A), Representative histograms show the expression of CD16, NKG2D, NKp46, 2B4, and DNAM-1 on NK cells expanded using K562, K562-mIL21, 721.221, and 721.221-mIL21. (FIG. 3B), Representative histograms show the expression of CD69, CD94, CD8a, and NKG2C on NK cells expanded using K562, K562-mIL21, 721.221, and 721.221-mIL21. (FIG. 3C), Representative histograms show the expression of NKG2A, CTLA-4, KLRG1, and PD-1 on NK cells expanded using K562, K562-mIL21, 721.221, and 721.221-mIL21. (FIG. 3D), Representative histograms show the expression of LIR1, TIM-3, TIGIT, and LAG-3 on NK cells expanded using K562, K562-mIL21, 721.221, and 721.221-mIL21. (FIG. 3E), Representative histograms show the expression of KIR, KIR2DL1, KIR2DL2/L3, KIR3DL1, and KIR3DL2 on NK cells expanded using K562, K562-mIL21, 721.221, and 721.221-mIL21. The MFIs are indicated in the respective histograms.

(FIG. 4A), Quantitative data show cytotoxic activity of expanded NK cells against K562 cells using the CFSE/7-AAD cytotoxicity assay. K562 cells were labeled with CFSE and then incubated with expanded NK cells for E:T ratios ranging from 1:4 to 4:1 for 4 hours. Next, 7-AAD was used to determine the lysis of K562 cells. (FIG. 4B), Quantitative data show the percentage of expanded NK cells expressing CD107a following no stimulation, stimulation with K562, and stimulation with PMA/Ionomycin, for 2 hours. (FIG. 4C), Quantitative data show the cytotoxic activity of expanded NK cells against 721.221 cells using CFSE/7-AAD cytotoxicity assay. 721.221 cells were labeled with CFSE and then incubated with expanded NK cells for E:T ratios ranging from 1:4 to 4:1 for 4 hours. Next, 7-AAD was used to determine the lysis of 721.221 cells. (FIG. D), Quantitative data show the percentage of expanded NK cells expressing CD107a following no stimulation, stimulation with 721.221, and stimulation with PMA/Ionomycin, respectively, for 2 hours. The means±SD are shown in (FIG. 4A) and (FIG. 4C), and means+SD are shown in (FIG. 4B) and (FIG. 4D). (FIG. 4E) Gating strategies for NK cell mediated cytotoxicity using the CFSE/7-AAD approach. After incubation of NK cells with CFSE-labeled target cells for 4 hours, dead cells were gated on 7-AAD positive subsets. (FIG. 4F) Representative flow cytometry dot plots of the percent of 7-AAD positive cells in CFSE labeled K562 cells following incubation with expanded NK cells at different effector:target (E:T) cell ratios. (FIG. 4G) Gating strategies for cell surface CD107a assays. (FIG. 4H) Representative dot plots of the percent of expanded NK cells expressing CD107a following no stimulation (NK cell only, negative control group), stimulation with K562, and PMA/Ionomycin (positive control group). *** $p<0.001$, ns $p>0.05$.

(FIG. 5B), Representative dot plots show the percentage of expanded NK cells in CD19-CAR-positive cells on the indicated day post expansion. PBMCs were stimulated with irradiated 721.221-mIL21 on day 0 and transduced with CD19-CAR retrovirus on day 7. Purities of NK cells in CD19-CAR-positive cells were examined every 3 to 4 days. (FIG. 5C) Dynamic time-lapsed expansion data of the fold expansion of CD19-CAR NK cells from 3 donors. CD19-CAR-modified NK cells were expanded with irradiated K562, K562-mIL21, 221, and 221-mIL21 feeder cells for 21 days. (FIG. 5D) Quantitative data of the fold expansion of CD19-CAR NK cells from 3 donors on day 21 of expansion. (FIG. 5E) Dynamic time-lapsed expansion data of the purity of NK cells 544 within CD19-CAR positive cells from 3 donors. NK cells were expanded with irradiated 545 K562, K562-mIL21, 221, and 221-mIL21 feeder cells, respectively. (FIG. 5F) Quantitative data of the percent of NK cells within CD19-CAR positive cells from 3 donors on day 21 post expansion. The means (solid lines) with 95% CI (gray band) are shown in (FIG. 5C) and (FIG. 5D).

(FIG. 6A) Representative flow cytometry dot plots of the percent of CD19-CAR positive cells in NK cells at the indicated days. CBMCs were stimulated with irradiated feeder cells on day 0 and transduced with CD19-CAR retrovirus on day 7. (FIG. 6B) Quantitative data for the percent of CD19-CAR positive cells in NK cells expanded from CBMCs (n=3). (FIG. 6C) Quantitative data for the cytotoxic activity of expanded CD19-CAR CB-NK cells against Raji cells using the CFSE/7-AAD cytotoxicity assay. Target cells were labeled with CFSE and then incubated with expanded CD19-CAR CB-NK cells at E:T ratios ranging from 5:1 to 0.3125:1 for 4 hours. Next, 7-AAD was used to detect the lysis of target cells. (FIG. 6D) Quantitative data for the cytotoxic activity of expanded CD19-CAR CB-NK cells against Daudi cells using the CFSE/7-AAD cytotoxicity assay.

(FIG. 7A) Diagram of the experimental design of the Daudi lymphoma xenograft model. Male and female NSG mice (n=5) were i.v. injected with $2\times10^6$ Daudi-FFLuc cells in 100 μL of PBS via tail vein on day −4. Beginning on day 0, mice were injected (i.v.) with $1\times10^7$ 221-mIL21 expanded- or K562-mIL21 expanded-CD19-CAR NK cells in 100 μL of PBS and injected (i.p.) with IL-2 (50,000 Unit/mouse) and IL-15 (10 ng/mouse) in 150 μL of PBS at days 0, 3, 7, and 10. Animals were imaged using the IVIS system twice a week for tumor cell tracking. (FIG. 7B) Representative images of tumor burden at indicated time points. The range of fluorescence intensity is from $1\times10^5$ to $2\times10^6$ units of photons/sec/cm$^2$/sr. (FIG. 7C) Quantitative data of tumor burden at indicated time points. Mice were imaged at the indicated days to evaluate tumor burden expressed as quantified bioluminescence (average light intensity), which represents tumor growth. (FIG. 7D) Quantitative data of mice body weights at the indicated days. (FIG. 7E) Diagram of the experimental design of the Raji lymphoma xenograft model. Male and female NSG mice (n=10) were i.v. injected with $2\times10^6$Raji-FFLuc-GFP cells in 100 μL of PBS via tail vein on day 0. On day 2 and day 4, mice were injected (i.v.) with $1\times10^7$K562-mIL21 expanded-CD19-CAR NK cells, 221-mIL21 expanded-CD19-CAR NK cells, and 221-mIL21 expanded-CD19-CAR-IL15 NK cells, respectively, in 100 μL of PBS and injected (i.p.) with IL-2 (50,000 Unit/mouse) and IL-15 (10 ng/mouse) in 150 μL of PBS. Animals were imaged using the IVIS system once a week for tumor cell tracking. (FIG. 7F) Representative images of tumor burden at indicated time points. The range of fluorescence intensity is from $5\times10^5$ to $1\times10^7$ units of photons/sec/cm$^2$/sr for day 7 and from $2\times10^7$ to $5\times10^8$ units of photons/sec/cm$^2$/sr for day 14 and day 21. (FIG. 7G) Kaplan-Meier survival curves of tumor-bearing mice after treatment with PBS, K562-mIL21 expanded-CD19-CAR NK cells, 221-mIL21 expanded-CD19-CAR NK cells, and 221-mIL21 expanded-CD19-CAR-IL15 NK cells, respectively. The p-value was analyzed by log-rank (Mantel-Cox) Test. (FIG. 7H) Quantitative data of tumor burden at indicated time points. Mice were imaged at the indicated days to evaluate tumor burden expressed as quantified, which represent tumor growth. (FIG. 7I) Quantitative data of mice body weights at the indicated days.

(FIG. 8A), the IL-21 construct contains the human IgG1 Fab' domain, CD28 transmembrane domain, intracellular domain of 4-1BB, and intracellular domain of CD3 zeta. (FIG. 8B) Feeder cells were irradiated with a dose of 100 Gray (10000 Rad), and then PBMCs were co-cultured with irradiated feeder cells with IL-2 and IL-15 for NK cell expansion.

(FIG. 10A), Representative dot plots show the purity of NK cell expanded with two different types of feeder cell on indicated day post expansion detected by flow cytometry. PBMCs were stimulated with irradiated wild-type 721.221 (top panel) and 721.221-mIL-15Rα on day 0, respectively. The purities of NK cell were checked on day 7, day 14, and day 21. (FIGS. 10B and 10C), Quantitative data show fold expansion (FIG. 10B) and purity (FIG. 10C) of NK cells from 7 donors expanded with irradiated wild-type 721.221 and 721.221-mIL-15Rα for 21 days, respectively.

(FIG. 11A) Representative dot plots show the purity of T cell expanded with two different types of feeder cell on indicated day post expansion detected by flow cytometry. PBMCs were stimulated with irradiated K562-mIL21 (top panel) and 721.221-mIL21 (low panel) on day 0, respectively. The purities of NK cell were checked on day 7, day 14, and day 21. Quantitative data show fold expansion (left panel) and purity (right panel) of T cells from 11 donors expanded with irradiated K562-mIL21 and 721.221-mIL21 for 21 days, respectively. (FIG. 11B) Representative dot plots show the purity of T cell expanded with two different types of feeder cell on indicated day post expansion detected by flow cytometry. Cord blood monocytes were stimulated with irradiated K562-mIL21 (top panel) and 721.221-mIL21 (low panel) on day 0, respectively. The purities of NK cell were checked on day 7, day 14, and day 21. Quantitative data show fold expansion (left panel) and purity (right panel) of T cells from 11 donors expanded with irradiated K562-mIL21 and 721.221-mIL21 for 21 days, respectively. (FIG. 11C) Representative dot plots show the purity of T cell expanded with two different types of feeder cell on indicated day post expansion detected by flow cytometry. PBMCs from patients with anaplastic large cell lymphoma were stimulated with irradiated 721.221-mIL21 feeder cells. The purities of T cells were checked on day 7, day 20, and day 28, respectively.

(FIG. 13A) PBMCs were stimulated with irradiated K562-mIL21 and 221-mIL21 feeder cells. NK cells were purified from expanded cells using flow cytometry on day 7 and day 14 for RNA sequencing (RNA-Seq). Principal component analysis (PCA) plots of sample-to-sample distances of NK cells expanded with K562-mIL21 or 221-mIL21 feeder cells on day 7 and day 14. (FIG. 13N) Heat map of genes associated with development and maturation of NK cells. Heat maps were generated using z-scores derived from transformed RNA-seq counts using regularized-logarithm transformation (r log). Each column represents a biological replicate.

(FIG. 14A) Dynamic time-lapsed expansion data for the percent of T cells (CD3+CD56−) from PBMCs (n=11) expanded with irradiated K562, K562-mIL21, 221, and 221-mIL21 feeder cells for 21 days. (FIG. 14B) Quantitative data for the percent of T cells (CD3+CD56−) from PBMCs (n=11) expanded with the indicated feeder cells on day 21. (FIG. 14C) Dynamic time-lapsed expansion data for the percent of CD3+CD56+ from PBMCs (n=11) expanded with irradiated K562, K562-mIL21, 221, and 221-mIL21 feeder cells for 21 days. (FIG. 14D) Quantitative data for the percent of CD3+CD56+ from PBMCs (n=11) expanded with indicated feeder cells on day 21. (FIG. 14E) Dynamic time-lapsed expansion data for the percent of CD3−CD56− from PBMCs (n=11) expanded with irradiated K562, K562-mIL21, 221, and 221-mIL21 feeder cells for 21 days. (FIG. 14F) Quantitative data for the percent of CD3−CD56− from PBMCs (n=11) expanded with indicated feeder cells on day 21. Mean (solid lines) with 95% CI (gray band) are shown in (FIGS. 14A, 14C, and 14E). * p<0.05,  p<0.01, * p<0.001, ns p>0.05.

(FIG. 15A) Representative flow cytometry dot plots of the purity of NK cells expanded with different feeder cells at indicated days post expansion. Cord blood mononuclear cells (CBMCs) were either stimulated with irradiated K562-mIL21 or 221-mIL21 on day 0, and the purities of NK cells were checked on day 7 and then subsequently checked every 3 to 4 days. (FIG. 15B) Dynamic time-lapsed expansion data for the fold expansion of NK cells from CBMCs from 9 donors expanded with either irradiated K562-mIL21 or 221-mIL21 feeder cells for 21 days. (FIG. 15C) Quantitative data for the fold expansion of NK cells from CBMCs from 9 donors on 21 days. (FIG. 15D) Dynamic time-lapsed expansion data for the purity of NK cells from CBMCs from 9 donors expanded with irradiated K562-mIL21 and 221-mIL21 feeder cells for 21 days. (FIG. 15E) Quantitative data for the purity of NK cells from CBMCs from 9 donors on 21 days. (FIG. 15F) Dynamic time-lapsed expansion data for the percent of T cells (CD3+CD56−) from CBMCs (n=9) expanded with irradiated K562, K562-mIL21, 221, and 221-mIL21 feeder cells for 21 days. (FIG. 15G) Quantitative data for the percent of T cells (CD3+CD56−) from CBMCs (n=9) expanded with indicated feeder cells on day 21. (FIG. 15H) Dynamic time-lapsed expansion data for the percent of CD3+CD56+ from CBMCs (n=9) expanded with irradiated K562, K562-mIL21, 221, and 221-mIL21 feeder cells for 21 days. (FIG. 15I) Quantitative data for the percent of CD3+CD56+ from CBMCs (n=9) expanded with indicated feeder cells on day 21. (FIG. 15J) Dynamic time-lapsed expansion data for the percent of CD3−CD56− from CBMCs (n=9) expanded with irradiated K562, K562-mIL21, 221, and 221-mIL21 feeder cells for 21 days. (FIG. 15K) Quantitative data for the percent of CD3−CD56− from CBMCs (n=9) expanded with indicated feeder cells on day 21. Mean (solid lines) with 95% CI (gray band) are shown in (FIGS. 15B, 15D, 15F, 13H, and 15J). ** p<0.01, ns p>0.05.

(FIG. 16A) Representative histograms of the expression of NKG2D, NKp46, 2B4, and CD226 on NK cells expanded from cord blood mononuclear cells using 221-mIL21 (red) and K562-mIL21 (green) feeder cells. NK cells from freshly isolated cord blood mononuclear cells from the same donor is also shown (blue). (FIG. 16B) Representative histograms of the expression of CD69, CD94, CD8a, and CD16 on NK cells expanded from cord blood mononuclear cells using 221-mIL21 (red) and K562-mIL21 (green) feeder cells. NK from freshly isolated cord blood mononuclear cells from the same donor is also shown (blue). (FIG. 16C) Representative histograms of the expression of NKG2A, NKG2C, KIR, and KIR3DL1 on NK cells expanded from cord blood mononuclear cells using 221-mIL21 (red) and K562-mIL21 (green) feeder cells. NK from freshly isolated cord blood mononuclear cells from the same donor is also shown (blue). (FIG. 16D) Quantitative data for the cytotoxic activity of expanded CB-NK cells against K562 cells using the CFSE/7-AAD cytotoxicity assay. K562 cells were labeled with CFSE and then incubated with expanded CB-NK cells at E:T ratios ranging from 5:1 to 0.3125:1 for 4 hours. Next, 7-AAD was used to detect the lysis of K562 cells.

(FIG. 17A) Representative flow cytometry dot plots of the percent of CD19-CAR positive cells in NK cells at the indicated time points. PBMCs were stimulated with irradiated feeder cells on day 0 and transduced with CD19-CAR retrovirus on day 7. (FIG. 17B) Quantitative data for the percent of CD19-CAR positive cells in NK cells expanded from PBMCs (n=3). (FIG. 17C) Dynamic time-lapsed expansion data for the percent of T cell (CD3+CD56−) in CD19-CAR positive cells (n=3). (FIG. 17D) Quantitative data for the percent of T cell (CD3+CD56−) in CD19-CAR positive cells (n=3) on day 21. (FIG. 17E) Dynamic time-lapsed expansion data for the percent of CD3+CD56+ in CD19-CAR positive cells (n=3). (FIG. 17F) Quantitative data for the percent of CD3+CD56+ in CD19-CAR positive cells (n=3) on day 21. (FIG. 17G) Dynamic time-lapsed expansion data for the percent of CD3−CD56− in CD19-CAR positive cells (n=3). (FIG. 17H) Quantitative data for the percent of CD3−CD56− in CD19-CAR positive cells (n=3) on day 21. Mean (solid lines) with 95% CI (gray band) are shown in (FIGS. 17C, 17E, and 17G).

(FIG. 18A-18D) Dot plots of the GSEA for genes between NK cells expanded with 221-mIL21 and K562-mIL21 feeder cells on day 7 (FIGS. 18A-18B) and day 14 (FIGS. 18C-18D) using gene ontology (GO) biological process (BP) datasets in the Molecular Signatures Database (MSigDB). (FIG. 18E) Gene set enrichment analysis (GSEA) of cellular amino acid metabolic processes in NK cells that were expanded with 221-mIL21 feeder cells compared to those that were expanded with K562-mIL21 feeder cells on day 14. NES, normalized enrichment score; p.adjust, FDR-adjusted p-value. (FIG. 18F) GSEA of glycolysis in NK cells that were expanded with 221-mIL21 feeder cells compared to those that were expanded with K562-mIL21 feeder cells on day 14 using Hallmark datasets in the Molecular Signatures Database (MSigDB). NES, normalized enrichment score; p.adjust, FDR-adjusted p-value. (FIG. 18G) GSEA of lymphocyte activation in NK cells that were expanded with 221-mIL21 feeder cells compared to those that were expanded with K562-mIL21 feeder cells on day 14. NES, normalized enrichment score; p.adjust, FDR-adjusted p-value. (FIG. 18H) GSEA of lymphocyte differentiation in NK cells that were expanded with 221-mIL21 feeder cells compared to those that were expanded with K562-mIL21 feeder cells on day 14. NES, normalized enrichment score; p.adjust, FDR-adjusted p-value. (FIG. 18I) GSEA of cell-cell adhesion in NK cells that were expanded with 221-mIL21 feeder cells compared to those that were expanded with K562-mIL21 feeder cells on day 14. NES, normalized enrichment score; p.adjust, FDR-adjusted p-value.

(FIGS. 19A-19B) Heat map of GSEA-identified genes of cellular amino acid metabolic processes. (FIG. 19C) Heat map of GSEA-identified genes of glycolysis. (FIGS. 19D-19E) Heat map of GSEA-identified genes of lymphocyte activation. (FIGS. 19E-19F) Heat map of GSEA-identified genes of lymphocyte differentiation. (FIGS. 19G-19I) Heat map of GSEA-identified genes of cell-cell adhesion. Heat maps were generated using z-scores derived from transformed RNA-seq counts using regularized-logarithm transformation (r log). Each column represents a biological replicate.

SEQUENCES

Figure 1A:
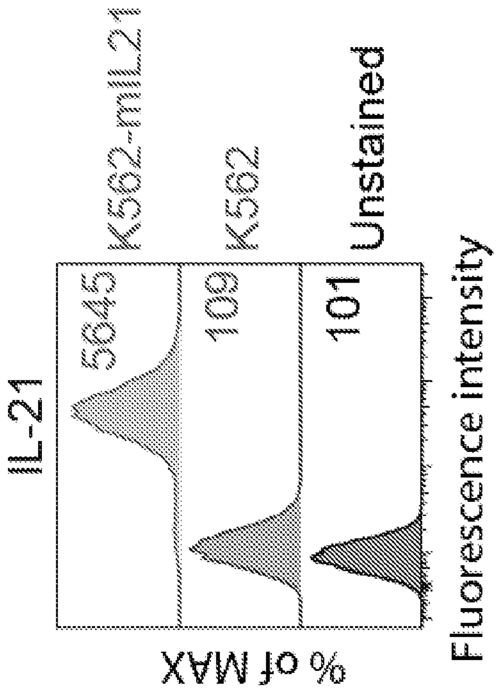
FIGS. 1A-1F. Characterization of K562 and 721.221 cells expressing membrane IL-21.

The Sequence Listing is submitted as an ASCII text file in the form of the file named Sequence_Listing.txt, which was created on Aug. 19, 2021, and is 72,239 bytes, which is incorporated by reference herein.

Any nucleic acid and amino acid sequences provided herein are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is an exemplary nucleic acid sequence of the extracellular domain from interleukin (IL)-21.

SEQ ID NO: 2 is an exemplary amino acid sequence of the extracellular domain from IL-21.

SEQ ID NO: 3 is an exemplary nucleic acid sequence of a construct for transducing cells with membrane-bound (m)IL-21.

SEQ ID NO: 4 is an exemplary nucleic acid sequence of IL-15Rα.

SEQ ID NO: 5 is an exemplary amino acid sequence of IL-15Rα.

SEQ ID NO: 6 is an exemplary nucleic acid sequence of IL-15.

SEQ ID NO: 7 is an exemplary amino acid sequence of IL-15.

SEQ ID NO: 8 is an exemplary nucleic acid sequence of IL-2.

SEQ ID NO: 9 is an exemplary amino acid sequence of IL-2.

SEQ ID NO: 10 is an exemplary nucleic acid sequence of IL-27.

SEQ ID NO: 11 is an exemplary amino acid sequence of IL-27.

SEQ ID NO: 12 is an exemplary nucleic acid sequence of IL-12B.

SEQ ID NO: 13 is an exemplary amino acid sequence of IL-12B.

SEQ ID NO: 14 is an exemplary nucleic acid sequence of IL-12 p35.

SEQ ID NO: 15 is an exemplary amino acid sequence of IL-12 p35.

SEQ ID NO: 16 is an exemplary nucleic acid sequence of IL-12 p40.

SEQ ID NO: 17 is an exemplary amino acid sequence of IL-12 p40.

SEQ ID NO: 18 is an exemplary nucleic acid sequence of IL-18.

SEQ ID NO: 19 is an exemplary amino acid sequence of IL-18.

SEQ ID NO: 20 is an exemplary nucleic acid sequence of IL-18.

SEQ ID NO: 21 is an exemplary amino acid sequence of IL-18.

SEQ ID NO: 22 is an exemplary nucleic acid sequence of IL-33.

SEQ ID NO: 23 is an exemplary amino acid sequence of IL-33.

SEQ ID NO: 24 is an exemplary nucleic acid sequence of IL-7.

SEQ ID NO: 25 is an exemplary amino acid sequence of IL-7.

SEQ ID NO: 26 is an exemplary nucleic acid sequence of MICA.

SEQ ID NO: 27 is an exemplary amino acid sequence of MICA.

DETAILED DESCRIPTION

Described herein are modified 721.221 cells that express one or more cytokines or cytokine receptors (e.g., IL-15 receptor alpha (IL-15Rα) and/or membrane-bound IL-21) and methods of expanding immune cells using the modified 721.221 cells. The modified 721.221 cells can be used to effectively expand NK cells or T cells (including CAR-modified NK cells or T cells), as shown herein.

In combination with recombinant IL-15 and IL-2 and the modified 721.221 cells, primary NK cells were expanded by about 39,663-fold after three weeks of expansion. Furthermore, transduction with a retrovirus coding for a CAR molecule specific for CD19 protein resulted in the expansion of primary NK cells from both peripheral blood and cord blood. Therefore, a platform for the expansion of human primary NK cells and genetically modified CAR-NK cells is described.

Compared with previous NK expansion systems (Denman et al., PLoS One 7:e30264 (2012); Fujisaki et al., Cancer Res 69:4010-7 (2009)), the 721.221-mIL-21 cells used for NK expansion described herein include three distinct advantages. The number of expanded NK cells is significantly higher using the technique described herein (about a 39,663-fold increase in 721.221-mIL-21 cells vs. a 3588-fold increase using K562-mIL-21 cells) with the combination of the membrane form of IL-21 with two soluble cytokines in the cell culture, in which NK cells were efficiently propagated in vitro. The 721.221-mIL-21 expanded NK cells further feature higher purity with enhanced cytotoxicity compared with K562-mIL-21 expanded NK cells. Moreover, herein CAR-NK cells are derived from cord blood (CB) using the 721.221-mIL-21 NK expansion ready availability of CB from a CB bank and 2) use of CB-derived CAR-NK cells as an off-the-shelf CAR product.

I. Terms

Unless otherwise noted, technical terms are used according to conventional usage. Definitions of common terms in molecular biology may be found in Benjamin Lewin, Genes VII, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The singular forms "a," "an," and "the" refer to one or more than one, unless the context clearly dictates otherwise. For example, the term "comprising an interleukin" includes single or plural interleukins and is considered equivalent to the phrase "comprising at least one interleukin." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers (for the sequence present on Feb. 20, 2019). In case of conflict, the present specification, including explanations of terms, will control. In addition, the materials, methods, and examples are illustrative only and not intended to be limiting.

To facilitate review of the various embodiments of this disclosure, the following explanations of specific terms are provided.

721.221 cells: Also referred to as LCL 721.221 or ATCC® CRL1855™ cells, 721.221 cells are B lymphocytes derived from a human Epstein-Barr virus-transformed cell line. 721.221 cells do not express class I histocompatibility antigens (also known as major histocompatibility complex (MHC) class I molecules). Methods of producing 721.221 cells are known in the art (see, e.g., Shimiz et al., Proc Natl Acad Sci USA., 85(1):227-31, 1988, incorporated by reference in its entirety).

Activating receptor ligand: Ligands that bind receptors of natural killer (NK) or T cells, thereby activating the NK or T cell. Examples of activating receptor ligands include UL16-binding protein (ULBP)-1, ULPB-2, and/or major histocompatibility complex (MHC) class I chain-related protein A (MIC-A).

Autoimmune disorder: A disorder in which the immune system produces an immune response (e.g., a B cell or a T cell response) against an endogenous antigen, with consequent injury to tissues. The injury may be localized to certain organs, such as thyroiditis, or may involve a particular tissue at different locations, such as Goodpasture's disease, or may be systemic, such as lupus erythematosus.

In some examples, autoimmune diseases include systemic lupus erythematosus, Sjogren's syndrome, rheumatoid arthritis, type I diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, rubulavirus, and Evan's syndrome.

Cancer: Also referred to as a "malignant tumor" or "malignant neoplasm," cancer refers to any of a number of diseases characterized by uncontrolled, abnormal proliferation of cells. Cancer cells have the potential to spread locally or through the bloodstream and lymphatic system to other parts of the body (e.g., metastasize) with any of a number of characteristic structural and/or molecular features. A "cancer cell" is a cell having specific structural properties, lacking differentiation, and being capable of invasion and metastasis. Indolent and high grade forms are included. In some examples, the cancer is a solid cancer (such as sarcomas (e.g., rhabdomyosarcoma, osteogenic sarcoma, Ewing's sarcoma, chondrosarcoma, and alveolar soft part sarcoma); carcinomas (e.g., colorectal carcinoma and hepatocellular carcinoma (HCC),); and lymphomas, such as Hodgkin's or non-Hodgkin's lymphoma, for example, diffuse large B-cell, follicular, chronic lymphocytic, small lymphocytic, mantle cell, Burkitt's, cutaneous T-cell, AIDS-related, or central nervous system lymphoma); neuroblastoma; gynecological cancer (such as ovarian cancer); breast cancer; liver cancer (e.g., hepatocellular carcinoma (HCC),); lung cancer; prostate cancer; skin cancer; bone cancer; pancreatic cancer; brain cancer (neuroblastoma); head or neck cancer; kidney cancer (such as Wilms' tumor); retinoblastoma; adrenocortical tumor; desmoid tumors; desmoplastic small round cell tumor; endocrine tumors; and/or blood cancer (such as myeloma, such as multiple myeloma; lymphoma, such as Hodgkin's or non-Hodgkin's lymphoma, for example, diffuse large B-cell, follicular, chronic lymphocytic, small lymphocytic, mantle cell, Burkitt's, cutaneous T-cell, AIDS-related, or central nervous system lymphoma; or leukemia, such as acute lymphocytic leukemia (ALL) or acute myeloid leukemia (AML)).

Chimeric antigen receptor (CAR): A chimeric fusion protein having an extracellular domain that is fused via a transmembrane domain to an intracellular signaling domain capable of activating a T cell. CAR molecules can include an extracellular domain (ectodomain) with two (or more) targeting domains that are functionally different from each other (multispecific CAR) and that bind to two different sites on a target (multi-targeted). For example, one targeting domain of a multispecific CAR can be a cell surface receptor, such as CD19 (e.g., a multispecific CD19-based CAR). In another example, one targeting domain of a multispecific CAR can be a cell surface receptor, such as CD19, and the second targeting domain can be an antibody or a fragment thereof, such as a scFv (i.e. a multispecific CD19-scFv CAR). In some embodiments, the CD19-scFv CAR binds two different target sites (i.e. a multi-targeted CD19-scFv). A monofunctional CAR contains only a single functional element in the targeting extracellular domain. In some particular embodiments, a portion of the CAR's extracellular binding domain is derived from a murine or humanized monoclonal antibody.

The intracellular signaling domain of CAR molecules include two different cytoplasmic signaling domains. For example, one signaling domain can be a cytoplasmic effector function signaling domain and the second signaling domain can be a cytoplasmic co-stimulatory signaling domain. Linkers can connect domains to each other (for example, the two targeting domains) or they can connect one domain to another domain (for example, the ligand-binding domain to the transmembrane domain). CARS are also known as chimeric immune receptors, zetakines, and universal T cell receptors.

Methods of making CARS are available (see, e.g., Park et al., Trends Biotechnol., 29:550-557, 2011; Grupp et al., N Engl J Med., 368:1509-1518, 2013; Han et al., J. Hematol Oncol., 6:47, 2013; PCT Pubs. WO 2012/079000, WO 2013/059593; and U.S. Pub. 2012/0213783, each of which is incorporated by reference herein in its entirety.)

Contacting: Placement in direct physical association, including both a solid and liquid form. In one example, contacting includes association between a substance or cell (such as a cytokine or feeder cells) in a liquid medium and one or more other cells (such as NK cells or T cells in culture). Contacting can occur in vitro with isolated cells or tissue or in vivo by administering to a subject.

Culturing or Cell culture: Growth of a population of cells in a defined set of conditions (such as culture medium, extracellular matrix, temperature, and/or time of culture) in vitro. In some examples, a cell culture includes a substantially pure culture (for example, isolated 721.221 cells or isolated NK cells). In additional examples a cell culture includes a mixed culture, such as co-culture of two or more types of cells (for example a culture of NK cells with feeder cells). In further examples, a cell culture includes cells grown in contact with an extracellular matrix.

Culture Medium: A synthetic set of culture conditions with the nutrients necessary to support the viability, function, and/or growth of a specific population of cells, such as 721.221 cells. Culture media generally include components such as a carbon source, a nitrogen source, and a buffer to maintain pH. Additional components in culture media also may include one or more of serum, cytokines, hormones, growth factors, protease inhibitors, protein hydrolysates, shear force protectors, proteins, vitamins, glutamine, trace elements, inorganic salts, minerals, lipids, and/or attachment factors.

Cytokine: Proteins made by cells that affect the behavior of other cells, such as lymphocytes. In one embodiment, a cytokine is an interleukin, a molecule that regulates cell growth, differentiation, and motility (e.g., to stimulate immune responses, such as inflammation). In other embodiments, the cytokine can be an activating receptor ligand, TRL ligand, or receptors thereof. In some examples, the cytokine includes molecules known to stimulate or co-stimulate cell expansion (e.g., NK or T cell expansion). The term "cytokine" is used as a generic name for a diverse group of soluble proteins and peptides that act as humoral regulators at nanomolar to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNF-α), interleukin (IL)-2, IL-7, IL-15, IL-21, including membrane-bound IL-21 (mIL-21), interferon (IFN)γ, IFNα, IFNβ, IL-12, IL-33, IL-27, IL-18, IL-1 family molecules (e.g., IL-1α, IL-1β, IL-1Rα, IL-18, IL-36Rα, IL36α, IL36β, IL-36γ, IL-37, IL-38, IL-33, toll receptor (TLR) ligands, activating receptor ligands (e.g., UL16 binding protein (ULBP)-1, ULPB-2, major histocompatibility complex (MHC) class I chain-related protein A (MIC-A)), IL-1 family molecules, Fc receptors, intercellular adhesion molecule 1 (ICAM-1), CD8α, 2B4 (also known as cluster of differentiation 244 (CD244)), intercellular adhesion molecule 1 (ICAM-1), CD8α, CD40, CD28, 4-1BB ligand (4-1BBL), OX40L, TRX518, CD3 antibody, and CD28 antibody.

Effective amount: A quantity of a specified agent sufficient to achieve a desired effect, for example, in a subject being treated with that agent. In some examples, an effective amount of an expanded NK cell or T cell (e.g., a chimeric antigen receptor (CAR)-NK cell or CAR-T cell) disclosed herein is an amount sufficient to treat or inhibit a disease or disorder in a subject (such as a tumor, viral infection, autoimmune disease, or transplant rejection). In other examples, an effective amount is an amount of an expanded NK cell or T cell (e.g., a chimeric antigen receptor (CAR)-NK cell or CAR-T cell) sufficient to reduce or ameliorate one or more symptoms of a disease or disorder in a subject. The effective amount (for example, an amount ameliorating, inhibiting, and/or treating a disorder in a subject) will be dependent on, for example, the particular disorder being treated, the subject being treated, the manner of administration of the composition, and other factors.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

Feeder cells: Cells that provide support for another cell type in ex vivo or in vitro culture. Feeder cells may provide one or more factors required for survival, growth, and/or differentiation (or inhibiting differentiation) of the cells cultured with the feeder cells. Typically feeder cells are irradiated or otherwise treated to prevent their proliferation in culture. In some examples disclosed herein, NK cells are cultured with feeder cells, such as irradiated modified 721.221 cells (e.g., mIL-21-expressing 721.221 cells).

Heterologous nucleic acid: A nucleic acid introduced into a cell, for example, by transduction or transfection. A 'heterologous' nucleic acid or protein refers to a nucleic acid or protein originating from a different genetic source. For example, a nucleic acid or protein that is heterologous to a cell originates from an organism or individual other than the cell in which it is expressed and includes synthesized nucleic acids (e.g., mRNA). In other examples, a heterologous nucleic acid or protein originates from a cell type other than the cell in which it is expressed (for example, a nucleic acid or protein not normally present in 721.221 cells is heterologous to 721.221 cells). In further examples, a heterologous nucleic acid includes a recombinant nucleic acid, such as a protein-encoding nucleic acid operably linked to a promoter from another gene and/or two or more operably linked nucleic acids from different sources.

Immune system disorder: A disease or disorder that is associated with a pathological immune response in a subject (see Intl. Patent Pub. No. WO 2013/192294 and U.S. Patent Pub. No. 2011/00811323, both of which are incorporated herein by reference). Examples include immunodeficiency (e.g., primary or hereditary immunodeficiency and immunodeficiencies associated with other conditions, such as immunosuppression associated with, for example, HIV, old age, and cancer), cytokine storm, allergies, asthma, various types of inflammation, and autoimmune disorders.

Infectious disease: Also known as transmissible disease or communicable disease, infection disease are illnesses resulting from an infection. Infections are caused by infectious agents, including viruses, viroids, prions, bacteria; nematodes, such as parasitic roundworms and pinworms; arthropods, such as ticks, mites, fleas, and lice; fungi, such as ringworm; and other macroparasites, such as tapeworms and other helminths. Hosts fight infections using the immune system, such as the innate response (e.g., in mammals), which involves inflammation, followed by an adaptive response. Medications used to treat infections include antibiotics, antivirals, antifungals, antiprotozoals, and antihelminthics. Specific examples of infectious diseases include human immunodeficiency syndrome (HIV), hepatitis B virus (HBV), tuberculosis (TB), and malaria.

Inhibiting or treating a condition: "Inhibiting" a condition refers to inhibiting the full development of a condition or disease, for example, a tumor. Inhibition of a condition can span the spectrum from partial inhibition to substantially complete inhibition (e.g., including, but not limited to prevention) of a disease (such as a tumor, viral infection, autoimmune disease, or transplant rejection). In some examples, the term "inhibiting" refers to reducing or delaying the onset or progression of a condition. "Treatment" refers to a therapeutic intervention that ameliorates a sign or symptom of a disease or condition after it has begun to develop. A subject to be administered an effective amount of the disclosed NK cells or T cells (e.g., CAR-NK cells or CAR-T cells) can be identified by standard diagnosing techniques for such a disorder, for example, presence of the disease or disorder or risk factors to develop the disease or disorder.

Isolated: An "isolated" or "purified" biological component (such as a cell, nucleic acid, peptide, protein, protein complex, or virus-like particle) has been substantially separated, produced apart from, or purified away from other components (for example, other biological components in the cell or the organism in which the component naturally occurs). Cells, nucleic acids, peptides and proteins that have been "isolated" or "purified" thus include cells, nucleic acids, and proteins purified by standard purification methods.

The term "isolated" or "purified" does not require absolute purity; rather, it is intended as a relative term. Thus, for example, an isolated biological component is one in which the biological component is more enriched than the biological component is in its natural environment within a cell, organism, sample, or production vessel (for example, a cell culture system). Preferably, a preparation is purified such that the biological component represents at least 50%, such as at least 70%, at least 80%, at least 90%, at least 95%, or greater, of the total biological component content of the preparation.

Natural Killer (NK) cells: Cells of the immune system that kill target cells in the absence of a specific antigenic stimulus and without restriction according to MHC class. Target cells can be tumor cells or cells harboring viruses. NK cells are characterized by the presence of CD56 and the absence of CD3 surface markers. NK cells typically comprise approximately 10 to 15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the cytotoxic T lymphocyte (CTL) response by down-regulating MHC class I presentation. In addition to being involved in direct cytotoxic killing, NK cells also serve a role in cytokine production, which can be important to control cancer and infection. Tissue-resident memory NK cells are included.

In some examples, a "CAR-NK cell" is an NK cell transduced with a heterologous nucleic acid encoding or expressing a CAR.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, PA, 21$^{st}$ Edition (2005), describes compositions and formulations suitable for pharmaceutical delivery of one or more therapeutic compositions, such as one or more modified NK cells and/or additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Subject: A living multi-cellular vertebrate organism, a category that includes both human and non-human mammals (such as veterinary animals, including dogs and cats, as well as mice, rats, rabbits, sheep, horses, cows, and non-human primates).

T Cell: A white blood cell critical to the immune response. T cells include, but are not limited to, CD4+ T cells and CD8+ T cells. A CD4+ T lymphocyte is an immune cell that expresses CD4 on its surface. These cells, also known as helper T cells, help orchestrate the immune response, including antibody responses as well as killer T cell responses. Th1 and Th2 cells are functional subsets of helper T cells. Th1 cells secrete a set of cytokines, including interferon-gamma, and whose principal function is to stimulate phagocyte-mediated defense against infections, especially related to intracellular microbes. Th2 cells secrete a set of cytokines, including interleukin (IL)-4 and IL-5, and whose principal functions are to stimulate IgE and eosinophil/mast cell-mediated immune reactions and to downregulate Th1 responses. In further examples, T cells can include regulatory T cells (Tregs), NKT cells, tumor infiltrating lymphocytes (TIL), other unconventional T cells (e.g., MAIT, γδ T cells, and CD8αα+ IELs), innate lymphoid cells (ILCs), tissue-resident memory T cells, or any vaccine-primed T cells. Similar to CD4+ T cells, Tregs also express CD4 but are distinguished by expression of TGFβ. Tregs can aid in treating immune disorders, such as autoimmune disease, chronic graft versus host disease (GVHD), diabetes, systemic lupus erythematosus, obesity, and encephalitis, as well as facilitate organ transplant acceptance. NKT cells coexpress an αβ T-cell receptor as well as a variety of molecular markers that are typically associated with NK cells, such as CD161. NKT cells can recognize lipids and glycolipids presented by CD1d molecules, and, thus, NKT cells can be used to recognize glycolipids from organisms such as *Mycobacterium*, which causes tuberculosis.

In some examples, the T cell can be genetically modified, such as a "CAR-T cell", which is a T cell transduced with a heterologous nucleic acid encoding or expressing a CAR, or can be a chimeric cytokine receptor (CCR)-expressing T cell, which is a T cell transduced with a heterologous nucleic acid encoding a CCR (see, e.g., PCT Pat. Pub. No. WO 2017/029512, incorporated herein by reference in its entirety).

Toll-like receptor (TRL) ligands: TLR ligands are evolutionarily conserved, and include pathogen-associated molecules, such as bacterial cell-surface lipopolysaccharides (LPS), lipoproteins, lipopeptides, and lipoarabinomannan; proteins, such as flagellin from bacterial flagella; double-stranded RNA of viruses; unmethylated CpG islands of bacterial and viral DNA; CpG islands in the eukaryotic DNA promoters; as well as other RNA and DNA molecules.

Transformed: A transformed cell is a cell into which has been introduced a nucleic acid molecule by molecular biology techniques. As used herein, the term transformation encompasses all techniques by which a nucleic acid molecule might be introduced into such a cell, including transduction with viral vectors, transformation with plasmid vectors, and introduction of naked DNA by electroporation, lipofection, and particle gun acceleration (e.g., 'transfection').

Vector: A nucleic acid molecule allowing insertion of foreign or heterologous nucleic acid into a cell without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and/or translation of an inserted gene or genes. In some non-limiting examples, the vector is a viral vector, such as a retroviral vector or lentiviral vector.

II. Overview of Several Embodiments

Described herein are modified (e.g., genetically-engineered) 721.221 cells and methods of expanding immune cells (such as NK cells, T cells, or genetically modified NK cells or T cells) using an irradiated modified 721.221 cell line (a B cell line derived by mutagenesis that does not express MHC class I molecules or expresses a low level of MHC class I molecules; (Shimizu et al., Proc Natl Acad Sci USA 85:227-31 (1988)), expressing at least one of membrane-bound IL-21 (mIL-21), IL-2, IL-12, IL-33, IL-27, IL-18, IL-7, mIL-7, IL-15, mIL-15, an IL-1 family cytokine, a TLR ligand, ULBP-1, ULPB-2, Fc receptors, 2B4 (also known as CD244), intercellular adhesion molecule 1 (ICAM-1), CD8α, and/or MIC-A. Also disclosed are methods of producing the modified 721.221 cells, for example by transducing or transfecting the cells with a nucleic acid encoding the membrane-bound IL-21 (mIL-21), IL-2, IL-12, IL-33, IL-27, IL-18, IL-7, mIL-7, IL-15, mIL-15, IL-1 family cytokine, a TLR ligand, ULBP-1, ULPB-2, Fc receptors, 2B4 (also known as CD244), intercellular adhesion molecule 1 (ICAM-1), CD8α, and/or MIC-A. The modified 721.221 cells are used in methods of expanding primary NK cells or T cells, or modified NK cells or T cells (such as CAR-NK or CAR-T cells). Finally, the expanded cells are used in methods of treating a disease or disorder, such as cancer, infectious disease, or immune disease.

Recent studies have shown that the 4-1BB (also known as CD137) ligand (4-1BBL/CD137L)- and IL-21-expressing K562 cells as feeder cells can be used to rapidly expand NK cells in vitro (Denman et al., PLoS One 7:e30264 (2012)). However, characterization and application of these cells for the treatment of patients is essential to ensure that the cells are functional and healthy. In addition, specific NK cell expansion is also needed to advance NK cell immunotherapy in vivo. One potential issue regarding NK cell expansion in vitro using irradiated feeder cells in the presence of cytokine IL-2 is that naïve immune cells become exhausted or senescent after rapid proliferation and differentiation (Keir et al., Annu Rev Immunol 26:677-704 (2008)). Indeed, CAR-modified immune cells express exhaustion markers such as PD-1 (John et al., Oncoimmunology 2:e26286 (2013); Cherkassky et al., J Clin Invest 126:3130-44 (2016); Chong et al., Blood (2016); Gargett et al., Mol Ther 24:1135-49 (2016)). To solve the problem of immune cell exhaustion, one approach is to block PD-1 signaling in CAR-modified T cells (Cherkassky et al., J Clin Invest 126:3130-44 (2016). Another potential strategy is to alter the metabolic pathway in CAR-modified T cells (Ping et al., Protein Cell (2017)) or reinforce lymphocyte metabolism (Lim W A and June C H, Cell 168:724-40 (2017)), given the essential metabolic signaling in T cells (Buck et al., J Exp Med 212:1345-60 (2015)).

In previous techniques, expansion of CAR-modified T and NK cells requires in vitro stimulation of genetically modified T and NK cells using antibodies and cytokines. Such antibody- and cytokine-driven activation and expansion may negatively alter CAR-T/NK cell functions. For example, CAR-modified immune cell exhaustion can be induced by the end of an extensive expansion program, which is evident by up-regulation of PD-1, TIM-3, and LAG-3 in CAR T cells (Long et al., Nat Med 21:581-90 (2015)). Therefore, new modification and expansion strategies without induction of exhaustion may be developed in vivo, given that immune cell exhaustion is a major factor for compromised immune responses against tumor and virus during chronic antigen stimulation (Wherry E J, Nat Immunol 12:492-9 (2011); Virgin et al., Cell 138:30-50 (2009)). Additionally, expansion of CAR-modified immune cells for clinical applications takes at least 2-3 weeks, which is a significant hurdle for some patients. The "sleeping beauty transposon", or piggBac system, which is capable of delivering large (9.1-14.3 kb), transposable elements without a significant reduction in T cell efficacy (Guerrero et al., Chin J Cancer 33:421-33 (2014); Singh et al., Immunol Rev 257:181-90 (2014); Maiti et al., J Immunother 36:112-23 (2013)), in combination with genetically engineered artificial cells expressing membrane-bound IL-15 and 4-1BB ligands has been used for CAR-modified T cell immunotherapy.

III. Modified 721.221 Cells and Methods of Production

Disclosed herein are modified (e.g., genetically-engineered) 721.221 cells that express one or more of a cytokine (e.g., membrane-bound interleukin-21 (mIL-21), IL-21, IL-2, IL-12, IL-33, IL-27, IL-18, IL-7, mIL-7, IL-15, mIL-15, a toll receptor (TLR) ligand, or an activating receptor ligand (e.g., UL16 binding protein (ULBP)-1, ULPB-2, major histocompatibility complex (MHC) class I chain-related protein A (MIC-A)), IL-1 family molecules, Fc receptors, intercellular adhesion molecule 1 (ICAM-1), CD8α, 2B4 (also known as cluster of differentiation 244 (CD244)), intercellular adhesion molecule 1 (ICAM-1), and CD8α), including CD40, CD28, 4-1BB ligand (4-1BBL), OX40L, TRX518, CD3 antibody, and CD28 antibody. Herein, these cells are referred to as 'modified 721.221 cells.' In some embodiments, the modified 721.221 cells further express IL-15 receptor a (IL-15Rα). In one example, the modified 721.221 cells express mIL-21. In other examples, the modified 721.221 cells express mIL-21 and IL-15Rα.

721.221 cells are B lymphocytes characterized by transformation with human Epstein-Barr virus and do not express class I histocompatibility antigens (also known as major histocompatibility complex (MHC) class I molecules), or express low levels of MHC I molecules. 721.221 cells are also referred to as LCL 721.221 (also previously referred to as ATCC® CRL-1855™ cells). 721.221 cells can be produced by any method used in the art. An exemplary method of producing 721.221 cells is described in Shimiz et al., Proc Natl Acad Sci USA., 85(1):227-31, 1988 (incorporated by reference in its entirety).

In some embodiments, the modified 721.221 cells include a heterologous nucleic acid encoding one of more of mIL-21, IL-2, IL-12, IL-33, IL-27, IL-18, IL-7, mIL-7, IL-15, mIL-15, a TLR ligand, ULBP-1, ULPB-2, MIC-A, IL-1 family molecules, Fc receptors, 2B4 (also known as CD244), intercellular adhesion molecule 1 (ICAM-1), and/or CD8α. In some embodiments, the nucleic acid encodes a protein that facilitates expansion of immune cells, such as natural killer (NK) cells or T cells. In some examples, the nucleic acid encodes a cytokine or cytokine receptor (e.g., an interleukin or interleukin receptor), such as mIL-21, mIL-15, IL-7, IL-2, IL-12, IL-33, IL-27, IL-18, IFNα, IFNβ, IFNγ, IL-1 family molecules, or a receptor therefor (e.g., IL-15Rα; see, e.g., Wu et al., Front Immunol, 8:930, 2017, incorporated herein by reference in its entirety), toll-like receptor (TLR) ligands, activating receptor ligands (such as ULBP-1, ULPB-2, MIC-A, Fc receptors, 2B4 (also known as CD244), intercellular adhesion molecule 1 (ICAM-1), and/or CD8α), CD40, CD28, 4-1BB ligand (4-1BBL), OX40L, TRX518, CD3 antibody, and CD28 antibody. In further examples, the cytokine or cytokine receptor is membrane-bound (e.g., membrane-bound IL-21 or membrane-bound IL-15). In specific, non-limiting examples, the modified 721.221 cells include a nucleic acid encoding mIL-21. In other non-limiting examples, the modified 721.221 cells include heterologous nucleic acids encoding mIL-21 and IL-15Rα. In further, non-limiting examples, the modified 721.221 cells include heterologous nucleic acids encoding membrane-bound ICAM-1, Fc receptor, CD8α, ULBP-1, ULPB-2, or MIC-A.

In some examples, the nucleic acid encoding mIL-21 includes or consists of a nucleic acid with at least 90% identity (such as at least 90%, 91%, 92%, 93%, 94%, 95%, 96%, 97%, 98%, 99%, or 100% identity) to SEQ ID NO: 1 and/or encodes a protein including or consisting of an amino acid sequence with at least 95% identity (such as at least 95%, 96%, 97%, 98%, 99%, or 100% identity) to SEQ ID NO: 2. In some examples, the nucleic acid encoding IL-15Rα includes or consists of a nucleic acid with at least 90% identity (such as at least 90%, 91%, 92%, 93%, 94%, 95%, 96%, 97%, 98%, 99%, or 100% identity) to SEQ ID NO: 4 and/or encodes a protein including or consisting of an amino acid sequence with at least 95% identity (such as at least 95%, 96%, 97%, 98%, 99%, or 100% identity) to SEQ ID NO: 5.

Further disclosed herein are methods of producing the modified 721.221 cells described herein. Modified or recombinant 721.221 cells can be produced by transducing or transfecting 721.221 cells with at least one heterologous nucleic acid (such as a nucleic acid encoding one or more of mIL-21, IL-2, IL-12, IL-33, IL-27, IL-18, IL-7, mIL-7, IL-15, mIL-15, a TLR ligand, ULBP-1, ULPB-2, MIC-A, IL-1 family molecules, Fc receptors, 2B4, ICAM-1, CD8α, CD40, CD28, 4-1BB ligand (4-1BBL), OX40L, TRX518, CD3 antibody, or CD28 antibody), and, in some examples, also IL-15Rα. In specific, non-limiting examples, the modified 721.221 cells include a heterologous nucleic acid encoding mIL-21. In other non-limiting examples, the modified 721.221 cells include heterologous nucleic acids encoding mIL-21 and IL-15Rα. In further, non-limiting examples, the modified 721.221 cells include heterologous nucleic acids encoding membrane-bound ICAM-1, Fc receptor, CD8α, ULBP-1, ULPB-2, or MIC-A.

In some examples, the 721.221 cells are transduced or transformed with a vector (such as a lentivirus or retrovirus vector) that includes the at least one heterologous nucleic acid. For example, the 721.221 cells can be transduced or transfected with at least 1, at least 2, at least 3, at least 4, at least 5, at least 6, at least 7, at least 8, at least 9, at least 10, or more heterologous nucleic acids, or about 1-2, 1-3, 1-5, 1-7, or 1-10 heterologous nucleic acids, or about 1, 2, or 3 heterologous nucleic acids.

Any method of transduction or transfection can be used, such as viral transduction (e.g., using a retrovirus, such as MoMLV or lentivirus) or non-viral transduction, mRNA transfection, or nanoscale nucleic acid delivery (e.g., chemical dendrimers, DNA dendrimers, nanospheres, nanolayers, nanorods, and nanotubes).

In some embodiments, the disclosed methods utilize a viral vectors for delivery of the at least one heterologous nucleic acid to 721.221 cells. Examples of suitable virus vectors include retrovirus (e.g., MoMLV or lentivirus), adenovirus, adeno-associated virus, vaccinia virus, and fowlpox vectors. In specific examples, a retroviral system is used to introduce one or more heterologous nucleic acids into 721.221 cells. In some examples, a MoMLV vector can be used, such as an SFG retroviral vector. The SFG vector is derived from a murine leukemia virus (MLV) backbone. This type of Murine leukemia virus (MLV)-based retroviral vector is frequently used gene delivery vehicles and has been widely used in clinical trials. Current SFG vectors are fully optimized for gene expression for lymphocyte genetical modification, protein expression, and viral titer.

In some examples, the SFG vector is a gamma retroviral vector that is pseudotyped with the RD114 envelope. RD114 pseudotyped transient retroviral supes can be generated by triple transfection of Peq-Pam plasmid (Moloney GagPol; e.g., at about 4.69 μg), RDF plasmid (RD114 envelope; e.g., at about 3.125 μg), and SFG-VRCO1 plasmid (e.g., at about 4.69 μg) into cells (e.g., 293T cells, for example, using GeneJuice (Novagen). Supernatant can be harvested (e.g., after about 48 and 72 hours). High-titer producer lines were generated by multiple transduction of Monkey and Human lymphocytes.

The heterologous nucleic acid introduced can be a nucleic acid encoding any cytokine, activating receptor ligand, or receptor or fragment thereof, such as IL-21 (e.g., to produce mIL-21), IL-15Rα, IL-2, IL-12, IL-33, IL-27, IL-18, IL-7, TLR ligands, ULBP-1, ULBP-2, MIC-A, IL-1 family molecules, Fc receptors, 2B4, ICAM-1, CD8α, CD40, CD28, 4-1BB ligand (4-1BBL), OX40L, TRX518, CD3 antibody, and/or CD28 antibody. In specific examples, the nucleic acid encodes mIL-21, IL-15Rα, or a combination thereof. In other non-limiting examples, the nucleic acid encodes membrane-bound ICAM-1, Fc receptor, CD8α, ULBP-1, ULPB-2, or MIC-A.

In embodiments where at least one heterologous nucleic acid comprises a nucleic acid that encodes a membrane-bound cytokine, the at least one heterologous nucleic acid can comprise cytokine of interest and additional heterologous nucleic acid sequences (e.g., in the same or separate vector), for example, to form a membrane-bound cytokine. For example, the at least one heterologous nucleic acid can comprise at least one extracellular sequence, at least one transmembrane sequence, and/or at least one intracellular sequence can be used (e.g., in the same vector).

In some examples, at least one heterologous nucleic acid comprises at least two extracellular sequences, at least three extracellular sequences, at least four extracellular sequences, or at least five extracellular sequences or about 1-2, 1-3, or 1-5 extracellular sequences. The at least one extracellular sequence can include the cytokine of interest for membrane, such as an interleukin. In specific examples, the interleukin is IL-21. In some examples, at least one extracellular sequence can include an extracellular fragment from an IgG sequence. In some examples, at least one extracellular sequence can include an extracellular fragment from a CD8a sequence. In some examples, at least one heterologous nucleic acid comprises at least two extracellular sequences. In specific examples, the at least two extracellular sequences include a cytokine of interest, such as IL-21, and an extracellular fragment from an IgG sequence.

In some examples, at least one heterologous nucleic acid comprises at least two transmembrane sequences, or at least three transmembrane sequences or about 1-2 or 1-transmembrane sequences. In some examples, at least one transmembrane sequence can include a transmembrane fragment from a CD28 sequence. Other transmembrane sequences can also be used, such as a transmembrane sequence from CD40L or 2B4. In some examples, at least one heterologous nucleic acid comprises at least two intracellular sequences, at least three intracellular sequences, at least four intracellular sequences, at least five intracellular sequences, or at least six intracellular sequences, or about 1-2, 1-3, or 1-6 intracellular sequences. In some examples, at least one intracellular sequence can include an intracellular fragment from a CD28 sequence, an intracellular fragment from a 4-1BB sequence, and/or an intracellular fragment from a CD3ζ sequence. In some examples, the nucleic acid construct includes or consists of a nucleic acid with at least 90% identity (such as at least 90%, 91%, 92%, 93%, 94%, 95%, 96%, 97%, 98%, 99%, or 100% identity) to SEQ ID NO: 3.

Techniques for the in vitro isolation and enrichment of 721.221 cells are described herein. In some example, bulk 721.221 cells or 721.221 cell subsets can be isolated for by enriching procedures, such as through the use of immunomagnetic beads or flow sorting. The isolated 721.221 cells may be grown in cell culture medium. In one example, the medium is RPMI-1640 (CORNING®) containing 10% (v/v) fetal bovine serum (FBS) and 100 U/mL Penicillin-Streptomycin (CORNING®). The isolated 721.221 cells can be analyzed by flow cytometry for the expression of the at least one transgene, such as mIL-21 and/or IL-15Rα. In some examples, the methods include arresting proliferation of 721.221 cells, such as by contact with arresting reagents or conditions. In some examples, 721.221 cell proliferation is arrested by irradiation (e.g., γ-irradiation, such as at a dose of at least 1,000, at least 2,000, at least 3,000, at least 5,000, at least 7,000, at least 8,000, at least 9,000, at least 10,000, at least 11,000, at least 12,000, or at least 15,000 or about 1,000-15,000, 2,000-12,000, 1,000-5,000, 5,000-10,000, or 8,000-12,000, or about 10,000 Rad) or by contact with mitomycin-C (MC).

Modified 721.221 cells can be identified using various techniques known to one skilled in the art. In some examples, the modified 721.221 cells are identified using flow cytometry or immuno-magnetic methods. For example, detectable antibodies (e.g., by fluorescent or metal labeling) can be used to bind modified 721.221, which express, for example, a surface-expressed cytokine, TRL ligand, or activating receptor ligand of interest. In some examples, flow cytometry or magnetic beads can then be used to identify modified 721.221 cells.

IV. Methods of Expanding Immune Cells Utilizing the Modified 721.221 Cells

Disclosed herein are methods of expanding NK or T cells using the modified 721.221 cells disclosed herein. In particular examples, the methods disclosed herein are utilized to expand CAR-modified NK or T cells.

Techniques for the in vitro or ex vivo isolation and enrichment of NK or T cells are described herein. Exemplary procedures are described in US Pat. App. Publ. No. 2014/0086890, WO Pat. Pub. No. 2017/127729, and US Pat. Pub. No. 2013/0315884 incorporated herein by reference in their entireties. One of ordinary skill in the art can identify additional methods for expanding NK or T cells, for example, as described in Childs et al., *Hematol. The Education Program* 2013:234-246, 2013; U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 2006/0121005 incorporated herein by reference in their entireties.

Mononuclear cells are collected from a subject (such as a healthy subject, a donor subject, or a subject with a cancer, immune disorder, or infectious disease) or from a donor HLA-matched to the subject to be treated. In some examples, mononuclear cells are collected by an apheresis procedure. The mononuclear cells are enriched for NK or T cells, for example, by negative depletion using an immunomagnetic bead strategy. In other examples, the mononuclear cells comprise PMBCs, for example, isolated using a polysaccharide technology, such as a Ficoll®-based separation method (GE® Healthcare).

In some examples, NK cells are optionally enriched by depleting the mononuclear cell sample of T cells, B cells, monocytes, dendritic cells, platelets, macrophages, and erythrocytes utilizing a mixture of biotinylated monoclonal antibodies. In some examples, The non-NK cells in the sample are removed with magnetic beads coupled to streptavidin, resulting in an enriched preparation of NK cells. An exemplary commercially available kit for this method is Dynabeads® Untouched™ Human NK Cells kit (ThermoFisher Scientific, Waltham, MA).

In some examples, T cells are enriched by depleting the mononuclear cell sample of NK cells, B cells, monocytes, dendritic cells, platelets, macrophages, and erythrocytes utilizing a mixture of biotinylated monoclonal antibodies. In some examples, The non-NK cells in the sample are removed with magnetic beads coupled to streptavidin, resulting in an enriched preparation of NK cells. An exemplary commercially available kit for this method is EASY-SEP™ Human T Cell Isolation Kit (STEMCELL™ technologies, Cambridge, MA). In some examples, The non-NK cells in the sample are removed with magnetic beads coupled to streptavidin, resulting in an enriched preparation of NK cells.

In some examples, NK or T cells are enriched by positive selection. In some examples, the methods include enriching for NK cells, such as by positive selection of $CD56^+$ NK cells, for example utilizing magnetic beads conjugated to an anti-CD56 antibody (such as CD56 MicroBeads, Miltenyi Biotec, Inc., Auburn, CA). In other examples, a two-step method including negative depletion (such as T cell depletion) followed by positive selection of $CD56^+$ NK cells is used for enriching NK cells. In other examples, the methods include enriching for T cells, such as by positive selection of CD4+ T cells or CD8+ T cells, for example utilizing magnetic beads conjugated to an anti-CD4 or anti-CD8 antibody (such as CD4 or CD8 MicroBeads, Miltenyi Biotec, Inc., Auburn, CA). In other examples, a two-step method including negative depletion (such as NK cell depletion) followed by positive selection of $CD4^+$ T cells or CD8+ T cells is used for enriching T cells. One of ordinary skill in the art can identify other methods that can be used to prepare an enriched population of NK or T cells.

The isolated NK or T cells can be analyzed by flow cytometry for the expression of markers. In some examples, the markers can be used to assay for purity of the isolated cells. In some examples, CD56 can be used as a marker, for example, to analyze NK cells. In some examples, CD8 or CD4 can be used as a marker, for example, to analyze T cells.

In some embodiments, NK cells or T cells are expanded in vitro. In some examples, enriched NK cells or T cells can be used for expansion. In other examples, NK cells or T cells are expanded using a heterogeneous pool of cells, such as a population of cells derived from a sample, such as a tissue, fluid, or blood sample. In some examples, the population of cells comprises peripheral blood mononuclear cells (PMBCs). The population of cells (e.g., PMBCs) can be generated from any tissue, fluid, or blood sample can be used, for example, peripheral blood, cord blood, ascites, menstrual blood, or bone marrow. In specific examples, the population of cells comprises PBMCs from healthy donors, cord blood mononuclear cells from healthy donors, or PBMCs from non-Hodgkin lymphoma (NHL) patients.

In some examples, to enhance expansion, the NK cells or T cells are expanded with the modified 721.221 cells disclosed herein (e.g., 721.221 cells expressing mIL-21). The modified 721.221 cells disclosed herein are utilized as feeder cells for the NK or T cells. Any amount of cells for expansion and feeders cells can be used. In some examples, the amount of cells for expansion (e.g., PMBCs) can include at least about $10^1$, at least about $10^2$, at least about $10^3$, at least about $10^4$, at least about $10^5$, at least about $10^6$, at least about $10^7$, at least about $10^8$, at least about $10^9$, or at least about $10^{10}$, about $10^1$-$10^{10}$, $10^4$-$10^8$, or about $10^6$, such as $5\times10^6$ cells. In some examples, the cells for expansion (e.g., a population of cells comprising NK cells or T cells, such as PMBCs) can be contacted with at least about $10^1$, at least about $10^2$, at least about $10^3$, at least about $10^4$, at least about $10^5$, at least about $10^6$, at least about $10^7$, at least about $10^8$, at least about $10^9$, or at least about $10^{10}$, about $10^1$-$10^{10}$, $10^5$-$10^9$, or about $10^6$, such as $1\times10^7$ cells feeder cells (e.g., modified 721.221 cells, for example, 721.221 cells expressing mIL-21). In some examples, the ratio of cells for expansion (e.g., PMBCs) to the feeder cells can be at least about 1:1 to about 1:50, for example, at least about 1:1, at least about 1:2, at least about 1:5, at least about 1:6, at least about 1:7, at least about 1:8, at least about 1:9, at least about 1:10, at least about 1:15, at least about 1:20, at least about 1:25, at least about 1:30, at least about 1:35, at least about 1:40, at least about 1:45, or at least about 1:50 or about 1:2, about 1:7, about 3:20, or about 1:20. In some examples, further reagents are used to enhance expansion, such as additional cytokines, for example, IL-2, IL-5, IL-7, IL-8, and/or IL-12.

The cells for expansion (e.g., a population of cells comprising NK cells or T cells, such as PMBCs) are contacted with feeder cells and/or other expansion-enhancing reagents (e.g., IL-2, IL-5, IL-7, IL-8, and/or IL-12) for at least about 1-40 days, such as at least about 1, at least about 3, at least about 5, at least about 7, at least about 10, at least about 14, at least about 21, at least about 28, at least about 35, about 10-30, 10-20, 20-30, or 15-25, or about 14 days (e.g., for T cell expansion) or about 21 days (e.g., for NK cell expansion, such as CAR-NK cells).

The expanded NK cells or T cells (e.g., enriched or in a heterogeneous population of cells, such as PMBCS) produced using the techniques disclosed herein (e.g., by contacting the NK cells or T cells with feeder cells, such as modified 721.221 cells, for example, expressing mIL-21) can be superior to control expansion techniques, where feeder cells, such as the modified 721.221 cells (e.g., expressing mIL-21), are not used. In some examples, expansion using the techniques disclosed herein can enhance expansion by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, 1-20-fold, 5-15-fold, 1-5-fold, 5-10-fold, 10-15-fold, or about 10-fold.

In some examples, cytotoxicity of the expanded NK cells or T cells can be evaluated. Cytotoxicity can be evaluated at any time, such as after the expanded NK cells or T cells are expanded or, optionally, the expanded NK cells or T cells can be transduced (for example, to express chimeric antigen receptor (CAR)). In some examples, to evaluate cytotoxicity against tumor cells, animal models can be used, such as animal models expressing a detectable tumor marker (e.g., a bioluminescent tumor marker, such as luciferase, for example, ffluc.Daudi tumor cells). In specific examples, the NK or T cells exhibit superior cytotoxicity, for example, against tumor cells, compared with control NK or T cells produced without the methods disclosed herein. For example, the NK or T cells produced using the disclosed methods can exhibit greater cytotoxicity, for example, against tumor cells, by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, or at least about 10-fold, about 0.5-10-fold, 1-5-fold, or 5-10-fold, or about 3-fold greater toxicity. In some examples, chromium release assays can be used to assess NK cell cytotoxicity against cell targets. One of ordinary skill in the art can identify other methods to assess the isolated NK cell population (for example, purity, viability, and/or activity).

In some embodiments, the NK or T cells can be further transduced to express a protein of interest. In specific examples, the NK or T cells can be transduced to express a CAR. The modified NK or T cells are then expanded using the modified 721.221 cells and methods disclosed herein. The NK or T cells can be transduced at any time throughout the methods described herein, such as before expansion or during expansion. In specific examples, the NK or T cells can be transduced with CAR during expansion, for example, at least about ¼, ⅓, ½, or ¾ of the duration of the expansion process. In a specific, non-limiting example, the NK or T cells can be transduced with CAR at about ⅓ of the duration of expansion, for example, where the expansion process occurs over 21 days, the NK or T cells can be transduced with CAR at about day 7. In other examples, NK or T cells expanded using the modified 721.221 cells disclosed herein are subsequently modified to express a CAR.

In specific examples, the NK or T cells can be transduced with viral vectors comprising the CAR of interest for delivery therein. Examples of suitable virus vectors include retrovirus (e.g., MoMLV or lentivirus), adenovirus, adeno-associated virus, vaccinia virus, and fowlpox vectors. In specific examples, a retroviral system is used to introduce the CAR into NK or T cells. In some examples, a MoMLV vector can be used, such as an SFG retroviral vector. In some examples, the CAR can comprise proteins or fragments thereof from at least one heterologous nucleic acid can comprise at least one extracellular sequence, at least one transmembrane sequence, and/or at least one intracellular sequence can be used (e.g., in the same or different vectors).

In some examples, at least one heterologous nucleic acid comprises at least two extracellular sequences, at least three extracellular sequences, at least four extracellular sequences, or at least five extracellular sequences or about 1-2, 1-3, or 1-5 extracellular sequences. The at least one extracellular sequence can include any CAR of interest, such as a CD19 or kappa light chain sequence. In some examples, at least one extracellular sequence can include an extracellular fragment from an IgG sequence. Other extracellular sequences can be used, including extracellular sequences from CD8a or CD28. In some examples, at least one heterologous nucleic acid comprises at least two extracellular sequences. In specific examples, the at least two extracellular sequences include a CAR of interest, such as CD19 or kappa, and an extracellular fragment from an IgG sequence.

In some examples, at least one heterologous nucleic acid comprises at least two transmembrane sequences, or at least three transmembrane sequences or about 1-2 or 1-transmembrane sequences. In some examples, at least one transmembrane sequence can include a transmembrane fragment from a CD28 sequence. Other transmembrane sequences can be used, such as a 4-1BB sequence. In some examples, at least one heterologous nucleic acid comprises at least two intracellular sequences, at least three intracellular sequences, at least four intracellular sequences, at least five intracellular sequences, or at least six intracellular sequences, or about 1-2, 1-3, or 1-6 intracellular sequences. In some examples, at least one intracellular sequence can include an intracellular fragment from a CD28 sequence, an intracellular fragment from a 4-1BB sequence, and/or an intracellular fragment from a CD3 sequence.

Additional CARs can be used, for example, LL1 (anti-CD74), GD2 antigen, CD5 antigen, CD57 antigen, LL2 or RFB4 (anti-CD22), veltuzumab (hA20, anti-CD20), rituxumab (anti-CD20), obinutuzumab (GA101, anti-CD20), lambrolizumab (anti-PD1), nivolumab (anti-PD1), MK-3475 (anti-PD1), AMP-224 (anti-PD1), pidilizumab (anti-PD1), MDX-1105 (anti-PD-LI), MEDI4736 (anti-PD-L1), MPDL3280A (anti-PD-LI), BMS-936559 (anti-PD-L1), ipilimumab (anti-CTLA4), trevilizumab (anti-CTL4A), RS7 (anti-epithelial glycoprotein-1 (EGP-1, also known as TROP-2)), PAM4 or KC4 (both anti-mucin), MN-14 (anti-carcinoembryonic antigen (CEA, also known as CD66e or CEACAM-5), MN-15 or MN-3 (anti-CEACAM-6), Mu-9 (anti-colon-specific antigen-p), Immu 31 (an anti-alpha-fetoprotein), RI (anti-IGF-1R), A19 (anti-CD19), TAG-72 (e.g., CC49), Tn, 1591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin), BWA-3 (anti-histone H2A/H4), LG2-1 (anti-histone H3), MRA12 (anti-histone PRI-1 (anti-histone H2B), LG11-2 (anti-histone H2B), LG2-2 (anti-histone H2B), and trastuzumab (anti-ErbB2), carbonic anhydrase IX, B7, CCL19, CCL21, CSAp, HER-2/neu, BrE3, CDI, CD1a, CD2, CD3, CD4, CDS, CDS, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD47, CD52, CD54, CD55, CD59, CD64, CD67, CD70, CD72, GPC-3, CD74, CD79a, CDS0, CD83, CD95, CD126, CD133, CD137, D138, CD147, CD154, CD127 (also known as B7-H3), CEACAM-5, CEACAM-6, CTLA4, alpha-fetoprotein (AFP), VEGF (e.g., AVASTIN®, fibronectin splice variant), ED-B fibronectin (e.g., L19), EGP-1 (TROP-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO family proteins, HMGB-1, hypoxia inducible factor (HIF), HM1 0.24, HER-2/neu, insulin-like growth factor (ILGF), IFN family proteins, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, ganglio-sides, Fas-L, HCG, the HLA-DR antigen to which L243 binds, CD66 antigens (i.e., CD66a-d or a combination thereof), MAGE, mCRP, MCP-1, MIP-1A, MIP-18, macrophage migration-inhibitory factor (MIF), MUC1, MUC2, MUC3, MUC4, MUC5ac, placental growth factor (P1GF), PSA (prostate-specific antigen), PSMA, PAM4 antigen, PD1 receptor, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, and TI01. Other CARs are possible, such as multispecific CARs (e.g., bispecific or trispecific CARS, such as including one or more CAR disclosed herein)

IV. Methods and Compositions for Treating or Inhibiting a Condition

Disclosed herein are methods of treating a subject with a disease or disorder by administering NK or T cells produced by the methods described herein to the subject (e.g., CAR-modified NK or T cells). In specific, non-limiting examples, NK cells are administered. The non-modified NK or T cells or modified (e.g., CAR-modified) NK or T cells described herein can be administered either to animals or to human subjects. In particular examples, the NK or T cells (or CAR-NK or CAR-T cells) are from a non-HLA matched donor, including an unrelated individual. In other examples, the NK or T cells (or CAR-NK or CAR-T cells) are from the subject being treated (e.g., are autologous). In some embodiments, the disease or disorder is a cancer (e.g., solid cancer (such as sarcomas (e.g., rhabdomyosarcoma, osteogenic sarcoma, Ewing's sarcoma, chondrosarcoma, and alveolar soft part sarcoma); carcinomas (e.g., colorectal carcinoma); and lymphomas, such as Hodgkin's or non-Hodgkin's lymphoma, for example, diffuse large B-cell, follicular, chronic lymphocytic, small lymphocytic, mantle cell, Burkitt's, cutaneous T-cell, AIDS-related, or central nervous system lymphoma); neuroblastoma; gynecological cancer (such as ovarian cancer); breast cancer; liver cancer; lung cancer; prostate cancer; skin cancer; bone cancer; pancreatic cancer; brain cancer (neuroblastoma); head or neck cancer; kidney cancer (such as Wilms' tumor); retinoblastoma; adrenocortical tumor; desmoid tumors; desmoplastic small round cell tumor; endocrine tumors; and/or blood cancer (such as myeloma, such as multiple myeloma; lymphoma, such as Hodgkin's or non-Hodgkin's lymphoma, for example, diffuse large B-cell, follicular, chronic lymphocytic, small lymphocytic, mantle cell, Burkitt's, cutaneous T-cell, AIDS-related, or central nervous system lymphoma; or leukemia, such as acute lymphocytic leukemia (ALL) or acute myeloid leukemia (AML))), immune disorder (e.g., an autoimmune disorder or transplant rejection), or infectious disease (for example, cytomegalovirus, adenovirus, respiratory syncytial virus, Epstein-Barr virus, or HIV infection).

The expanded NK or T cells produced as described herein can be incorporated into pharmaceutical compositions. Such compositions typically include a population of NK or T cells (such as modified NK or T cells) and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (see, e.g., *Remington: The Science and Practice of Pharmacy*, The University of the Sciences in Philadelphia, Editor, Lippincott, Williams, & Wilkins, Philadelphia, PA, $21^{st}$ Edition, 2005). Examples of such carriers or diluents include, but are not limited to, water, saline, Ringer's solutions, dextrose solution, balanced salt solutions, and 5% human serum albumin. Liposomes and non-aqueous vehicles such as fixed oils may also be used. Supplementary active compounds can also be incorporated into the compositions. Actual methods for preparing administrable compositions are known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, PA, $21^{st}$ Edition (2005). In one non-limiting example, the transduced NK cells are suspended in PLASMA-LYTE™ multiple electrolyte solution.

In some examples, the composition includes about $10^4$ to $10^{12}$ of the NK or T cells (for example, about $10^4$-$10^8$ cells, about $10^6$-$10^8$ cells, or about $10^6$-$10^{12}$ cells). For example, the composition may be prepared such that about $10^4$ to $10^{10}$ NK or T cells cells/kg (such as about $10^4$, $10^5$, $10^6$, $10^7$, or $10^8$ cells/kg) are administered to a subject. In specific examples, the composition includes at least $10^4$, $10^5$, $10^6$, or $10^7$ NK cells. The population of NK or T cells is typically administered parenterally, for example intravenously; however, injection or infusion to a tumor or close to a tumor (local administration) or administration to the peritoneal cavity can also be used. One of skill in the art can determine appropriate routes of administration.

Multiple doses of the population of NK or T cells can be administered to a subject. For example, the population of NK or T cells can be administered daily, every other day, twice per week, weekly, every other week, every three weeks, monthly, or less frequently. A skilled clinician can select an administration schedule based on the subject, the condition being treated, the previous treatment history, and other factors.

In additional examples, the subject is also administered at least one, at least one, at least two, at least three, or at least four cytokine(s) (such as IL-2, IL-15, IL-21, and/or IL-12) to support survival and/or growth of the NK or T cells. In specific, non-limiting examples, at least one cytokine includes IL-2 and IL-15 (e.g., to support survival and/or growth of NK cells). The cytokine(s) are administered before, after, or substantially simultaneously with the NK or T cells. In specific examples, at least one (e.g., IL-2 and/or IL-2) is administered simultaneously, for example, with NK cells.

In some examples, the methods include treating or inhibiting a hyperproliferative disorder, such as a hematological malignancy or a solid tumor. Examples of hematological malignancies include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), T-cell large granular lymphocyte leukemia, polycythemia vera, lymphoma, Hodgkin's lymphoma, non-Hodgkin's lymphoma (indolent and high grade forms; includes diffuse large B-cell, follicular, chronic lymphocytic, small lymphocytic, mantle cell, Burkitt's, cutaneous T-cell, AIDS-related, or central nervous system lymphoma), multiple myeloma, Waldenstrom's macroglobulinemia, heavy chain disease, myelodysplastic syndrome, hairy cell leukemia, and myelodysplasia. Unmodified or modified (e.g., CAR-modified) NK or T cells can be administered. In specific examples, unmodified NK or T cells expanded using the methods herein can be administered to treat or inhibit lymphoma, such as B cell lymphoma; gynecological cancer, such as ovarian cancer; breast cancer; liver cancer; lung cancer; or blood cancer, such as myeloma or leukemia, for example, multiple myeloma, ALL, or AML).

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoma (includes indolent and high grade forms; Hodgkin's lymphoma; and non-Hodgkin's lymphoma, such as diffuse large B-cell, follicular, chronic lymphocytic, small lymphocytic, mantle cell, Burkitt's, cutaneous T-cell, AIDS-related, or central nervous system lymphoma), pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma, and retinoblastoma).

In particular examples, hematological malignancies that can be inhibited or treated by the methods disclosed herein include but are not limited to multiple myeloma, chronic lymphocytic leukemia, acute lymphocytic leukemia, acute myeloid leukemia, chronic myelogenous leukemia, pro-lymphocytic/myelocytic leukemia, plasma cell leukemia, NK cell leukemia, Waldenstrom macroglobulinemia, Hodgkin's lymphoma, and non-Hodgkin's lymphoma (indolent and high grade forms; includes diffuse large B-cell, follicular, chronic lymphocytic, small lymphocytic, mantle cell, Burkitt's, cutaneous T-cell, AIDS-related, or central nervous system lymphoma). In additional particular examples, solid tumors that can be treated or inhibited by the methods disclosed herein include lung carcinoma, prostate cancer, pancreatic cancer (for example, insulinoma), breast cancer, colorectal adenocarcinoma or squamous cell carcinoma, neuroblastoma, testicular cancer (such as seminoma), and ovarian cancer. In specific, non-limiting examples, the subject has chronic myelogenous leukemia, acute monocytic leukemia, or non-Hodgkin's lymphoma (indolent and high grade forms; includes diffuse large B-cell, follicular, chronic lymphocytic, small lymphocytic, mantle cell, Burkitt's, cutaneous T-cell, AIDS-related, or central nervous system lymphoma). One of ordinary skill in the art can select NK cells or T cells expressing an appropriate transgene for treating a subject with particular tumors or other disorders.

In some examples, the subject (such as a subject with a tumor or hyperproliferative disorder) is also administered one or more chemotherapeutic agents and/or radiation therapy. Such agents include alkylating agents, such as nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine); antimetabolites such as folic acid analogs (such as methotrexate), pyrimidine analogs (such as 5-FU or cytarabine), and purine analogs, such as mercaptopurine or thioguanine; or natural products, for example vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Additional agents include platinum coordination complexes (such as cis-diamine-dichloroplatinum II, also known as cisplatin), substituted ureas (such as hydroxyurea), methyl hydrazine derivatives (such as procarbazine), and adrenocrotical suppressants (such as mitotane and aminoglutethimide); hormones and antagonists, such as adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytarabine), carmustine, busulfan, lomustine, carboplatinum, cisplatinum, cyclophosphamide (Cytoxan®), daunorubicin, dacarbazine, 5-fluorouracil, fludarabine, hydroxyurea, idarubicin, ifosfamide, methotrexate, mithramycin, mitomycin, mitoxantrone, nitrogen mustard, paclitaxel (or other taxanes, such as docetaxel), vinblastine, vincristine, VP-16, while newer drugs include gemcitabine (Gemzar®), trastuzumab (Herceptin®), irinotecan (CPT-11), leustatin, navelbine, rituximab (Rituxan®) imatinib (STI-571), Topotecan (Hycamtin®), capecitabine, ibritumomab (Zevalin®), and calcitriol.

In some examples, the methods include treating or inhibiting a blood cancer (includes indolent and high grade forms; includes such as myeloma, such as multiple myeloma; lymphoma, such as Hodgkin's or non-Hodgkin's lymphoma, for example, diffuse large B-cell, follicular, chronic lymphocytic, small lymphocytic, mantle cell, Burkitt's, cutaneous T-cell, AIDS-related, or central nervous system lymphoma; or leukemia, such as acute lymphocytic leukemia (ALL) or acute myeloid leukemia (AML)). For example, the methods can include selecting a subject with a blood cancer. The methods can also include administering any of the CAR-modified lymphocytes disclosed using the methods disclosed herein, thereby treating the blood cancer. For example, CD19-CAR-modified NK cells produced using 721.221 cells. In some examples, modified 721.221 cells expressing mIL-21 and/or IL-15Rα can be used to produce the CD19-CAR-modified NK cells administered.

In specific, non-limiting examples, the methods include treating or inhibiting leukemia (such as acute lymphocytic leukemia (ALL) or acute myeloid leukemia (AML)). For example, the methods can include selecting a subject with leukemia. The methods can also include administering any of the CAR-modified lymphocytes disclosed using the methods disclosed herein, thereby treating the leukemia, for example, CD19-CAR-modified NK cells produced using 721.221 cells. In some examples, modified 721.221 cells expressing mIL-21 and/or IL-15Rα can be used to produce the CD19-CAR-modified NK cells administered.

In some examples, the methods include treating or inhibiting solid tumors (indolent and high grade forms; includes sarcomas, carcinomas, and lymphomas (such as Hodgkin's or non-Hodgkin's)). For example, the methods can include selecting a subject with a solid tumor. The methods can also include administering any of the CAR-modified lymphocytes disclosed using the methods disclosed herein, thereby treating the solid tumor. For example, CD19-CAR-modified NK cells produced using 721.221 cells. In some examples, modified 721.221 cells expressing mIL-21 and/or IL-15Rα can be used to produce the CD19-CAR-modified NK cells administered.

In specific, non-limiting examples, the methods include treating or inhibiting lymphoma (includes indolent and high grade forms; includes Hodgkin's and non-Hodgkin's lymphoma). For example, the methods can include selecting a subject with lymphoma. The methods can also include administering any of the CAR-modified lymphocytes disclosed using the methods disclosed herein, thereby treating the lymphoma, for example, CD19-CAR-modified NK cells produced using 721.221 cells. In some examples, modified 721.221 cells expressing mIL-21 and/or IL-15Rα can be used to produce the CD19-CAR-modified NK cells administered.

In specific, non-limiting examples, the methods include treating or inhibiting non-Hodgkin's lymphoma (includes indolent and high grade forms; includes diffuse large B-cell, follicular, chronic lymphocytic, small lymphocytic, mantle cell, Burkitt's, cutaneous T-cell, AIDS-related, or central nervous system lymphoma). For example, the methods can include selecting a subject with non-Hodgkin's lymphoma. The methods can also include administering any of the CAR-modified lymphocytes disclosed using the methods disclosed herein, thereby treating the non-Hodgkin's lymphoma. For example, CD19-CAR-modified NK cells produced using 721.221 cells. In some examples, modified 721.221 cells expressing mIL-21 and/or IL-15Rα can be used to produce the CD19-CAR-modified NK cells administered.

In some examples, the methods include treating or inhibiting an immune system condition. The immune system condition can be any type of immune system condition, such as a cytokine storm, an immune system disorder (e.g., an inflammatory or autoimmune disorder) or can be immune system conditions associated with another condition and/or disease (e.g., human immunodeficiency virus infection or exposure to microgravity). In some non-limiting examples, the immune system condition is an inflammatory disorder. In specific embodiments, the inflammatory disorder can be rheumatoid arthritis, chronic obstructive pulmonary lung disease, inflammatory bowel disease, or systemic lupus erythematosus. In other examples, the immune system condition is an autoimmune disorder. In certain embodiments, the autoimmune disorder is type I diabetes, multiple sclerosis, lupus erythematosus, myasthenia gravis, ankylosing spondylitis, celiac disease, Crohn's disease, Graves' disease, Hashimoto's thyroiditis, transplant rejection, or autoimmune uveitis. Modified or unmodified NK or T cells expanded using the methods disclosed herein can be used. In specific examples, modified (e.g., CAR-modified) NK or T cells can be used, for example, to treat or inhibit rheumatoid arthritis, Crohn's disease, or transplant rejection.

In some examples, the subject (e.g., a subject with an immune disorder, such as an autoimmune disease, transplant rejection, or inflammatory disease) is also administered one or more immunomodulatory therapies (e.g., immunomodulatory biologics, such as muromonab, ipilimumab, abatacept, belatacept, tremelimumab, BMS-936558, CT-011, MK-3475, AMP224, BMS-936559, MPDL3280A, MEDI4736, MGA271, IMP321, BMS-663513, PF-05082566, CDX-1127, anti-OX40, huMAb, OX40L, and TRX518, e.g., Yao et al., Nat Rev Drug Discov, 12(2): 130-146, 2013, and Kamphorst et al., Vaccine, 33(0 2): B21-B28, 2015, both of which are incorporated herein by reference in their entireties; modulatory cytokines, such as IL-7; mTOR modulatory agents, such as rapamycin; antimicrobial therapy, such as vaccination, antifungals, and/or antibiotics), anti-inflammatory agents (NSAIDS; antileukotrines; immune selective anti-inflammatory derivatives, ImSAIDs; bioactive compounds with anti-inflammatory activities, such as plumbagin and plumericin; and/or steroids), disease-modifying antirheumatic drugs (DMARDs, such as methotrexate, sulfasalazine, leflunomide, hydroxychloroquine, tofacitinib, infliximab, etanercept, adalimumab, certolizumab, golimumab, tocilizumab, anakinra, abatacept, and/or rituximab), antimalarial drugs (e.g., chloroquine and hydroxychloroquine), medical procedures (including surgery and stem cell transplantation); immunosuppressive agents (e.g., for preventing rejection of transplanted organs or tissues, treating autoimmune diseases, and/or inflammatory diseases; e.g., glucocorticoids, such as prednisone, dexamethasone, and hydrocortisone; cytostatics, such as alkylating agents and antimetabolites; antibodies, such as Atgam, thymoglobuline, and T-cell receptor- and IL-2 receptor-directed antibodies; immunophilin-targeting agents, such as cyclosporin, tacrolimus, sirolimus, and everolimus; interferons (IFNs), such as IFNλ and IFNβ; opioids; TNF binding proteins, such as infliximab, etanercept, and adalimumab; mycophenolate; and small biological agents, such as fingolimod and myriocin), immune tolerance therapy (e.g., for treating subjects at risk for tissue or organ transplantation rejection, subjects with allergies, and/or subjects with autoimmune disease; e.g., T or B cell-targeting or T or B cell-suppressing drugs, such as CAMPATH-1H, calcineurin inhibitors, rituximab, epratuzumab, belimumab, and atacicept; anti-cluster of differentiation (CD)3 antibodies; abatacept; induction of hematopoietic chimerism, such as mixed hematopoietic chimerism, in which the bone marrow of an organ or a tissue recipient is replaced with the donor's bone marrow or a mixture of the donor and recipient bone marrow to reduce organ or tissue transplant rejection; antigen desensitization; see Nepom et al., Immunol Rev; 241(1): 49-62, 2011, incorporated herein by reference), antihistamines, helminthic therapies (e.g., deliberate infestation of the subject with a helminth or with the ova of a helminth for treating immune disorders).

In some examples, the methods include treating or inhibiting an infectious disease by administering a therapeutically effective amount of a composition disclosed herein to a subject. In some aspects, the infectious disease is selected from among arboviral infections, botulism, brucellosis, candidiasis, campylobacteriosis, chickenpox, *Chlamydia*, cholera, coronovirus infections, *Staphylococcus* infections, coxsackie virus infections, Creutzfeldt-Jakob disease, cryptosporidiosis, *cyclospora* infection, cytomegalovirus infections, Epstein-Barr virus infection, dengue fever, diphtheria, ear infections, encephalitis, influenza virus infections, parainfluenza virus infections giardiasis, gonorrhea, *Haemophilus influenzae* infections, hantavirus infections, viral hepatitis, herpes simplex virus infections, HIV/AIDS, *Helicobacter* infection, human papillomavirus (HPV) infections, infectious mononucleosis, legionellosis, leprosy, leptospirosis, listeriosis, lyme disease, lymphocytic choriomeningitis, malaria, measles, marburg hemorrhagic fever, meningitis, monkeypox, mumps, mycobacteria infection, *Mycoplasma* infection, norwalk virus infection, pertussis, pinworm infection, pneumococcal disease, *Streptococcus pneumonia* infection, *Mycoplasma pneumoniae* infection, *Moraxella catarrhalis* infection, *Pseudomonas aeruginosa* infection, rotavirus infection, psittacosis, rabies, respiratory syncytial virus infection (RSV), ringworm, rocky mountain spotted fever, rubella, salmonellosis, SARS, scabies, sexually transmitted diseases, shigellosis, shingles, sporotrichosis, streptococcal infections, syphilis, tetanus, trichinosis, tuberculosis, tularemia, typhoid fever, viral meningitis, bacterial meningitis, west Nile virus infection, yellow fever, adenovirus-mediated infections and diseases, retrovirus-mediated infectious diseases and yersiniosis zoonoses. For example, the infectious disease can be influenza, parainfluenza, respiratory syncytial virus.

Unmodified or modified (e.g., CAR-modified) NK or T cells expanded using the methods disclosed herein can be used to treat or inhibit infectious disease. In specific examples, CAR-modified NK or T cells expanded using the disclosed methods can be used to treat or inhibit HIV, such as using CARs based on HIV antibodies VRC01, 2G12, 2F5, 4E10, 3BNC117, 10-1074, VRC01LS, VRC07-532LS, 3BC176, PG16, NIH45-46G54W, PG9, PG16, PGT145, PGDM1400, PGT121, PGT124, PGT128, PGT135, 8ANC195, 10E8, and/or PD-1. In specific examples, CAR-modified NK or T cells expanded using the disclosed methods can be used to treat or inhibit HBV, such as using CARS targeting HBsAg (e.g., GENBANK® nos. KP972453.1 or KP972454.1) and/or HB1.

In some examples, the subject (e.g., a subject with an infectious disease, such as HIV) is also administered one or more anti-infection agents (e.g., antibodies, antifungals, antivirals, and/or antiparasitics). In specific examples, the infectious disease is HIV, and the subject is also administered antiretroviral agents, such as nucleoside and nucleotide reverse transcriptase inhibitors (nRTI), non-nucleoside reverse transcriptase inhibitors (NNRTI), protease inhibitors, entry inhibitors (or fusion inhibitors), maturation inhibitors, or a broad spectrum inhibitors, such as natural antivirals. Exemplary agents include lopinavir, ritonavir, zidovudine, lamivudine, tenofovir, emtricitabine, and efavirenz.

EXAMPLES

The following examples are provided to illustrate certain particular features and/or embodiments. These examples should not be construed to limit the disclosure to the particular features or embodiments described.

The clinical success of chimeric antigen receptor (CAR)-modified T cells requires engineering of autologous T cells harvested from patients, which limits the broader implementation of CAR cell therapy. Development of allogeneic, universal cell products will significantly broaden their application and reduce costs. The unique biology of NK cells allows them to serve as a safe and effective alternative immunotherapeutic strategy to CAR-modified T cells in the clinic.

Figure 12:
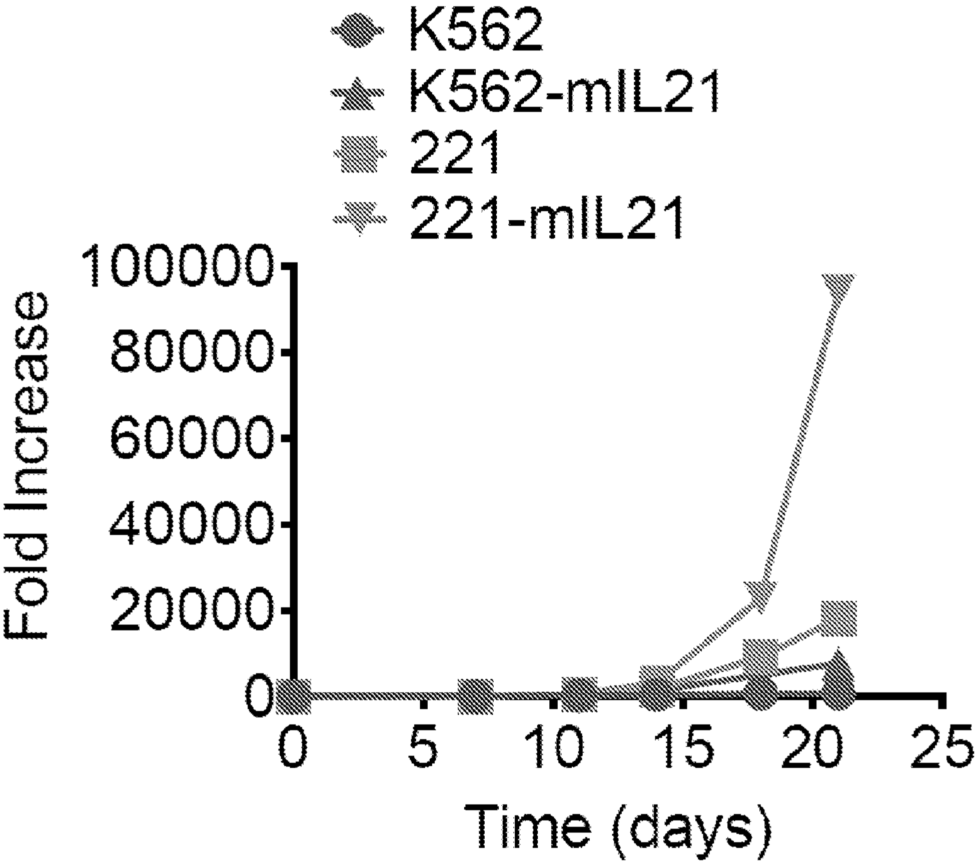
FIG. 12. Primary human NK cell expansion with four different types of feeder cells. PBMCs were stimulated with irradiated K562, K562-mIL21, 721.221, and 721.221-mIL21, quantitative data show fold-expansion of NK cells.

Described herein is an approach for expansion of NK and CAR-modified NK cells from both peripheral and cord blood. Herein, 721.221-based artificial antigen-presenting cells (APC) with membrane-bound interleukin (IL)-21 (mIL-21) were developed to propagate clinical-grade NK and CAR-modified NK cells. In contrast to K562-based APC with mIL-21, by day 21, the capability of propagating NK cells with 721.221-expressed mIL-21 feeder cells (ranging from a 5335- to 94170-fold expansion; e.g., FIG. 12) was superior to K562 with mIL-21 feeder cells (ranging from 662- to 7743-fold expansion). The 721.221-mIL-21-expanded NK cells and K562-mIL-21-expanded NK cells were similar in phenotype. However, a superior cytotoxicity from 721.221-mIL-21-expanded NK cells was observed. In conclusion, development of off-the-shelf NK cell products derived from cord blood or peripheral blood with superior functionalities, persistence, and proliferation will support their clinical use for adoptive immunotherapy. This approach provides the immunotherapy field with a powerful tool to expand primary NK and CAR-modified NK cells for clinical application.

Example 1—Methods and Materials

Antibodies and Reagents. PE and APC anti-human CD3 antibody (clone OKT3, BIOLEGEND®), FITC, BV605, PE/Cy7, and BV 510 anti-human CD56 antibody (clone HCD56, BIOLEGEND®), PE anti-human CD69 antibody (clone FN50, BIOLEGEND®), PE/Cy7 anti-human CD8a antibody (clone HIT8a, BIOLEGEND®), AF647 anti-human IL-21 antibody (clone 3A3-N2, BIOLEGEND®), APC/Fire 750 anti-human CD226 antibody (DNAM-1) (clone 11A8, BIOLEGEND®), APC/Fire 750 anti-human KLRG1 (MAFA) antibody (clone SA231A2, BIOLEGEND®), BV 421 anti-human CD335 (NKp46) antibody (clone 9E2, BIOLEGEND®), PE/Cy7 anti-human CD158b (KIR2DL2/L3, BIOLEGEND®) antibody (clone DX27, BIOLEGEND®), PE/Cy7 anti-human CD244 (2B4) antibody (clone C1.7, BIOLEGEND®), PE anti-human CD152 (CTLA-4) antibody (clone BNI3), APC anti-human CD366 (Tim-3) antibody (clone F38-2E2), PerCP/Cy5.5 anti-human TIGIT (VSTM3) antibody (clone A15153G), FITC anti-human CD223 (LAG-3) antibody (clone 11C3C65, BIOLEGEND®), and PerCP/Cy5.5 anti-human CD94 (clone DX22, BIOLEGEND®) were purchased from BIOLEGEND® (San Diego, CA, USA). APC anti-human CD16 antibody (clone B73.1, BD™ Biosciences), FITC anti-human CD3 antibody (clone UCHT1, BD™ Biosciences), BV480 anti-human CD85j antibody (LIR-1) antibody (clone GHI/75, BD™ Biosciences), BV711 anti-human CD314 (NKG2D) antibody (clone 1D11, BD™ Biosciences), and FITC anti-human CD107a antibody (clone H4A3, BD™ Biosciences) were purchased from BD™ Biosciences (San Jose, CA, USA). FITC anti-human KIR/CD158 antibody (clone 180704, R&D SYSTEMS®), PE anti-human KIR2DL1/KIR2DS5 antibody (clone 143211, R&D SYSTEMS®), APC anti-human KIR3DL1 antibody (clone DX9, R&D SYSTEMS®), AF405 anti-human KIR3DL2/CD158k antibody (clone 539304, R&D SYSTEMS®), APC anti-human NKG2A/CD159a antibody (clone 131411, R&D SYSTEMS®), and PE anti-human NKG2C/CD159c antibody (clone 134591, R&D SYSTEMS®) were purchased from R&D SYSTEMS®. AF647 goat anti-human IgG F(ab')2 fragment antibody was purchased from Jackson ImmunoResearch (West Grove, PA, USA).

Cell lines. The 721.221 cell line was a gift. The 293T, K562, and Daudi cell lines were purchased from AMERICAN TYPE CULTURE COLLECTION® (ATCC®). To establish K562-mIL21 and 721.221-mIL21 cells, K562 and 721.221 cells were each transduced with IL-21 retrovirus, and membrane IL-21-positive cells were then sorted using a FACS ARIA™ II cell sorter (BD™ Biosciences) by AF647 mouse IgG1 anti-human IL-21 (clone 3A3-N2). To establish the Daudi-FFluc cell, CD19-positive Daudi cells were transduced with a lentiviral vector encoding FFLuc, as previously described (Xiong et al., Mol Ther 26:963-75 (2018)). The K562, 721.221, K562-mIL21, 721.221-mIL21, Daudi, and Daudi-FFluc cells were cultured in RPMI-1640 (CORNING®) supplemented with 10% (v/v) fetal bovine serum (FBS) and 100 U/mL Penicillin-Streptomycin (CORNING®) at 37° C. under 5% (v/v) $CO_2$. For NK cell expansion, K562, 721.221, K562-mIL21, and 721.221-mIL21 cells were irradiated at a dose of 10,000 Rad, washed with PBS, and then used as the feeder cells. 293T was cultured in DMEM (CORNING®) supplemented with 10% (v/v) fetal bovine serum (FBS) and 100 U/mL penicillin-streptomycin (CORNING®) at 37° C. under 5% (v/v) $CO_2$.

Primary NK cell expansion. PBMCs were isolated from buffy coats (Gulf Coast Regional Blood Center) using Lymphocyte Separation Medium (CORNING®). For NK cell expansion, 5×106 PBMCs were cultured with 1×107 10000 Rad-irradiated feeder cells in 35 ml complete RPMI-1640 media with 200 U/ml IL-2 (PEPROTECH®) and 5 ng/ml IL-15 (PEPROTECH®) in G-REX® 6 multi-well cell culture plate (Wilson Wolf). Media were changed every 3-4 days, and $2\times10^7$ cells were kept in each well for continued culture. Total cell numbers were counted using trypan blue. To determine the percentage of NK cells, cells were stained for CD3 and CD56 followed by flow cytometry analysis.

Transduction of expanded NK cells with CD19-CAR. To produce CD19-CAR retrovirus, 293T cells were transfected with a combination of plasmid containing CD19-specific scFv, RDF, and PegPam3, as previously described (Xiong et al., Mol Ther 26:963-75 (2018)). NK cells were harvested on day 7 of expansion and transduced with CD19-CAR retrovirus (using an SFG backbone) in plates coated with RETRONECTION®. Two days later, cells were transferred to G-REX® 6 multi-well cell culture plate and maintained in 35 ml complete RPMI-1640 media with 200 U/ml IL-2 (PeproTech) and 5 ng/ml IL-15 (PeproTech). The media were changed every 3-4 days and $2\times10^7$ cells were kept in each well for continued culture. The total cell numbers were counted using trypan blue. To determine the percentage of NK cells and expression of CAR, cells were stained for CD3, CD56, and an anti-human IgG(H+L) F(ab')2 fragment and then analyzed by flow cytometry.

Flow Cytometry Analysis. PBMCs and expanded NK cells were stained with fluorescence-conjugated antibodies in FACS staining buffer (PBS with 1% FBS) on ice for 30 minutes, washed with PBS, and analyzed on a FACS LSRII or an LSRFORTESSA® flow cytometer (BD™). The PMT voltages were adjusted and compensation values were calculated before data collection. Data were acquired using FACS DIVA™ software (BD™) and analyzed using FLOWJO® software (Tree Star).

Flow Cytometry-based NK Cytotoxicity Assays. K562 and 721.221 cells were each used as target cells to determine NK cell cytotoxicity. The target cells were harvested and stained with 5 uM CELLTRACE™ CFSE (INVITROGEN®) in PBS for 20 minutes. The staining was stopped by adding complete RPMI-1640 media and then washed using PBS twice. Expanded NK cells were harvested and cocultured with 2×105 CFSE-labeled target cells at 5 different E:T ratios (effector:target; 4:1, 2:1, 1:1, 0.5:1, and 0.25:1, respectively) in V-bottomed 96-well plates in complete RPMI-1640 media. After 4 hours of incubation at 37° C. and 5% $CO_2$, cells were stained with 7-AAD (EBIOSCIENCE™) and then analyzed by flow cytometry. Target cells ($CFSE^+$) were gated, and the percent of 7-$AAD^+$ was then used to calculate NK cell cytotoxicity using (Experimental−Spontaneous Dead)/(100−Spontaneous Dead)×100%.

NK Degranulation assay (CD107a). Expanded NK cells ($5\times10^5$) were incubated with $1.5\times10^5$ K562 cells in V-bottomed 96-well plates in complete RPMI-1640 media at 37° C. for 2 hours. Afterward, cells were harvested; washed; stained for CD3, CD56, and CD107a with GOLGISTOP™ for 30 minutes; and analyzed by flow cytometry. (See, e.g., Zheng et al., J Allergy Clin Immunol 135, 1293-1302, (2015), incorporated herein by reference).

Animal Studies. All animal experiments were approved by the Houston Methodist Research Institute Institutional Animal Care and Use Committee (IACUC). NOD.Cg-Prkdcscid Il2rgtmlWjl/SzJ (NSG) mice from Jackson Laboratory were used for all in vivo experiments. To establish a human lymphoma xenograft model, both male and female NSG mice (8-weeks-old) were i.v. injected with $2\times10^6$ FFLuc-Daudi cells in 100 μL of PBS via tail vein. Beginning on day 0, the mice were injected (i.v.) with $1\times10^7$ 721.221-mIL21 expanded- or K562-mIL21-expanded CD19-CAR NK cells in 100 μL of PBS and then injected (i.p.) with IL-2 (50,000 Unit/mouse) and IL-15 (10 ng/mouse) in 150 μL of PBS at days 0, 3, 7, and 10. Isoflurane-anesthetized animals were imaged using the IVIS® system (IVIS®-200, PERKINELMER®, Waltham, MA, USA) 10 min after 150 mg/kg D-luciferin (GOLD BIOTECHNOLOGY®, St. Louis, MO, USA) per mouse administered intraperitoneally (i.p.). The photons emitted from the luciferase-expressing tumor cells were quantified using LIVING IMAGE® software 64 (CALIPER® Life Sciences, Hopkinton, MA, USA). A pseudo-color image representing light intensity (blue least intense and red most intense) was generated and superimposed over the grayscale reference image. A constant region of interest (ROI) was drawn over the whole animal, excluding the tail, and the intensity of the signal was measured as total photons per second. After effector CD19-CAR NK cell injections, animals were imaged twice a week for tumor cell tracking at the preclinical imaging core of the Houston Methodist Research Institute.

RNA-seq sample preparation, sequencing, and data analysis. NK cells were expanded among PBMCs with irradiated 221-mIL21 and K562-mIL21 cells as described before. On day 7 and day 14 of expansion, cells were collected and stained with PE-anti-CD3 and PE/Cy7-anti-CD56 antibodies on ice for 30 minutes. After washing with FACS staining buffer (PBS with 2% FBS) twice, cells were resuspended in FACS staining buffer and then CD3−CD56+ cells were sorted to a purity of >98% for each replicate using FACS Aria II cell sorter (BD Biosciences). Purified NK cells were directly lysed in Trizol reagent (Thermo Fisher Scientific) for RNA extraction using the manufacturer's protocol. RNA sequencing (RNA-seq) was performed on a BGISEQ-500 platform by BGI Group (Shenzhen, Guangdong, China). Clean reads in FASTQ format were obtained after filtering low quality reads (reads where more than 50% of the base's qualities are lower than 15), reads with adaptors, and reads with more than 10% unknown bases (N). FASTQ files were aligned to the hg38 human reference genome using STAR2.6.1d. The aligned files were processed using the GenomicAlignments package (v.1.20.0) to get count matrices. Genes with less than 10 reads median were pre-filtered in all comparisons as an initial step. Differentially expressed genes were identified using the DESeq2 package (v.1.24.0) and were defined as having an adjusted p-value <0.05 and a log 2 fold change ≥1 or ≤−1. The log 2 fold changes were shrunken using the lfcShrinkfunction and were then used to make MA-plots using ggpubr package (v.0.2.1). GSEAs were performed using MSigDB (Broad Institute) and clusterProfiler package (v.3.12.0). Heat maps were generated using z-scores derived from log transformed counts. All of the data analysis was performed using R (v.3.6.0).

Statistical Analysis. Data were represented as means±SEM. The statistical significance was determined using a two-tailed unpaired Student t test, a two-tailed paired Student t test, or a two-way ANOVA, where indicated. P<0.05 was considered statistically significant.

Figure 8A:
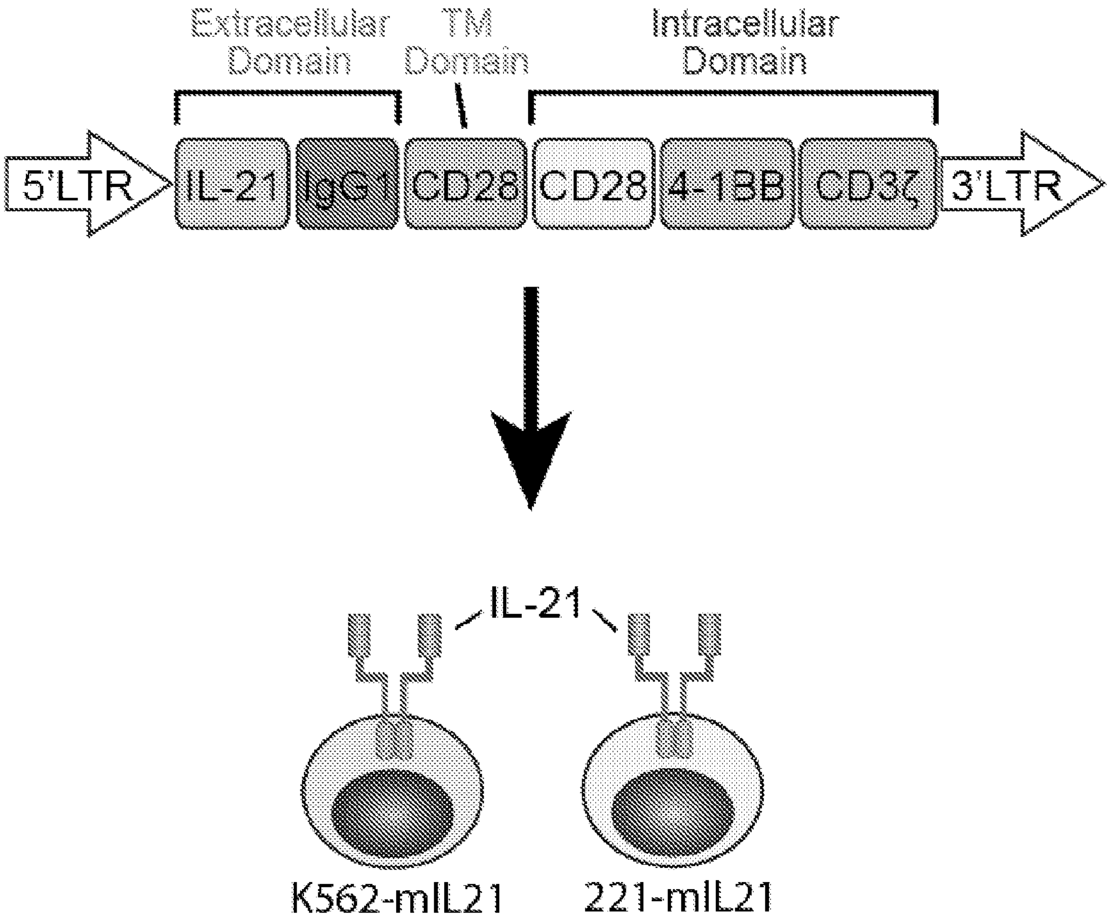
FIGS. 8A-8B. Schematic representation of exemplary recombinant retroviral vectors encoding human IL-21 and an exemplary method for NK cell expansion with 721.221.mIL-21 feeder cells.
Figure 9:
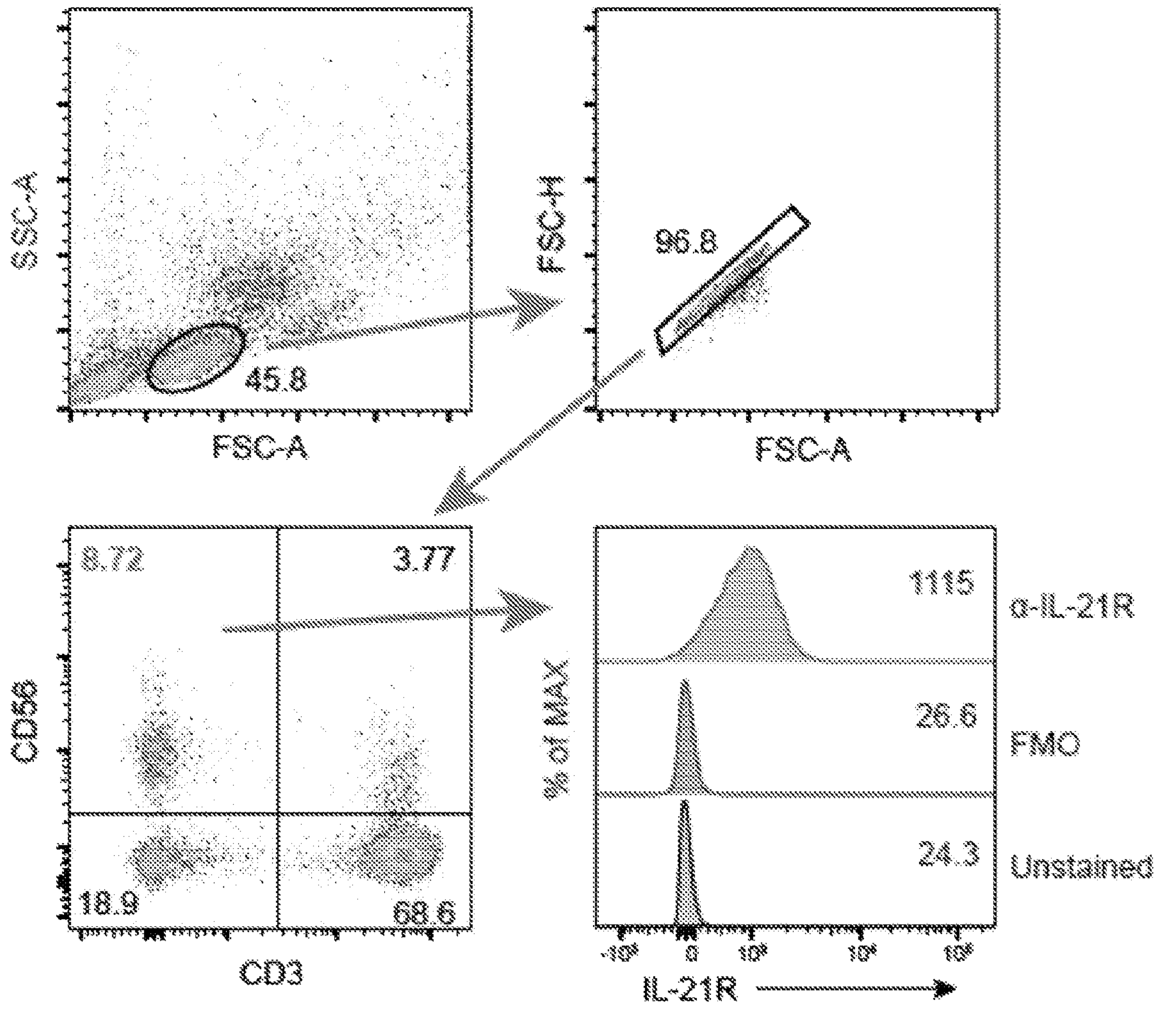
FIG. 9. Human primary NK cells express cell surface IL-21 receptors. Representative histograms show the expression of IL-21R on primary NK cells from PBMCs. The MFI is noted in the respective histograms.

Example 2—Generation of Membrane Form of IL-21 on Artificial Antigen Presenting Cell Lines Previous studies showed that IL-21 plays critical roles in NK cell proliferation (e.g., Denman et al., *PLoS One,* 7(1):e30264, 2012). An artificial antigen presenting cell line was developed using 721.221 cells expressing a membrane form of IL-21 without noticeable phenotype changes (FIG. 8A). The expression of the IL-21 receptor on human primary cells was also examined (FIG. 9).

Figure 1B:
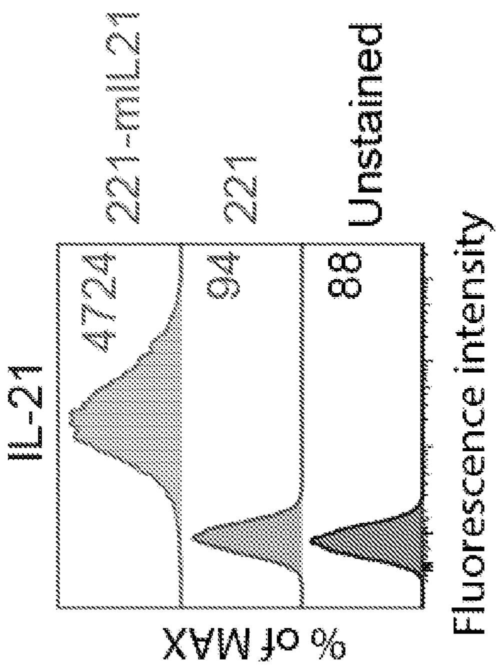
Figure 1C:
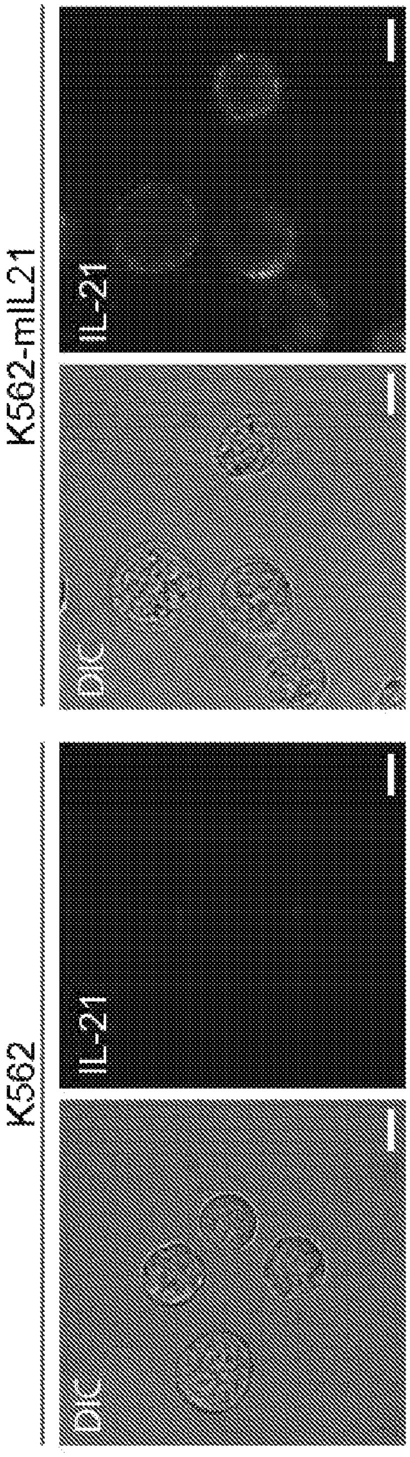
Figure 1D:
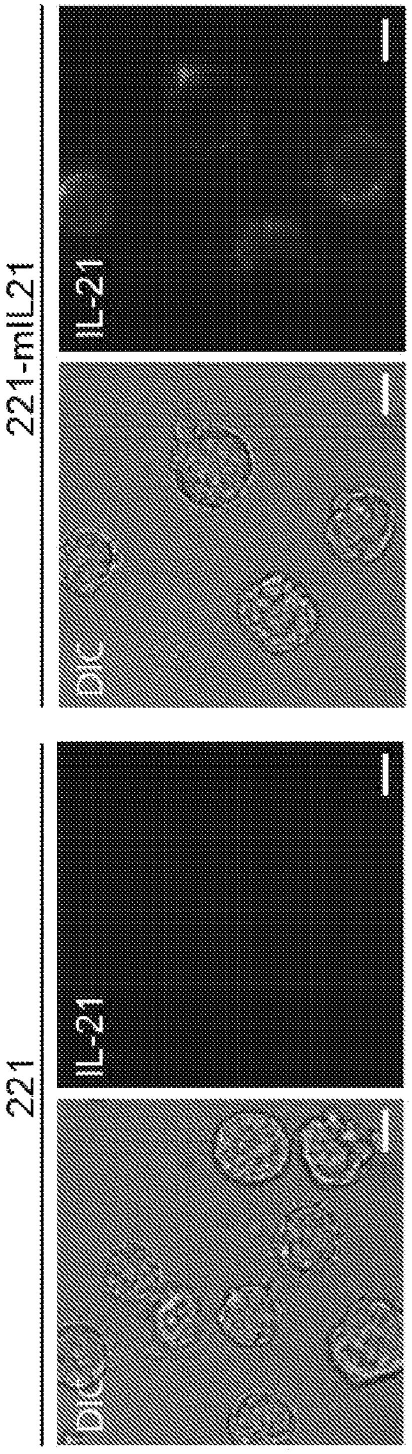
Figure 1E:
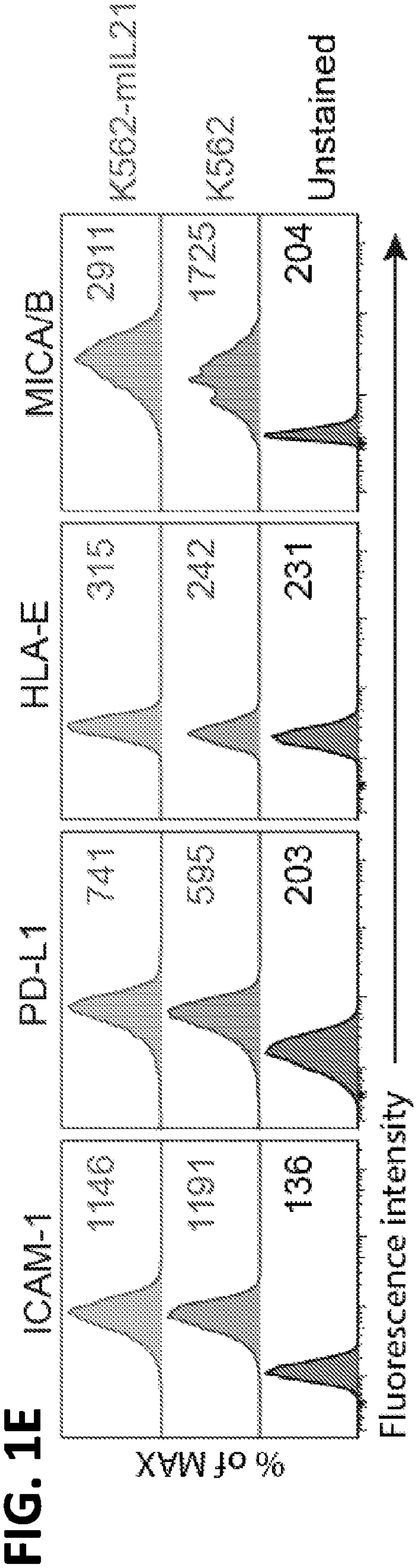
Figure 1F:
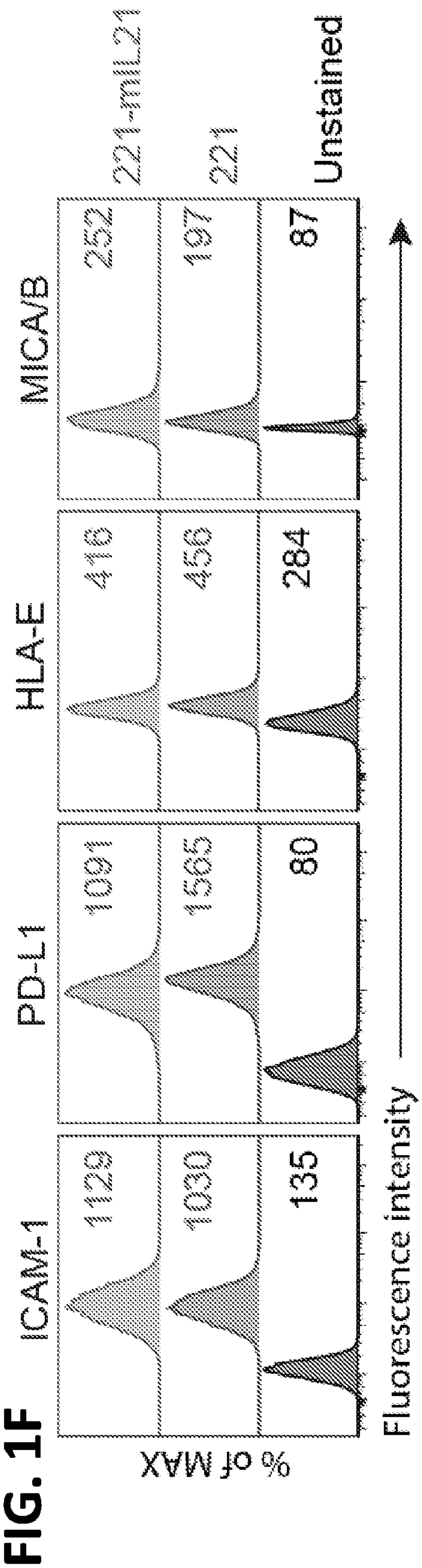
Figure 8B:
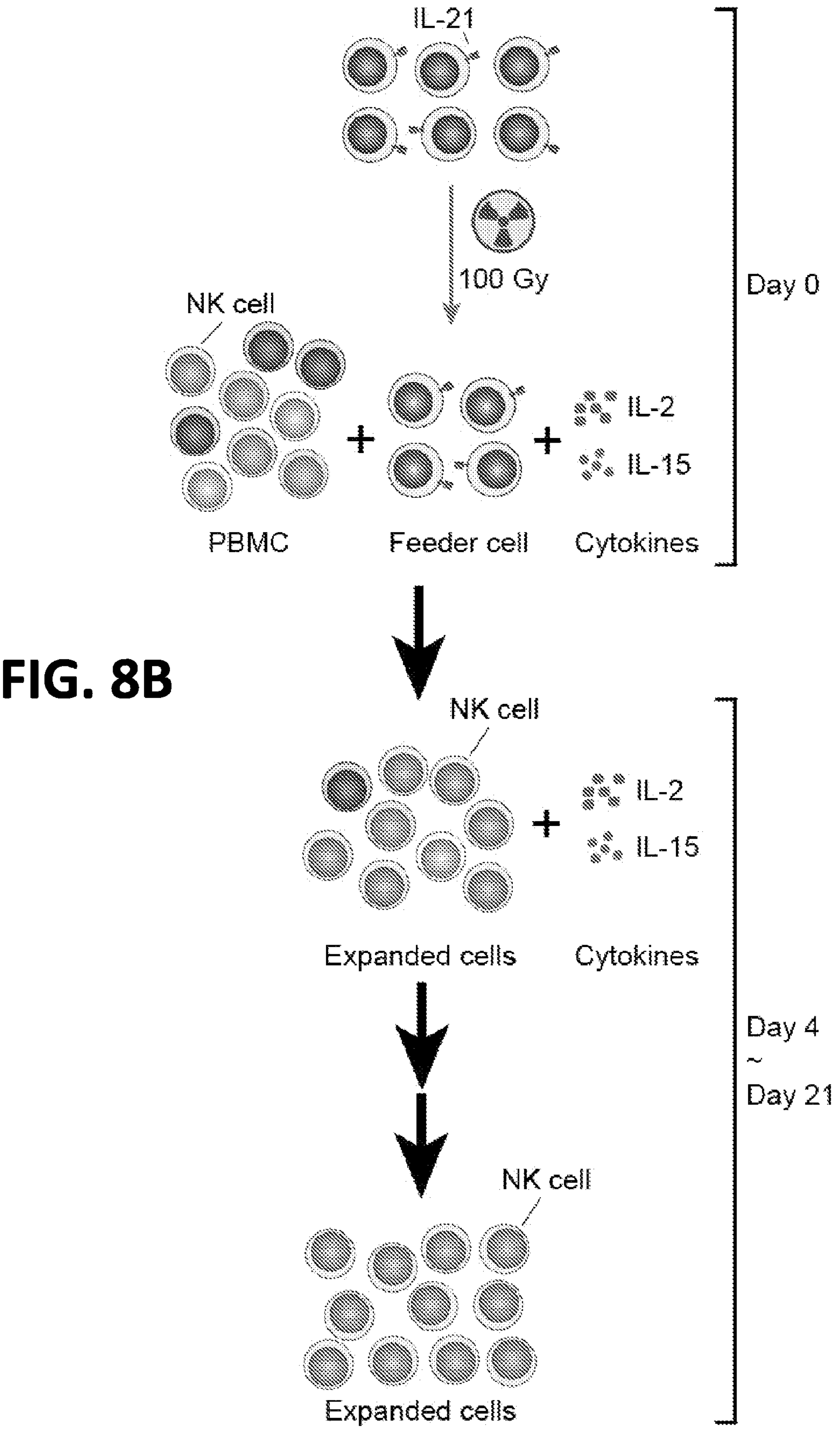

To expand human primary NK cells, PMBCs were isolated from peripheral blood or cord blood. The freshly isolated PBMCs were co-cultured with 721.221 cells expressing membrane IL-21 (221-mIL-21) in the presence of 200 U/mL IL-2 and 5 ng/mL IL-15 (FIG. 8B). As shown in FIGS. 8A-8B, IL-21 was cloned into the SFG vector that contains a human IgG1, CD28-transmembrane (TM) domain, CD28 intracellular domain, 4-1BB-Ligand, and CD3zeta (FIGS. 8A-8B). As a control, wild-type (WT) K562, K562-mIL-21, and WT 721.221 were included in the assays. K562 and 721.221 cells were transduced with IL-21 retrovirus and sorted using FACS by staining with anti-human IL-21 antibody. After 2 weeks of culture, the expression of IL-21 on K562-mIL21 and 721.221-mIL21 was examined using FACS. High levels of IL-21 were expressed on both K562-mIL21 (FIG. 1A) and 721.221-mIL21 cells (FIG. 1B). Both K562-mIL21 and 721.221-mIL21 cells were also stained with anti-IL21 antibody and mIL21 cells were also stained with anti-IL-21 antibody and evaluated for proper plasma membrane localization of the IL-21 protein by confocal microscopy (FIGS. 1C-1D). The membrane form of IL-21 molecules was expressed on the cell surface of K562-mIL21 (FIG. 1C) and 721.221-mIL21 cells (FIG. 1D). Human primary NK cell expression of IL-21 receptor (IL-21R) was verified (FIG. 9). To determine whether transduction of IL-21 molecules on the K562 and 721.221 cells alters expression of activating and inhibitory NK cell ligands. ICAM-1 (a ligand of LFA-1), PD-L1 (a ligand of PD-1), HLA-E (a ligand for CD94/NKG2A/C), and MICB (a ligand of NKG2D) were examined using flow cytometry. The level of expression was comparable between pre-transduction and after transduction (FIGS. 1E and 1F). In conclusion, membrane expression of IL-21 in K562 and 721.221 cells with comparable surface ligands was established.

Figure 2A:
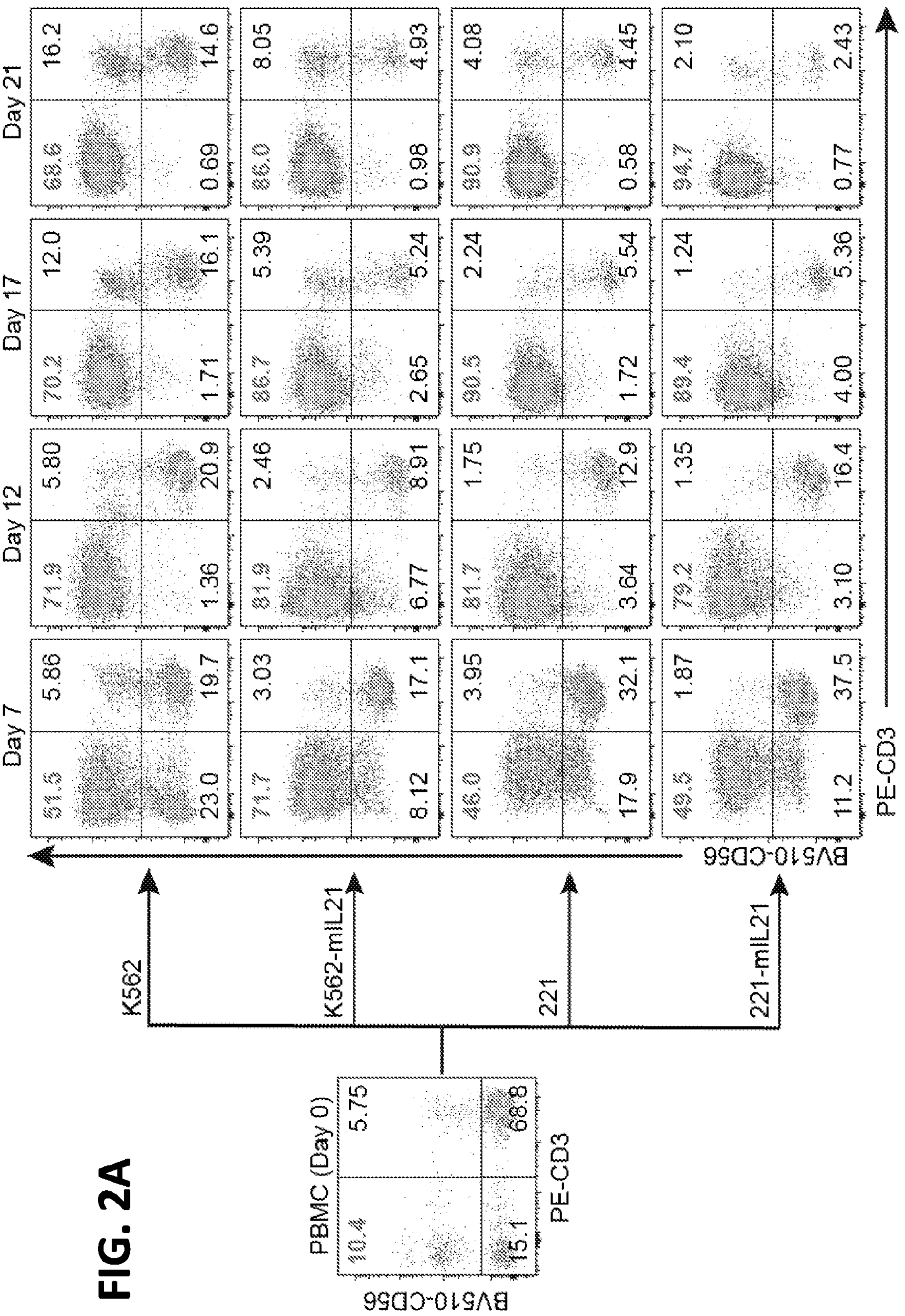
FIGS. 2A-2E. Primary human NK cell expansion with four different types of feeder cells.
Figure 2B:
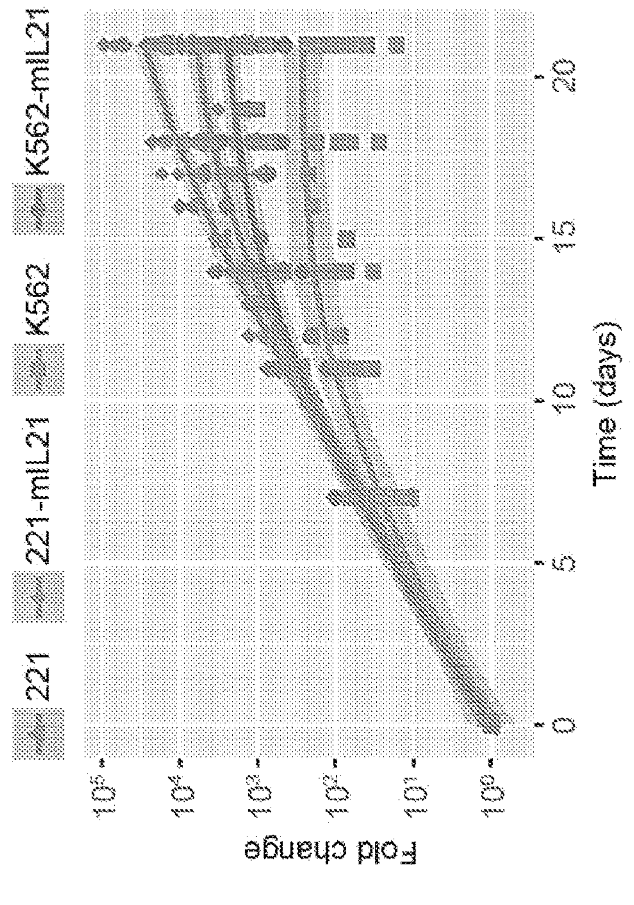
Figure 2C:
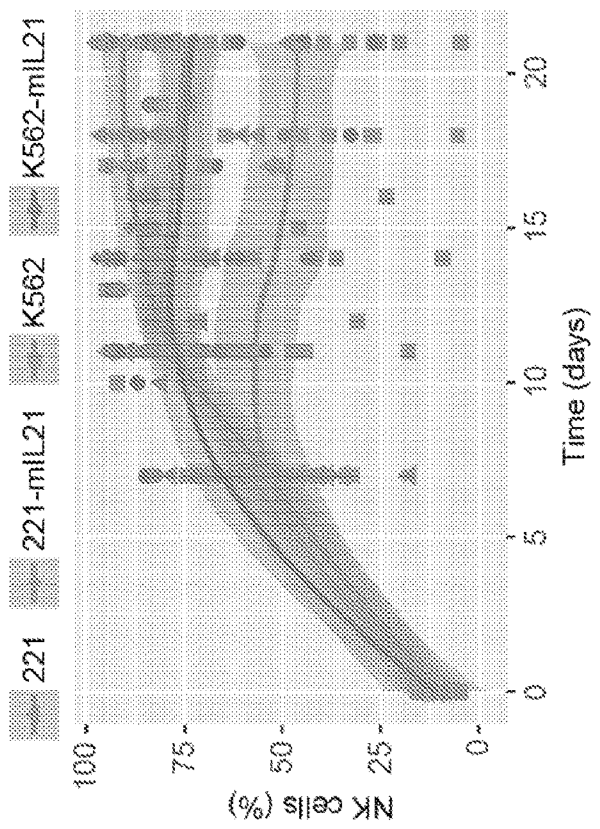
Figure 2E:
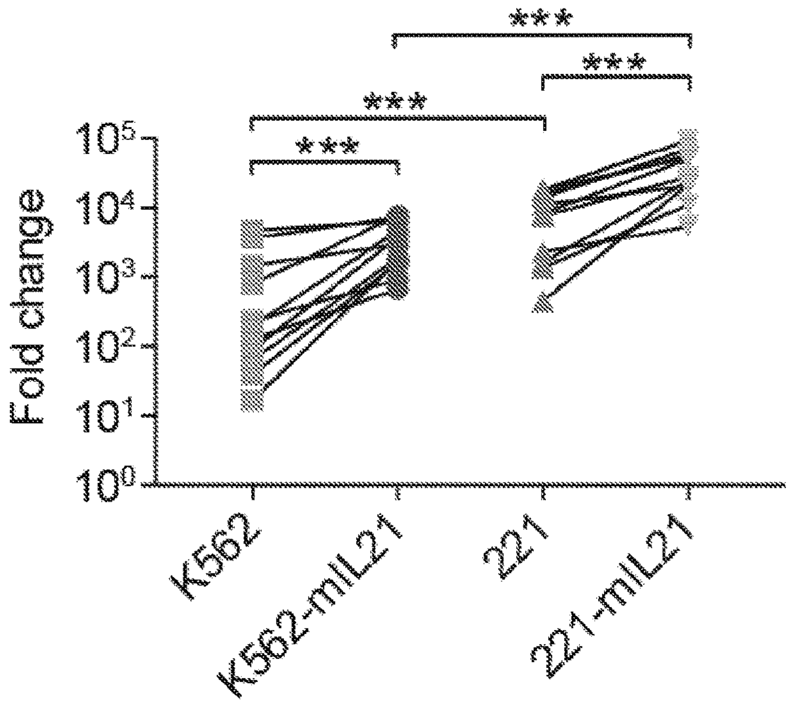
Figure 2D:
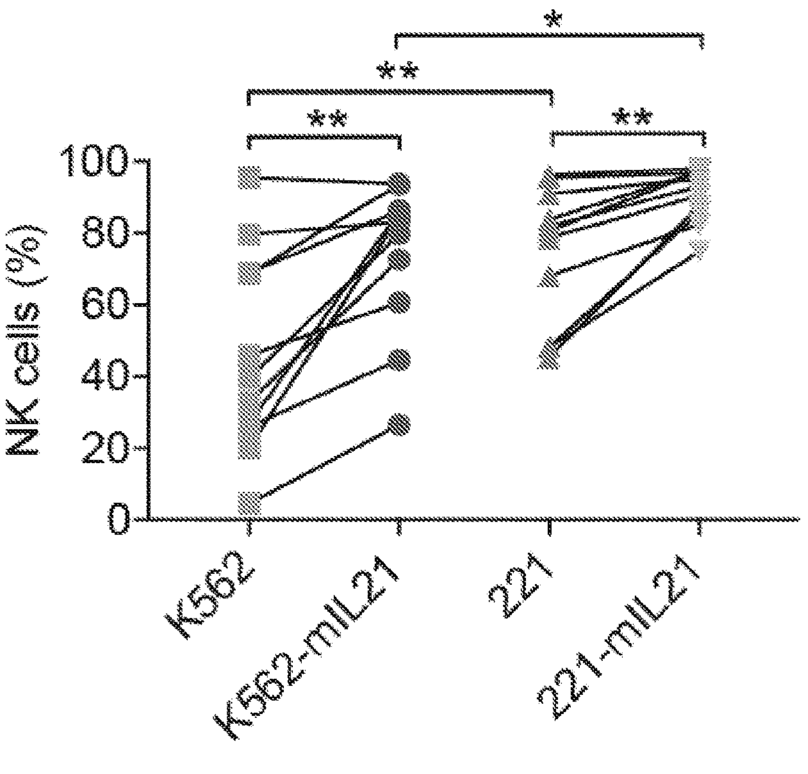

Example 3—Superior Propagation of NK Cells by 721.221-mIL21 Cells Among Different Types of Feeder Cells After establishment of the K562-, K562-mIL21, 721.221-, and 721.221-mIL21 cell lines as feeder cells, the best feeder cell line for expanding human NK cells was investigated. To expand primary human NK cells, PBMCs were isolated from buffy coat from healthy donors and cultured with feeder cells plus 200 U/ml IL-2 and 5 ng/ml IL-15, as described above. To compare the capacities for NK cell expansion, both K562-mIL21 and 721.221-mIL21 were compared directly. The WT-K562 and WT-221 cell lines were used as control groups. The initial number of NK cells and proportion of NK cells were 5 million and 10-20%, respectively. A representative NK expansion profile (FIG. 2A) at different time points (Day 0, Day 7, Day12, Day17, and Day 21) gated with CD3 and CD56 using flow cytometry data is shown. The dynamic number (FIG. 2B) and the proportion (FIG. 2C) of NK cells were significantly increased after 3 weeks of expansion by co-culturing PBMCs with different feeder cells. However, the fold-expanded NK cells with 721.221-mIL21 feeder cells (FIG. 2D) and purity (FIG. 2E) of expanded NK cells was significantly higher than for K562-mIL21 feeder cells. Additionally, the non-NK cells (including CD3+CD56−, CD3+CD56+, and CD3−CD56− cells) are decreased in the presence of mIL21-expressing feeder cells (FIGS. 14A-F). Thus, 721.221-mIL-21 cells are superior to K562-mIL21 cells as feeder cells for expanding human primary NK cells.

Example 4—Characteristics of Expanded NK Cells Derived from Peripheral Blood

Figure 3A:
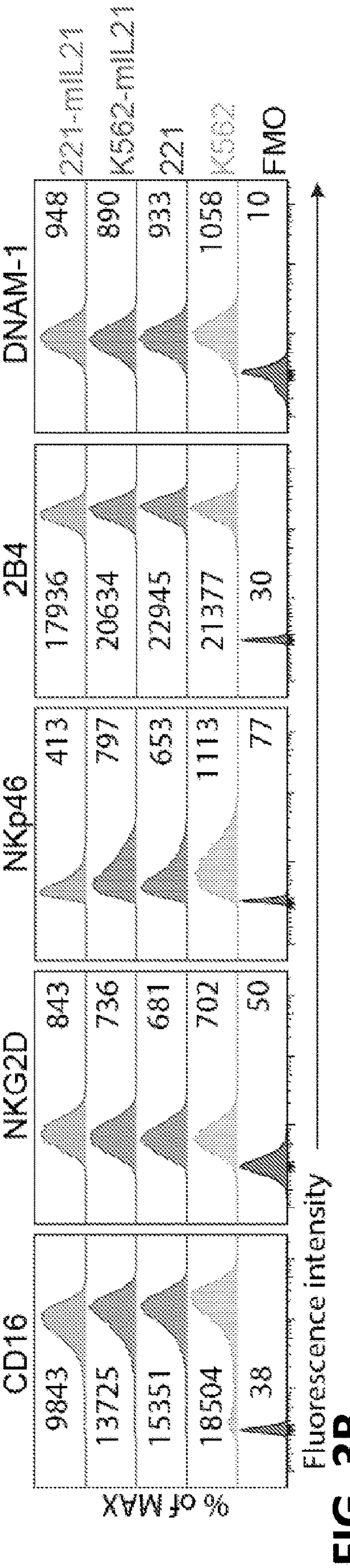
FIGS. 3A-3E. Phenotypes of NK cells expanded by different feeder cells.
Figure 3B:
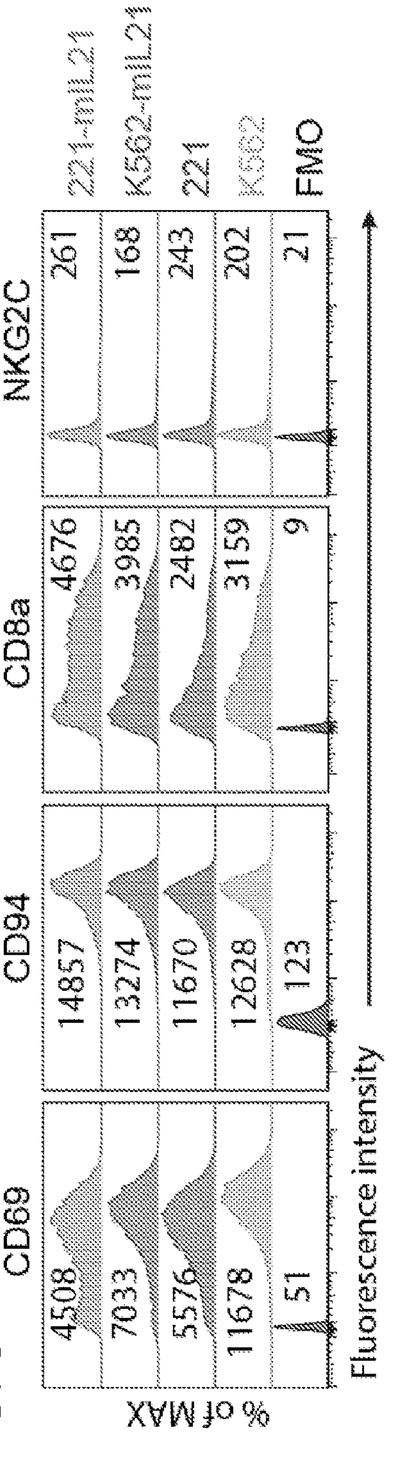
Figure 3C:
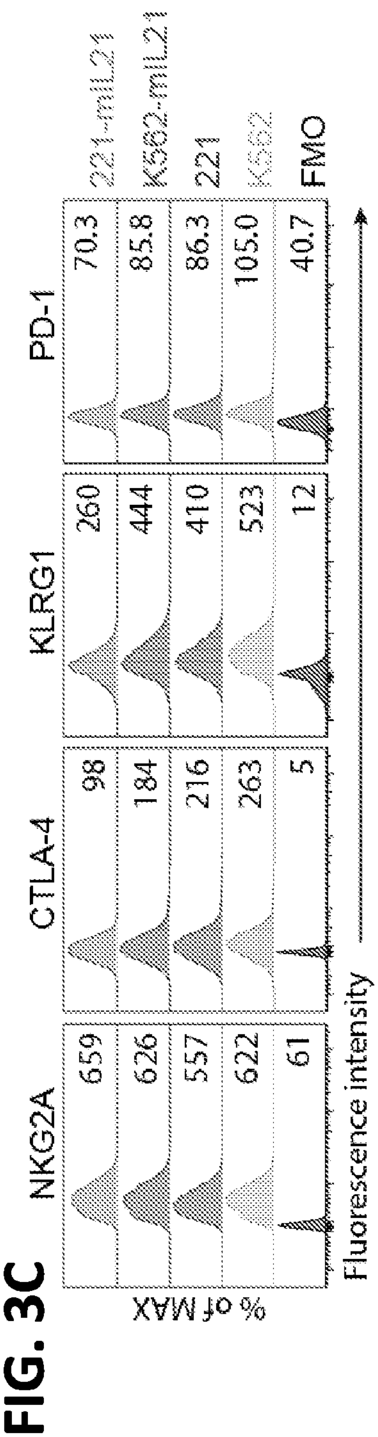
Figure 3D:
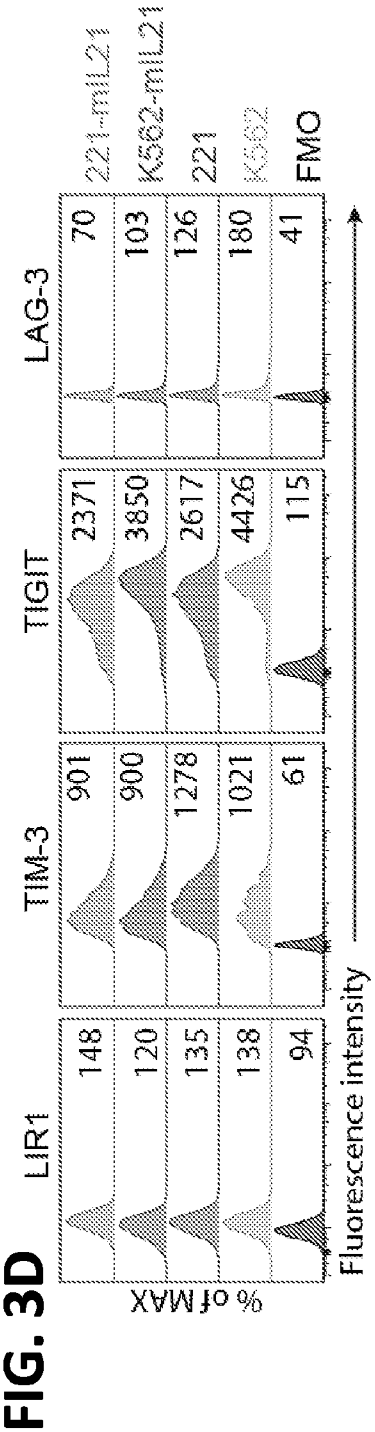
Figure 3E:
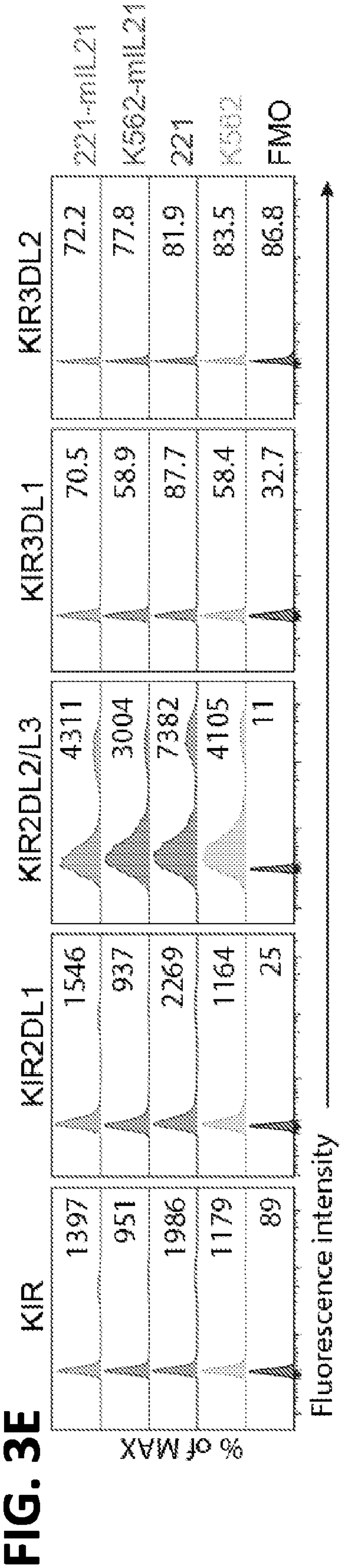

To determine the immunophenotying of expanded NK cells, K562-, K562-mIL21-, 721.221-, and 721.221-mIL21-expanded NK cells were examined using flow cytometry with antibodies against activating and inhibitory receptors. The activating receptors included CD16, NKG2D, NKP46, 2B4, DNAM-1, CD69, CD94, CD8α, and NKG2C (FIGS. 3A and 3B). The inhibitory receptors included NKG2A, CTLA-4, KIRG1, PD-1, LIR1, TIM-3, TIGIT, LAG-3, total KIR, KIR2DL1, KIR2DL2/L3, KIR3DL1, and KIR3DL2 (FIGS. 3C, 3D, and 3E). The expression of these activating and inhibitory receptors on the expanded NK cells is comparable. CD69, an activation marker of NK cells, was decreased in the 221-mIL21 expanded NK cells.

Figure 4B:
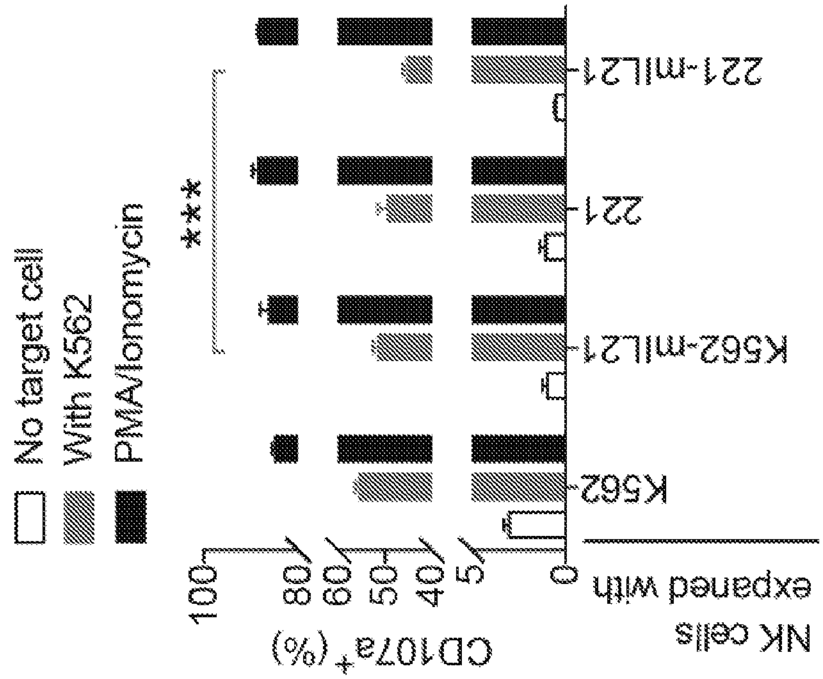
FIGS. 4A-4H. Functional comparison of NK cells against susceptible target cells.
Figure 4A:
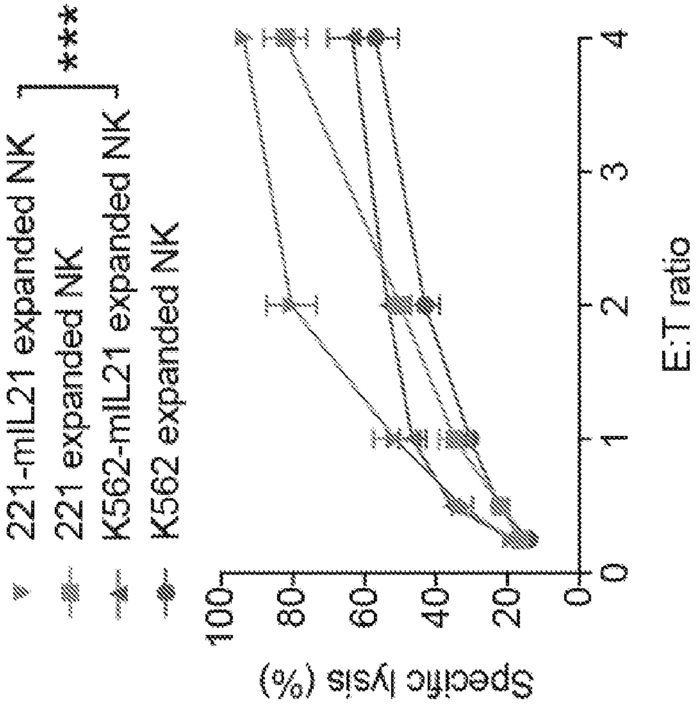
Figure 4C:
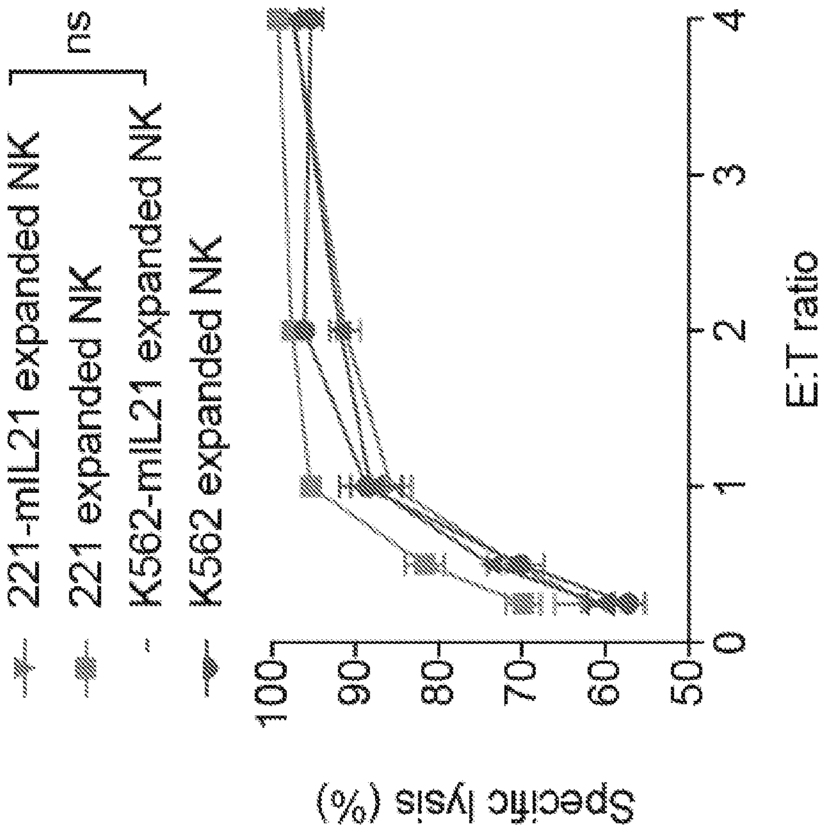
Figure 4D:
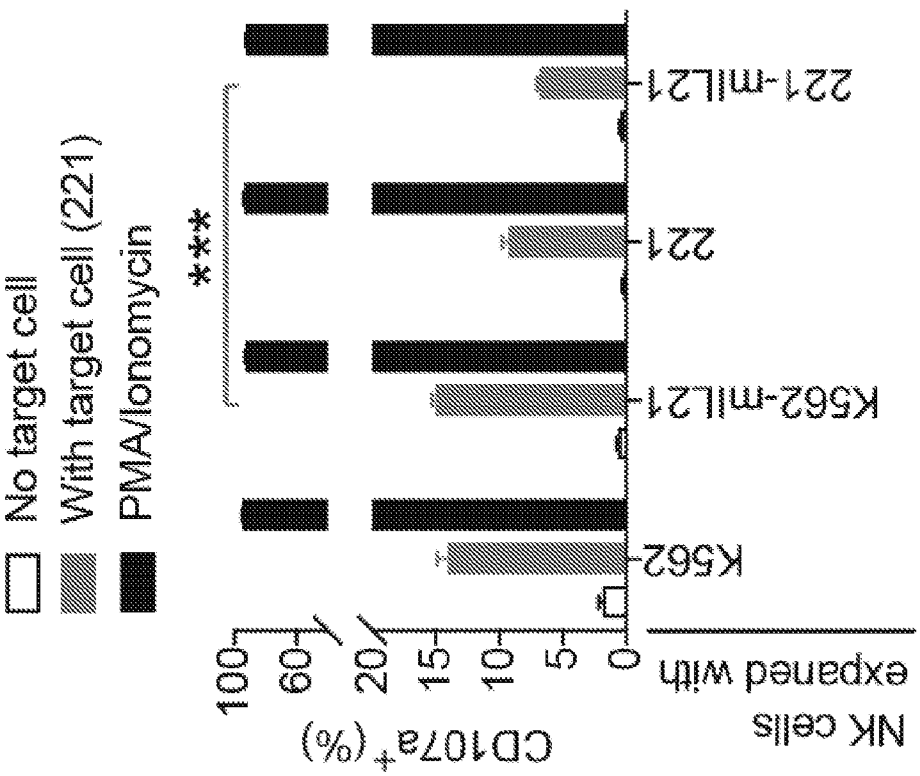
Figure 4E:
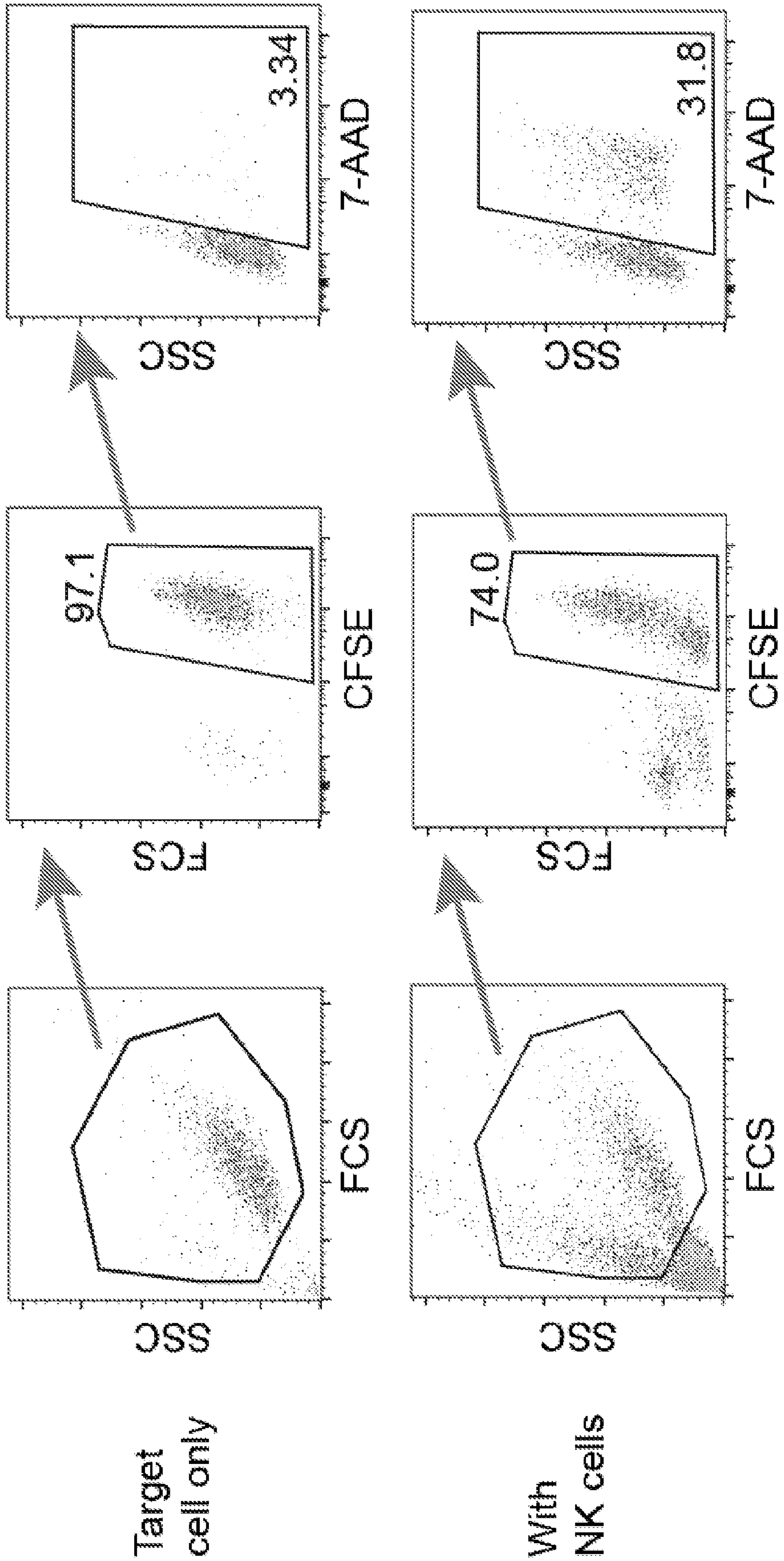
Figure 4F:
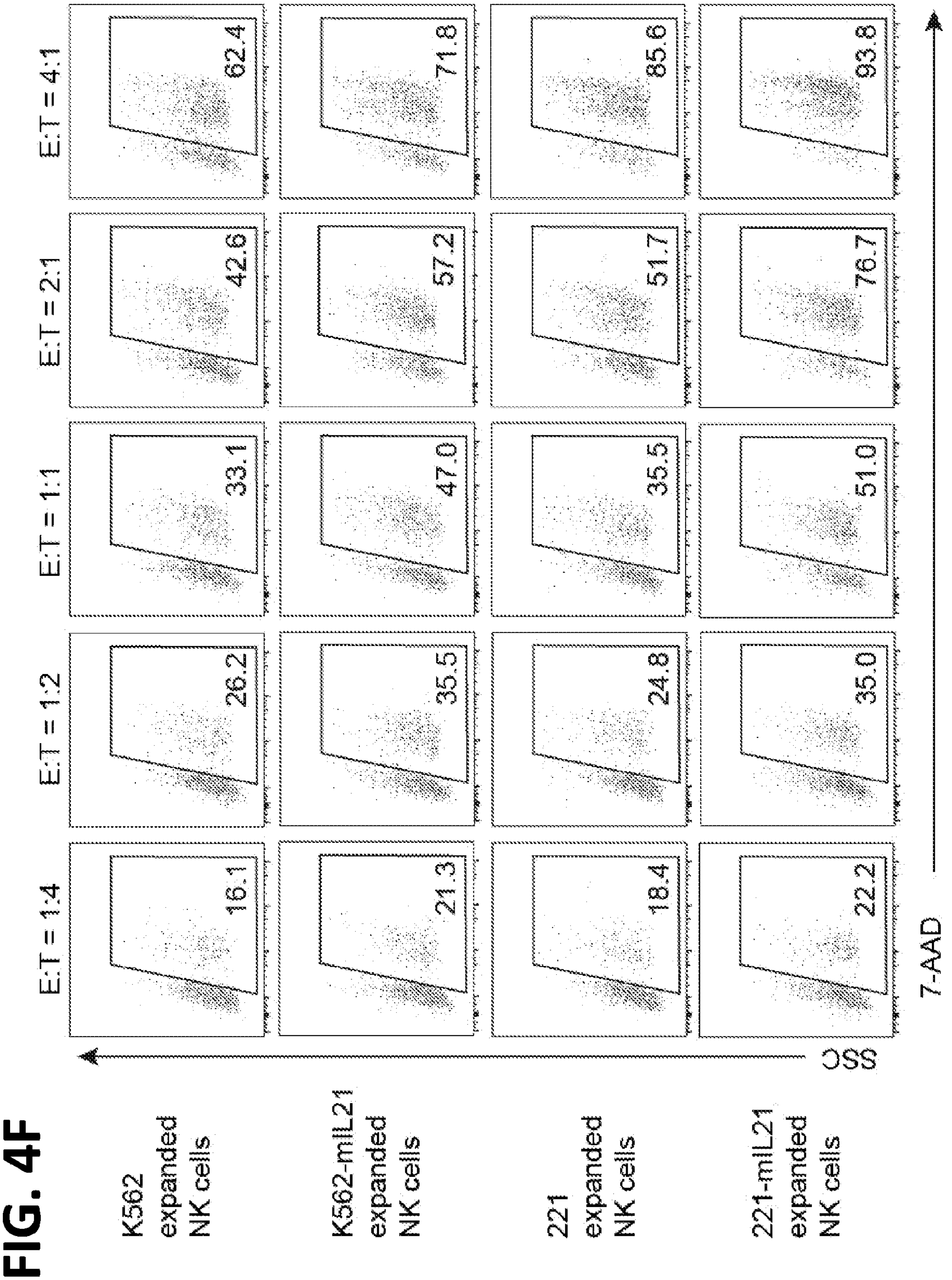
Figure 4G:
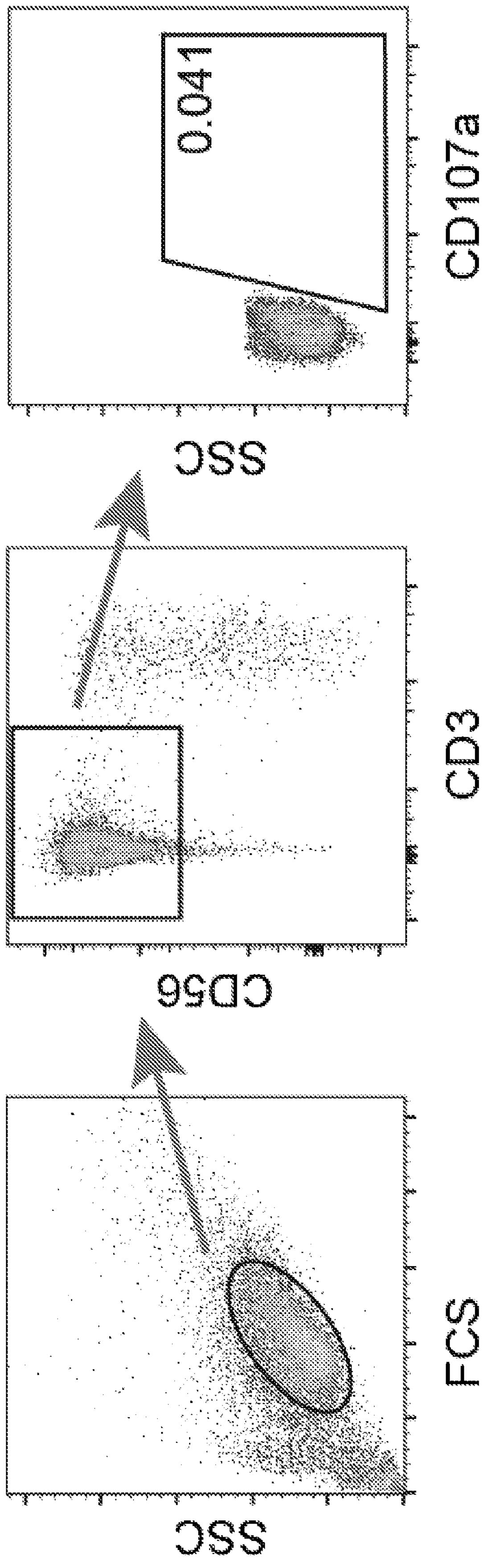
Figure 4H:
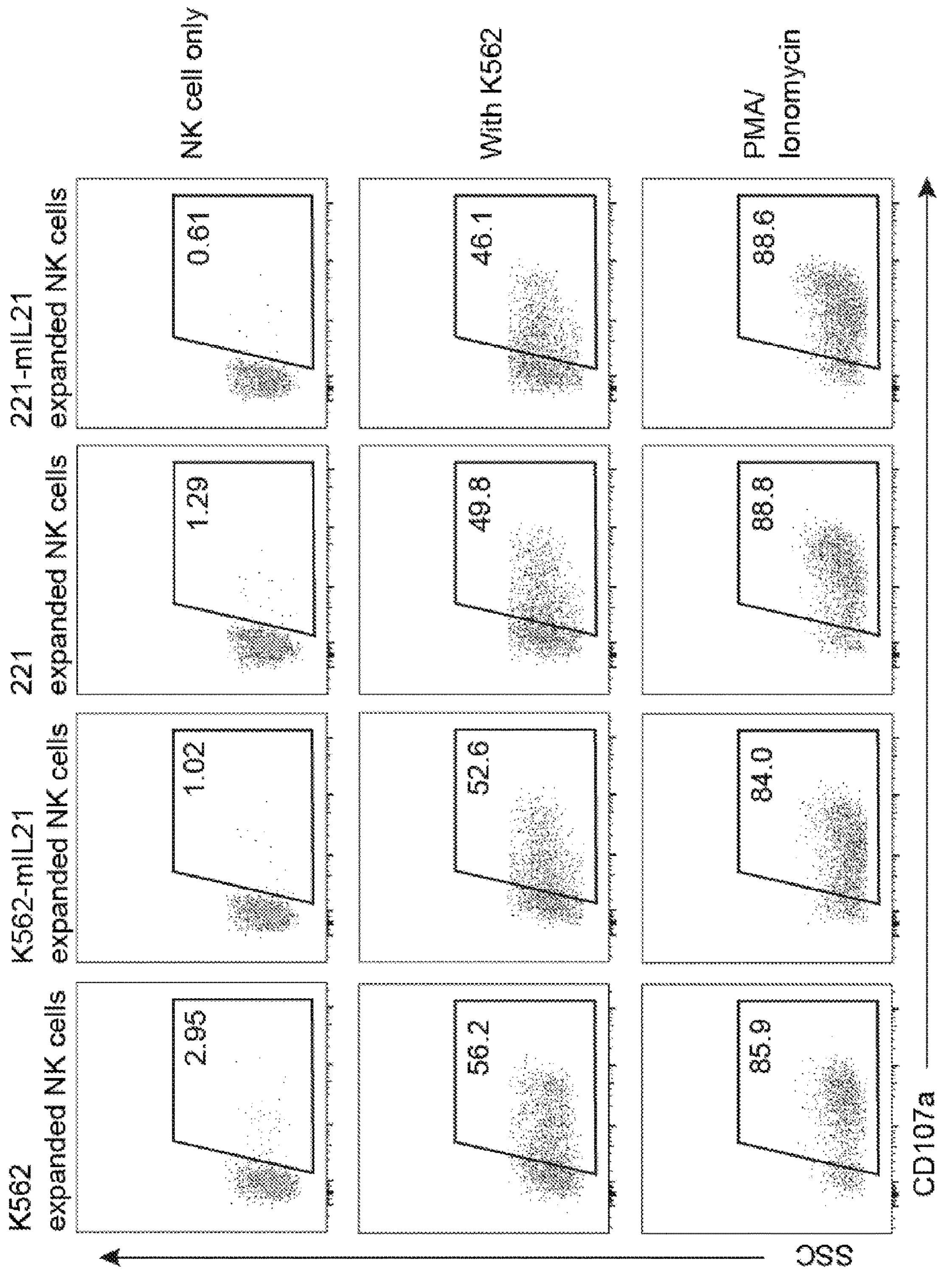

To examine similarities in function for the ex vivo expanded NK cells, the expanded NK cell cytotoxicity was investigated by co-culturing with NK-susceptible target cells 721.221 (FIGS. 4A and 4B) and K562 (FIGS. 4C and 4D). Interestingly, the NK cells expanded with 721.221-mIL-21 cells show superior cytotoxicity compared with NK cells expanded with K562-mIL-21 cells (FIG. 4A). To further confirm this observation, a CD107a assay was used to examine the surface level of CD107a molecules after NK degranulation. The comparable degranulation between K562-mIL-21- and 721.221-mIL-21-expanded NK cells was observation (FIG. 4B). No significant difference in cytotoxicity and degranulation was observed when co-culturing these expanded NK cells with WT K562 cells (FIGS. 4C and 4D).

To further examine whether NK cells isolated from cord blood (CB) can be expanded by this system, the expansion of NK number and purity of K562-mIL21 and 221-mIL21 was compared. Similar results were obtained (FIGS. 15A-15K). The immunophenotyping of expanded NK cells by K562-mIL2 land 221-mIL21 was also examined using by flow cytometry. CD69 expression was dramatically decreased in 221-mIL21 expanded NK cells with comparable cytotoxicity (FIGS. 16A-16D). In summary, expanded NK cells show similar phenotyping with freshly isolated human primary NK cells, and superior cytotoxicity.

Figure 5A:
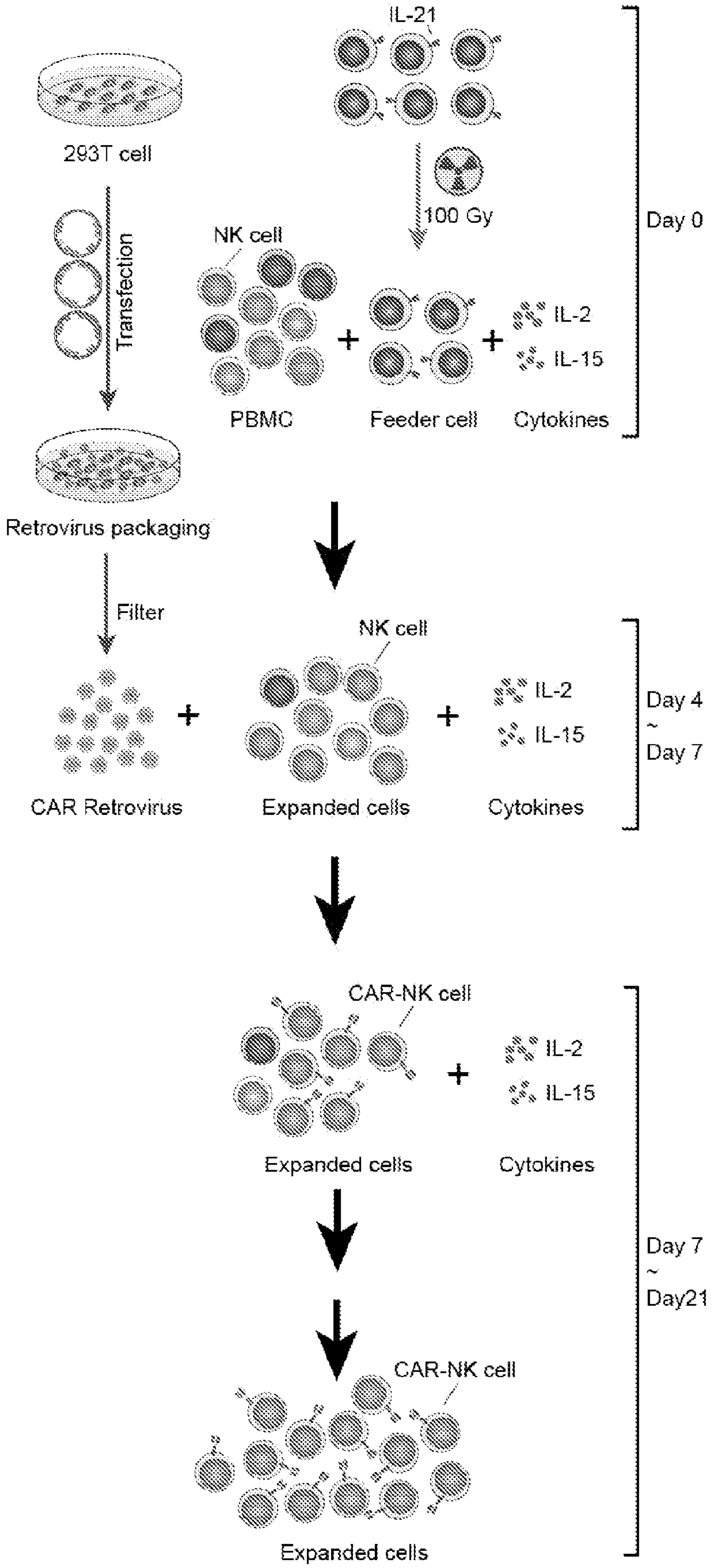
FIGS. 5A-5F. An exemplary method of expansion of CD19-CAR NK cells with 721.221-mIL21 is schematically illustrated in FIG. 5A. Briefly, 221.mIL21 cells were irradiated with a dose of 100 Gray (10000 Rad). PBMCs were then co-cultured with irradiated feeder cells in the presence of IL-2 and IL-15. In parallel, CD19-CAR retrovirus was produced by transfecting 293T cells. The expanded NK cells were transduced with CD19-CAR retrovirus at Day 7. Cells were cultured for 21 days.
Figure 5B:
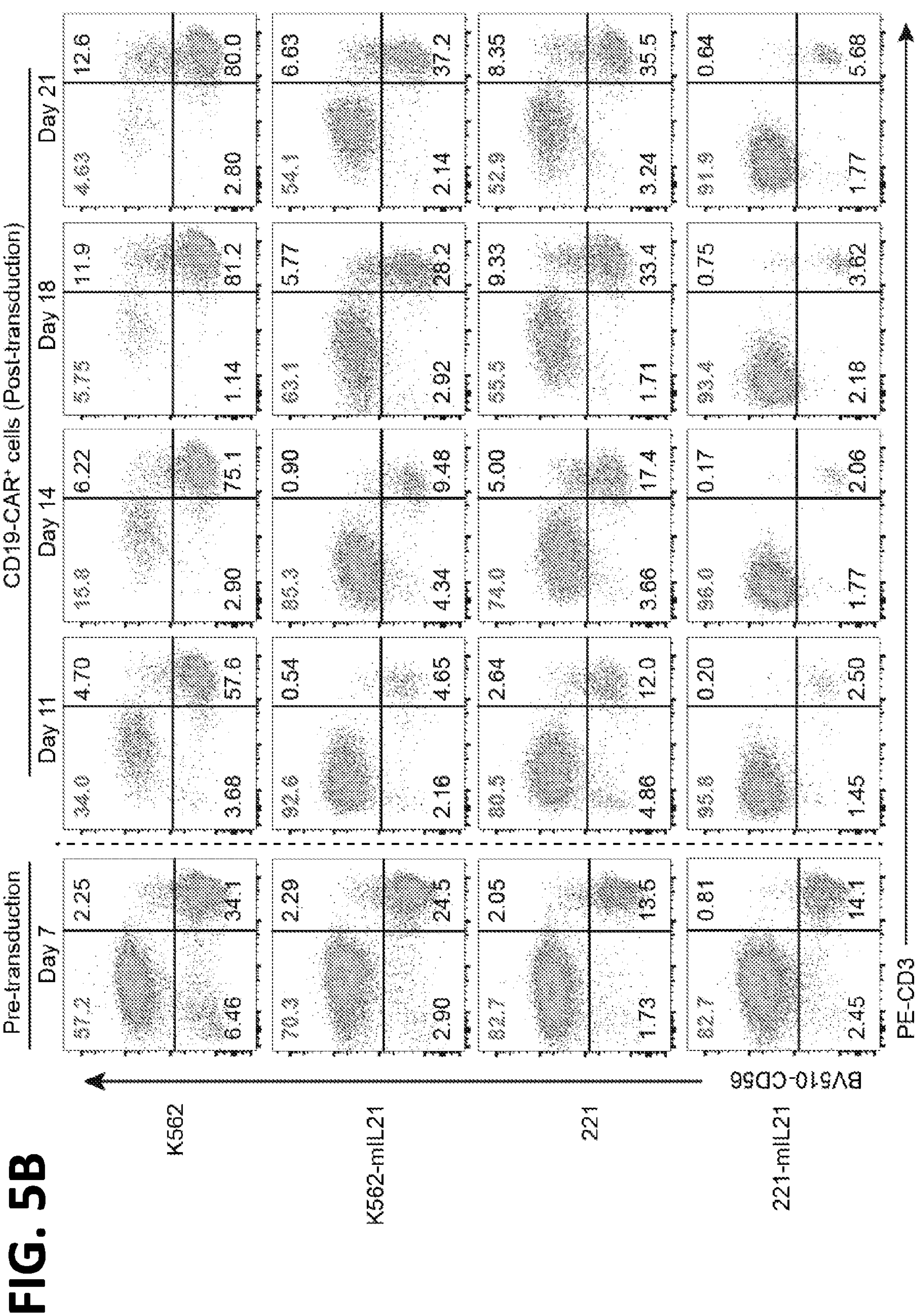
Figure 5D:
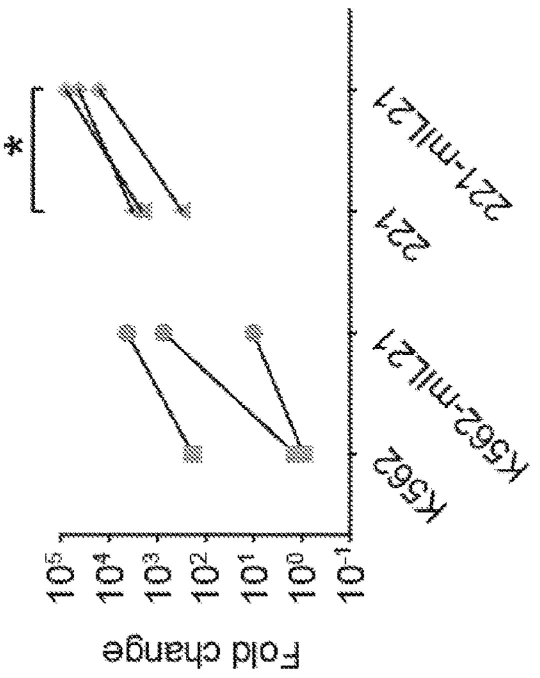
Figure 5C:
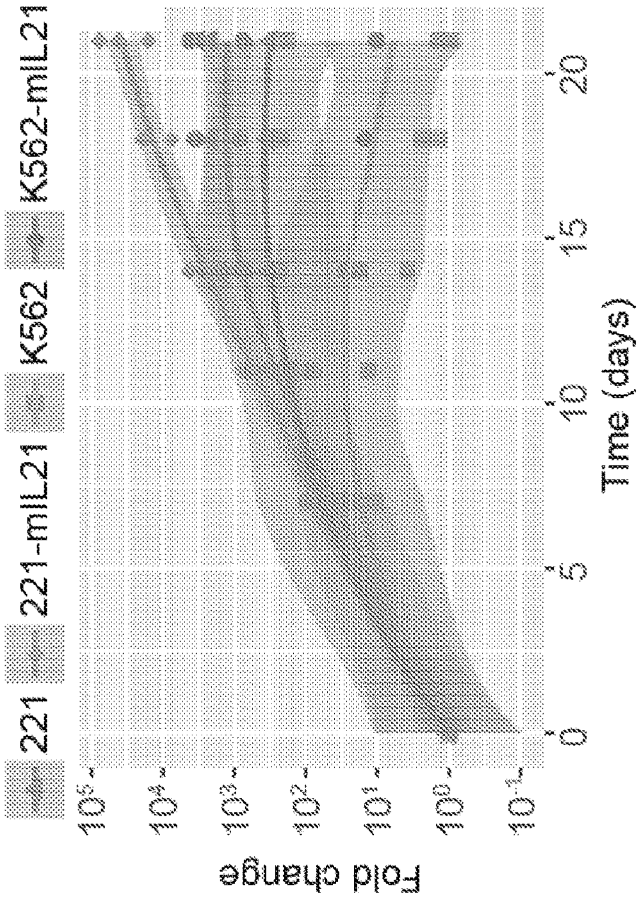
Figure 5F:
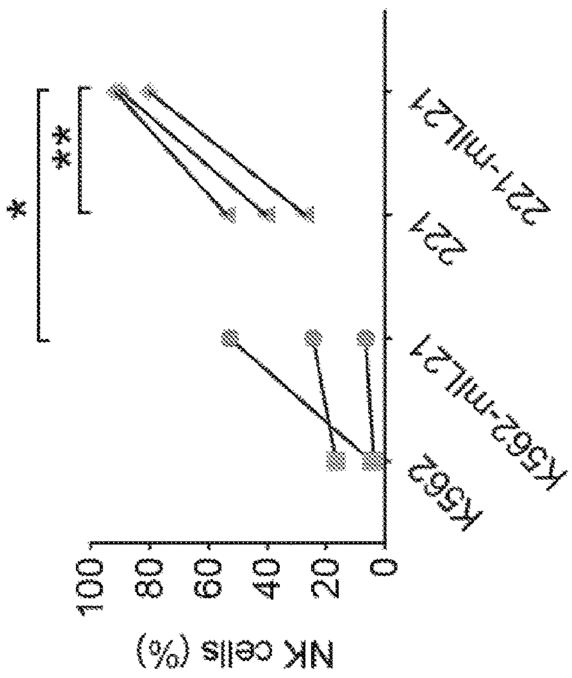
Figure 5E:
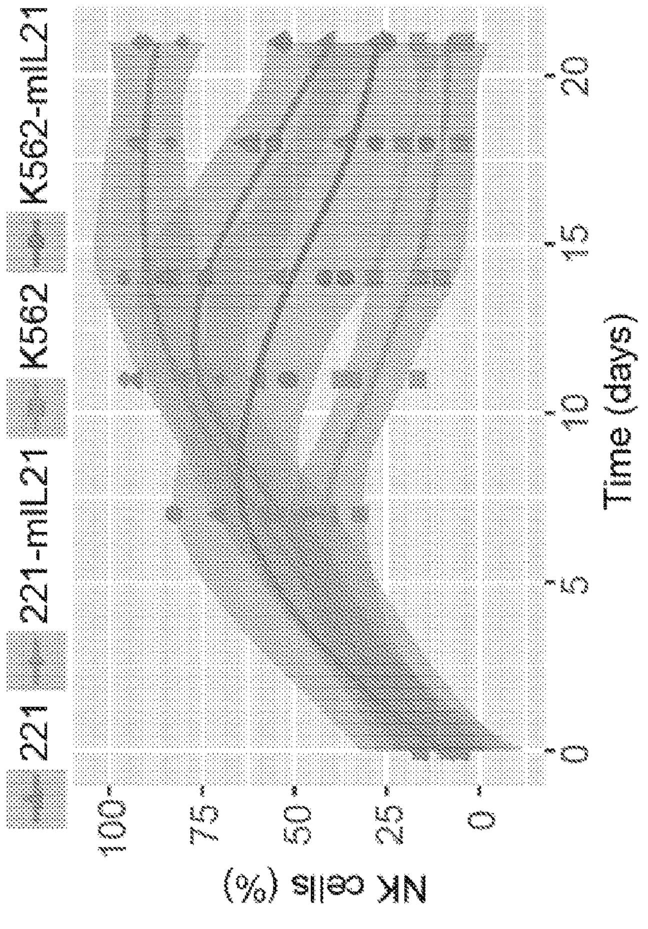

Example 5—Improved Peripheral Blood-Derived CAR-NK Expansion Using 721.221-mIL-21 Cells Whether the 721.221-mIL-21 feeder cells could expand CAR-NK cells in a similar way as non-genetically modified primary NK cells was also examined. To expand CAR-NK cells ex vivo, unfractionated PBMCs were stimulated for 7 days with 721.221-mIL-21 feeder cells in the presence of soluble IL-2 and IL-15, inducing rapid proliferation of NK cells and, in some cases, non-specific expansion of T cells (FIG. 5A). At day 7, expanded NK cells were transduced with CD19-CAR retrovirus. The dynamics of NK cell number and purity were examined at day 0, day 7, day 11, day 14, day 18, and day 21. A representative profile of ex vivo expanded NK cells from one donor shows superior NK number and purity (FIG. 5B). A quantitative analysis of NK cell number (FIG. 5C) and purity (FIG. 5D) from 5 donors shows that 721.221-mIL-21 feeder cells provide superior CD19-CAR-NK cell expansion. A quantitative analysis of NK cell number (FIGS. 5C-5D) and purity (FIGS. 5E-5F) from 3 donors shows that 221-mIL21 feeder cells provide superior CD19-CAR-NK cell expansion.

However, the percentage of CD19-CAR positive NK cells stimulated by K562-mIL21 was comparable to that of NK cells stimulated by 221-mIL21 cells (FIGS. 17A-17H). In contrast, non-NK cells (including CD3+CD56−, CD3+CD56+, and CD3−CD56− populations) were decreased in the presence of mIL21-expressing feeder cells (FIGS. 17A-17H). In conclusion, the 721.221-mIL-21 feeder cells show superior CAR-NK cell expansion capability compared with CAR-NK cells expanded with K562-mIL-21 feeder cells.

Figure 6A:
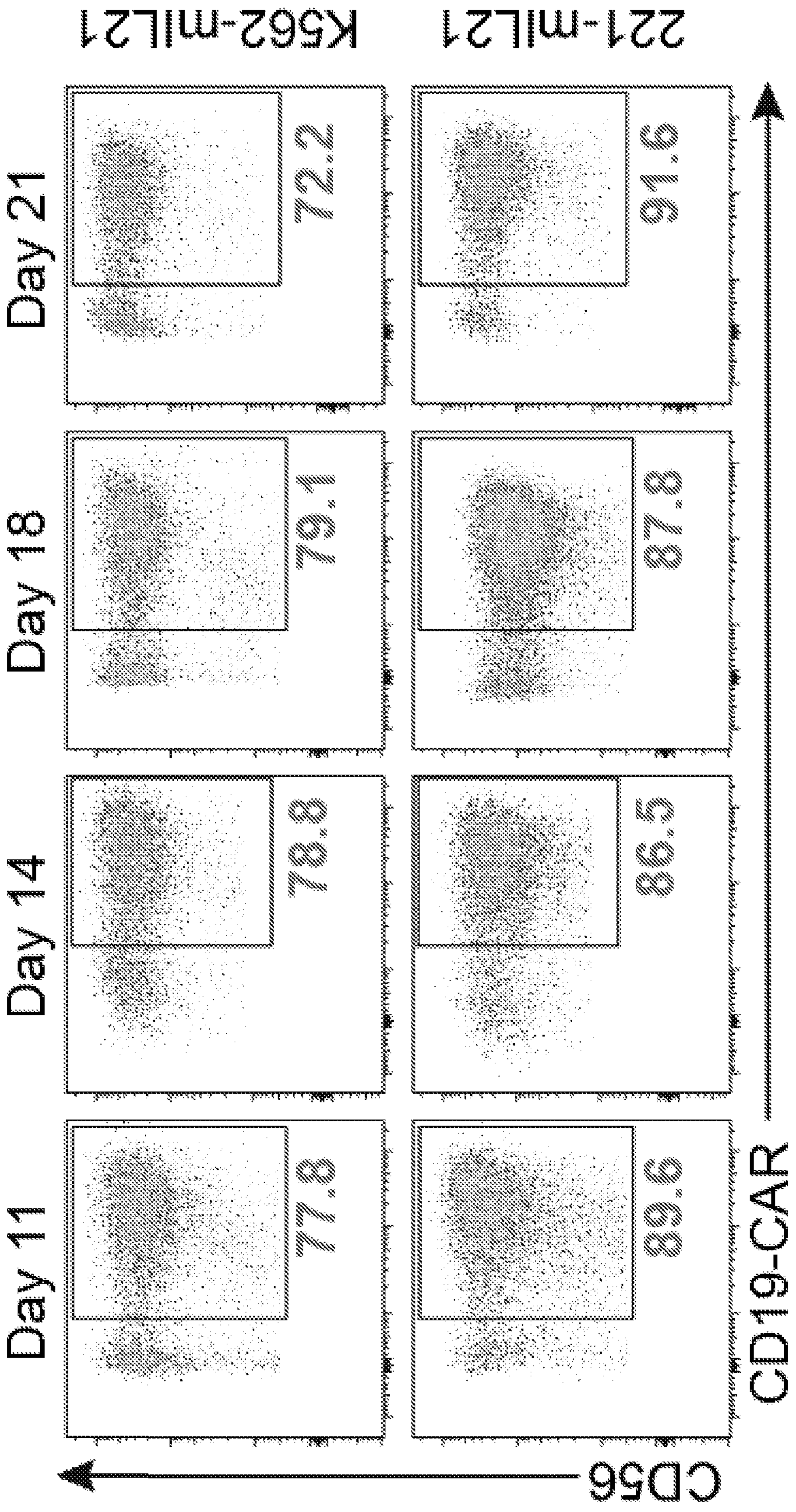
FIGS. 6A-6D. Expansion of Cord Blood (CB) derived NK and CAR-NK cells with 721.221-mIL21.

Example 6-721.221-mIL-21 Feeder Cells Exhibit a Superior Capacity to Expand Cord Blood-Derived Primary NK and CAR-NK Expansion Given multiple advantages of cord blood-derived NK and CAR-NK cells (Liu et al., Leukemia 32:520-31 (2018); Nahm et al., J Immunother 41:64-72 (2018); Balassa K and Rocha V, Expert Opin Bio Ther 18:121-34 (2018)), whether the 721.221-mIL-21 feeder cells could expand cord blood-derived NK cells and CAR-NK cells was examined. To expand CB-NK cells ex vivo, unfractionated CB-lymphocytes were stimulated for 7 days with 721.221-mIL-21 feeder cells in the presence of soluble IL-2 and IL-15, inducing rapid proliferation of NK cells (FIGS. 6A-6D). As a control, unfractionated CB-lymphocytes were stimulated with K562-mIL21 feeder cells in the presence of soluble IL-2 and IL-15 in a separate group. At day 7, expanded NK cells were transduced with CD19-CAR retrovirus. The dynamics of NK cell number and purity were examined at day 0, day 7, day 11, day 14, day 18, and day 21. A representative profile of ex vivo expanded NK cells from one donor shows superior NK number and purity (FIG. 6A). A quantitative analysis of NK cell number purity (FIG. 6B) from 3 donors shows that 721.221-mIL-21 feeder cells provide superior CD19-NK cell expansion.

Figure 6C:
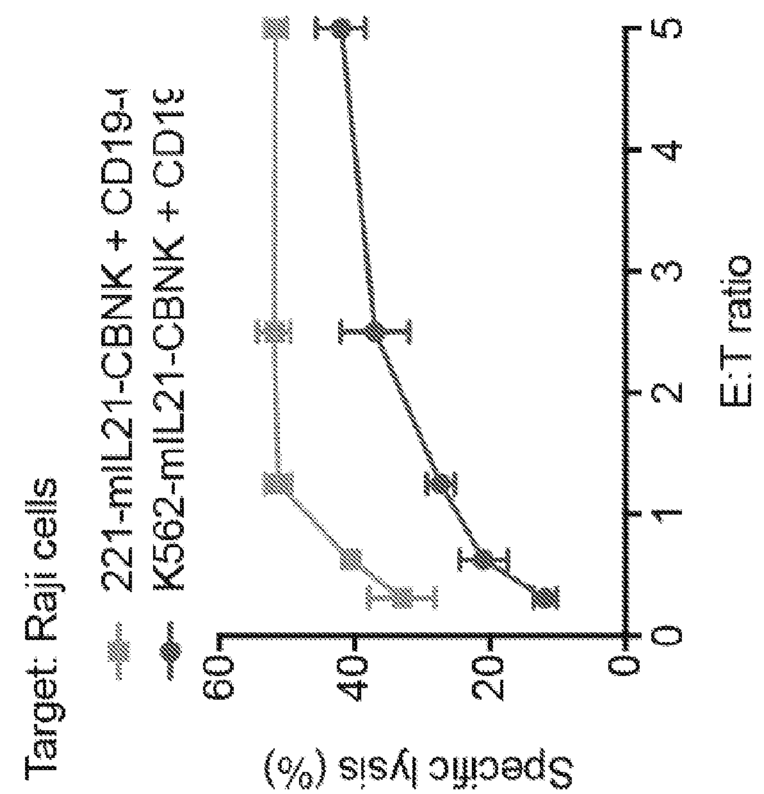
Figure 6B:
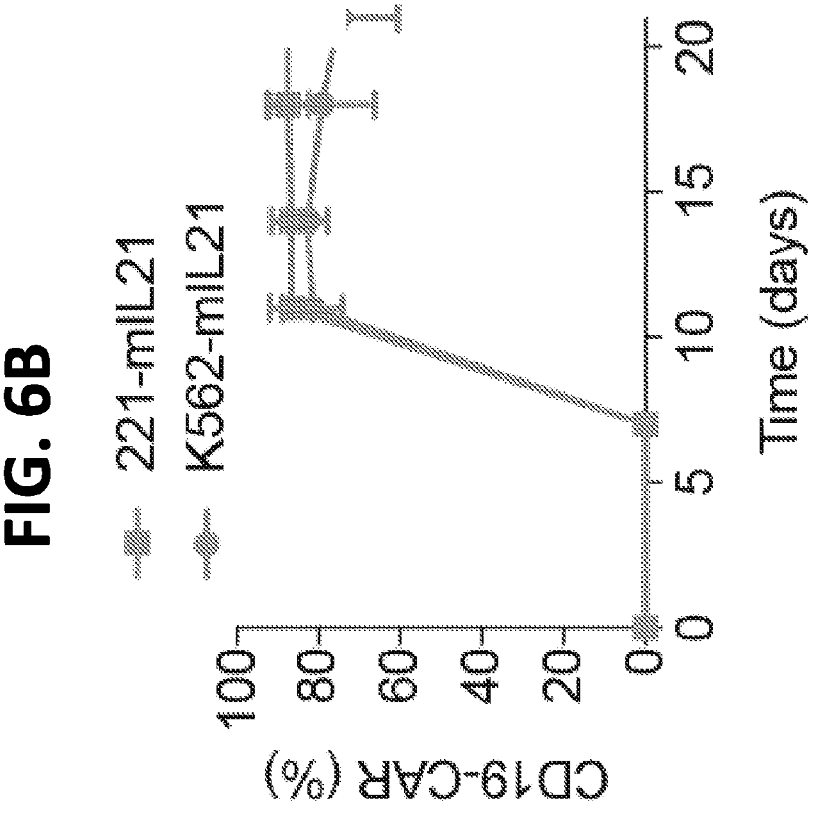
Figure 6D:
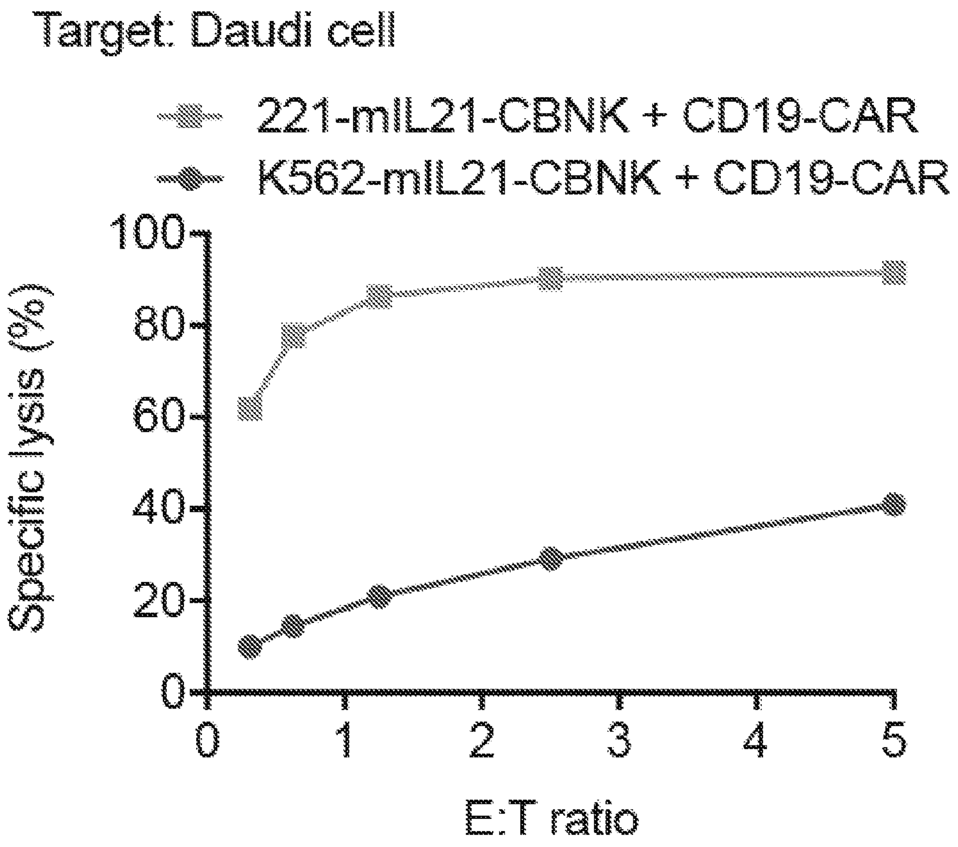

To examine whether these ex vivo expanded CD19-CAR.CB-NK cells exhibit similar functions, the expanded NK cell cytotoxicity was examined by co-culturing them with the NK susceptible Raji and Daudi cells. CD19-CAR.CB-NK cells expanded with 221-mIL21 cells show superior cytotoxicity compared with CD19-CAR.CB-NK cells expanded with K562-mIL21 cells (FIGS. 6C-6D). Therefore, the NK expansion approach with improved cord blood derived NK and CAR-NK expansion using 721.221-mIL-21 cells was successful.

Example 7—Effectiveness and Side Effects of Expanded CAR-NK Cells In Vivo

Figure 7A:
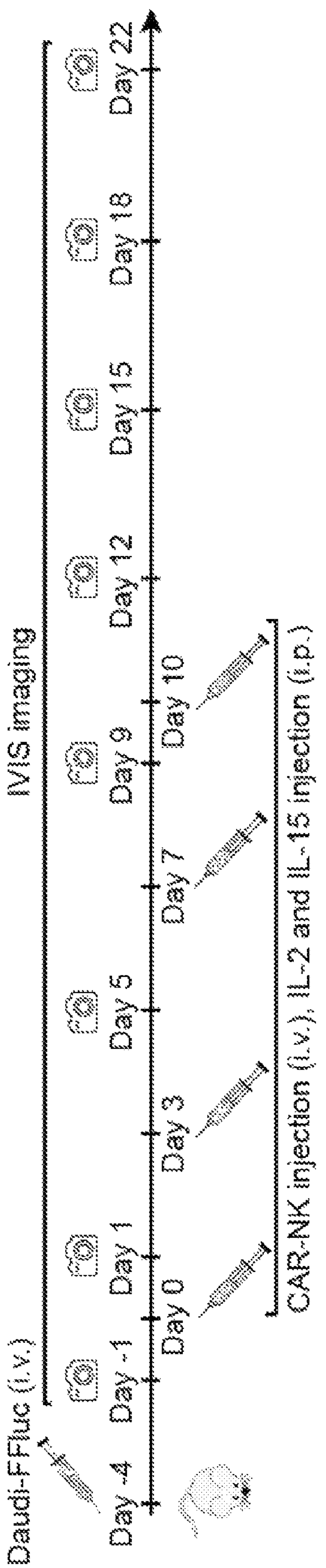
FIGS. 7A-7I. Superior anti-tumor activity from 221-mIL21 expanded CD19-CAR NK cells in a lymphoma xenograft model.
Figure 7E:
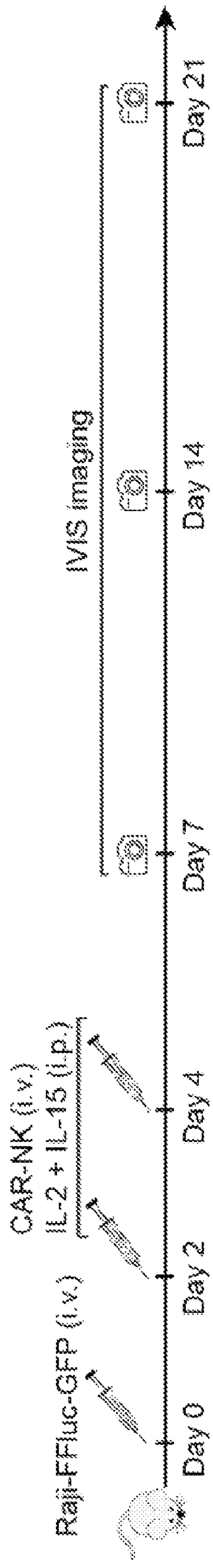
Figure 7B:
Figure 7C:
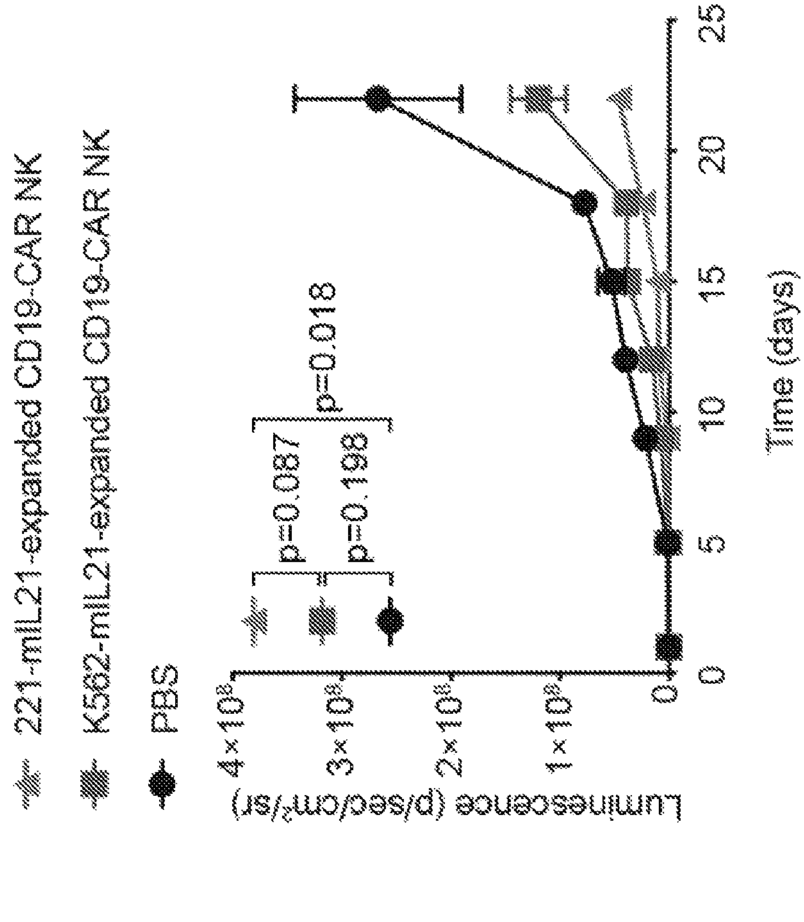
Figure 7D:
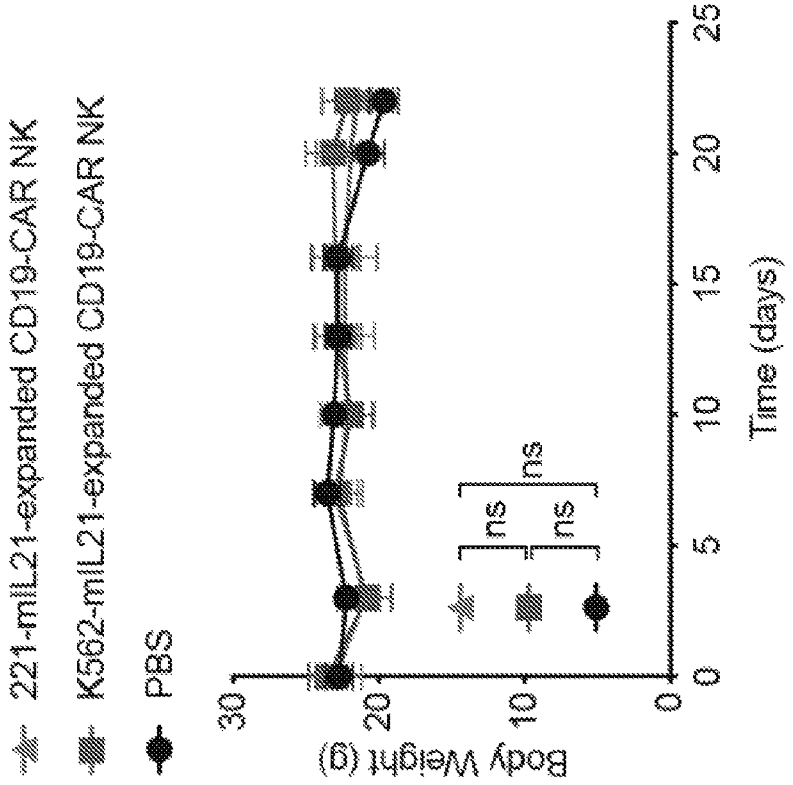
Figure 7F:
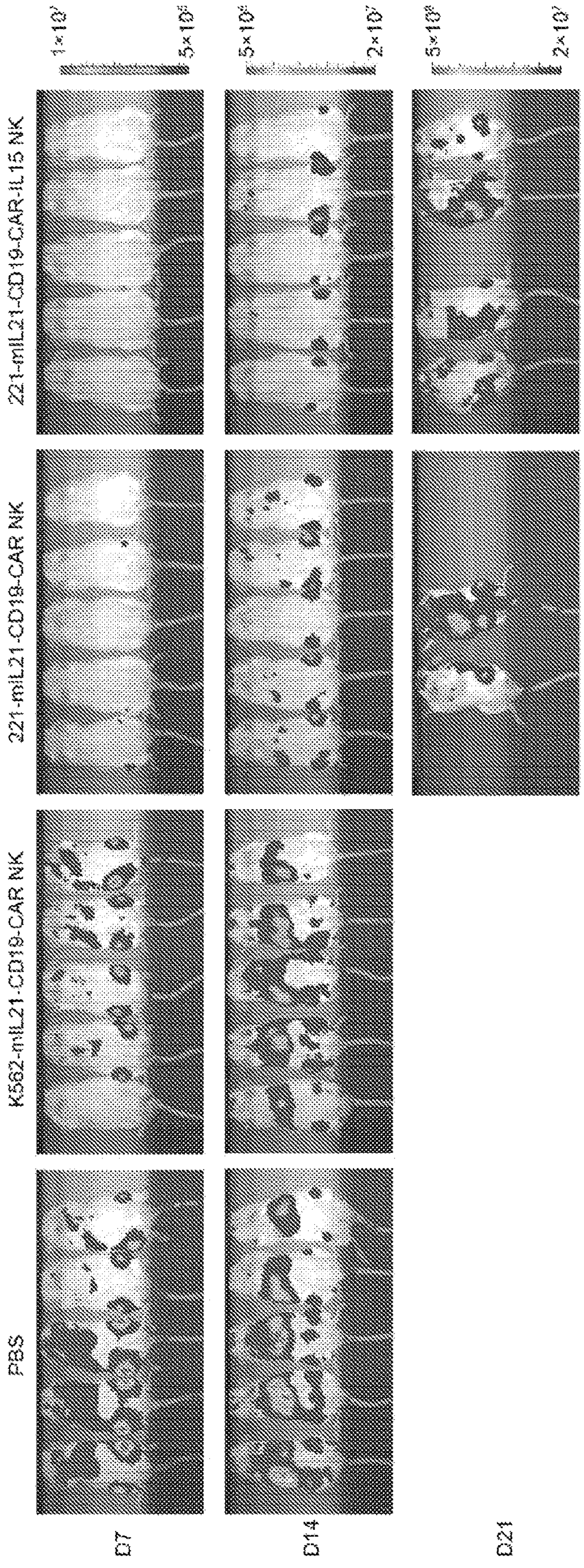
Figure 7G:
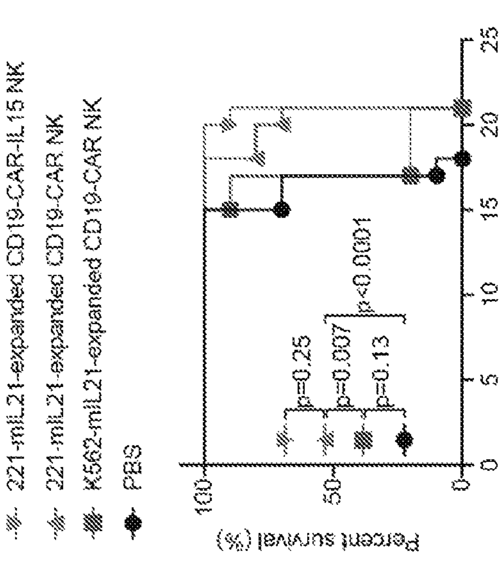
Figure 7H:
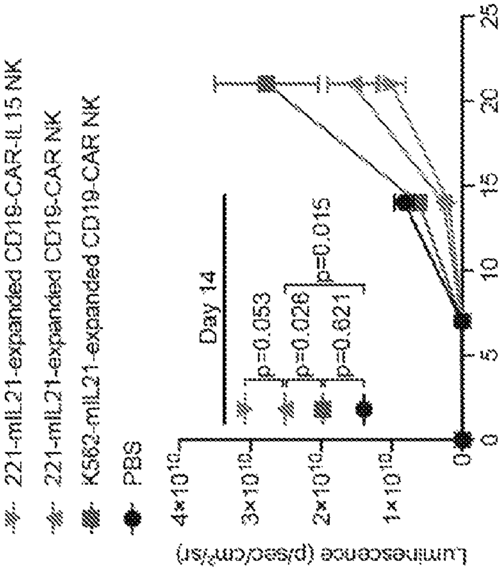
Figure 7I:
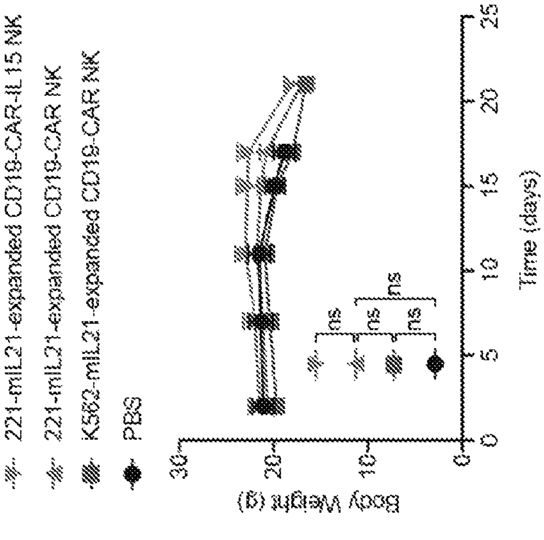

To further evaluate whether the expanded CD19-CAR-NK cells can kill tumor cells in vivo, the anti-tumor activities of 721.221-mIL-21 expanded CD19-CAR-NK cells and K562-mIL-21 expanded CD19-CAR-NK cells were compared using a lymphoma xenograft model in NSG mice (FIGS. 7A-7D). Luciferase-tagged Daudi (FFluc-Daudi) was implanted using intravenous (i.v.) tail vein injection. The tumor burden was assessed at the indicated points by measuring tumor-derived bioluminescence followed by CD19-CAR-NK infusion (FIG. 7A). Mice treated with 721.221-mIL-21 expanded CD19-CAR-NK cells show superior anti-tumor activities than K562-mIL-21 expanded CD19-CAR-NK after treatment (FIGS. 7B and 7C). Similar results for tumor growth inhibition (TGI) were obtained. To further evaluate the toxicity of the in vivo expanded CD19-CAR-NK cells, the body weight of the mice was quantified. No significant difference in body weight was observed (FIG. 7D), indicating the minimal side effects from the ex vivo expanded CD19-CAR-NK cells. In conclusion, 721.221-mIL-21 expanded CD19-CAR-NK cells show superior anti-tumor activities in vivo with minimal side effects.

Figure 10A:
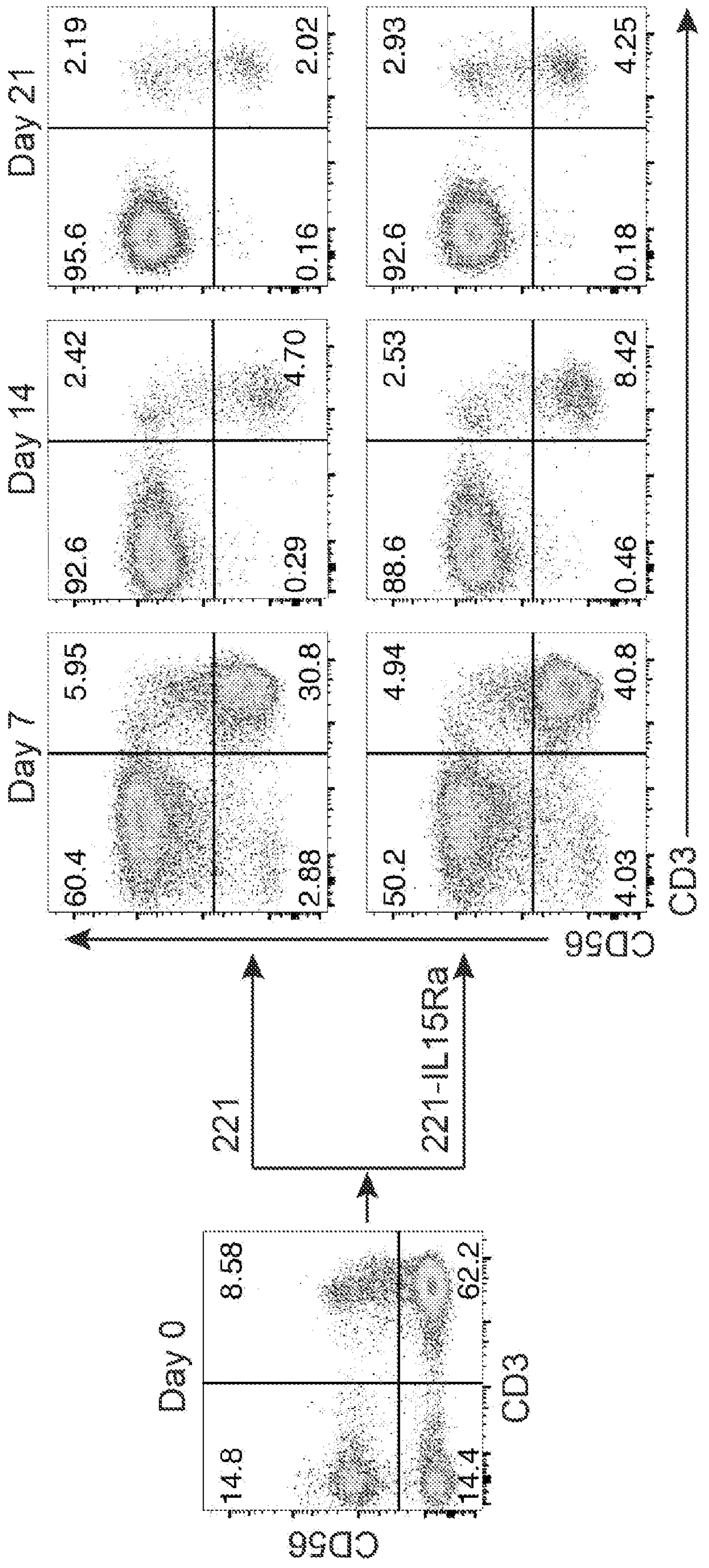
FIGS. 10A-10C. Primary human NK cell expansion with 721.221 cell expressing membrane IL-15 receptor alpha (221-mIL-15Rα).
Figure 10C:
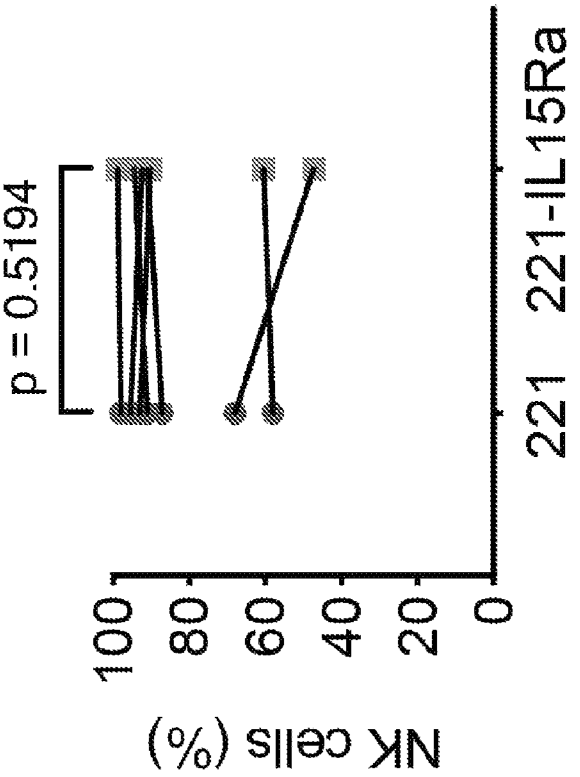
Figure 10B:
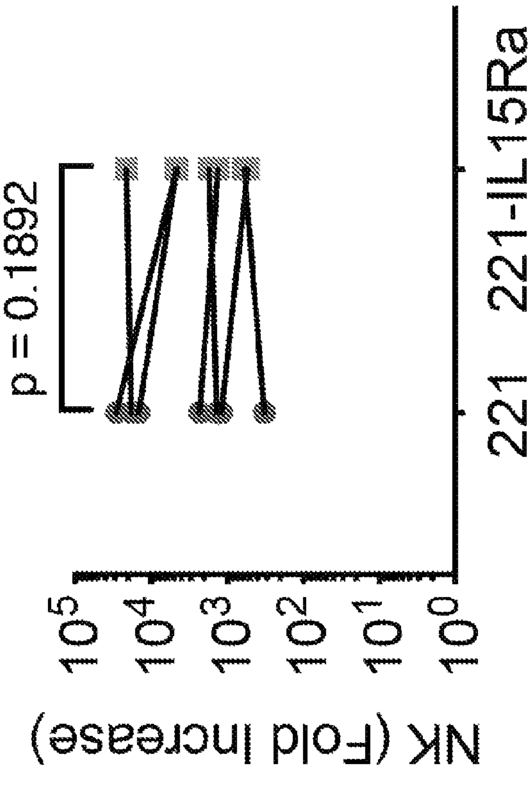

NK cell expansion capability was compared between wild-type 221 and 221 cell expressing trans-membrane presentation of IL-15. However, no significant difference in fold-NK expansion and purity of NK expansion was observed (FIGS. 10A-10C).

Example 8—Effectiveness of 221-mIL21 Cell Expansion of T Cells

Figure 11A:
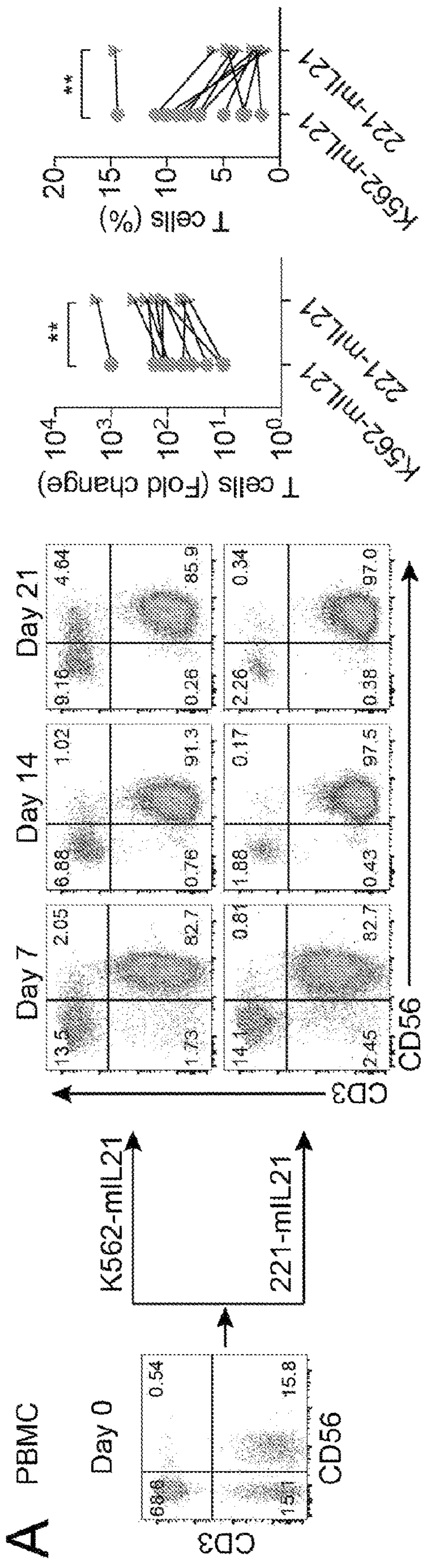
FIGS. 11A-11C. Primary human T cell expansion with 721.221 cell expressing membrane IL-21.
Figure 11B:
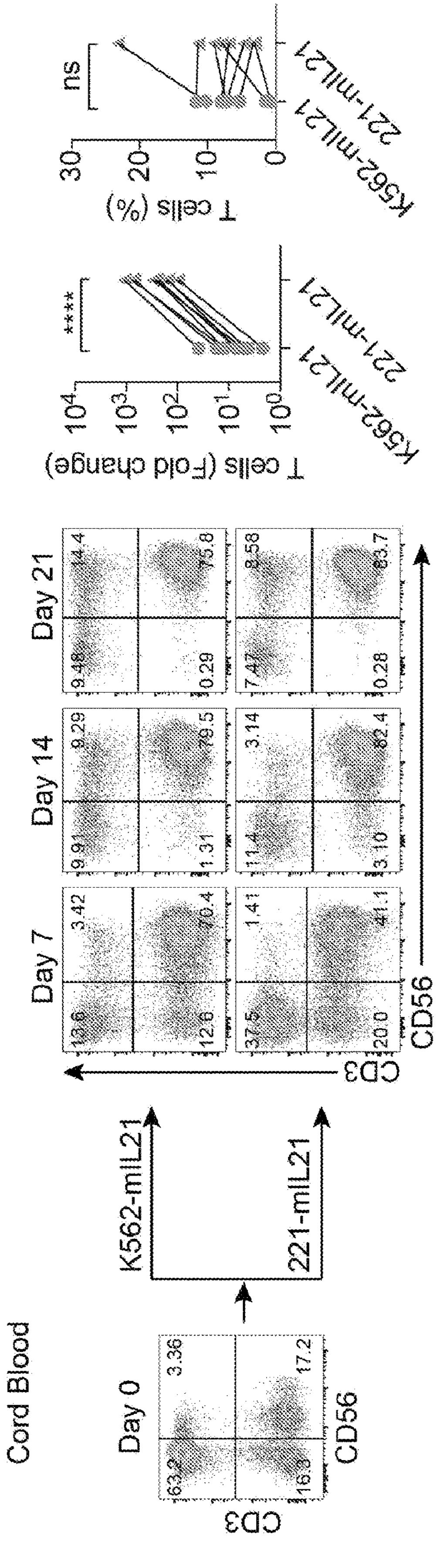
Figure 11C:
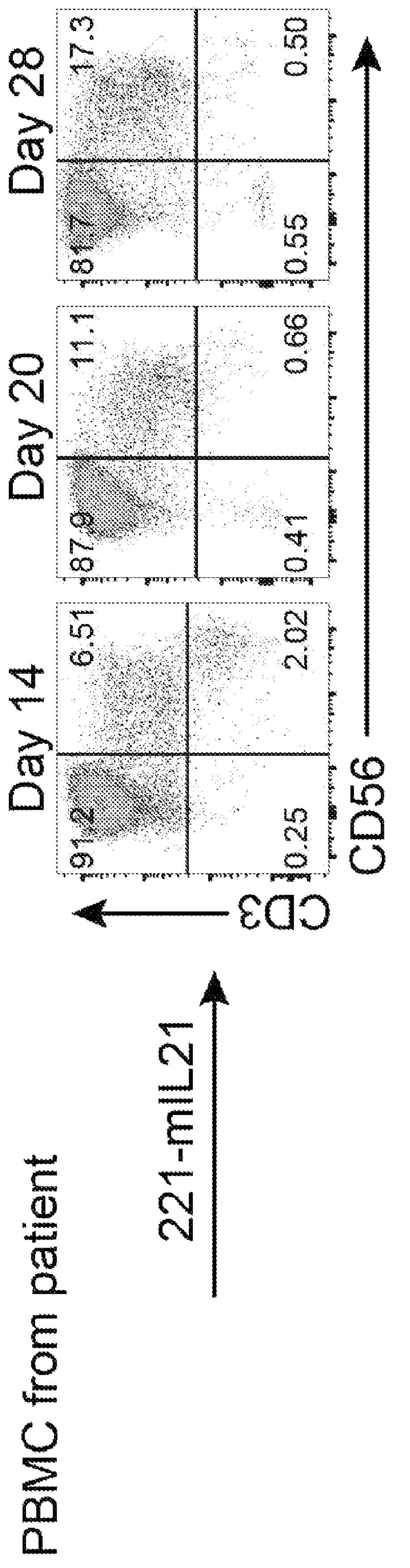

Expansion of T cells from different sources using 721.221-mIL21 was further tested. The CD3-positive T cell subsets from PBMCs and cord blood were examined. Both K562-mIL21 cells and 721.221-mIL21 cells can expand T cells. However, expansion using 721.221-mIL21 cells yielded a superior T cell fold increase from both PBMC and cord blood samples compared with K652-mIL21 cells (FIGS. 11A-11C). The percentage of T cells expanded from PBMCs by 721.221-mIL21 cells was lower than the percentage expanded using K562-mIL21 cells (FIG. 11A). No difference in T cell purity from cord blood between K652-mIL21 cells and 721.221-mIL21 cells was observed (FIG. 11B). Further, 721.221-mIL21 feeder cells preferably expanded CD4+ T cells from PBMCs of patient with anaplastic large cell lymphoma (ALCL, a rare type of non-Hodgkin lymphoma). After two-weeks of expansion by 721.221-mIL21 feeder cells, more than 90% of cells were CD4+, CD3+, and CD56− subsets (FIG. 11C).

Figure 13A:
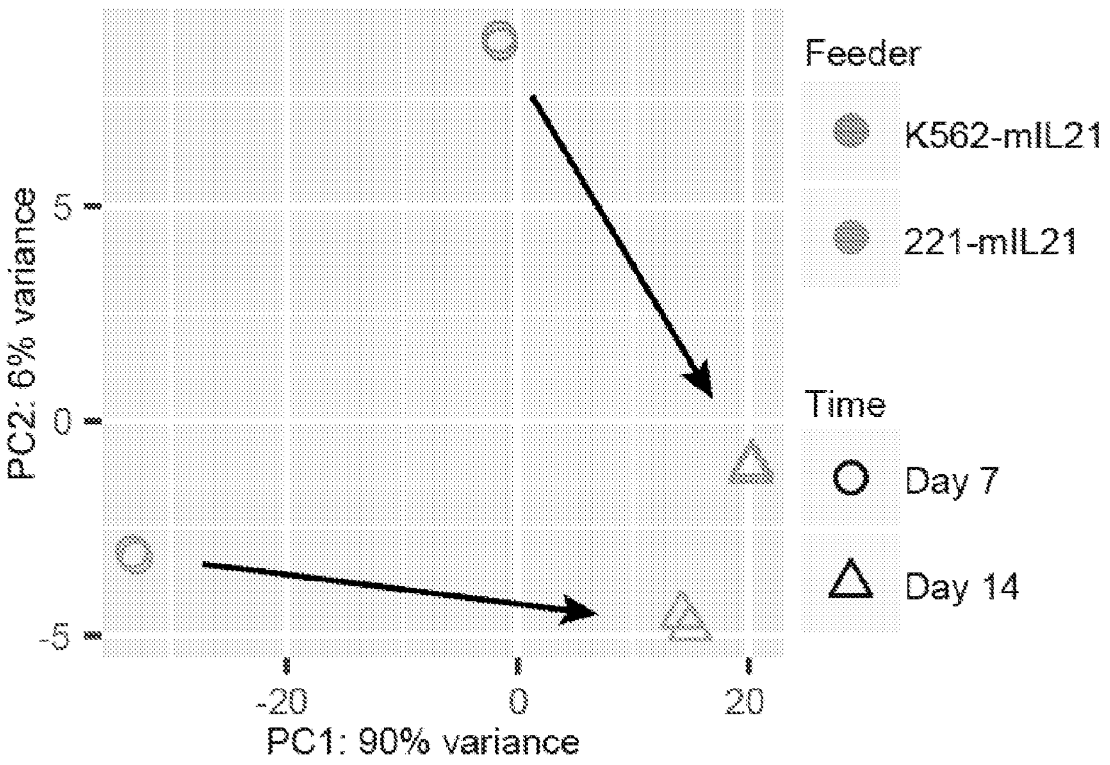
FIGS. 13A-13N. 221-mIL21 expanded NK cells show enriched metabolic pathways and immature phenotypes.

Example 9-221-mIL21 Feeder Cell Expansion System Promotes Less-Differentiated, Memory-Like NK Development To further investigate 221-mIL21 feeder cell expansion system inducing superior NK cell expansion capability and functions, RNA sequencing (RNA-Seq) experiments were performed using NK cells expanded by different feeder cell systems and at various time points. Briefly, PBMCs were stimulated with irradiated K562-mIL21 or 221-mIL21 feeder cells. Expanded NK cells from these two different expansion systems were sorted using flow cytometry on day 7 and day 14 for RNA-Seq. Principal component analysis (PCA) plots of sample-to-sample distances of NK cells expanded with K562-mIL21 or 221-mIL21 cells show a significant difference at day 7, compared with NK cells expanded at day 14 (FIG. 13A).

Figure 13C:
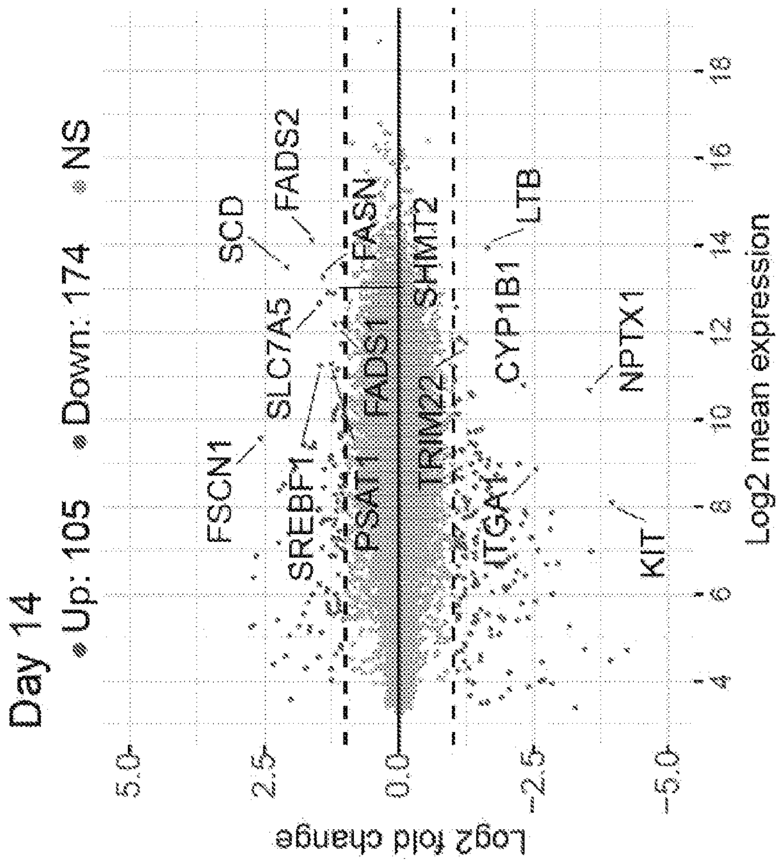
(FIG. 13C) MA plots of DEGs in NK cells that were expanded with 221-mIL21 feeder cells compared to those that were expanded with K562-mIL21 feeder cells on day 14. Top 15 significant DEGs are labeled on the MA-plot. Up, up-regulated DEGs, adjusted $p<0.05$ and log 2 fold change >=1; Down, down-regulated DEGs, adjusted $p<0.05$ and log 2 fold change <=−1; NS, not significant.
Figure 13B:
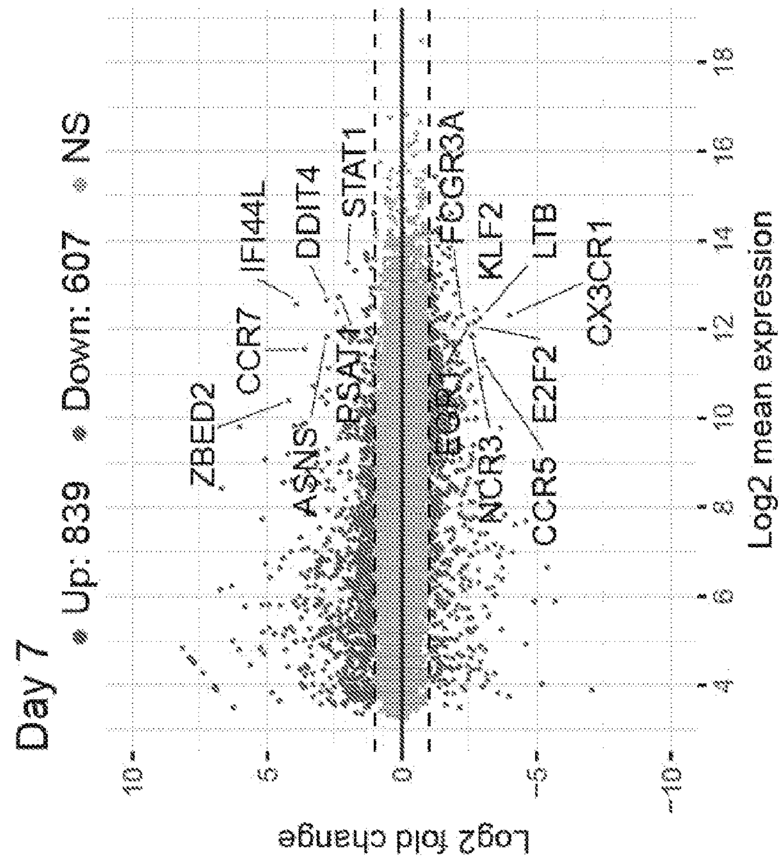
(FIG. 13B) Mean-average (MA) plots of differentially expressed genes (DEGs) in NK cells expanded with 221-mIL21 feeder cells compared to those that were expanded with K562-mIL21 feeder cells on day 7; p-values calculated using DESeq2. Top 15 significant DEGs are labeled on the MA-plot. Up, up-regulated DEGs, adjusted $p<0.05$ and log 2 fold change ≥1; Down, down-regulated DEGs, adjusted $p<0.05$ and log 2 fold change ≤−1; NS, not significant.
Figure 13E:
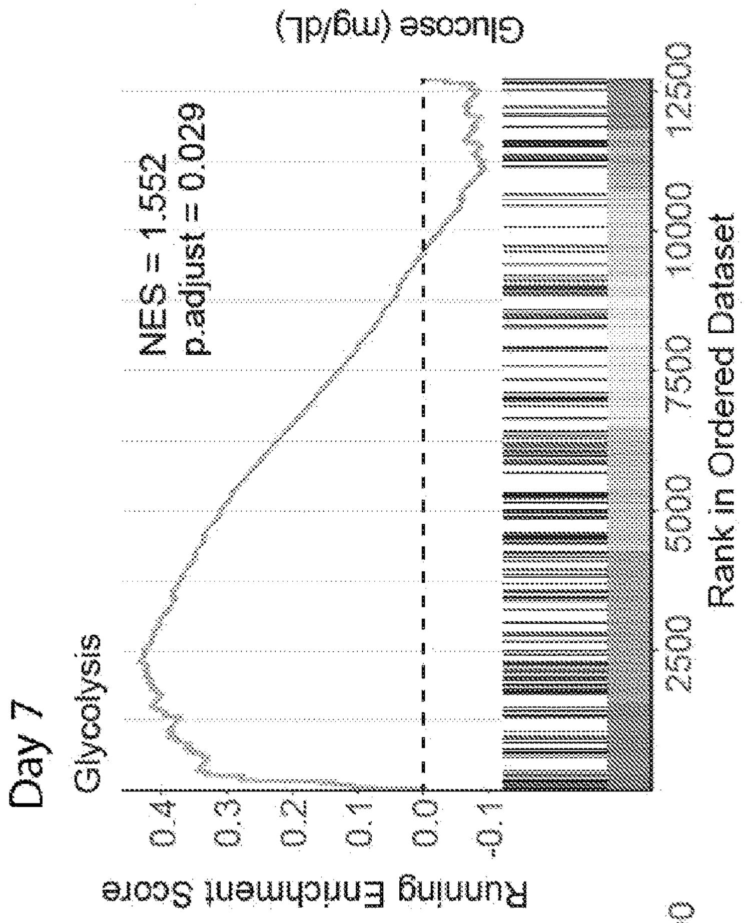
(FIG. 13E) GSEA of glycolysis in NK cells that were expanded with 221-mIL21 feeder cells compared to those that were expanded with K562-mIL21 feeder cells on day 7 using Hallmark datasets in the MSigDB. NES, normalized enrichment score; p.adjust, FDR-adjusted p-value.
Figure 13D:
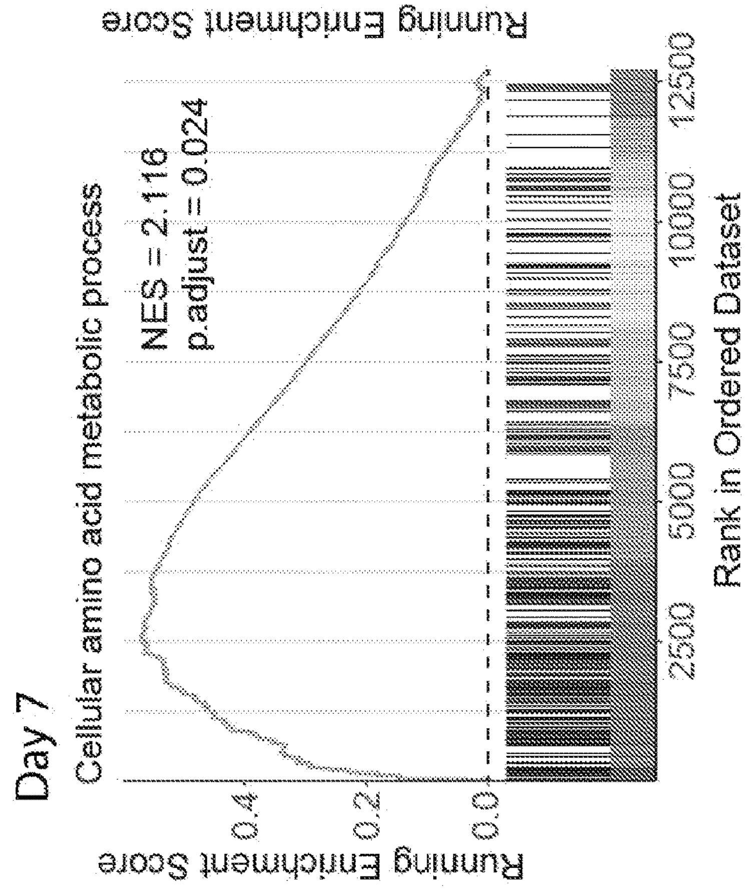
(FIG. 13D) Gene set enrichment analysis (GSEA) of cellular amino acid metabolic processes in NK cells that were expanded with 221-mIL21 feeder cells compared to those that were expanded with K562-mIL21 feeder cells on day 7 using gene ontology (GO) biological process (BP) datasets in the Molecular Signatures Database (MSigDB). NES, normalized enrichment score; p.adjust, false discovery rate (FDR)-adjusted p-value.
Figure 13G:
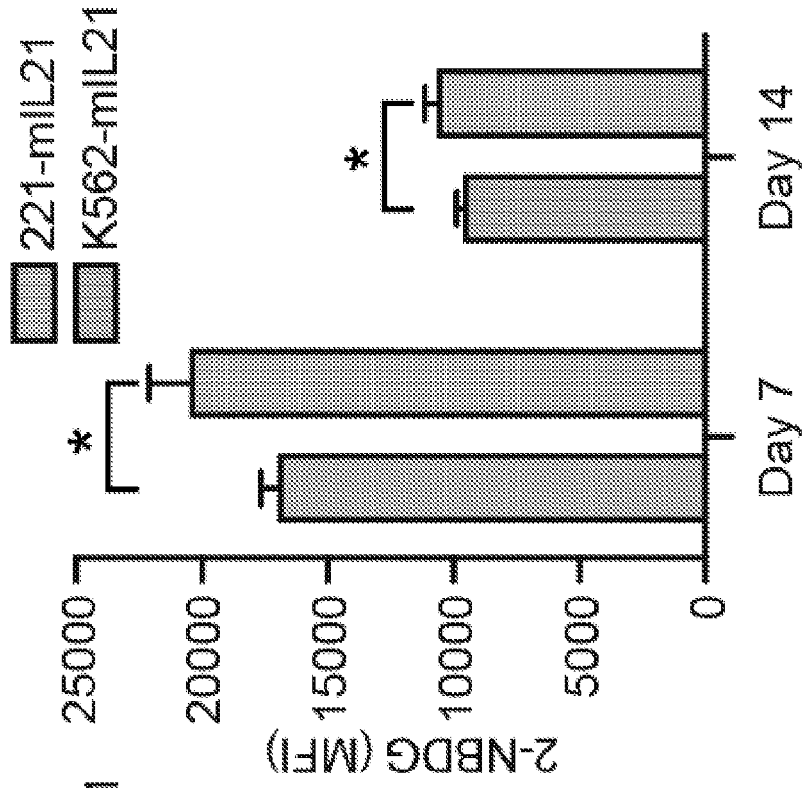
(FIG. 13G) Quantitative glucose uptake comparison of NK cells expanded with K562-mIL21 or with 221-mIL21 feeder cells on day 7 and day 14.
Figure 13F:
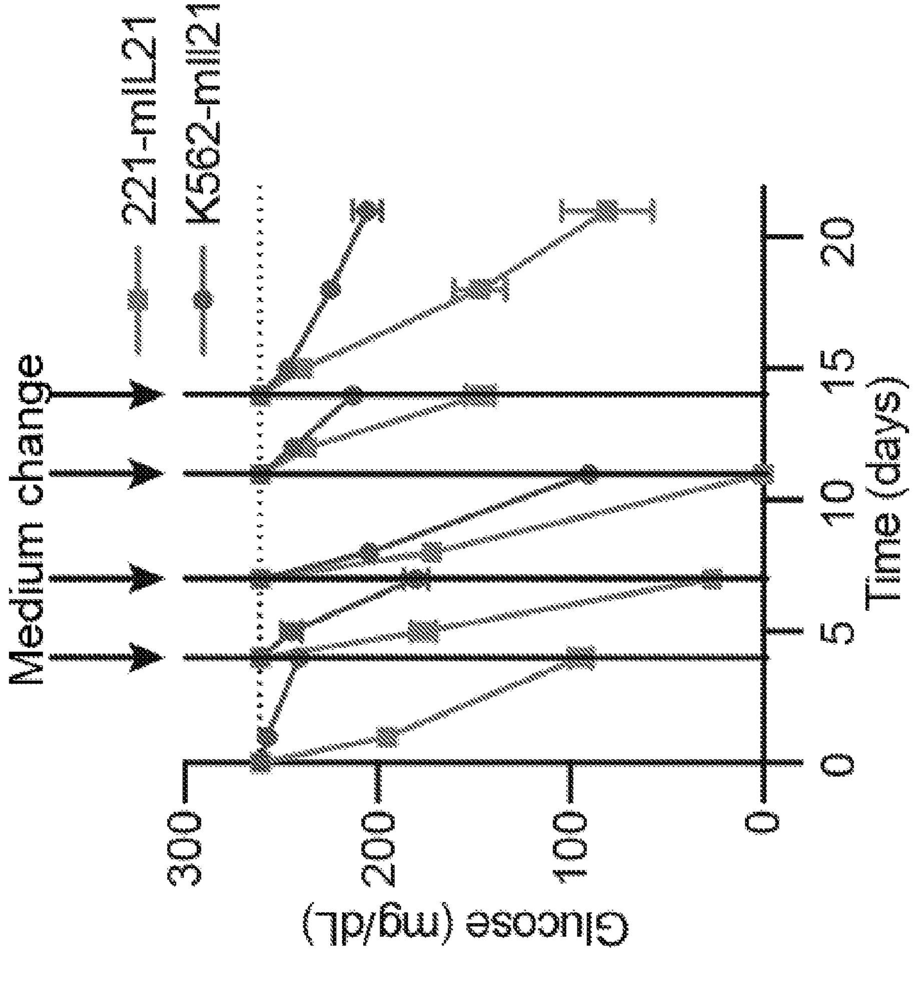
(FIG. 13F) Dynamic level of glucose in the media during NK cell expansion using either K562-mIL21 and 221-mIL21 as feeder cells. Arrows indicate the time points for media change.
Figure 18A:
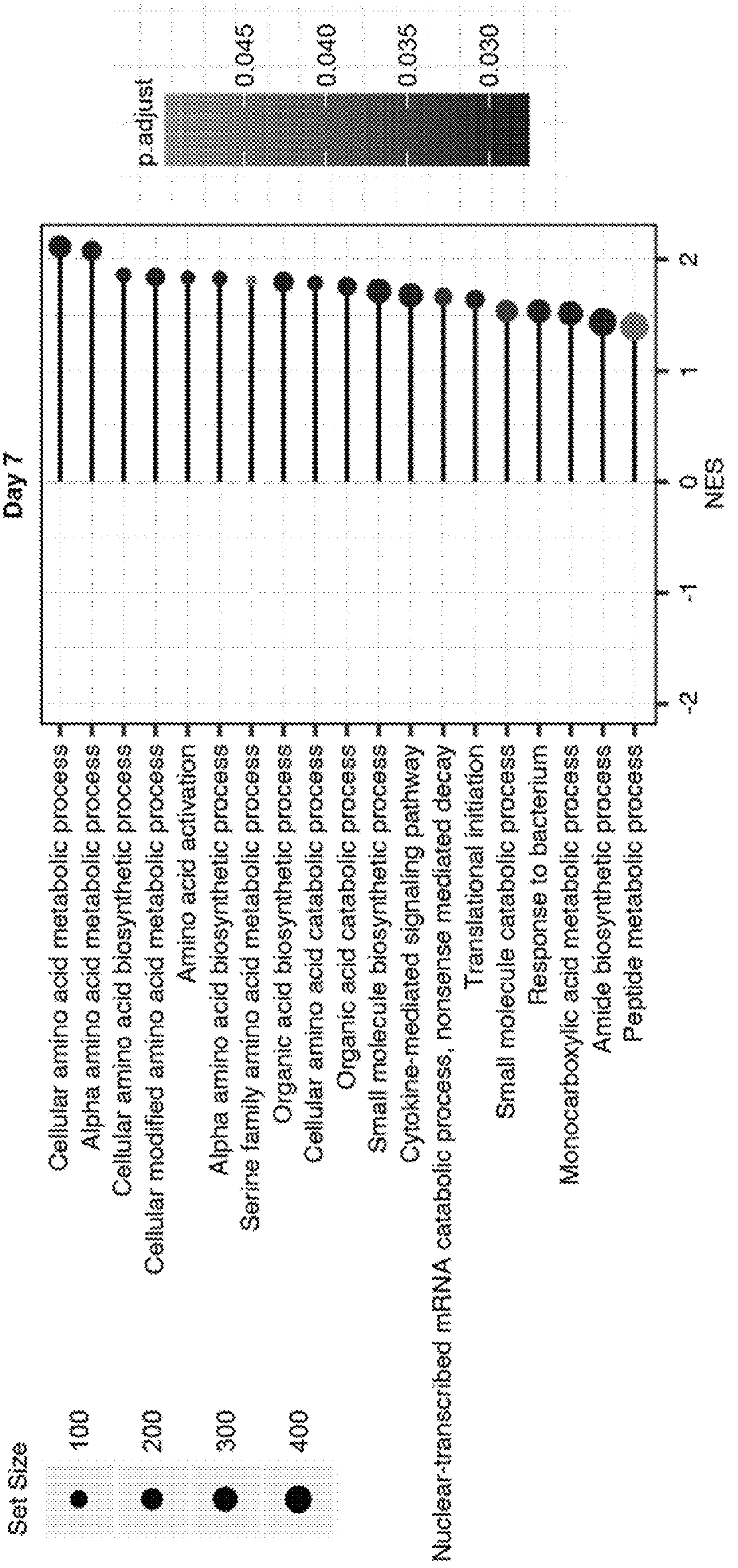
FIGS. 18A-18I. Enriched Metabolic pathways and immune Phenotypes of 221-expanded NK cells.
Figure 18B:
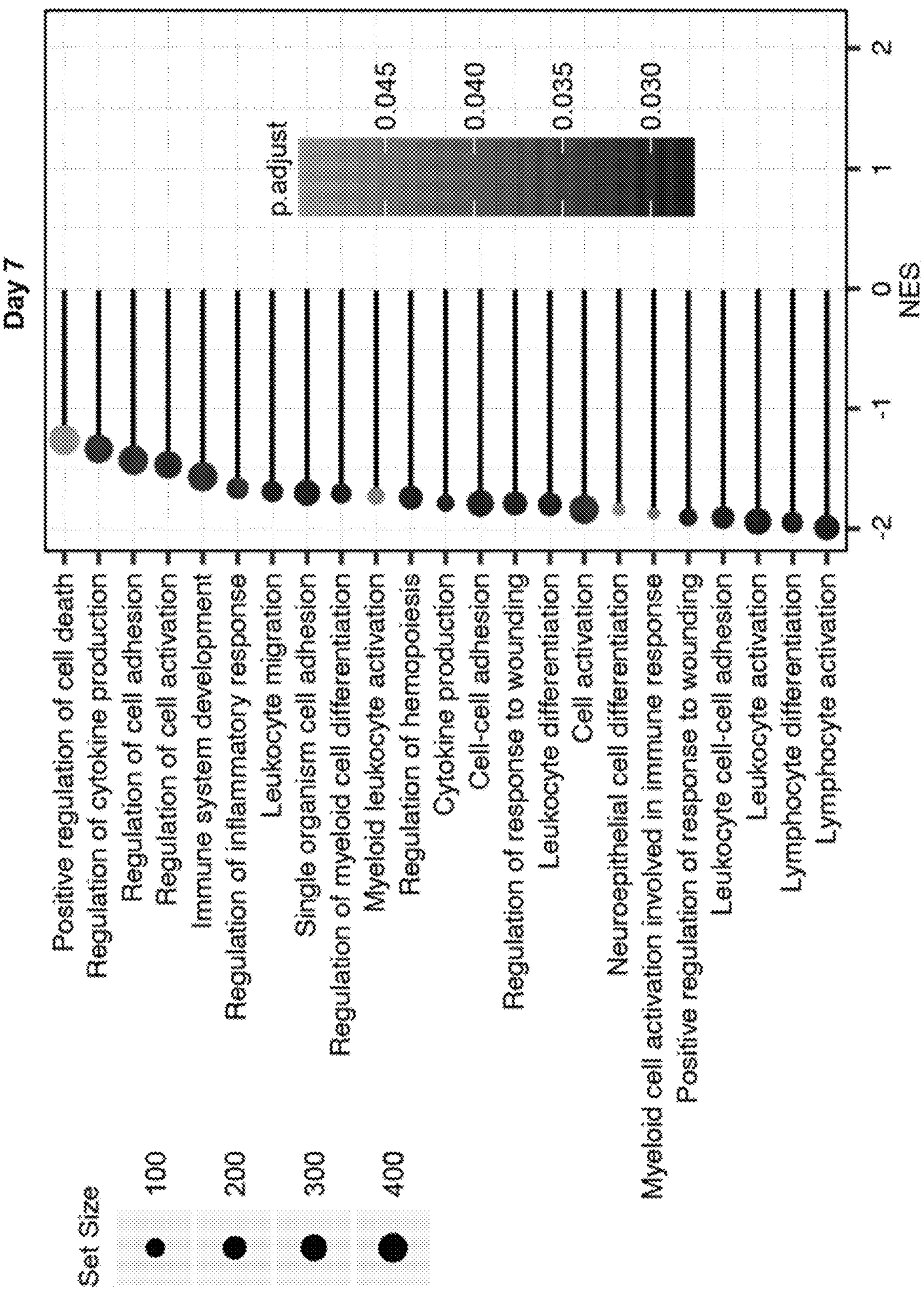
Figure 18C:
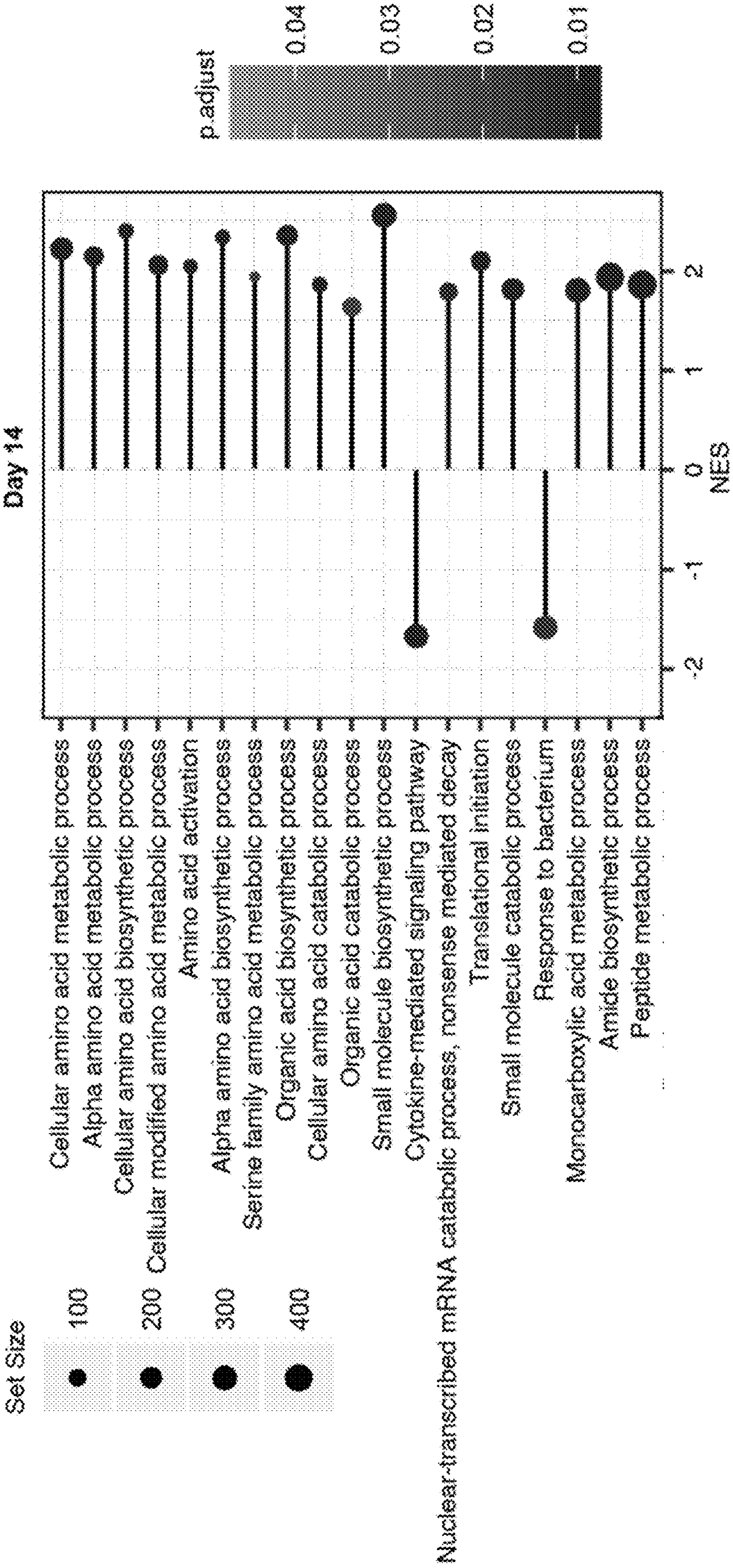
Figure 18D:
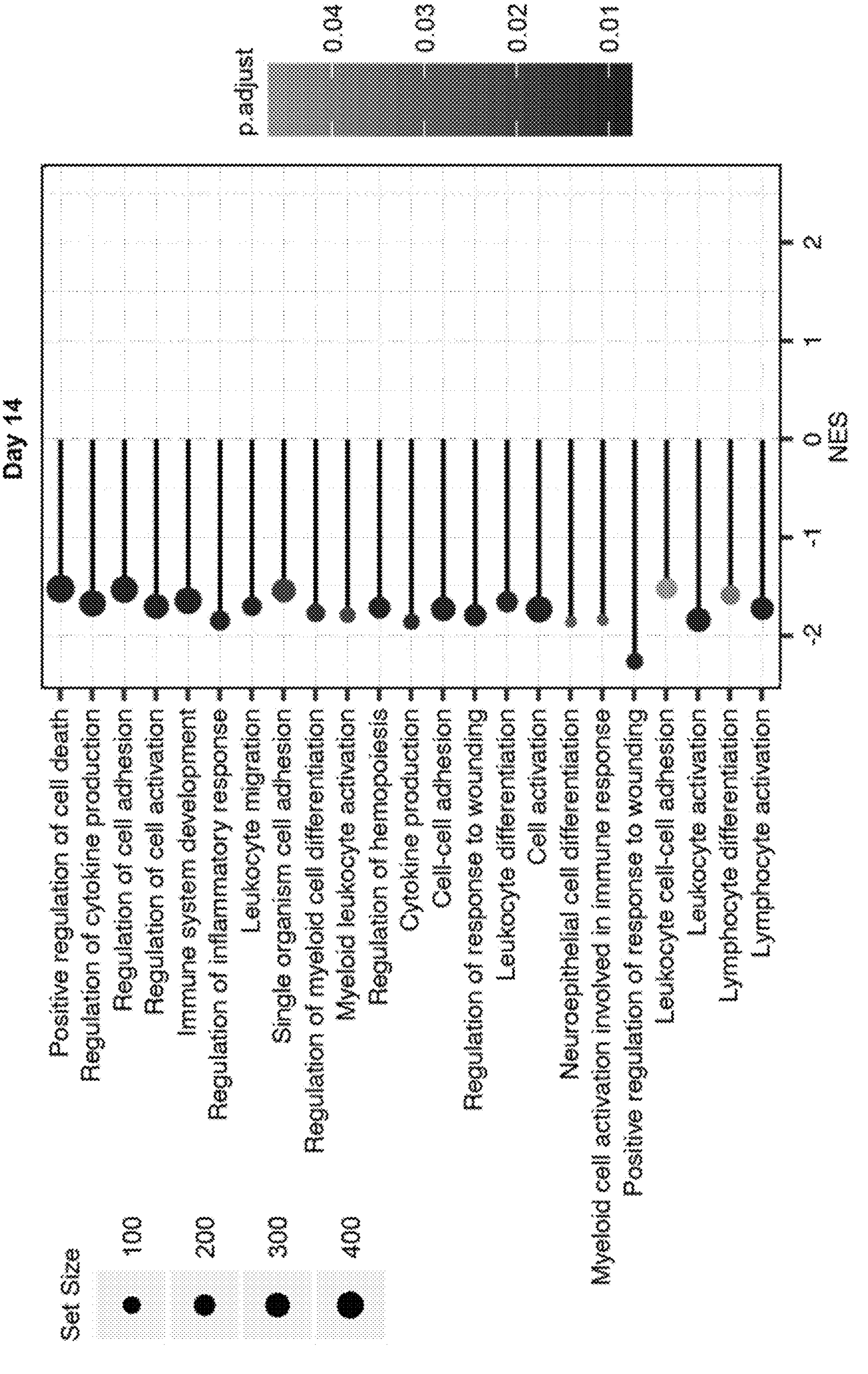
Figure 18F:
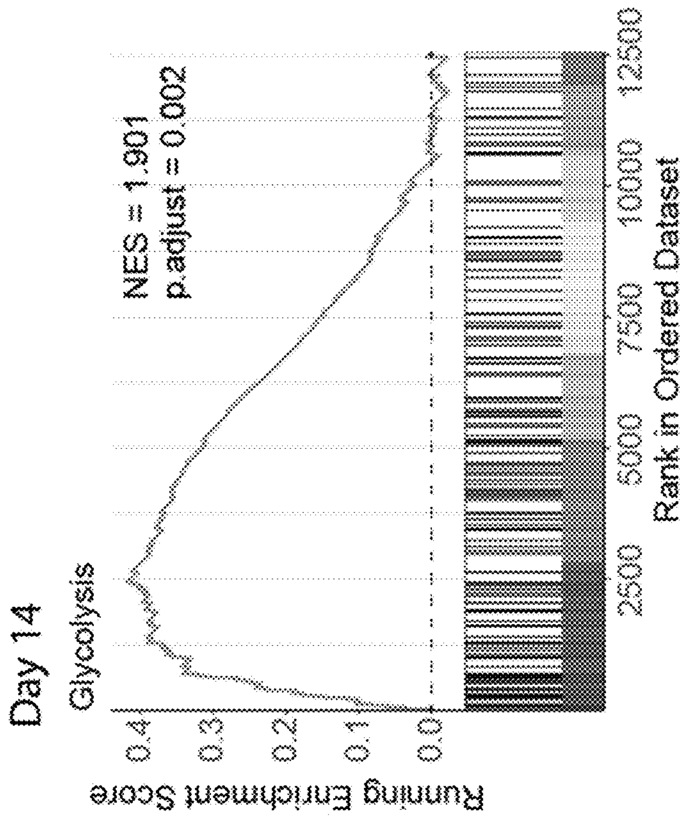
Figure 18E:
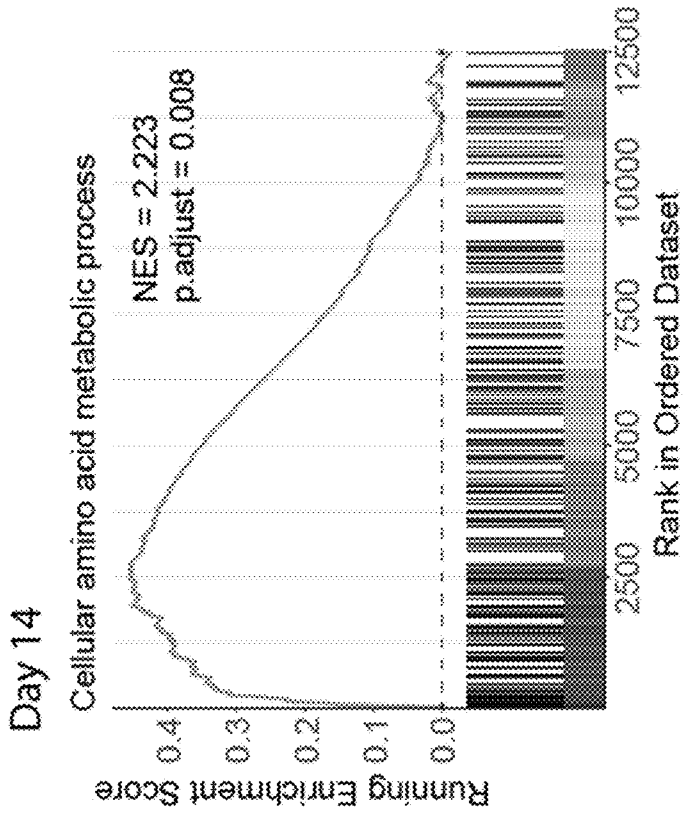
Figure 18H:
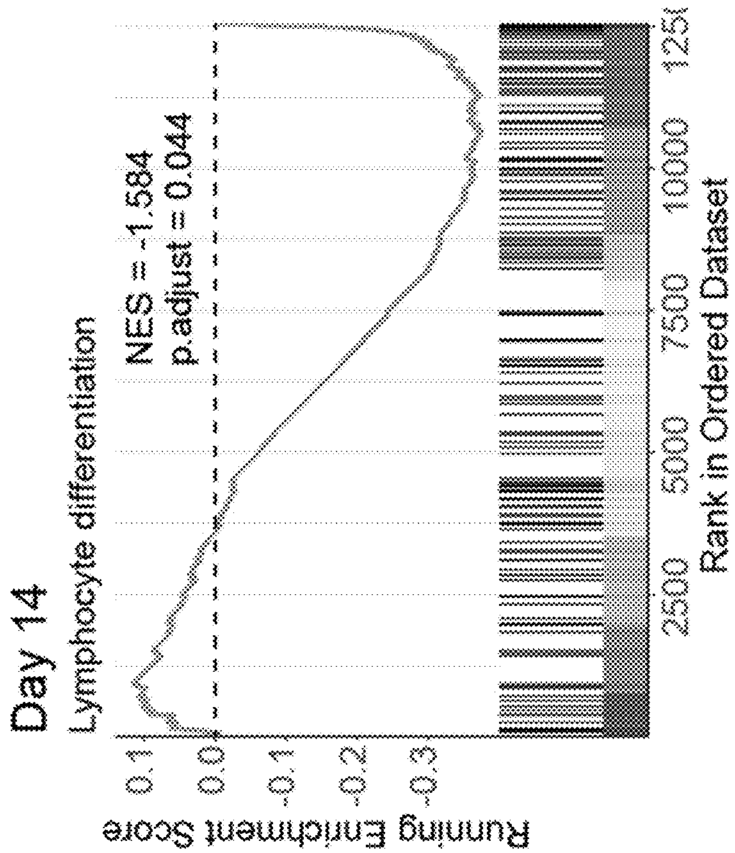
Figure 18G:
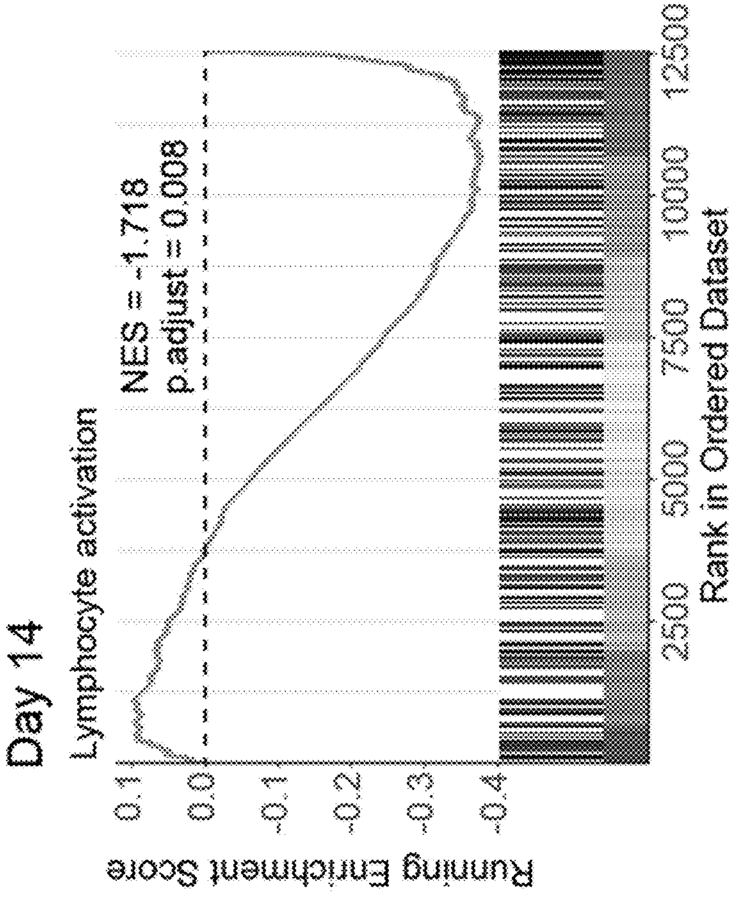
Figure 18I:
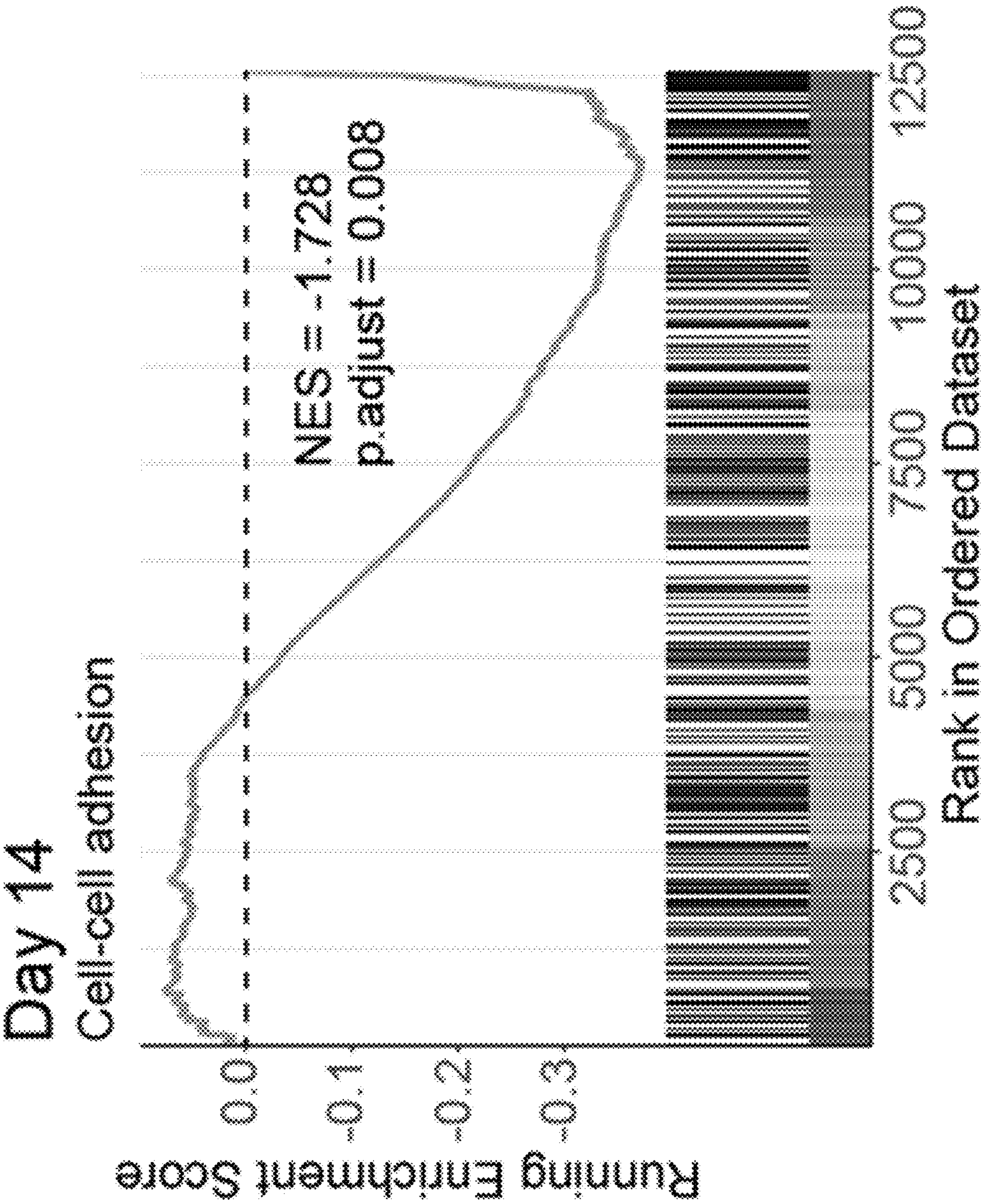
Figure 19A:
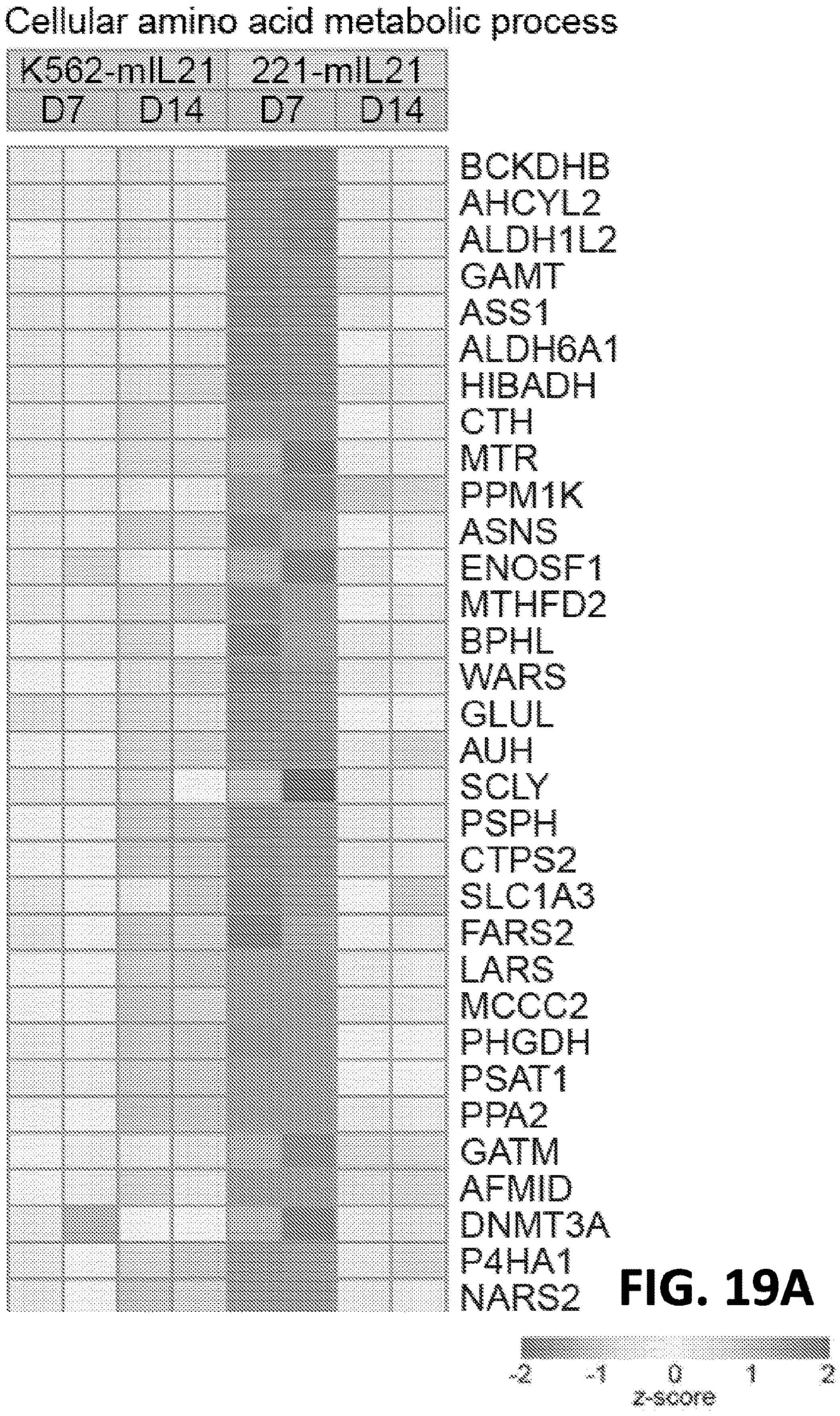
FIGS. 19A-19I. Heat maps of enriched metabolic pathways and immune phenotypes of expanded NK cells.
Figure 19B:
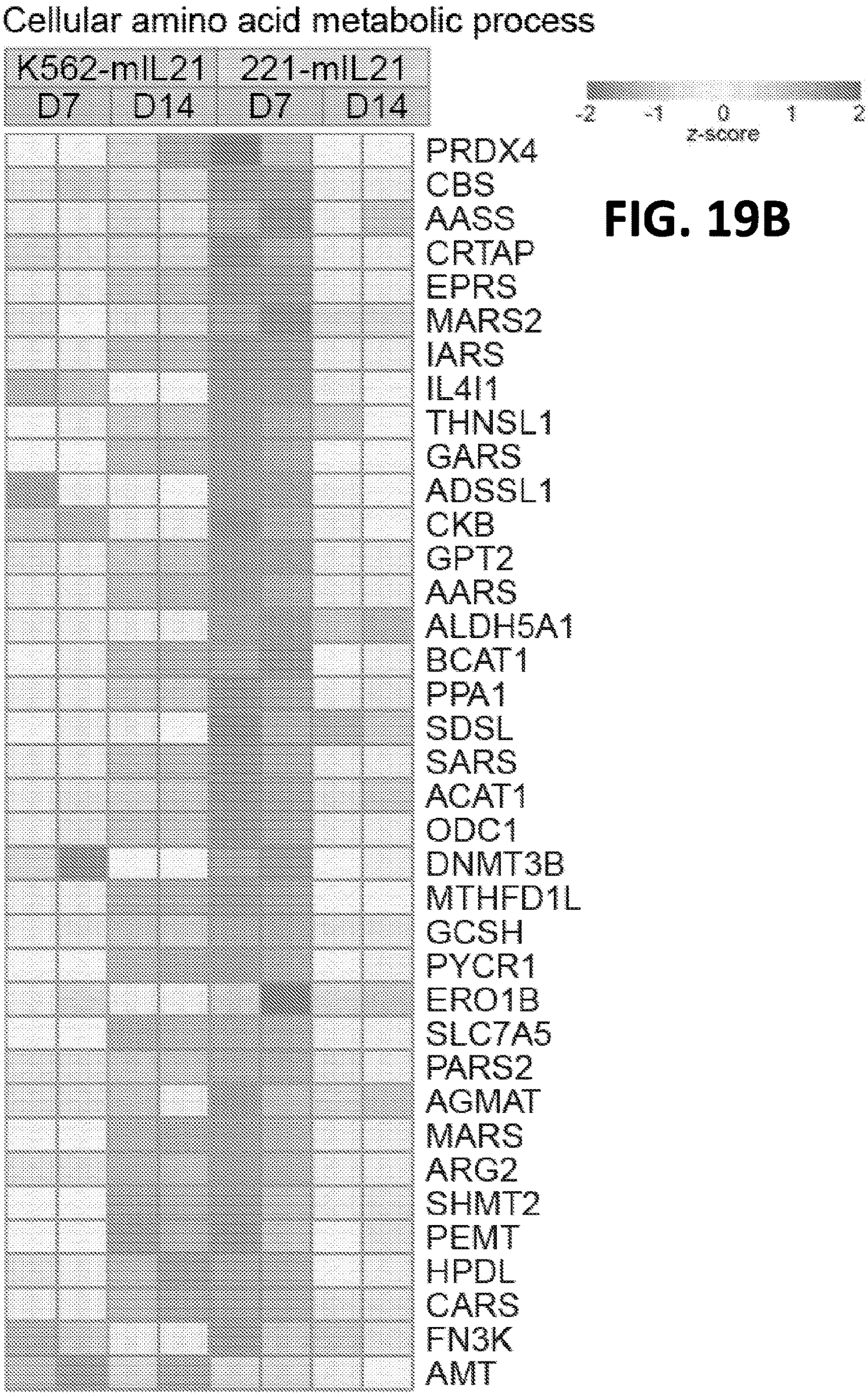
Figure 19C:
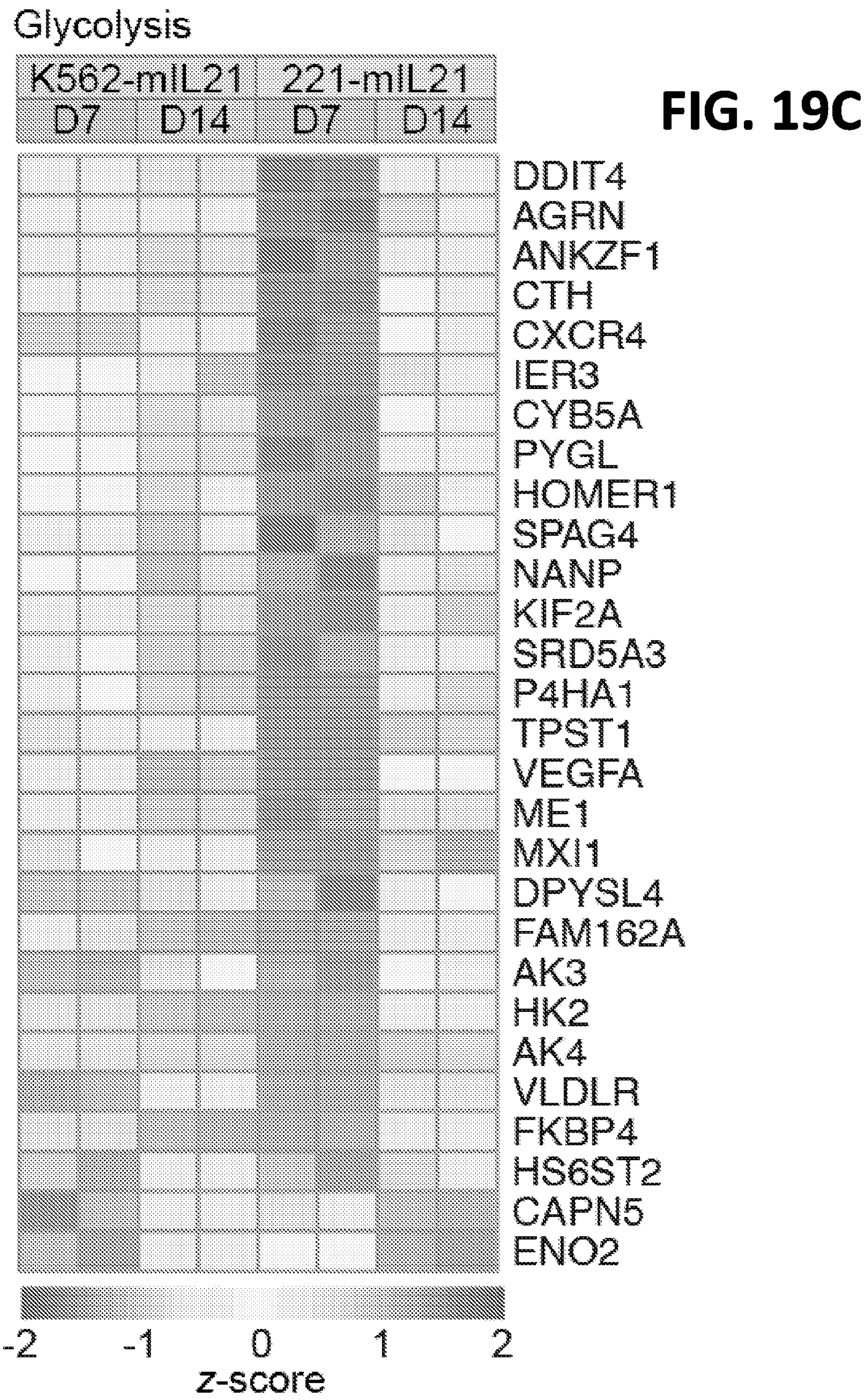
Figure 19D:
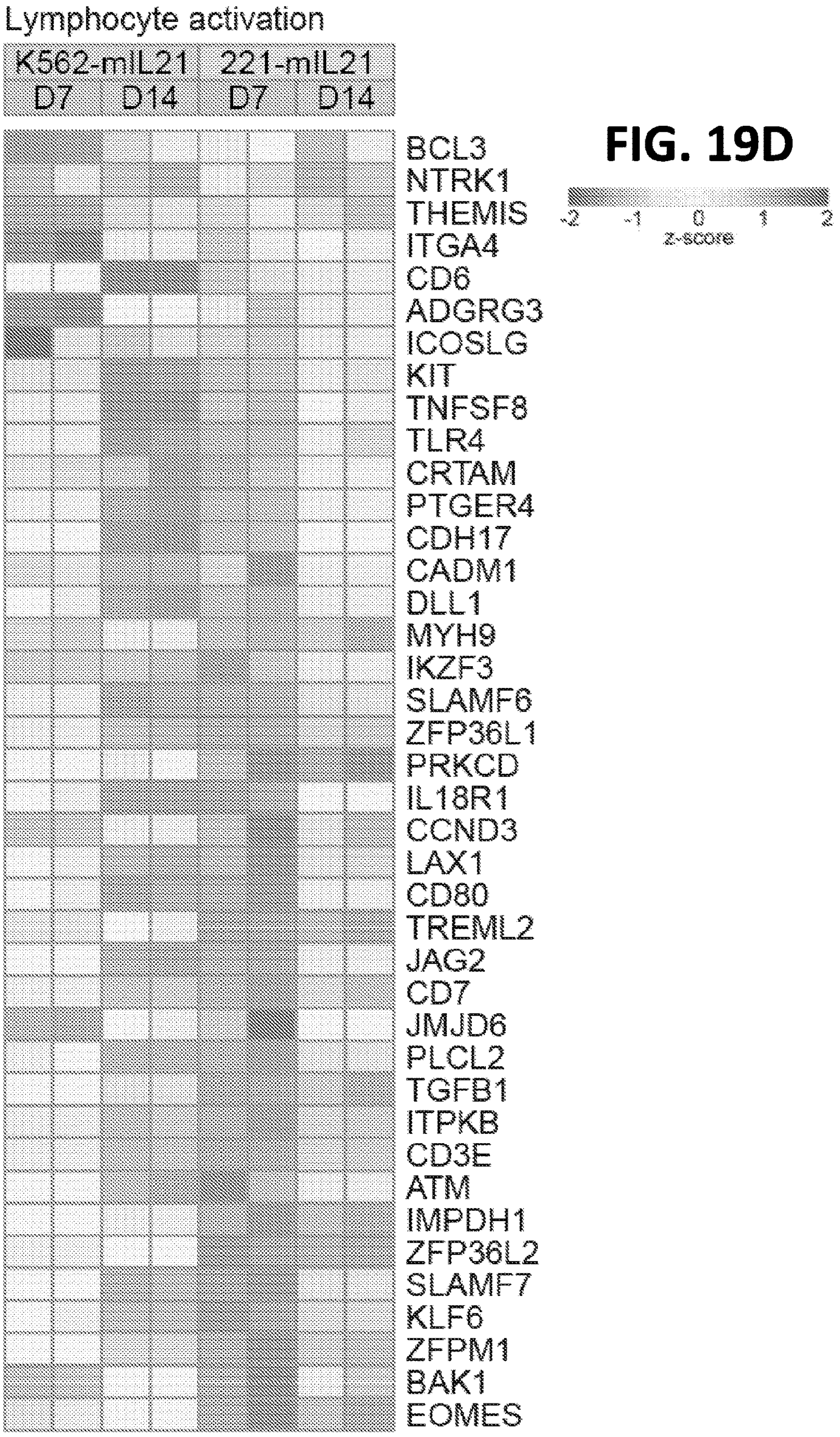
Figure 19E:
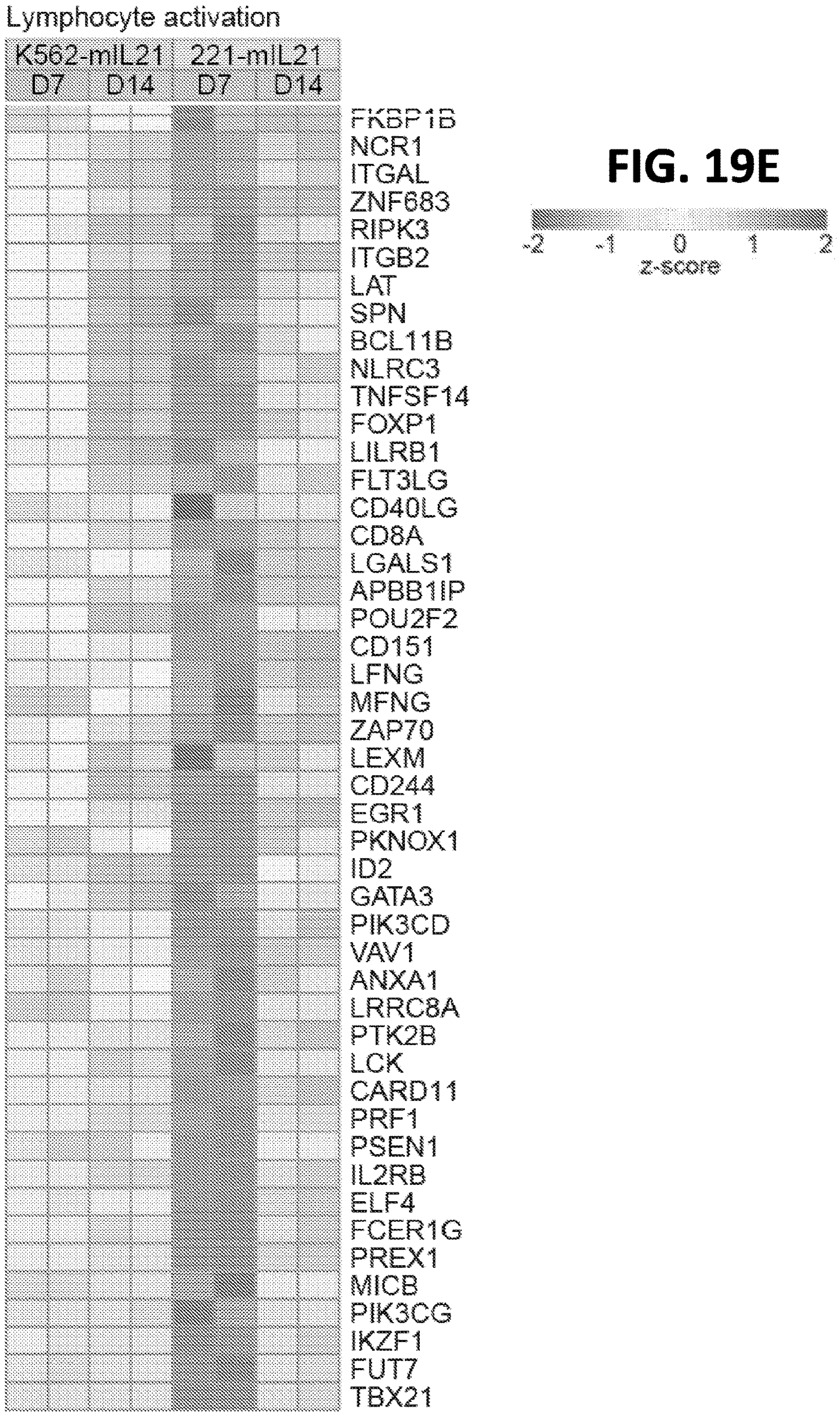
Figure 19F:
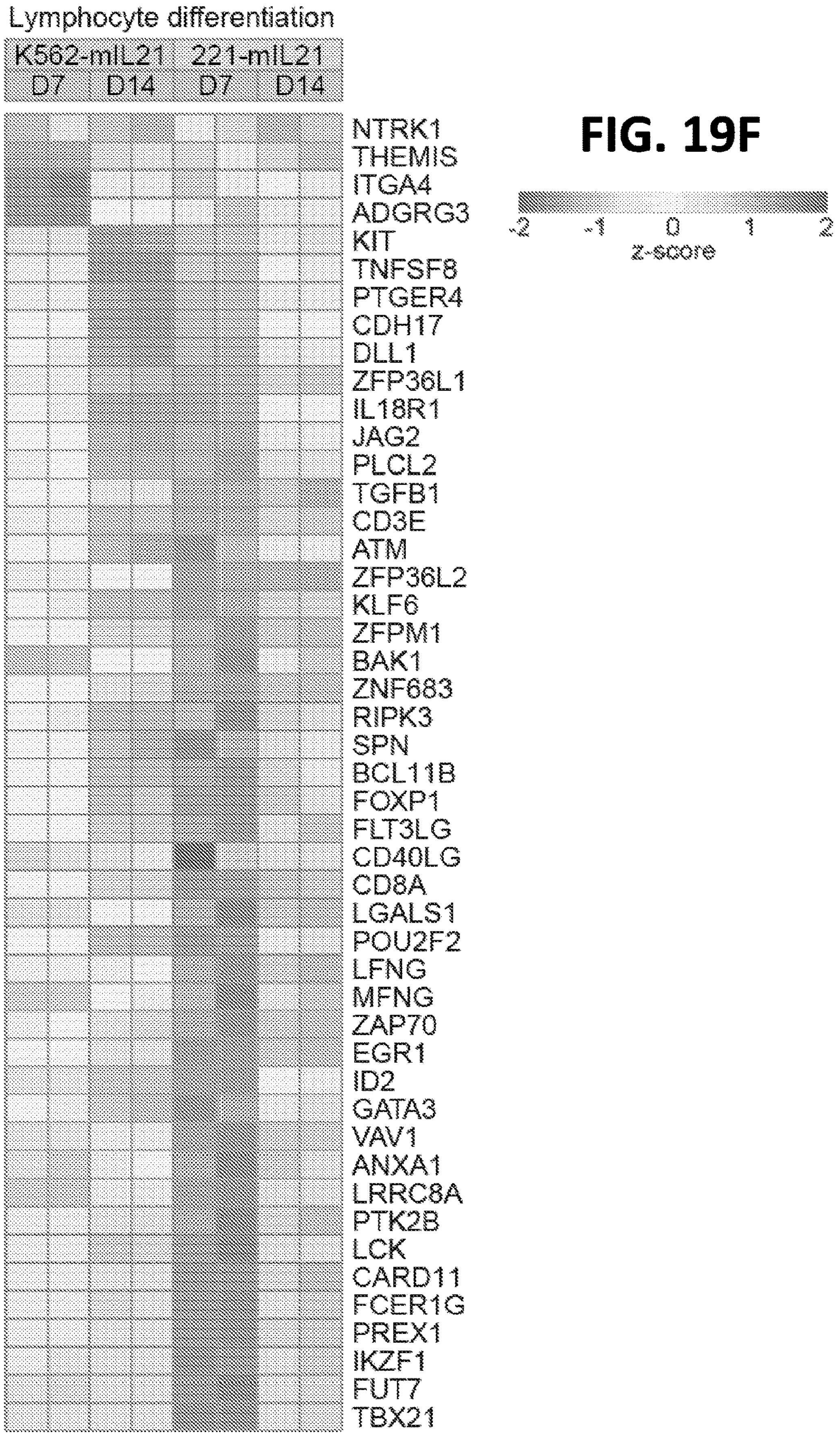
Figure 19G:
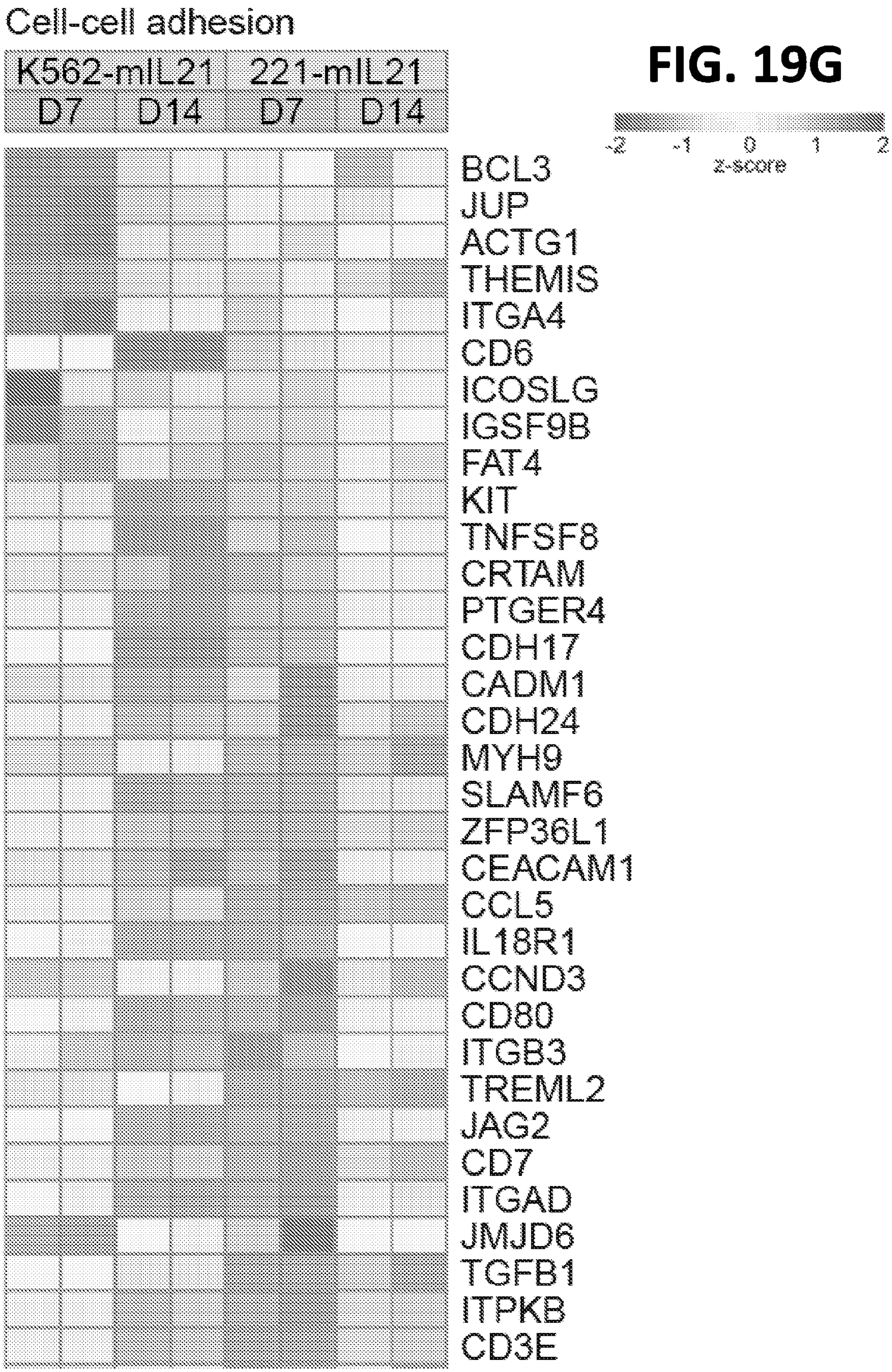
Figure 19H:
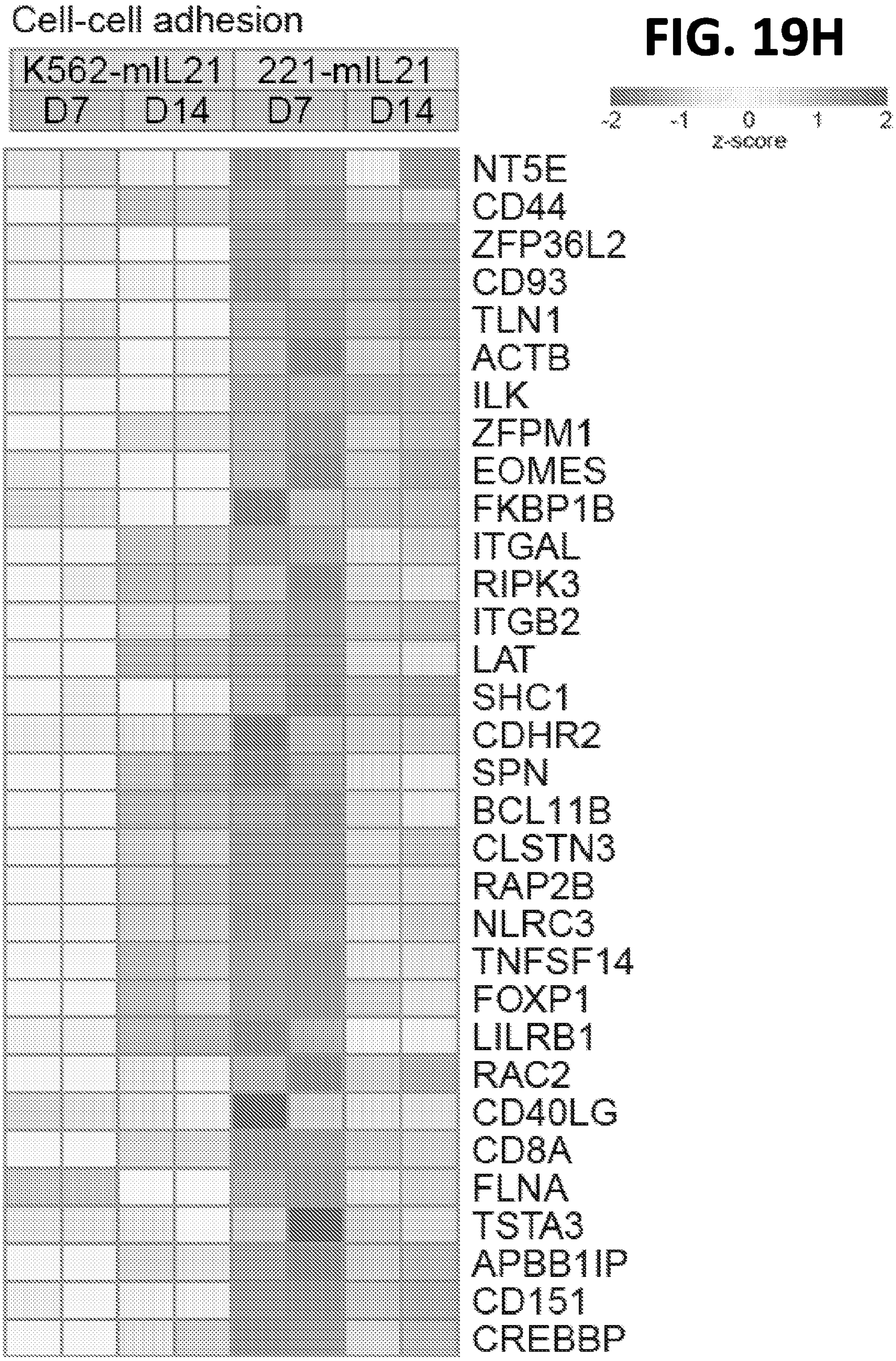
Figure 19I:
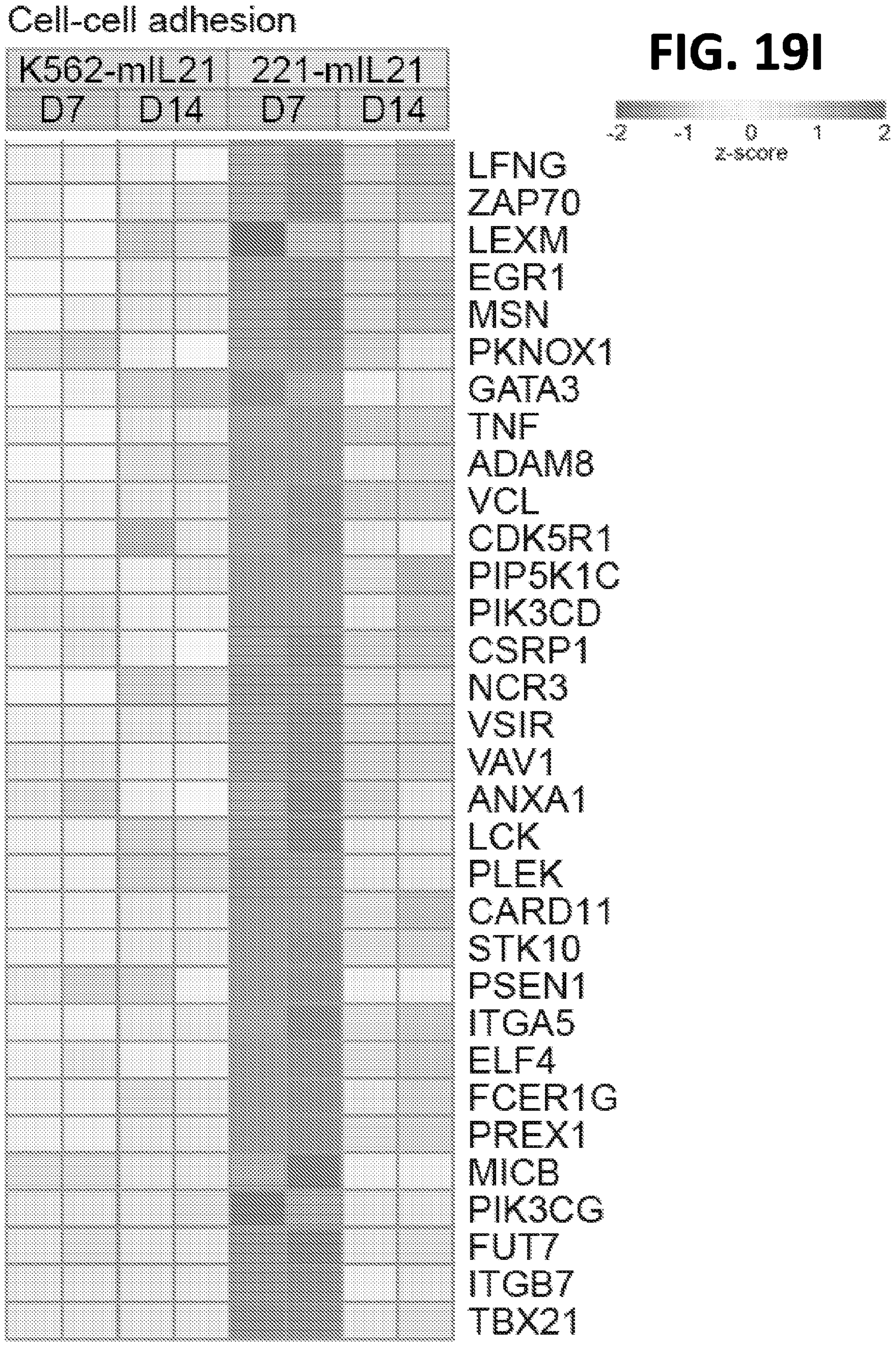

Therefore, the following RNA-Seq data analysis was focused on data at day 7. The numbers of differentially expressed genes (DEGs) in NK cells that were expanded with 221-mIL21 feeder cells on day 7 by mean average (MA) plots were significantly increased compared with those of NK cells expanded with K562-mIL21 on day 14 (FIGS. 13B and 13C). Gene set enrichment analysis (GSEA) using gene ontology (GO) biological process (BP) datasets and hallmark datasets in the Molecular Signatures Database (MSigDB) showed that gene signatures associated with cellular amino acid metabolic process and glycolysis were upregulated in NK cells that were expanded with the 221-mIL21 feeder cell expansion system on day 7 compared to NK cells expanded with the K562-mIL21 feeder cell expansion system, which has been further verified by glucose uptake assays (FIG. 13D-13H; FIGS. 18A-18C; FIGS. 19A-19C).

Figure 13H:
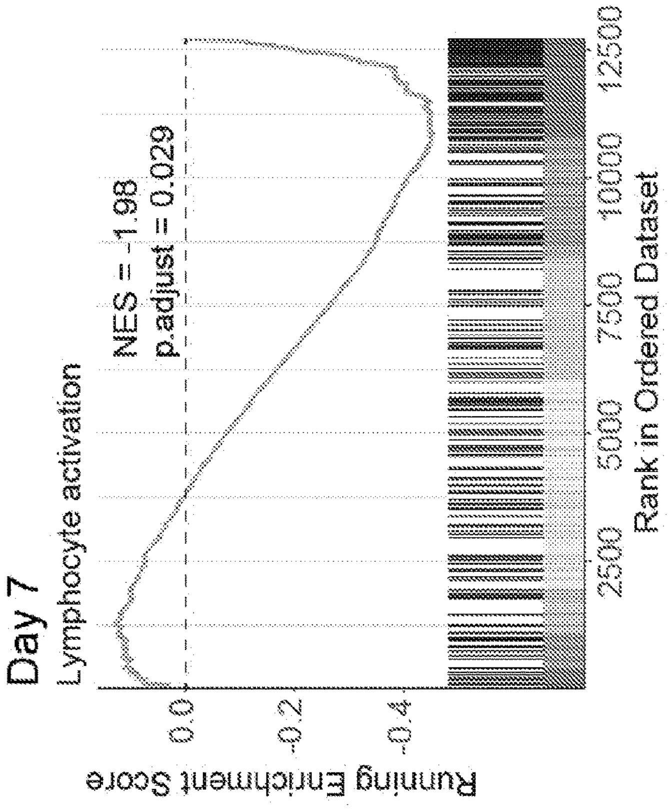
(FIG. 13H) GSEA of lymphocyte activation in NK cells that were expanded with 221-mIL21 feeder cells compared to those that were expanded with K562-mIL21 feeder cells on day 7 using GO_BP datasets in the MSigDB. NES, normalized enrichment score; p.adjust, FDR-adjusted p-value.
Figure 13I:
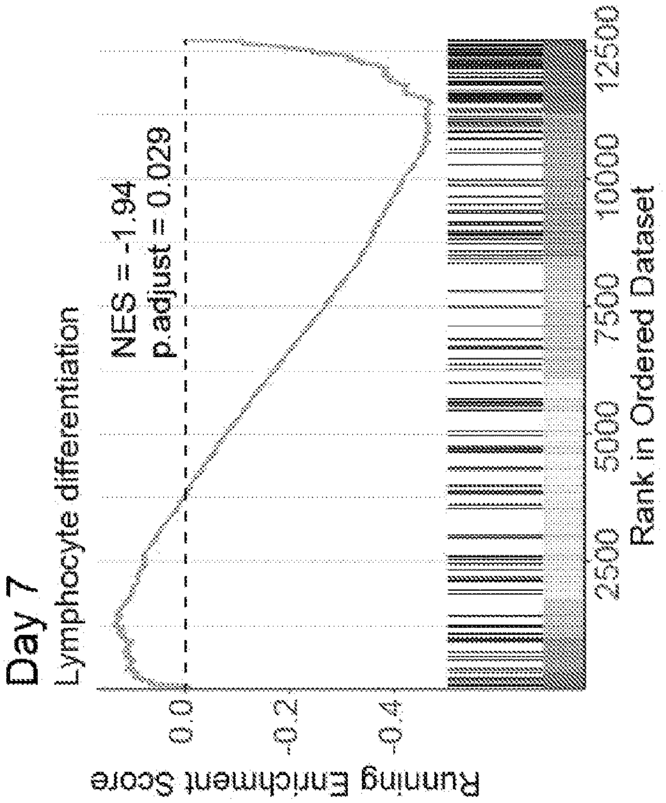
(FIG. 13I) GSEA of lymphocyte differentiation in NK cells that were expanded with 221-mIL21 feeder cells compared to those that were expanded with K562-mIL21 feeder cells on day 7 using GO_BP datasets in the MSigDB. NES, normalized enrichment score; p. adjust, FDR-adjusted p-value.
Figure 13J:
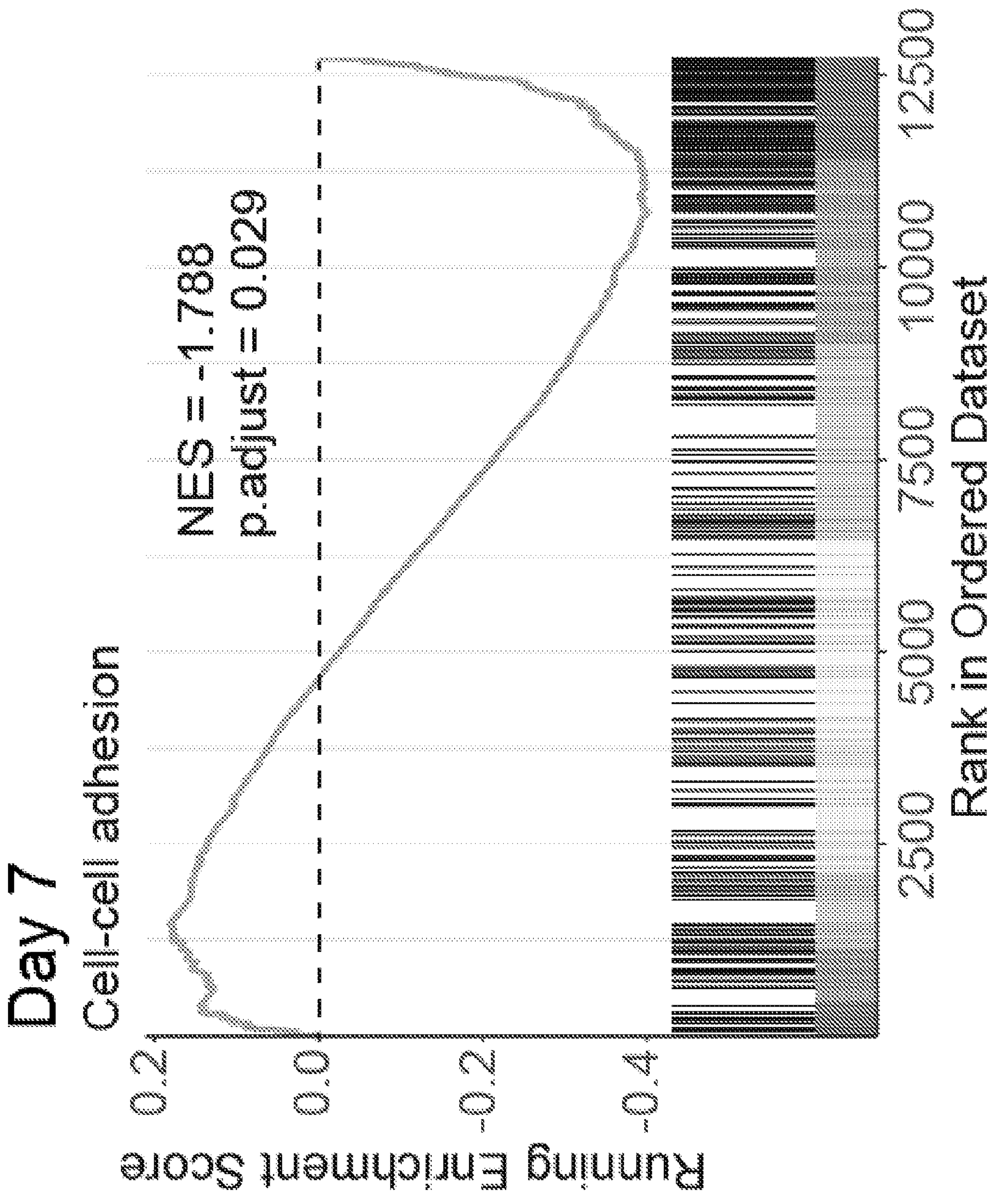
(FIG. 13J) GSEA of cell-cell adhesion in NK cells that were expanded with 221-mIL21 feeder cells compared to those that were expanded with K562-mIL21 feeder cells on day 7 using GO_BP datasets in the MSigDB. NES, normalized enrichment score; p. adjust, FDR-adjusted p-value.
Figure 13K:
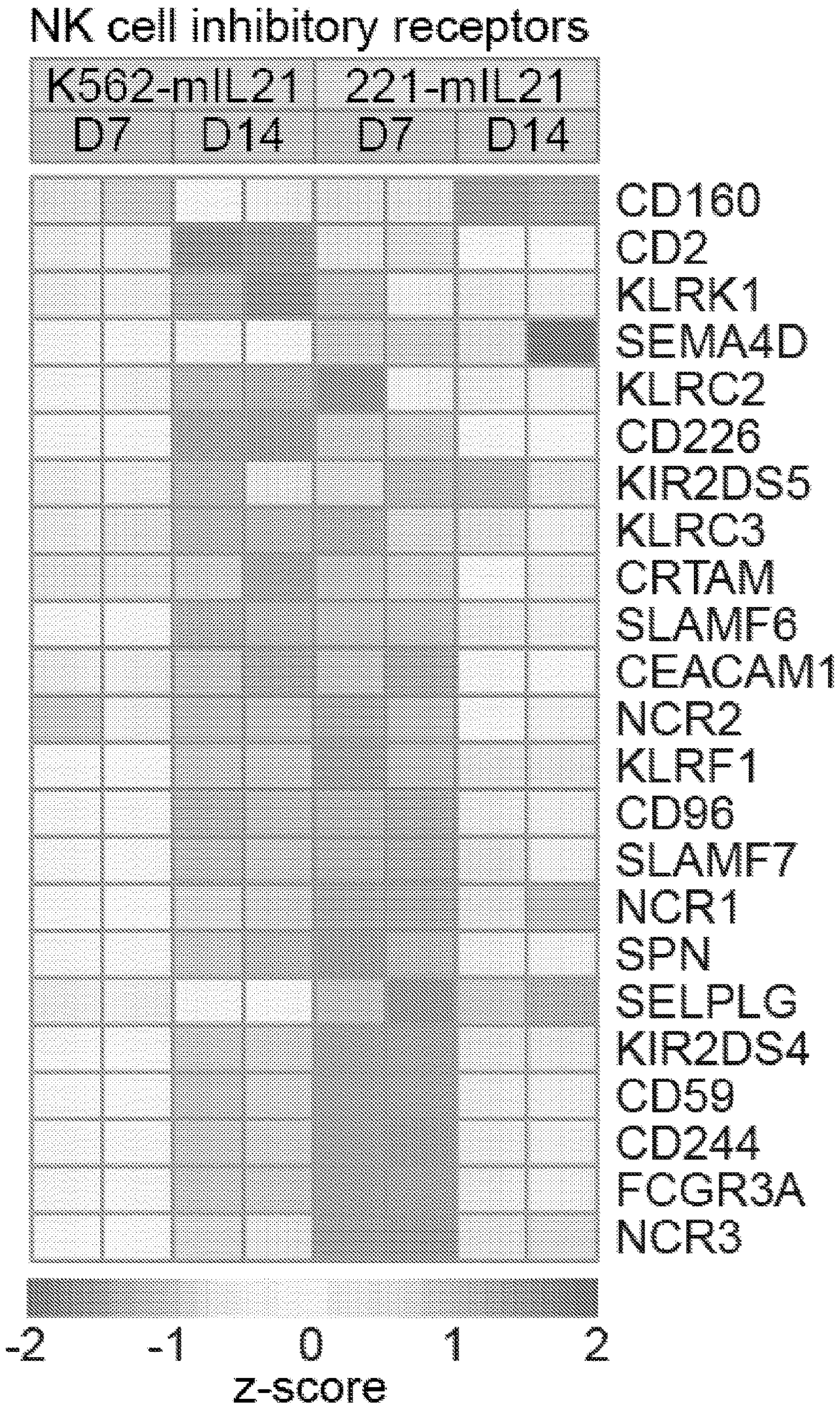
(FIG. 13K) Heat map of inhibitory receptor of NK cells.
Figure 13L:
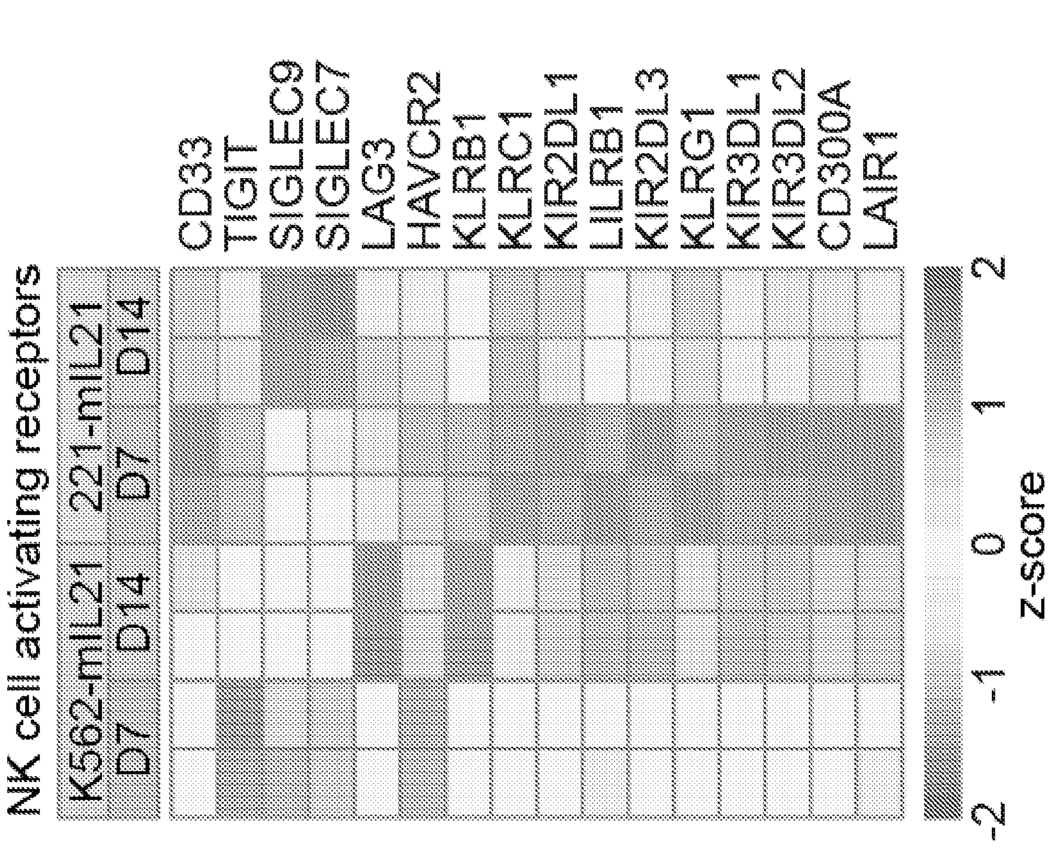
(FIG. 13L) Heat map of activating receptor of NK cells.
Figure 13M:
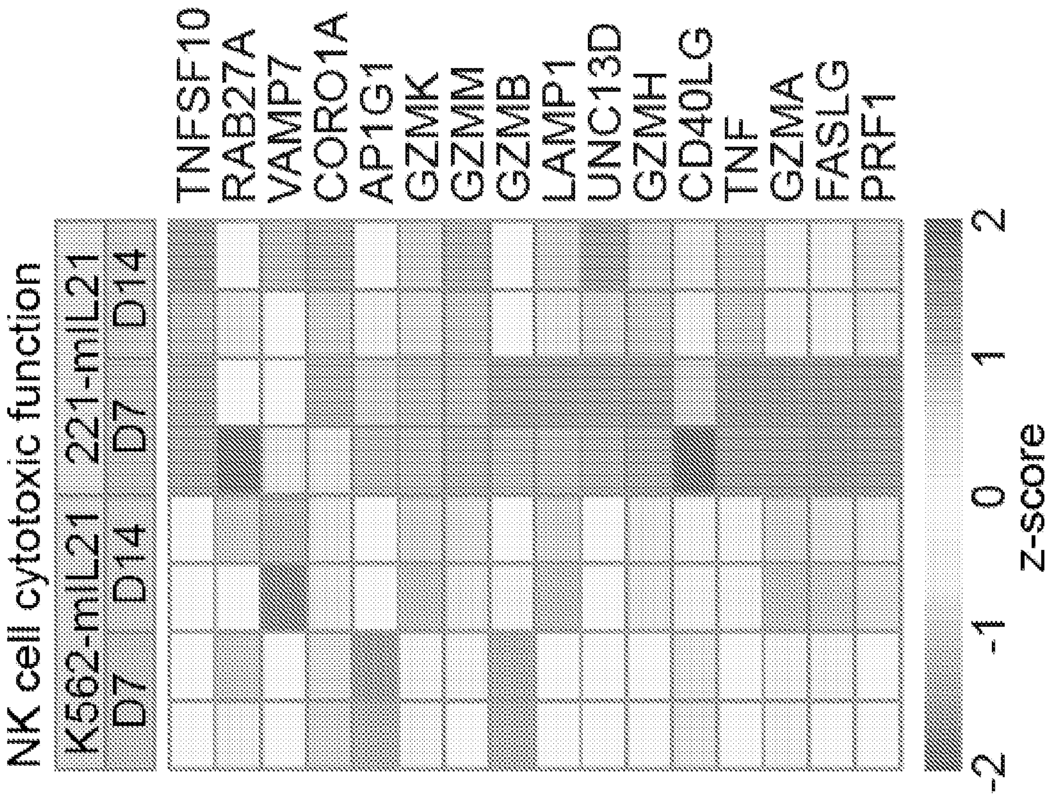
(FIG. 13M) Heat map of genes associated with cytotoxic function of NK cells.
Figure 13N:
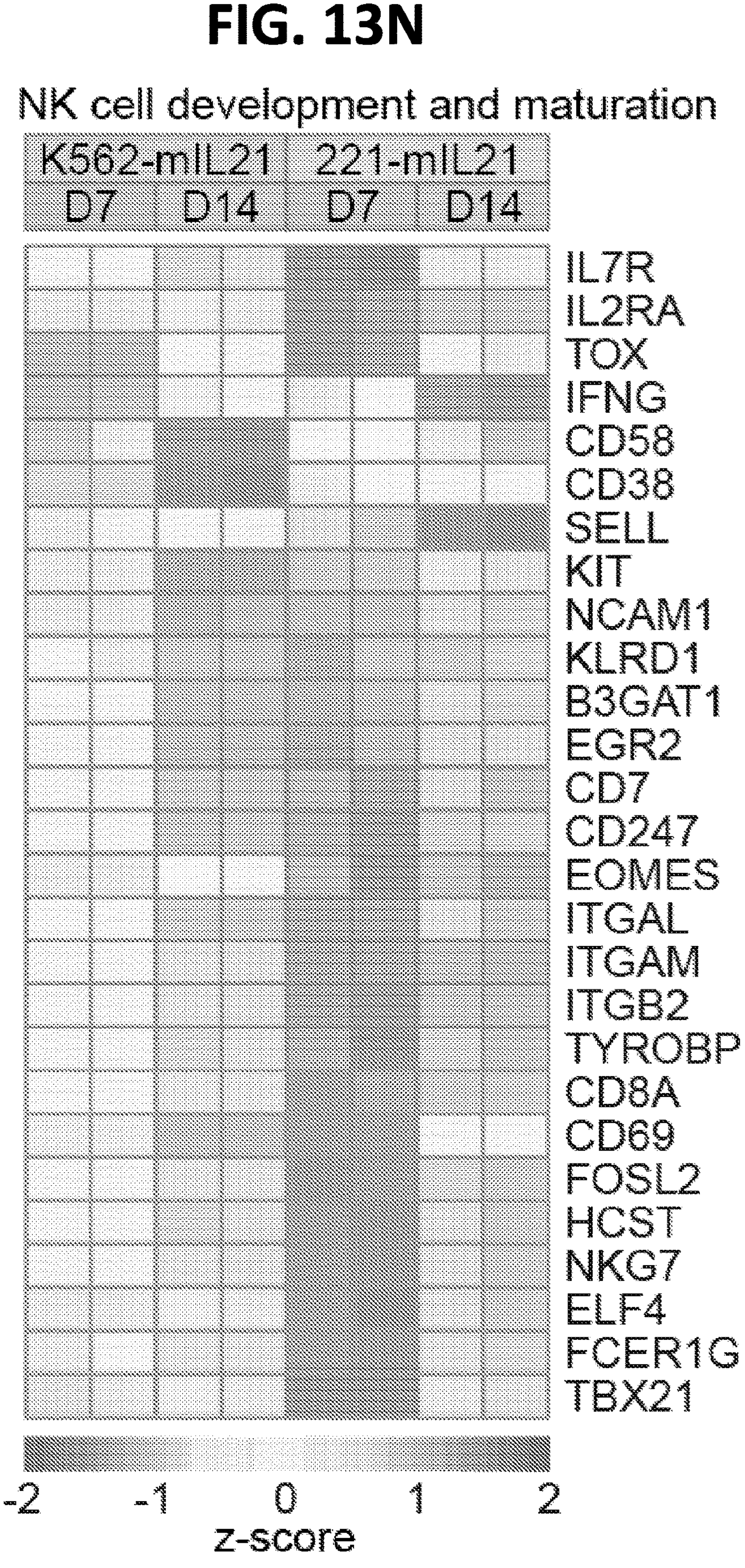
Figure 14B:
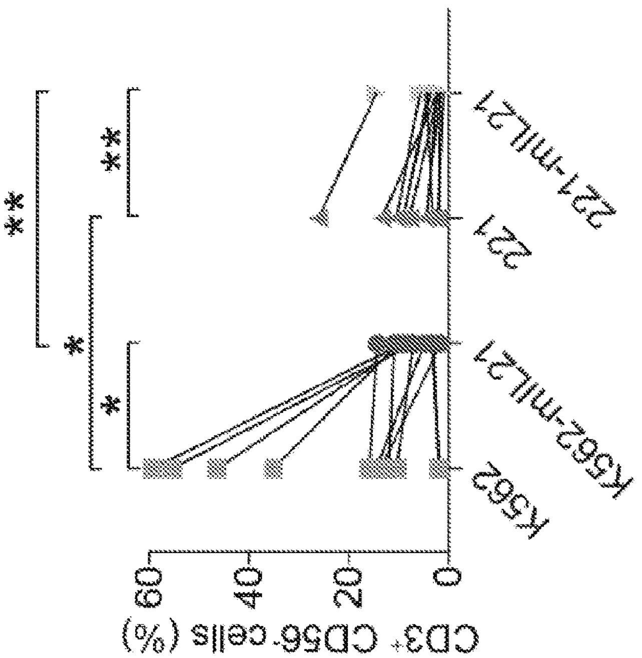
FIGS. 14A-14F. Dynamics of different cell population expansions among different types of feeder cell expansion systems.
Figure 14A:
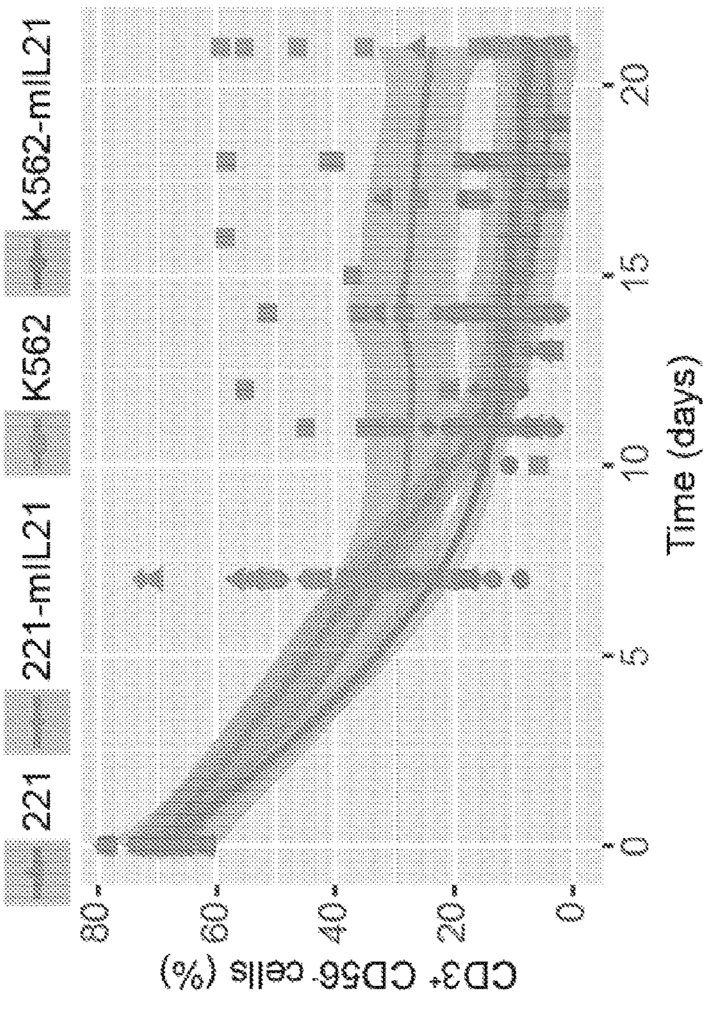
Figure 14C:
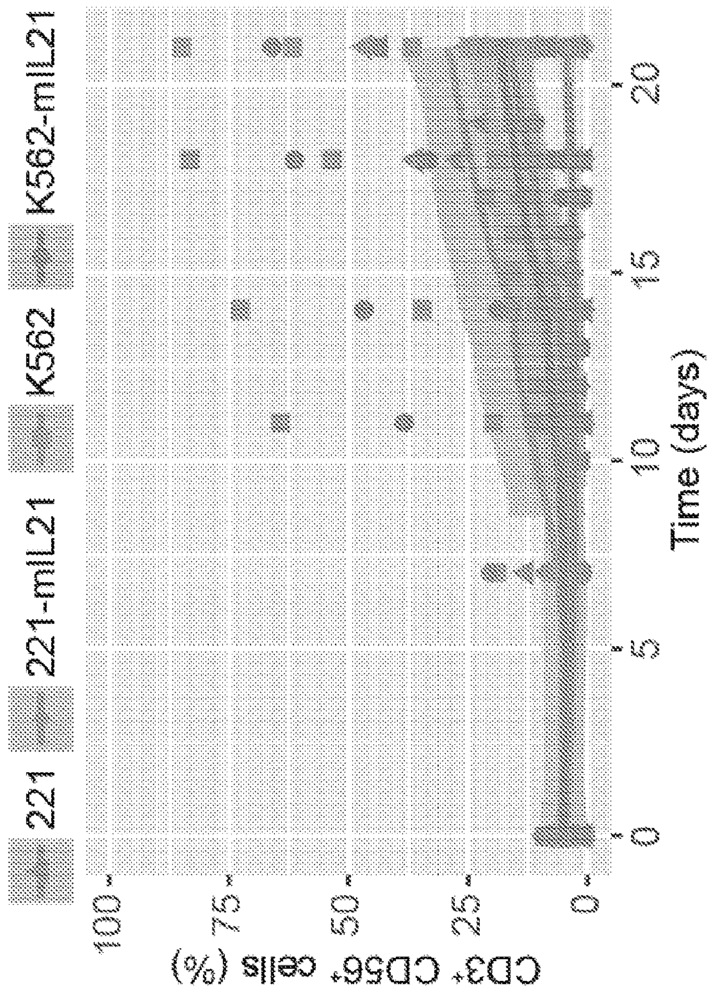
Figure 14D:
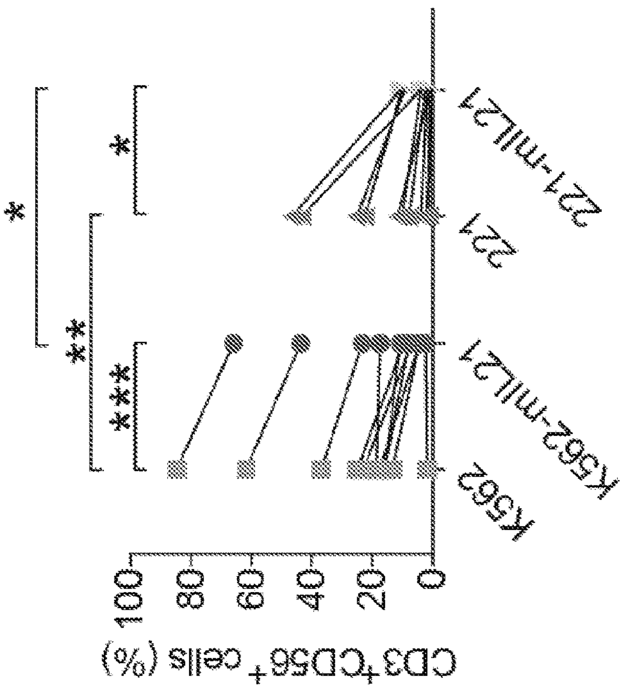
Figure 14F:
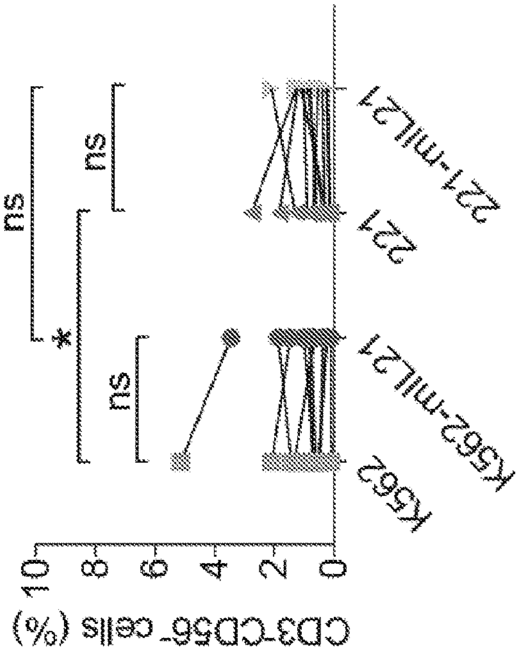
Figure 14E:
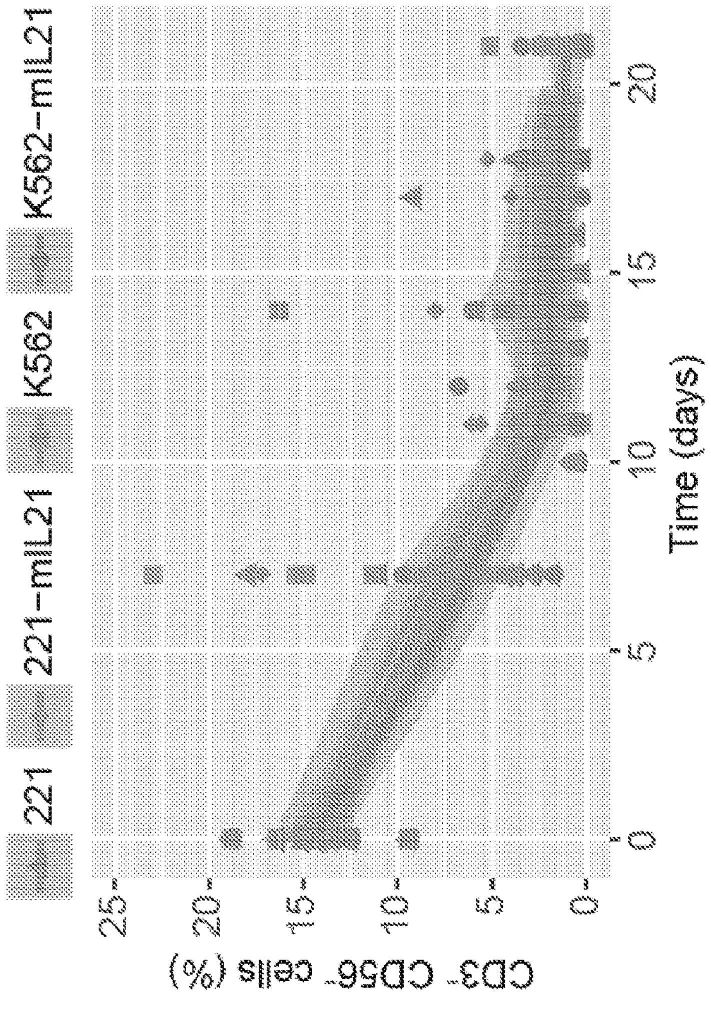
Figure 15A:
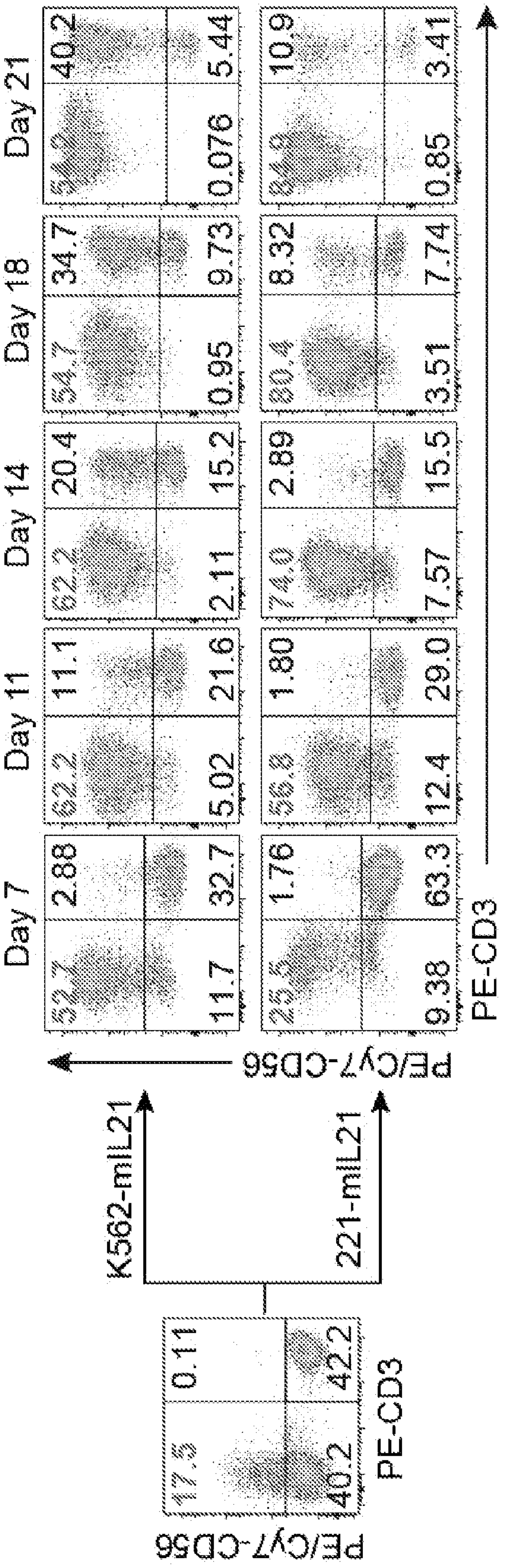
FIGS. 15A-15K. Figure S7. Improved cord blood derived NK cell expansion using 221-mIL21 cells.
Figure 15C:
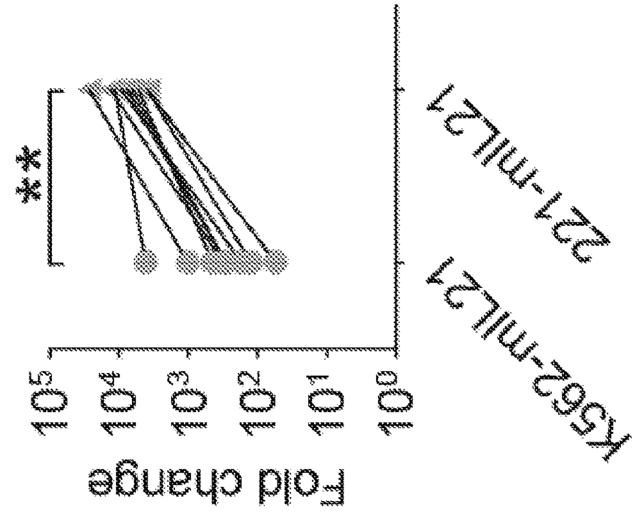
Figure 15B:
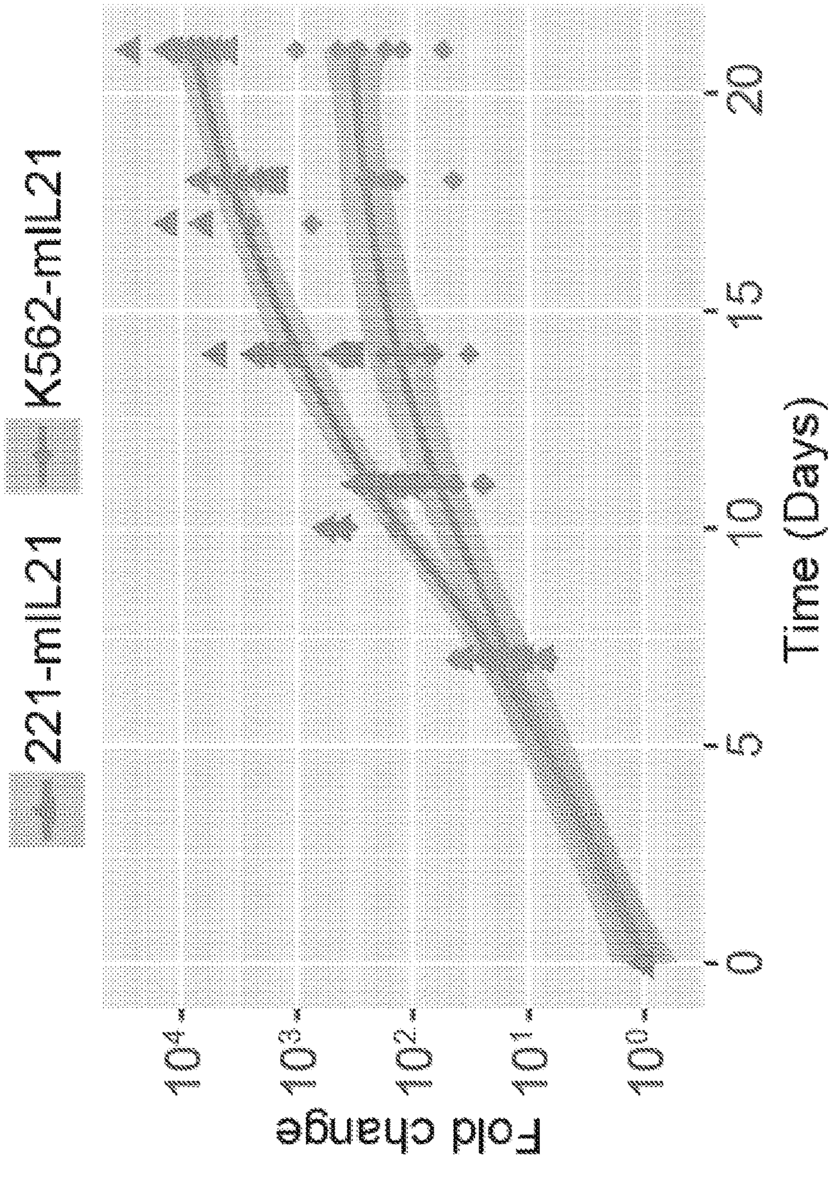
Figure 15D:
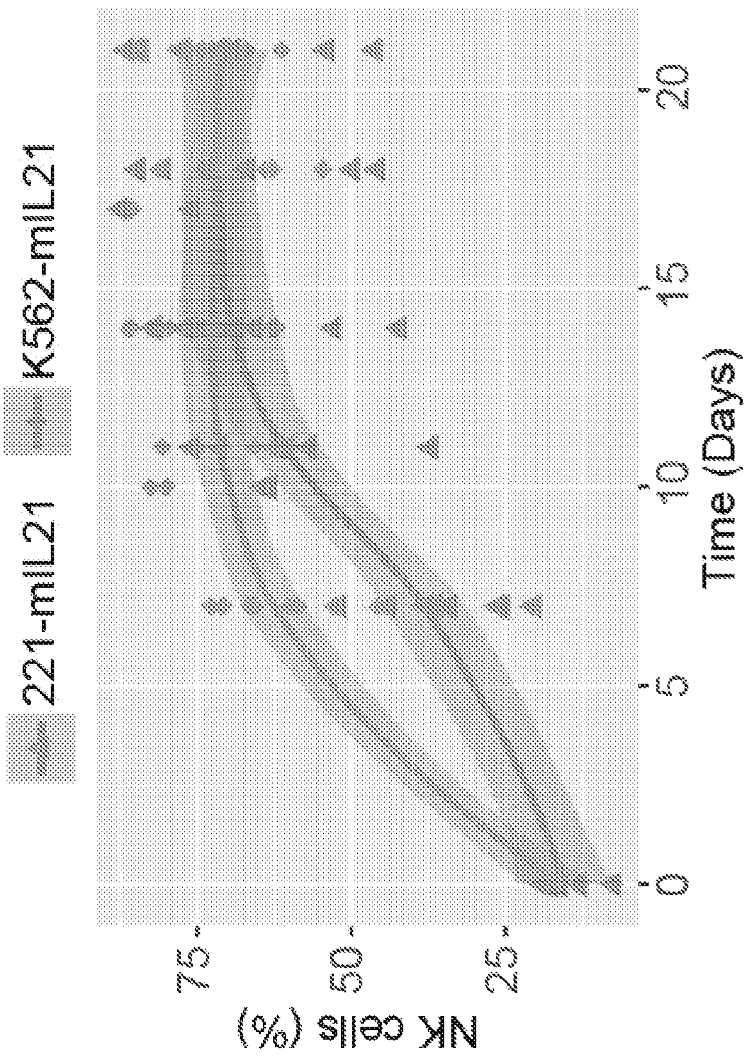
Figure 15E:
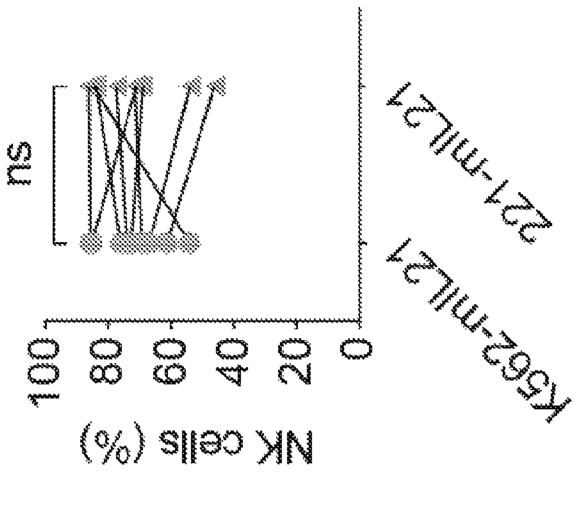
Figure 15F:
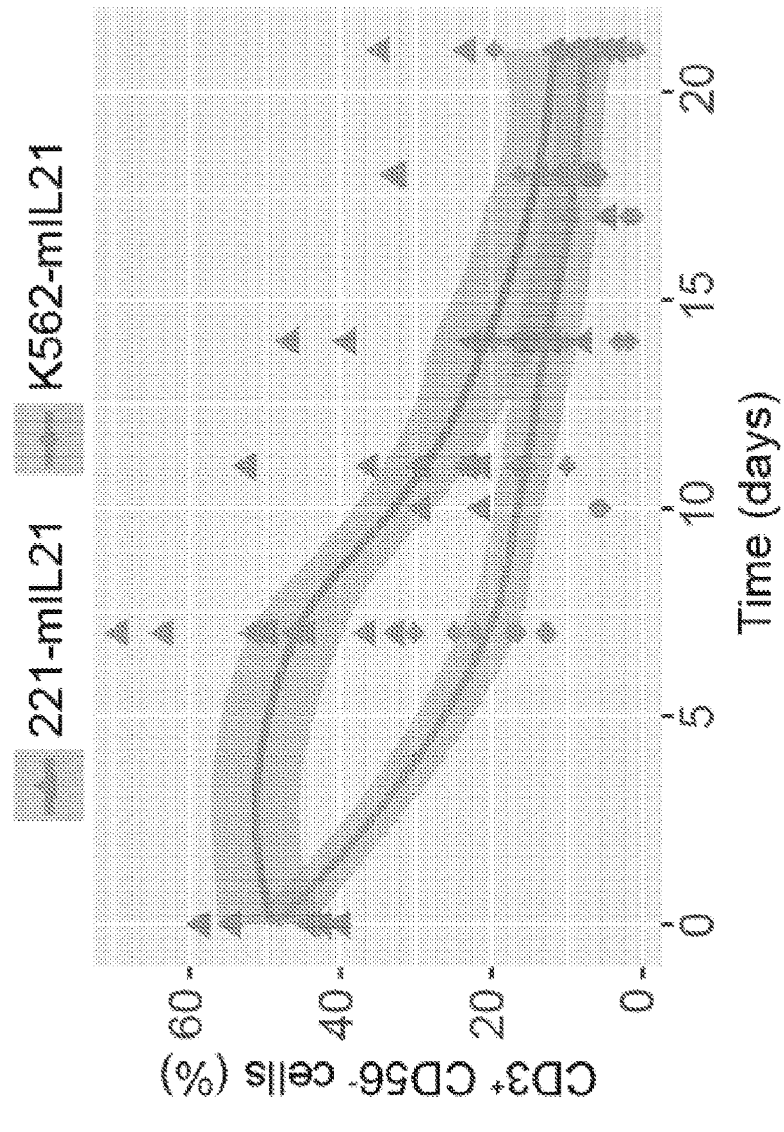
Figure 15G:
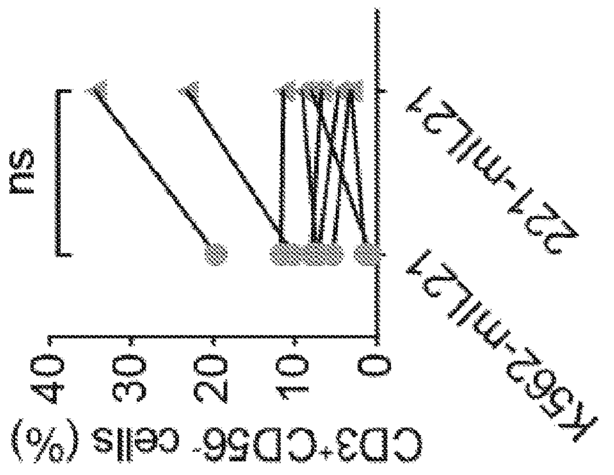
Figure 15I:
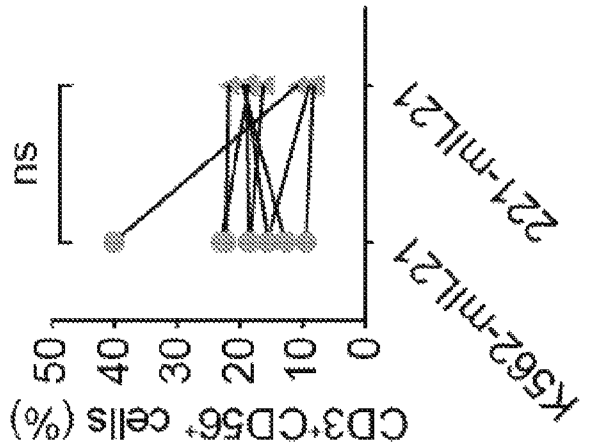
Figure 15H:
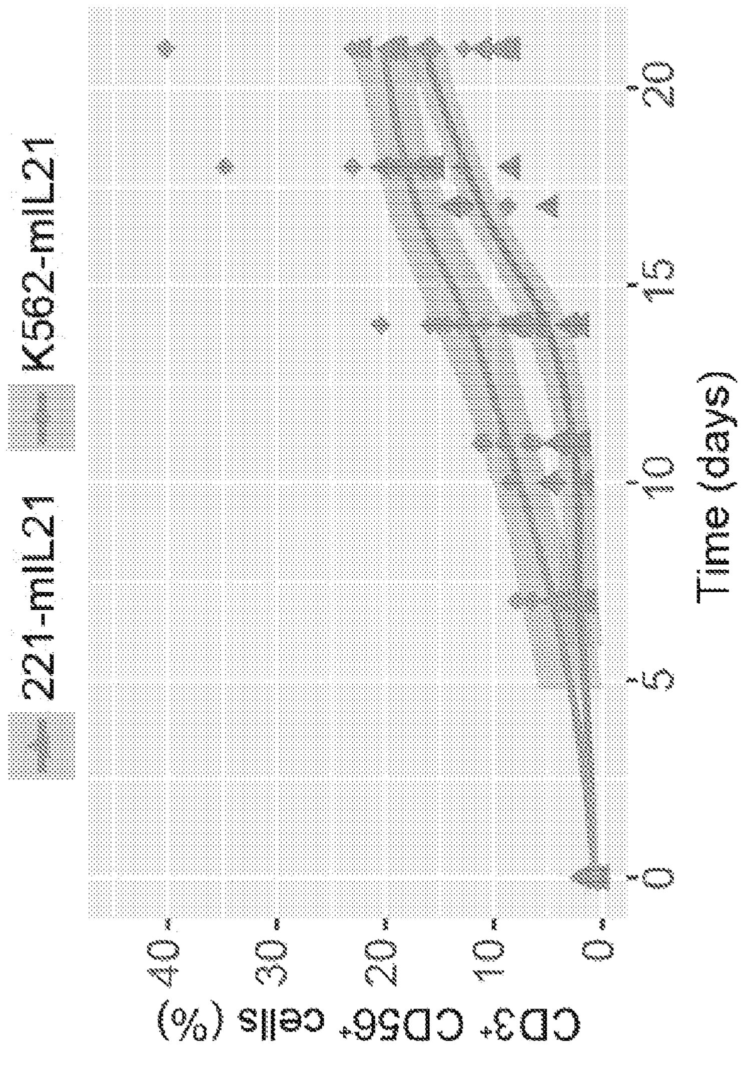
Figure 15K:
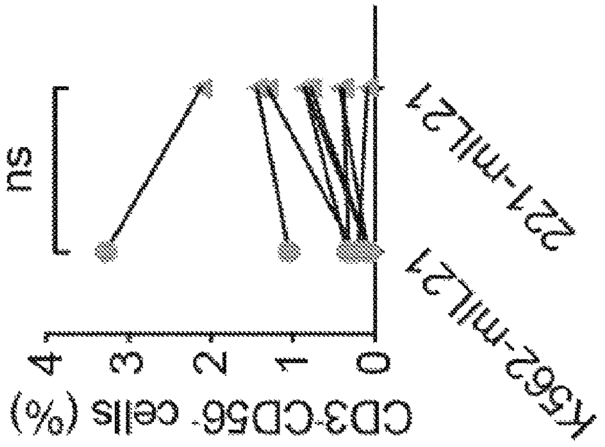
Figure 15J:
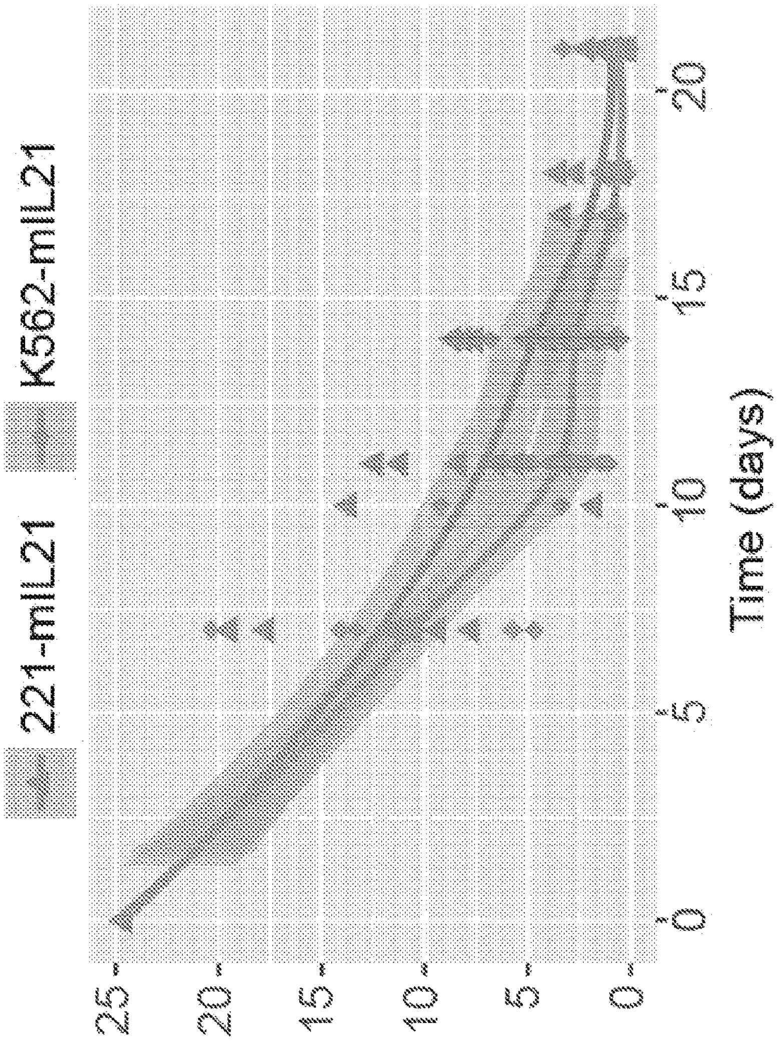
Figures 16A, 16B, 16C:
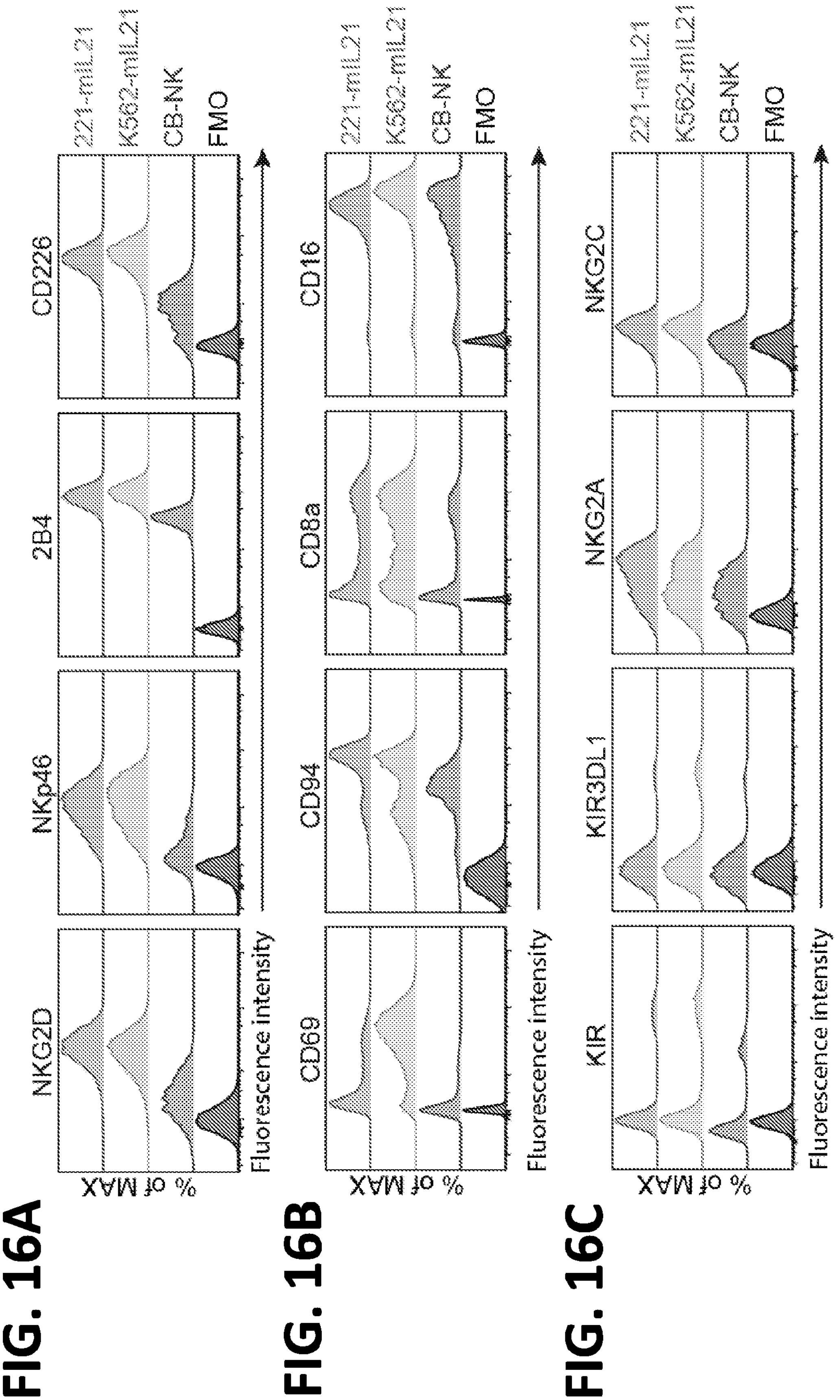
FIGS. 16A-16D. Phenotype and function of NK cells expanded from cord blood mononuclear cells using different feeder cell systems.
Figure 16D:
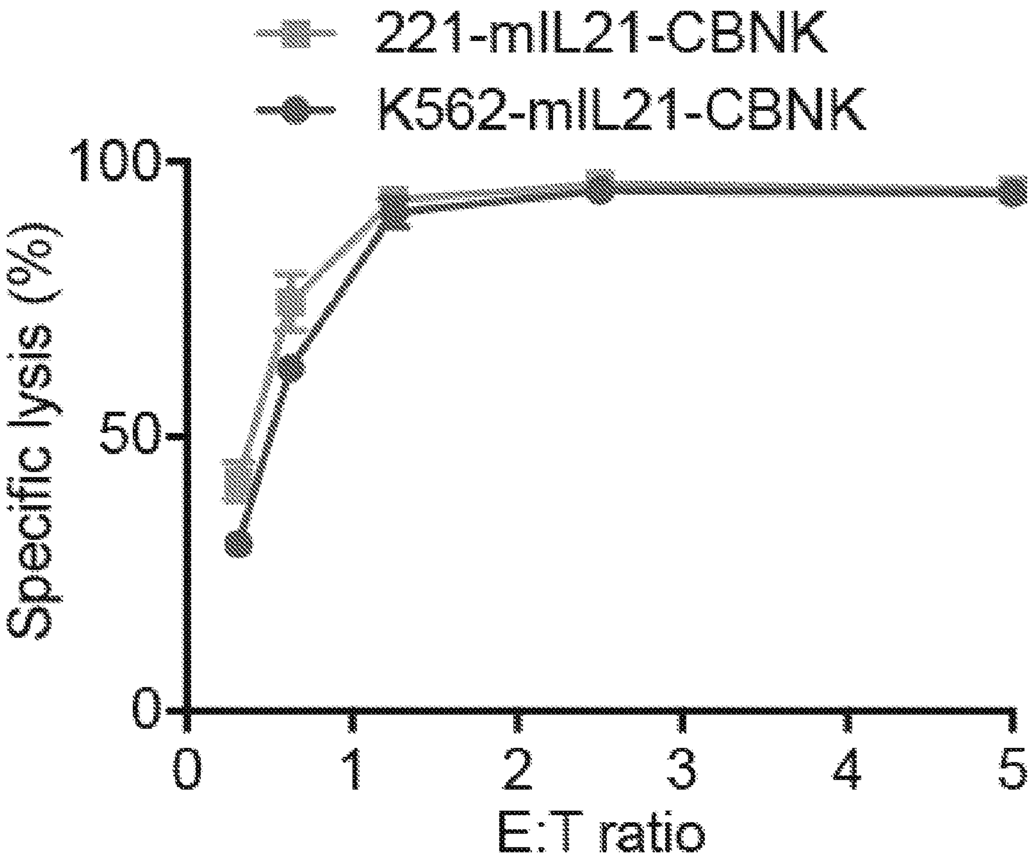
Figure 17A:
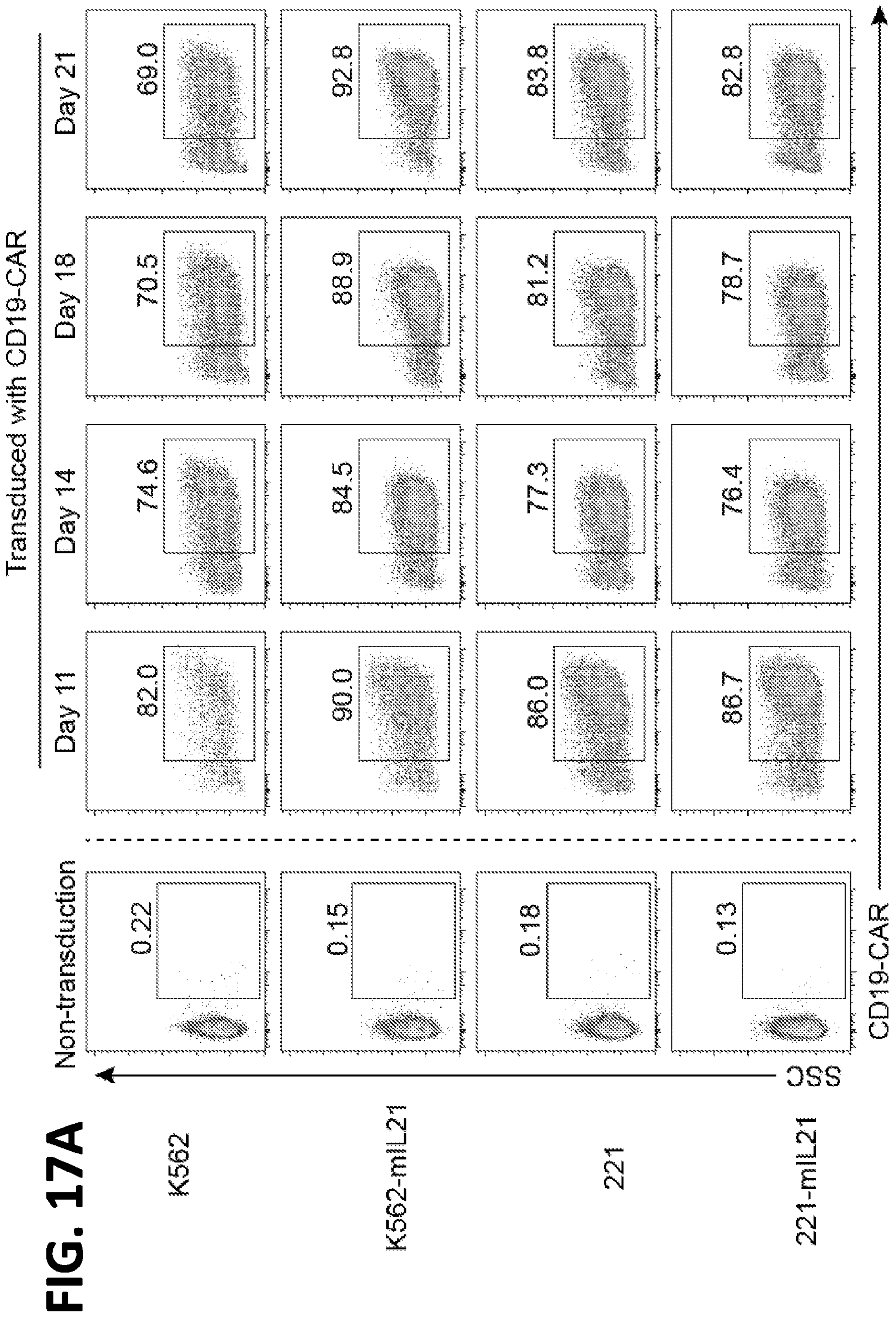
FIGS. 17A-17H. Expansion of CD19-CAR NK cells from PBMCs with different feeder cell systems.
Figure 17B:
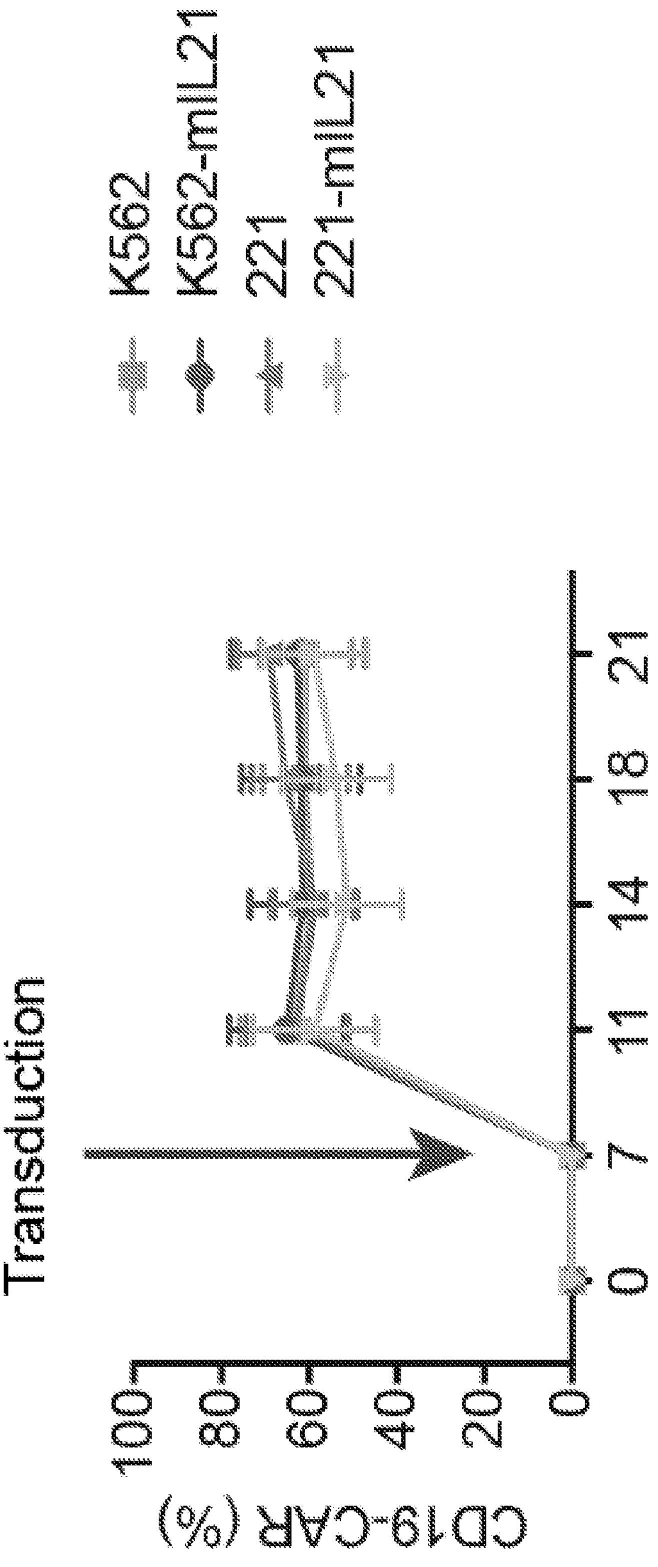
Figure 17D:
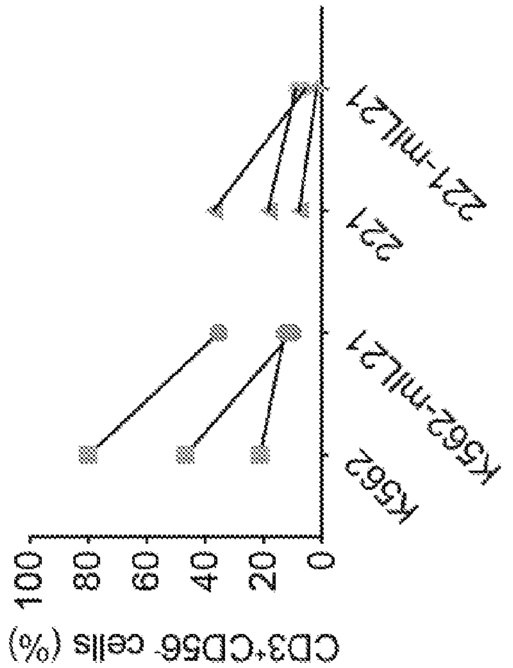
Figure 17C:
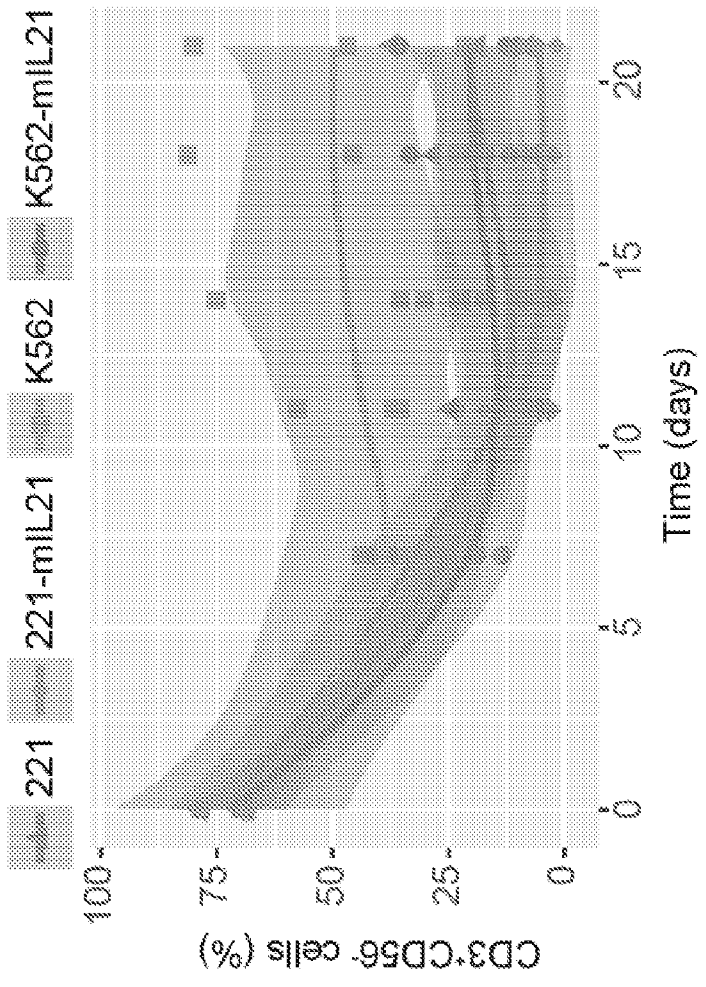
Figure 17F:
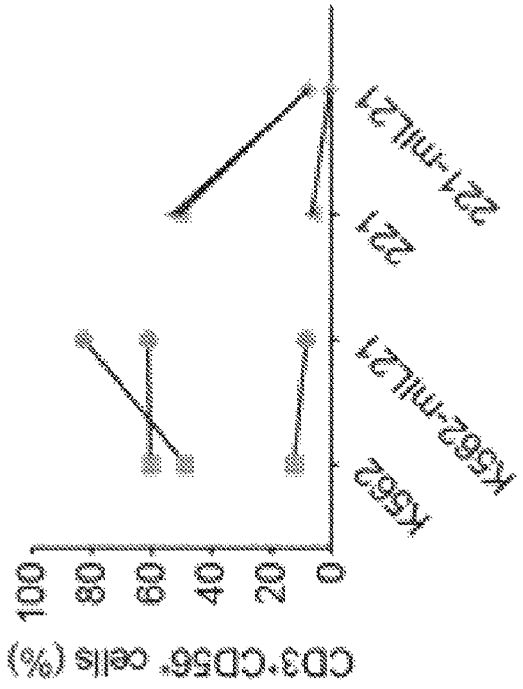
Figure 17E:
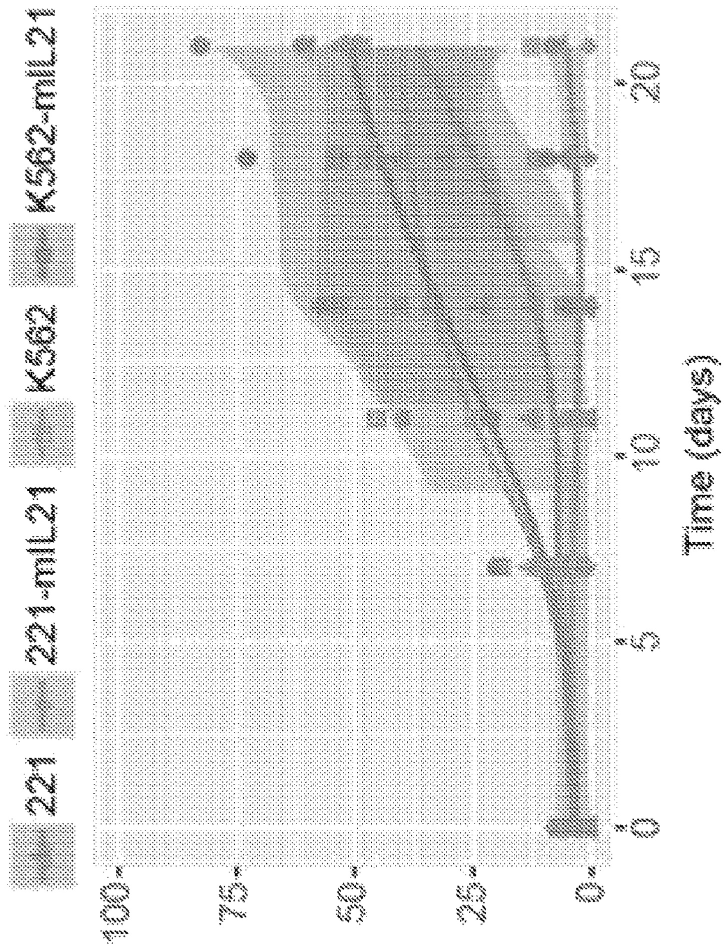
Figure 17H:
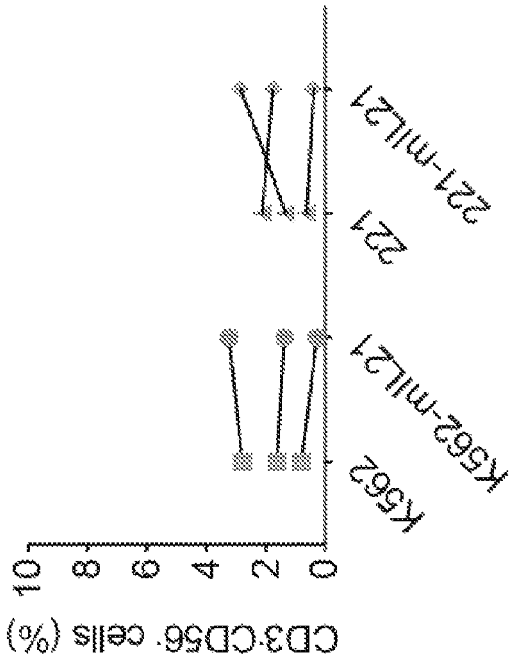
Figure 17G:
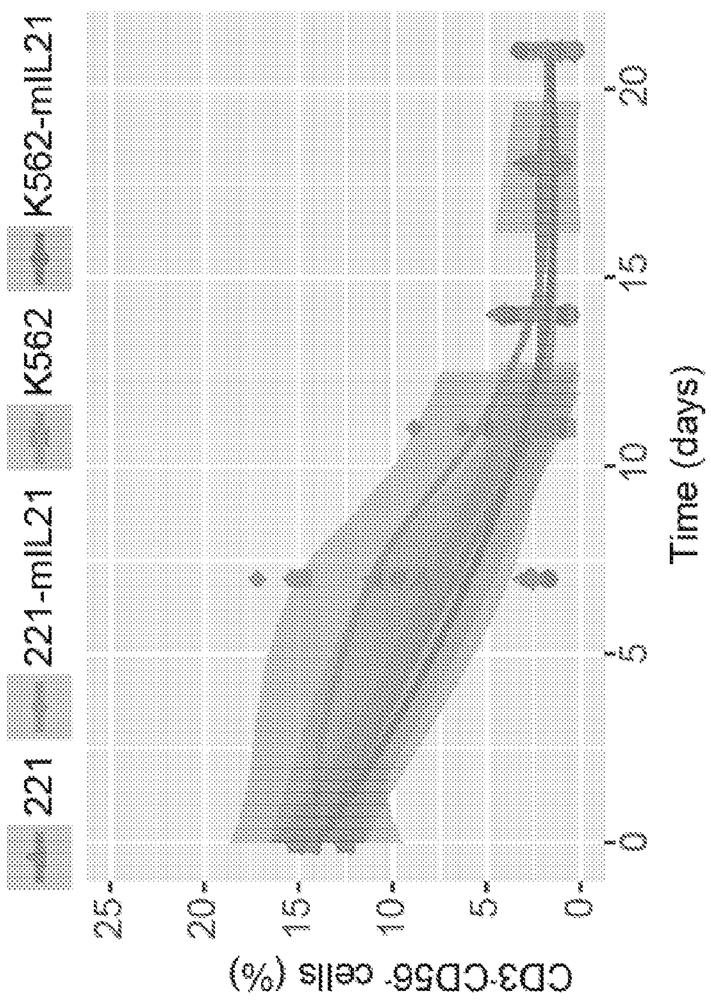

Unexpectedly, gene signatures of lymphocyte activation, lymphocyte differentiation, and cell-cell adhesion in NK cells expanded with the 221-mIL21 feeder cell expansion system on day 7 were significantly down-regulated compared to NK cells expanded with the K562-mIL21 feeder cell expansion system (FIG. 13H-13J; FIGS. 18A and 18D-18F), which can be further illustrated by heatmaps of NK cell development & maturation, inhibitory receptors, activating receptors, and cytotoxic function (FIG. 13K-13N; FIGS. 19D-19I). In conclusion, the 221-mIL21 feeder cell expansion system promotes a less-differentiated, memory-like, NK cell development.

In view of the many possible embodiments to which the principles of the disclosure may be applied, it should be recognized that the illustrated embodiments are only examples and should not be taken as limiting in scope. Rather, the scope is defined by the following claims. We, therefore, claim all that comes within the scope and spirit of these claims.

I claim:

1. A modified 721.221 cell expressing membrane-bound IL-21 (mIL-21), wherein the mIL-21 comprises an amino acid sequence comprising at least 90% or at least 95% sequence identity to SEQ ID NO: 2, and/or is encoded by a nucleic acid comprising a nucleic acid sequence comprising at least 90% or at least 95% sequence identity to SEQ ID NO: 1, wherein the mIL-21 is present in a construct further comprising an extracellular fragment from an IgG sequence, a transmembrane fragment from a CD28 sequence, an intracellular fragment from a CD28 sequence, an intracellular fragment from a 4-1BB sequence, and an intracellular fragment from a CD3ζ sequence.

2. The modified 721.221 cell of claim 1, wherein the mIL-21 is expressed in the 721.221 cell using a viral vector.

3. The modified 721.221 cell of claim 1, wherein the construct is encoded by a nucleic acid comprising at least 90% or 95% sequence identity to SEQ ID NO: 3.

4. The modified 721.221 cell of claim 1, wherein the cell further expresses at least one additional heterologous interleukin and/or interleukin receptor.

5. The modified 721.221 cell of claim 4, wherein the at least one additional heterologous cytokine, activating receptor ligand, TRL ligand, or receptor thereof comprises IL-15 receptor alpha (IL-15Rα).

6. The modified 721.221 cell of claim 1, further expressing at least one of IL-2, IL-12, IL-33, IL-27, IL-18, IL-7, mIL-7, IL-15, membrane-bound IL-15 (mIL-15), a toll-like receptor (TRL) ligand, UL16 membrane-binding protein (ULBP)-1, ULPB-2, and/or major histocompatibility complex (MHC) class I chain-related protein A (MIC-A).

7. A method of expanding a population of natural killer (NK) cells or T cells, comprising contacting a population of cells with the modified 721.221 cells of claim 1 and at least one cytokine for 1-40 days under conditions sufficient for cell expansion.

8. The method of claim 7, wherein the population of cells is from peripheral blood, cord blood, ascites, menstrual blood, or bone marrow.

9. The method of claim 7, wherein the population of cells comprises chimeric antigen receptor (CAR)-modified cells.

10. The method of claim 9, wherein the CAR-modified cells comprise CAR-modified T cells or CAR-modified natural killer (NK) cells.

11. The method of claim 7, wherein the population of cells and the modified 721.221 cells are contacted for at least 14-21 days.

12. A method of treating a cancer or an infectious or immune disease, comprising administering natural killer (NK) cells or T cells produced by the method of claim 7 to a subject with cancer or an infectious or immune disease, thereby treating the cancer or an immune disease.

13. A method of treating a cancer or an infectious or immune disease, comprising:

contacting a population of cells with the modified 721.221 cells of claim 1 and at least one cytokine for at least 14-21 days, thereby producing natural killer (NK) cells or T cells; and administering the NK cells or T cells to a subject with cancer or an infectious or immune disease, thereby treating the cancer or an immune disease.

14. The method of claim 13, wherein the cancer or immune disease comprises an autoimmune disease, a transplant rejection, a sarcoma, a neuroblastoma, a solid tumor, or a blood cancer.

15. The method of claim 13, wherein the population of cells is from a subject with cancer or immune disease.

16. The method of claim 13, wherein the population of cells comprise CAR-modified lymphocytes.

17. A method of producing a modified 721.221 cell, comprising:

transducing or transfecting a population of 721.221 cells with a nucleic acid encoding mIL-21, wherein the mIL-21 is encoded by a nucleic acid sequence comprising at least 90% or at least 95% sequence identity to SEQ ID NO: 1, and/or the mIL-21 comprises an amino acid sequence comprising at least 90% or at least 95% sequence identity to SEQ ID NO: 2;

isolating the cells that express the mIL-21; and irradiating the isolated cells, thereby producing the modified 721.221 cell, wherein the mIL-21 is present in a construct further comprising an extracellular fragment from an IgG sequence, a transmembrane fragment from a CD28 sequence, an intracellular fragment from a CD28 sequence, an intracellular fragment from a 4-1BB sequence, and an intracellular fragment from a CD32 sequence.

18. The method of claim 17, wherein the population of 721.221 cells is transduced with a viral vector comprising the nucleic acid encoding the m-IL21.

19. The method of claim 17, wherein the construct is encoded by a nucleic acid comprising at least 90% or 95% sequence identity to SEQ ID NO: 3.

20. The method of claim 17, wherein the population of 721.221 cells is further transduced or transfected with a nucleic acid encoding an additional heterologous cytokine, activating receptor ligand, TRL ligand, or receptor thereof, or IL-15Rα.

* * * * *